United States Patent
Markowitz

(10) Patent No.: US 7,432,050 B2
(45) Date of Patent: Oct. 7, 2008

(54) METHODS AND COMPOSITIONS FOR DETECTING COLON CANCERS

(75) Inventor: Sanford D. Markowitz, Pepper Pike, OH (US)

(73) Assignee: Case Western Reserve University, Cleveland, OH (US)

( * ) Notice: Subject to any disclaimer, the term of this patent is extended or adjusted under 35 U.S.C. 154(b) by 821 days.

(21) Appl. No.: 10/266,103

(22) Filed: Oct. 7, 2002

(65) Prior Publication Data

US 2004/0242510 A1     Dec. 2, 2004

Related U.S. Application Data

(60) Provisional application No. 60/327,537, filed on Oct. 5, 2001.

(51) Int. Cl.
*C12Q 1/68*     (2006.01)
*C12P 19/34*     (2006.01)
*C07H 21/04*     (2006.01)

(52) U.S. Cl. .......................... 435/6; 435/91.2; 536/24.33

(58) Field of Classification Search ...................... 435/6, 435/91.2; 536/23.1, 24.33

See application file for complete search history.

(56) References Cited

U.S. PATENT DOCUMENTS

| 5,786,146 | A | * | 7/1998 | Herman et al. | ................. | 435/6 |
| 6,017,704 | A | | 1/2000 | Herman et al. | ................. | 435/6 |
| 6,200,756 | B1 | | 3/2001 | Herman et al. | ................. | 435/6 |
| 6,265,171 | B1 | | 7/2001 | Herman et al. | ................. | 435/6 |
| 6,812,339 | B1 | * | 11/2004 | Venter et al. | ............. | 536/24.31 |
| 7,183,051 | B2 | * | 2/2007 | Androphy et al. | ............... | 435/6 |

FOREIGN PATENT DOCUMENTS

| WO | WO-01/68911 | 9/2001 |
| WO | WO-01/77375 | 10/2001 |
| WO | WO-01/92565 | 12/2001 |
| WO | WO-02/00927 | 1/2002 |

OTHER PUBLICATIONS

Lowe et al. A computer program for selection of oligonucleotide primers for polymerase chain reactions. Nucleic Acids Research, vol. 18, No. 7, pp. 1757-1761, 1990.*
Denissenko et al. Cytosine methylation determines hot spots of DNA damage in human P53 gene. Proc. Natl. Acad. Sci., vol. 94, pp. 3893-3898, 1997.*
Grand et al. Frequent deletion of hSNF5/INI1, a complement of the SWI/SNF complex, in chronic myeloid leukemia. Cancer Res., Vo. 59, pp. 3870-3874, 1999.*
Ahlquist, D.A. et al. Colorectal Cancer Screening by Detection of Altered Human DNA in Stool: Feasibility of Multitarget Assay Panel. Gastroenterology 119, 1219-1227 (Nov. 2000).
Deng, G. et al. Methylation of CpG in a Small Region of the hMLH1 Promoter Invariability Correlates with the Absence of Gene Expression. Cancer Res. 59, 2029-2033 (May 1, 1999).
Ding, H. et al. Characterization of a Helicase-Like Transcription Factor Involved in the Expression of the Human Plasminogen Activator Inhibitor-1 Gene. DNA Cell Biol. 15, 429-442 (1996).
Ding et al. Functional Interactions between Sp1 or Sp3 and the Helicase-like Transcription Factor Mediate Basal Expression from the Human Plasminogen Activator Inhibitor-1 Gene. J. Biol. Chem. 274, 19573-19580 (1999).
Dong, S.M. et al. Detecting Colorectal Cancer in Stool With the Use of Multiple Genetic Targets. J. Natl. Cancer Inst. 93, 858-865 (Jun. 6, 2001).
Esteller, M. et al. Detection of Aberrant Promoter Hypermethylation of Tumor Suppressor Genes in Serum DNA from Non-Small Cell Lung Cancer Patients. Cancer Res. 59, 67-70 (Jan. 1, 1999).
Gonzalgo, M.L. & Jones, P.A. Rapid quantitation of methylation differences at specific sites using methylation-sensitive single nucleotide primer extension (Ms-SNuPE). Nucleic Acids Res. 25, 2529-2531 (1997).
Herman, J.G. et al. Methylation-specific PCR: A novel PCR assay for methylation status of CpG islands. PNAS 93, 9821-9826 (Sep. 1996).
Herman, J. & Baylin, S. Methylation-Specific PCR. In Current Protocols in Human Genetics, N. Dracopoli, ed., John Wiler & Sons, Inc. vol. 2, pp. 10.6.1-10.6.10 (1998).
Hibi, K. et al. Molecular Detection of Genetic Alterations in the Serum of Colorectal Cancer Patients. Cancer Res. 58, 1405-1407 (1998).
Kane, M.F. et al. Methylation of the hMLH1 Promoter Correlates with Lack of Expression of hMLH1 in Sporadic Colon Tumors and Mismatch Repair-defective Human Tumor Cell Lines. Cancer Res. 57, 808-811 (1997).
Mahajan, M.C. & Weissman, S. DNA-dependent adenosine triphosphatase (helicase transcription factor) activates Beta-globin transcription in K562 cells. Blood 99, 348-356 (Jan. 1, 2002).
Moinova, H.R. et al. HLTF gene silencing in human colon cancer. PNAS 99, 4562-4567 (Apr. 2, 2002).
Muchardt, C. and Yaniv, M. ATP-dependent chromatin remodeling: SWI/SNF and Co. are on the job. J. Mol. Biol. 293, 187-198 (1999).
Sanchez-Cespedes, M. et al. Gene Promoter Hypermethylation in Tumors and Serum of Head and Neck Cancer Patients. Cancer Res. 60, 892-895 (Feb. 15, 2000).
Silva, J.M. et al. Aberrant DNA methylation of the p16INK4a gene in plasma DNA of breast cancer patients. Br. J. Cancer 80, 1262-1264 (1999).
Sudarsanam, P. and Winston, F. The Swi/Snf family. Trends Genet. 16, 345-351 (2000).
Toyota, M. et al. CpG island methylator phenotype in colorectal cancer. PNAS 96, 8681-8686 (Jul. 1999).
Toyota, M. et al. Distinct genetic profiles in colorectal tumors with or without the CpG island methylator phenotype. PNAS 97, 710-715 (Jan. 18, 2000).
Traverso, G. et al. Detection of APC Mutations in Fecal DNA From Patients with Colorectal Tumors. N.E. J. Med. 346, 311-320 (Jan. 31, 2002).

(Continued)

*Primary Examiner*—Suryaprabha Chunduru
(74) *Attorney, Agent, or Firm*—Ropes & Gray LLP

(57) ABSTRACT

This application describes methods and compositions for detecting and treating HLTF-associated neoplasia. Differential methylation of the HLTF nucleotide sequences has been observed in HLTF-associated neoplasia such as colon neoplasia.

15 Claims, 52 Drawing Sheets

OTHER PUBLICATIONS

Traverso, G. et al. Detection of proximal colorectal through analysis of faecal DNA. Lancet. 359, 403-404 (Feb. 2, 2002).

Veigl, M.L. et al. Biallelic inactivation of hMLH1 by epigenetic gene silencing, a novel mechanism causing human MSI cancers. PNAS 95, 8698-8702 (Jul. 1998).

Wong, I.H.N. et al. Detection of Aberrant p16 Methylation in the Plasma and Serum of Liver Cancer Patients. Cancer Res. 59, 71-73 (Jan. 1, 1999).

Xiong, Z. & Laird, P.W. Cobra: a sensitive and quantitative DNA methylation assay. Nucleic Acids Res. 25, 2532-2534 (1997).

Zhang, Q. et al. Molecular cloning and characterization of P113, a mouse SNF2/SWI2-related transcription factor. Gene 202, 31-37 (1997).

Hibi et al., "Methylation pattern of HLTF gene in digestive tract cancers", Int. J. Cancer, vol. 104, pp. 433-436 (2003).

* cited by examiner

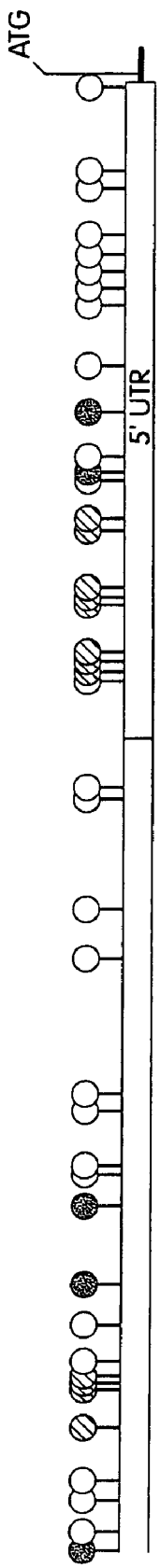
Fig. 2A
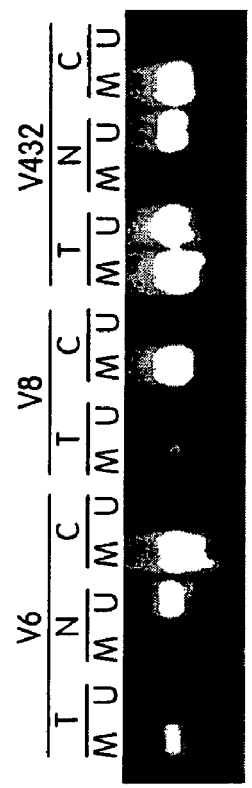
Fig. 2B
Fig. 2C

| CIMP STATUS | HLTF METHYLATED | HLTF NONMETHYLATED |
|---|---|---|
| CIMP+ | 20 | 11 |
| CIMP- | 8 | 25 |

Fig. 6A

| | HLTF METHYLATED | HLTF NONMETHYLATED |
|---|---|---|
| MLH1 METHYLATED | 20 | 6 |
| MLH1 NONMETHYLATED | 17 | 44 |

Fig. 6B

PRIMER SET (1277F + 1724R): Hpa II ASSAY.
PRIMER SETS: (1352MF + 1606MR), (1347UF + 1606MR), (1347UF + 1610UR): MS-PCR ASSAY.
(1352MF + 1627MR), (1347UF + 1627MR), (1347UF + 1631UR): MS-PCR ASSAY.
(1352MF(ASS) + 1607MR(ASS)), (1349UF(ASS) + 1611UR(ASS)): MS-PCR ASSAY.
(1352MF(ASS) + 1607MR(ASS) + 1611UR(ASS)): MS-PCR ASSAY.

mswmfkrdpvwkylqtvqyqvhgnfprlsyptffprfefgdvippddfltsdeevdsvlfgslrghvvglryytgvvnnn
emvalqrdpnnpydknaikvnnvngnqvghlkkelagalayimdnklaqiegvvpfgannaftmplhmtfwgkeenrkav
sdqlkkhgfklgpapktlgfnlesgwgsgragpsysmpvhaavqmtteqlktefdklfedlkeddkthemepaeaietpl
lphqkqalaw

Fig. 15

5'-
TGGCAGTTACATGGTGCCGCCTGTGCAGTCGGGCGCCACCACCAGCTTCCTGCCCTGTGCAGATTAAAAGGCCAGCTTCGG
GGACAGCAGCCTCCTCAACGCAAAGCAGCCCTGCCAGCGTCGGCTGTCGGCTGTCCAAGTTGACGGTCCAGGG
CCGCATTCTCCGGTCACCTCAGACTCTGGAGAGAGCCATGAGGCCTCAGAGCGCCCCTGCAGTTCCTGA
GAAAACAAGGCCTCCCCGTCCCCTGCTGAGCAGCCAAGTGCCCACGGGAAAATGGTCCGTCCACCATTTCAGGCAA
ACGCCCCCATAGCTGTAATAAACATGTGATTTTCCAAGAAGAAATTTCTTAAAAATAACAAAAGA
GGTGGGAGGGGACTCTAAGTTCCATTTAAGATTTTCCAAACTCGTTGTGTCTCATGCATACGCTGAGGCTTAACATGAA
AATTTGGAGCGAAAGTCCCACGGTTCACCACAGAAGTGCCACATTAGATGAGAAGAAATATCTCGGTAGCTCTAGGTCTCGTAAACC
GTGGAGCTCCTTAGTATAAGGCCCTATTAGTCGTAGGATAAAGGAAGAAAATAAGAGAAGAAGATACGGTAGAGCCT
TTAGAATGGGGTTCAGTCTTAGGACTCGTAGGATAAGTGCCACATTAGAAGGTCGTTCCCTCCGTTTGAGGCAGGGAATCAAACAAAA
CACCGGCACCGCAGGCACCGCAGTCGCACTCCTGGGCGCCTCGTGCCTTCCCCGCCGCGGGGCGGGGAGTTGCCCTTCCTTCTGTG
CCCGGATGAACCACCCTTGCAGCCCGACCCCCTCTCCTTTGAATGGCAGCCGTCTTTGGGCTTTCCTAGTGCCAGTCACAGAGCGACGCTGGTCTCCC
CTCTGACTGGTTTGGCTCCGCACTCTCCTTGTGATTGGGCTTCGACTCGCGGGACGTCGACTTACCTTCAGTCGTCGTCCTGATCCG
AGATTGTGTCAGAAGGAGACGTCCCGGCTTCAGGGCTGGAAGGAGGCGTATCAAGAGAGTGAAGGGGCGGAGGGGTGGG
GCGCTCGGAATTGTCCCCGGCTCCTCTTGTCATCCCACTCAGCGCCATGTGTTCAAGAGAGTGAAGGGGCGGAGGGGTGG
GAGCCGAGCGCCTCCTCTTGTCATCCCACTCAGCCGTCCCCAAATGAACCTGACCTTCCTCTGGGCCGTTCCTGCGGCGATTTG
GCGCTCGGTCTAACGGCCTGAGGCGTCCCCAAATGAACCTGACCGCCGGAGAAATAAATCATTGTCTTCGCTGGCGAGTAGGGGCT
TGCAGCTGTATTCGTTCTGTTGGTCGCATATGTCCAAATCTCTGTCACCGACTGTGGGGGCCTGGGGCTTAAAGCATCTCGGC
CCTAGGGCGAGTCCCGTGTTAGGACTTAGAACATCCATTAGATACCCATGTGCGCCAGGCATTGTCTCGGTGGAGGGCCGAGTAAGACA
CAGTGCTTATTTAACAAAACATCCATTAGATACCCATGTGCGCCAGGCATTGTCTCGGTGGAGGGCCGAGTAAGACA
GTCCTTGTCCCCAAGTGGCTCACAGCTTATCGTATGCACAGACGTGCAGATAAGTAGTTCTTAGGAGAGGCGCTAGTAGAGAT
ATGCCCACTTGCAAGGAAAACGCATCGCAAATTGGTATTTATGGTCATTCCCGAAACAGTTACACCTAATGGGTTTGGGGTTA
GACTCCCCTTCACTTTGTCCAATTGTCCAAATTGGTATTTATGGTCATTCCCGAAACAGTTACACCTAATGGGTTTGGGGTTA
TGCTTAAACCGGCGACGAAGGCGGGTACGGTGGCTTGGGCGTGGTGTTTGGATACCAGAATA
GGTGTTCGCTCGCAGGAGTTACAGTGATGATGCTGGAAAATTATAAACAACTTCTGTACATTA
ATAGTTGTATTTTTATAAGTCTTTATATAGCTCAATCCCTATTGAAATTTGGCATATGATTTCATTTTTAAATTATT
T-3'

Fig. 16

SENSE STRAND-METHYLATED (BISULFITE CONVERSION):

5'-GTTTAGTTTTAGGATTCGTAGGATAAAGGAAGGTCGTTTTTTCGTTTGAGGTAGGGAATTAAATAAAATAT*CG*TATCGTAGGTATCG
TAGTCGTATTTTTGGGGTTTT*CG*TCGCGTTCGTTTTTTGATTGGTTTTCGTATTTTTTTTCGTAGTT*CG*GAT
TTTTCGTCGTTTTTGAATGGTAGCGGGGCGAGTTGTTTTTTAGATGTGTAGAAGGAGACGGG*CG*T*CG*ACGTTTGATTGGAATTCG*CG*GCGATT
TTTTTTAGTCGTTAGTGTTATAGAGCGACGTTGGTTTTTT*CG*GTTTGATTGGAAGGAGGCGTATCGAGGCGG
TATTTTTAGT*CG*TG*CG*TTTTTGATT*CG*GCCGTTCCGAATTGTTT*CG*TTTTATTAGCGTTATGTTTTGGATGTTTAAGAGGTTAAGGGGCGGA
TTCGAAAACGATTTAGGGGAGTCGAGGCGTTTTTTTTGTATTTTATTAGCGTTATGTTTTGGATGTTTAAGAGGTGAAGGGGCGGA
GGGGGTGGGG-3'

SENSE STRAND-UNMETHYLATED (BISULFITE CONVERSION):

5'-GTTTAGTTTTAGGATTTGTAGGATAAAGGAAGGTGTTTTTTTGTTTGAGGTAGGGAATTAAATAAAATAT*TG*TATTGTAGGTATTG
TAGTTGTATTTTTGGGGTTT*TG*TTGTGTTTGTTTTTTGATTGGTTTTTGTATTTTTTTTTGTAGTT*TG*GAT
TTTTTGTTGTTTTGAATGGTAGTGGGGTGAGTTGTTTTTTAGATTGTGTAGAAGGAGATGGGT*GT*TGA*TG*TTTGATTGGTGTT*TG*TG*G*ATT
TTTTTTAGTTGTTAGTGTTATAGAGTGATGTTGGTTTTTTTGTT*T*GATTGGAAGGAGGTGTATTGAGGTGG
TATTTTTAGTTGTGTGTTTTTGATT*TG*GTTTGTTTTTTGAATTGTTT*TG*GTTTTATTAGTGTTATGTTTTTGATGTTTTATTAGTGTTATGTTTTTGATGTTTAAGAGGTGAAGGGGGTGGA
TTTGAAAATGATTTAGGGGAGTTGAGGTGTTTTTTTTGTATTTTATTAGTGTTATGTTTTTGATGTTTAAGAGGTGAAGGGGGTGGA
GGGGGTGGGG-3'

Fig. 18

COMPLEMENTARY STRAND-METHYLATED (BISULFITE CONVERSION):

3'--CAAATCAAAATCCTAAGCATCCTATTCCTTCCTTCCAGCAAAAAAGCAAACTCCATCCCTTAATTTATTTTATAGCCATAGCATCCATAGC
ATCAGCATAAAAACCCAAGCACCAAAGCGCAAGCAAACCCCGCCTCTTAAGCTACCTTAATAAAACATCAAGCTA
AAAAGCAGCAAAAACTTACCATCGCCCGCCTCAACAAAAACTAACACATCTTCCTGCCAAAGCATAAAAAAGCACTAACCC
AAAAAATCACAACAATAATATCTGCTGCAACCAAAAAATCTAACACATCTTCCTGCCAGCTGCAAACTAACCTAAGCGCGCGCTAA
ATAAAAATCAGCACGCGCAAGCCTTAAACAAAAGCCAAATCCCAAGCCCCAAACCTTCCTCCGCATAGCTCCGCC
AAGCTTTGCTAAATCCCCTCAGCTCCGCAATAAATCGCAATACAAAACCTACACAAATTCTCCACTTCCCCCGCCT
CCCCCACCCC-5'

COMPLEMENTARY STRAND-UNMETHYLATED (BISULFITE CONVERSION):

3'--CAAATCAAAATCCTAAACATCCTATTCCTTCCTTCCAACAAAAAAACAAACTCCATCCCTTAATTTATTTTATAACCATATAACATCCATAAC
ATCAACATAAAAACCCAAAACACCAAAACACAAACAAACCCCACCCCTTCTTAAACTACCTTAATAAAACATCAAAACTA
AAAACAACAAAAACTTACCATCACCCACCTCAACAAAAACTAACACATCTTCCTACAAACATAAAAAAACACTAACCC
AAAAAATCACAACAATAATATCTACTACAACCAAAAAATCTAACACTAACCTAAAACACACTAA
ATAAAAATCAACACAACAAACCTTAAACAAAAACAAATCCCAAACCTTCCTCCACATAACTCCACC
AAACTTTACTAAATCCCCTCAACTCCACAATAAATCACAATACAAAACCTACAATATCAAAATTCTCCACTTCCCCCACCT
CCCCCACCCC-5'

Fig. 19

5'-
TAGATGAGAAGAAATAAGAGAAGGATACGGTAGAGCCTTTAGAATGGGGTTCAGTCTTTAGGACTCGTAGGATAAAGGA
AGGTCGTTTCCCTCCGTTTGAGGCAGGGAATCAAAACAAACCGCAGGCACCGCAGTCGCACTCCTGGGCCT
CGTGGCTTTCCCGCGCCCGCCCTTGGGCGCCCTTGCAGCCCGGAACCACCCTTGCAGCCCGACCCCCGCCGT
CTTTGAATGGCAGCGGGGCGGAGTTGCCCCTCCCTTCGTGCTCTGACTGGTTTGGCTCCGCACTCTCCTCTTCGTGATTG
GCTTTCCTAGTGCCAGTCACAGAGCGACGCTGGTCTCCCAGATTGTTGCAGAAGGAGACGGCGTCGACGTCTGACTGA
CTCGCGGCGACTTACCTTTCAGTCGTCGTGCCTCGGCGCTCGTCCCGGATCCGGCGCTTCAGGCTGCGGGCCT
GGAAGGAGGCGTATCGAGGCGGCTCGAAAACGATCCAGGGAGCCGAGCGGCTCTCTGTCATCCCACTCAGCGCCATG
TCCTGATGTTCAAGAGAGTTCCTCTGCGTTCCCTGCGGATTGTGCAGCTGTATCGTTCTGTTGGTTAGGACTTGGAAATCTCTG
TGACCTTCCCGGCGTTCCTCTGCGTTCTCGGGGCTTAAAGCATCTCGGCCAGTGCTTTATTTAACAAAACATCATTAGATACCCACTG
GGAGAAATAAATGCATTGTCTTCGCTGGGGCTTAAAGCATCTCGGCCAGTGCTTTATTTAACAAAACATCATTAGATACCCACTG
TCACCGACTGTGGGGGCTGGAGGTGCGGTGAGGCCGAGTAAGACAGTGTCCTTGTCCCAAGTGCTCACAGTTTATCTGTATGCAC
TGCGCCAGGCATTGTCTCGGAGGCGCTGAGAGGCGCTAGTAGAGGCTAGTAGAGATATGCGCAAGGAAAACGCATGCAAATAAGCGAC
AGACGTGCAGATAAGTATTTGCAGAGTATTTGCAGAGAGATATGCAGTAGACTCCAGTAGACTCCAGTAGTTGCAATGGTATTTATG
TGTTCTTAGGAGAATGGAAACTTTTGCAATGGTATTTGCAATGGATCTTACACCTAATGGGTTTGGGTTATGCTTAAACCGGAAGGCTACGGAAGGGTACGGGTGGCTTGG
GTCATTCCCGAAATTCCCACGGTGGCCGTTGGTTTGGATACCAGAATACCAGAATACCAGAATACCAGAATAGGTGTTCTGCTCGCAGGGAGTTACAGTGATGGATGCTGGA
GGCCAATTCCCACGGTGGCCGTTGGTTTGGATACCAGAATACCAGAATAGGTGTTCTGCTCGCAGGGAGTTACAGTGATGGATGCTGGA
TGTATTTTCTGAAAATTATA-3'

Fig. 21

5'-
TAGATGACGAAGAAATAAGAGGAAGGATACGGTAGAGTTTTTAGAATTCGTAGAGTTTTTTTCGTTTGAGGTAGGGA
ATTAAATAAATATCGGTATCGTAGTCGTATCGTATTTTTGGGGTTTCGTGGTTTTTCGGCGTTCGTTTTGATGGAATTATTTTG
TAGTTCCGGATTTTCGTCGTTTTAGAATGGAGTCGGAGTTGTTTTTGTGTTTTGATTGGTTTCGTGATTGGGTTTTTAGTGT
TAGTTATACAGCGACGTTGGTTTTAGATTGTTGTAGAAGGAGAAGGCGAGTTCGGCGATTTATTTTAGTCGTGCGGATTCGGCGTT
CGGAATTTGTTTTCGGTTTAGGGTTGCGGGGTTCGGAAGGAGACGATTTAGGGAGGCGTTTTTTTGTATTTATTTAGCGT
TATGTTTTGGATGTTTAAGAGTGTAGTTGTTCGTTTCGTTATTCGGGTTCGGTCGTATATGTGCGAGAAATAAATTGATTTTCGTTTGCGT
GTTAGGGATTTGGGAAATTTTGTATTGTATCGATTGTGGGGTTTAAAGTATTCGGTTAGTGTTTATTAAATATTTATTGTCGTTAGG
TATTCGTTCGGTGGAGGGTCGAGTAAGTAGTTTTGTTTGTTTAGTGGTTTATATTTGTATGTATAGACGTGTAGTAGTATTGTAGAGAT
ATGGCGTTATTTGTAAGGAGAAACGTATCGTAAATAAGCGATTGTTTTTGGGTTTATGTTTTATATTTTATTGTTAAATTGG
TATTTATGGTTATTTCGAAATAGTTATATATTTAAGTTCGGGTTTGGGGTTTGGGGTTTAATTTTTGGAAAATTATA-3'
GTTTGGATATTAGAATAGGTGTTTTGTTCGTAGGGAGTTATAGTGATGATGTTGGATGTATTTTTGAAAATTATA-3'

Fig. 22

5'-
TAGATGAGAGAAGAAATAACAGACGAAGGATATGGTAGAGTTTTTTAGGATTTGTAGGATAAAGGAAGGTTGTTTTTTTGTTTGAGGTAGGGA
AITAAATAAAATATTGGTAGTTAGTTGTATTTGTTTGTTTTGGGGTGTGGAAGAATTGGATGAATTATTTTGT
AGTTTGGATTTTGTGTTTTGTTTGAATGGTAGTGGGGTGAGTTGTTTTTTTGTGTTTTGATTGGTGTTTTTTTTAGTGTTTA
GTTATAGAGTGATGTTGGTTTTTTAGATGTTGTGATTGGATTGGATGTGATTTATTTTAGTGTGTGATTTATTGGTGTTGG
AATTGTTTTTGGTTTAGGGTTGTGGGGTTTGAAGGTGTATTGAGGTGTTTGAAATGATTAGGGGAGTTGAGGTGTTTTTTGTTATTTATTAGTGTTAT
GTTTTGGATGTTTAAGAGGTTAAGGAGTGAAGGGGGTGAGGGGTGTTGGGGGGTGTTTTTAAATGAATTGATTTTTTGTGTTTTTTTTT
GGGTGATTGTGTAGTTGTTGTTTGTTGTTTGGAGAAATAAATGTATTGTTTTGTTTGAGTAGGGGTTTTAGGGTGAGTTTTGTGTTAG
GGATTTGGGAAATTTTGTAGTTGATTGTGGGGTTTAAAGTATTTTAGTGTTTATTAATAAATATTTATAGATATTTATTGTGTTAGTATTG
TGTTTGGTGGAGGGTTAGTGAGTAAATGTATTGTTTTGTGTTTTATATGTTTATGTGGTTAGTATTGTGAGGTGTTAGTAGTAGAGATATGTG
TTATTATTTGAAGAATATTGTAAATAAGTGATTGTTTTAGGAGAATGAGAAATTGTTGTAATTGTAATTGGTAATTGGTATTTA
TGGTTATTTGAATAGGGTTTAAGGGTTTAATGTTTGGGGTTTATGTTGAAGGTGGTGTTTGGGGTATGCGTATTTTTGGGGTTAATTTTTATTGGGTGTGGTTTGG
ATATTAGAATAGGTGTTTGTTTTTGTAGGGAGTTATAGTGATTGAATGATGTATTTTTTGGAAAATTATA-3'

```
3'-
ATTTATTTTTTTATTTTTTTTATGTTATTTGAAATTTATTTAAGTTAGAATTTGAGTATTTATTTTTTAGTAAAGGAGGTAAATTTGTTTTTAGTTT
GTTTGTTGGTTGTGGTTGTGTGGTGTAGTTGTGAGGATTTGAAAGGGTTGTGTGGTGAATTTGTTTATTTGGTTGGAATGTTGGGT
TTGGGGGTGGTAGAAATTTATTGTTTGTTTGTTTTGTTAATGGAGGAGAATATGAGATTGATTAAATTGAGGTGTGAGGAGAAGTATTAATTGAAACGATTATGTT
AGTGTTTTGTGATTAGAGGGTTAATAATGTTTTTTTTGTGTAGTTGTGAGATTGATTGATTGAGTGTTGTTGAGGATTAGGTTGTGAGTTT
TAAATAGGGGTTGAAGTTTGATGTTTTTTATTTTTGGATTTTTTGTATAGTTTGTTGAGTTTTGTTAGGTTTGTGAGGAGAATAGTAGGGTGAGTTGTGGTA
TAGGATTTATAAGTTTTATTTTTTGTTTATTTGTGAGTTAGATTGTGGATTTGTAGGGGTTCGAAGGTTCTGAAGAGAGTGTAAGGGAT
TTGTTGAAATATGTTGATATAAGTAAGATAATTAGTGTATATTGGTGGTTTATTTATGTAATAATAAATGTGATTGTTTATTTTTGAGGATTTGTTAGGTATAATTT
TTGAATTTTAGAGATAGTGTTGATATTTTGATTTTGATTTTGTTATGAATTTGTTATGAGTTTGATTTGTTAGTTAATTGTTTATGGGTGATATGTGTTGTAATA
TGAGTTATTTTGGTTTATTTGTTAGGAATAGGGTTTATTTAGTTGAGTGTTGAATAGAATATGTTTTGTATGTTTATTTATAAATGTTTTTGATTATTTTTATATGGT
GAATGTTTTTTGTGTAGTTTATTTATTGATAAGATTTTTGAAAAATGTTATGAGGTTATTGAGGGAAGTGAAAATGTAAATAGGTTAAATATAATAT
TAGTAAGGGTTTGTTAATGTGGATTATTTAAATTTAAATGAATTTGTTGTTGTTTATGTTGTTTATGTTATTGAATTTGGTTAAGGGTGTTATTGTATTAATTTATG
GTTTTATTTATAAGATGAGTGTGTTTTTAAGTTTATTATTTATGATTTATTATAAAAGATTTTTAATAT-5'
```

Fig. 25

| MSP4 (against Genetic-Anti-Sense Strand) | 1P-HLTF1581MF(ASS): | 5'-ACGTCGACGTCTAACTAAACTCGCGA-3' |
|---|---|---|
| | 13P-HLTF1713MR(ASS): | 5'-ATCGTTTTCGAGTCGTTTCGATACGTT-3' |
| | 2P-HLTF1575UF(ASS): | 5'-AAACAACATCAACATCTAACTAAACTCACA-3' |
| | 14P-HLTF1728UR(ASS): | 5'-TTTTGGTTTTTTTGATTGTTTTTGAGTTGT-3' |
| MSP5 (against Genetic-Anti-Sense Strand) | 1P-HLTF1581MF(ASS): | 5'-ACGTCGACGTCTAACTAAACTCGCGA-3' |
| | 5P-HLTF1827MR(ASS): | 5'-GACGTTTTAGTCGTTAGATCGAGC-3' |
| | 2P-HLTF1575UF(ASS): | 5'-AAACAACATCAACATCTAACTAAACTCACA-3' |
| | 6P-HLTF1829UR(ASS): | 5'-GGGGATGTTTTTAGGTTGTTAGATTGAGT-3' |
| MSP6 (against Genetic-Sense Strand) | 3P-HLTF1621MF: | 5'-GTCGTGCGTTTTTGATTCGGCGTTC-3' |
| | 7P-HLTF1873MR: | 5'-GCCCAAAAAACGCAAAAAAACGCG-3' |
| | 4P-HLTF1614UF: | 5'-TTTTTTAGTTGTGTGTTTTGATTGGTGTTT-3' |
| | 8P-HLTF1878UR: | 5'-AAATCACCCAAAAAACACAAAAAAACACCA-3' |
| MSP7 (against Genetic-Anti-Sense Strand) | 9P-HLTF1893MF(ASS): | 5'-GTTCTATTAATCGCATATATAACCGCCG-3' |
| | ALU(MB)2133FR(ASS): | 5'-TTGGGGATAAGGATTGTTTTATTTGGTTT-3' |
| | 10P-HLTF1890UF(ASS): | 5'-TTCATTCTATTAATCACATATATAACCACCA-3' |
| | ALU(MB)2133FR(ASS): | 5'-TTGGGGATAAGGATTGTTTTATTTGGTTT-3' |
| MSP8 (against Genetic-Anti-Sense Strand) | 15P-HLTF2201MF(ASS): | 5'-TACGCCACTTACAAAAAACGCATCG-3' |
| | 11P-HLTF2400MR(ASS): | 5'-TTTAAGTTATTATTCGTATTCGTTTTCGTCGTC-3' |
| | 16P-HLTF2197UF(ASS): | 5'-AATATACACCACTTACAAAAAAACACATCA-3' |
| | 12P-HLTF2403UR(ASS): | 5'-GGTTTTAAGTTATTATTTGTATTGTTTTTGTTGTT-3' |

Fig. 27

```
58381 aggtgagaac tgggcaaaag ttgtgaagca gcaattctgt tatatggaca gtgttctgct
58441 ttttaatcct atttagcttg tttcagaaat tctcacttttt gttgactgcc aacatacaaa
58501 gtaagggaaa ctcaagatat taagatggct gtatcagttc ttaaaatctg cagagcctgg
58561 ttcaaaatca gtcactccct tcagaagcag acatggcatc tgttccttgc ttgcttgttg
58621 gttgtgtacc tttcacgaga cctgaatttt agaattgccc agtgctgcca gagtgagtga
58681 gtgtaattct cctttcaggt aaagataggc tatctcaaca ctgctgagtg attcataaac
58741 atatcaacca atagcattaa cccattttat ttcctgtcct tagtgtctga agatgctcac
58801 cagttttctg tgtacagtaa ggcagcatgc taaaatgctt ttgttcagtt ctgtatattt
58861 gaaaatagca gtgtgttctc tgatggttac ctgcagtggc accctgtaca aaaaataaaa
58921 gacttattgc tgtatcttgg ttgtttaatt aaattaagga atttcaccat acaccttga
58981 acaaatctat tagggaattt ttcacaattt ttggaatttg tcatagttt aaaaaagtgt
59041 aaagcttgac attgggatat atgctttaaa aactggtatc tatgatttca atctaattgt
59101 ttttctgtga tggtgatgga tctgacagat cagaacaaac cgagatcaaa cttacatagt
59161 gtcatccaca ctgcacctct ctattaagtg ggtatttagc tatttagaat attttaacct
59221 taaagtcatt cctaactgtc agaatcaata ctgggtccag tccctactag tattttatct
59281 atgatttaaa atgatagaat ggaaaagcgt atttattaaa tttatagatc attctaggtt
59341 gtaagagatg gcaagctaaa gaagggtagg atccaagatg accttttaaa actaaaatga
59401 gtggtcagaa atgattctat ggaagaaaac aggacagtta accatgacag gaagaaactt
59461 tagaggtttg attgggcaaa agctgcaaag cttttgtgac ttagccttca aagtcaccct
59521 ccttattcat attgatgtga attaatatac aagcatatag acagcttaag tcaagaatgg
59581 ttggggccac cttgaaggct gttaccatag gagctcaata agaacctgag gatttaccta
59641 gaattataaa atattaaatg ataaatgact tctgaaacta gctatttgga ctggtgaaga
59701 atgagtcgct attgatcttc aagtacaatg aagcatttac caaagattta tttaagtgcc
59761 tccatgtgtc agatgctgtg gtacaaagaa ggacttctca aaattttagc tagtcagagg
59821 tctttctggc ttccgagtcc ctggttaaga tgaacagaaa cacagtcttc agatataaaa
59881 tgtcttattt ttgtggccat tcagttgcat tcaacgttaa tttttttctat ttactaccgt
59941 tcattctcta tttttacac agtagcataa caaagctcta aggtggaaaa gctgacatag
60001 ttttaaattt tttttttttt tttttttttt cttgaggcag agtcttgctc tgtcagtcag
60061 tcaccaggct ggagtgcagt ggtgcagtct cggctcactg caacctctgc ctcctggatt
60121 caagagattc tcctacctca gcctcctgag tagctgggac tacaggcacg caccaccacg
60181 cccagctaaa ttttgtattt ttagtagaga caggtttcac catgttgcca ggatggtctc
60241 aatctcttga cctcgtgatc caccggcctt ggcctcccaa agtgctggga ttacaggcgt
60301 gagccactgc acccagcaaa ttttaaattt tcaaataagt agtgaaggct attattaact
60361 tttggaatca gaaagaatga caagcttacc ataagacata gcatataatg ctgtcaagtt
60421 atttggctag aaaatcactg aactaaacat tcttttcctt ctatgatcta tgtcttaagg
60481 tgaagtatta actaacttttt ccatgtaaag ctatacaaat attggaaaat cttttctagg
60541 gagtccagaa tactaagggt tacttagtaa aatgtataaa aaggcaacag taattcaaat
60601 tacaagattt atatttgcag aggtgatcca tatatactta tccccttgca gtggctggta
60661 tgacctttgg ttgtaagaca aacttgccca caacagaggt caaatccatg cctttggaga
60721 ttagctccat ggtggatgga gctatggttt atgcataaag taaatgtttg tttaccttaa
60781 ttctccttat acccatattg tcctgctgta taacacattt tgcagatatt ttgaagttaa
60841 tgtgttaaaa acttgaggtt aaacatttga gttttttgtta agagccaaac atcaaatgtg
60901 cccttatatt tttaatgaat ctcatccaaa tgctaatgca taaaccttga caagtagtat
60961 aataaaaaca agaaaaaaat acagcaatgt ctttgccatt ccccaaaaca aagcacacac
61021 tgccgaagat cattagtact cactggtaac aaactacata gggttagttt gtatttccaa
```

Fig. 28

```
61081  ttctagagct gtaattttaa ggacaaaatg tacaatgatt gattaagagt gctatctgtg
61141  tatatatagg tattatcaca actccttttt ttcttccaga tgaagaaatt aattgggacc
61201  aatgttttta gatcaaggca ttttaaataa gcactcttga tttctgaaca agaatttcaa
61261  ccagctaaat tgagcaaaat aaagttagtt aggatatgag gacattattc tgttacagta
61321  atcttcatgt actctcaaaa aaatgtaaca cttgcataga aatgtcacaa ttaatgaagg
61381  attttatttg aagataaagt caaaattatg gcaccgagga aggtaataaa catttgaaat
61441  ttttattgat ttttaaattt aaaatccagt tttaaccaca aaattgtttg aatcacaagt
61501  ggtaatacaa tgtcttcaat attttctaa agttattttt ctatataata ataagacaac
61561  agcatagcat ataggaagtt ttcattccag tggctttttt atatatttat ccttcttagg
61621  aaggacaaat taaattgttt aaattaaact tttaaaatat aacaacatct aacagaactg
61681  tacaaaacaa agagacattt tttaaacaac ttgccaaact tacttatgag tgtgttttaa
61741  aaacaacttt gtaaatgtct gggcaaagaa gcaagctgtc ctcccttac cttcatagtg
61801  agtttgtaag gctttgtctt tgtaagcaga aagagtagac tgtgttgttt tttgccaaaa
61861  actgtttata cttaatctca ctgaagtatt gctatatgga gaacccatac tctgatcaac
61921  ttgattttt gtgtgtaatg cttgatctac caggtaactt cccaactgct cctaatgcta
61981  gcgggctaat cccacattat tattccacta tcatccctgc agaaaggtct tggttttgat
62041  gaaaatcagc cctttcctta cctgctactg cctcaaaaag ggaccaggaa gattctagct
62101  ggctaattca ctgttccctt tgagcaagaa aacggcacag ggagaaaagg acttatctgg
62161  tgagagattt ggcatatacc ttcaatgtgt gccctataac acaacattgt ctccgatctc
62221  atctttctat caaatgactt ccaacactct taagtctcag gtattcttaa atctgtatca
62281  tcaaacatga agcttctctt gtttgttaga gtaattaatc tttctttgga ttaaagtttc
62341  cctttgaaat aaaaccacct acctaatctg actgctaaat ttctagcttc tttgttttaa
62401  atatgctcag gagtcaaccc aaattctgca gcaaataagt ttgcttatta acaaaaaagt
62461  aaaaaaaaaa gaaaagaaaa aagatgacta attctacaga tagctgtaag gatgaattac
62521  tcaagttcaa aatcaaattc tgattctaaa cacataacaa ttgtttacat tcaggattaa
62581  gatgtcttta agagttgaaa cgactttgga gatcatccag cccaacttcc atccagatat
62641  cacgcctctc acatatagta gtcttctgaa ttataaaaat ttataagtt acttccaaaa
62701  aaagctacat aaataaaaat tatctattta tagaaatatc tatttagcag ttccataatt
62761  taaaatattc aaatcaaatt gggtaggact ggtttgcctc tcactcccac agactatatt
62821  tatacctcag acacagcaag ttacatttaa acaatgagtg tagtactact taactaaaat
62881  ggaaaaaata gtactcttaa cataatccct aatttttttca tgaacataaa actccaagtc
62941  atttatgtga actatatctc aatgtagctg taggaaaaat aaaaacctgt gctaacctgg
63001  actttggtct catttaagat ttggttctgg aatgcaaata tggttttga aagcccaata
63061  aaattaattc ttgtatagtc tgtatatatt gttacaagg actacaaaca ctgcatcaca
63121  aatcggaggc tttggtaaat aactaagtgt ccaacataga aataactat tggtcaaaa
63181  gtataaaagg tctgacctta tttgaaatac gaaaagctg agtacttgga agatacgtga
63241  aaatactcag catagatatt atgaaaagct gaataacaaa gtaacctttt ttctcaaatt
63301  atttcaggcc acagtatata acggaactta ttgctatttg aagtttcatt aaaaataggt
63361  tcatatatag aagaaattgt gtcagtaata cctcttcact aatataaaat atgccccttt
63421  tagaagacgt gttctctaga tctcatttct aaaactctgt atttttctca tttctaaaac
63481  ttaagtatcc aatcaaactg accttactaa aatcccacaa attataagtc aattaatgtt
63541  ctgatttcat taatttggc ttgttcatt tcgtcagcat ttggtttttt agttccaaag
63601  gctcctgctg caagttctct cttttgtttt tgtatttca gcatattttc ttcaacagag
63661  tccttttacaa tgaactttaa aaagaaaaaa aaaagttaag tagttttttaa ggcatagtat
63721  ttaaaatctt tattaaaaaa actaaatgaa agatttgcct aatggcaaaa accgcaatta
63781  cttttgcacc aaactataat aactatttaa tagaactgaa ctttgctttc cttacccaat
```

Fig. 28 (Cont.)

```
63841 atggttttct tatataaaga atatggctgt acgaatagaa gttacagatc acaagataag
63901 caaagcaata aagaaaaaaa aagcaaacta tataggcaac tctggcaaaa tgacttcagc
63961 attgtattaa aaaggccatt ctggccgggc acggtggctc acacctgtaa tcccagcact
64021 ttgggaggcc gaggcgggca gatcatgagg tcaggagatc gagaccatcc tggctaacac
64081 ggtgaaatgc catctctact aaaaaataga aaaagttagc cgggcatggt ggtgggcgcc
64141 tgtagtccca gctactcggg aggctgaggc aggagaatgg tgtgaacccg ggaggcggag
64201 cttgcagtaa gccgacattg cgccactgca ctccagcctg ggtgacagag cgacgtctca
64261 aaaaaaaaaa aaaaaaaaac aaaaaactat tcccagaaat tcaagaatga atctttagta
64321 taattcacaa cactaacaaa gagaaaaata aacgtgatc atctcattcc tgataaaaac
64381 ttgattttaa ataccccaa ctaggaatga atgtctcaac cttacatatt taatgtgaaa
64441 caataaaagt attctacaac aaaacagaaa caagtcaaga atggtcacta tctgctacta
64501 tttaacattg tttaagaaga cccaattact gcaataacta aagctatata ataaatttt
64561 actgaaatac atataagatc tacataaatg gagaaaggat actatgttcc tgtatggaaa
64621 cattcgttac ttataaagaa agatagttct cgaaagtaat aataaattca ataaatctca
64681 agatatctta aatgggattt tataactaaa atctaaagtt caattcaaga gcaataataa
64741 taaccaccaa tacaattttc aaaagggtc atcagaacat tttaccctat caggtatcaa
64801 aacttacttt aggaaaccat agttgttata agagtaatac tgccctaaga aaaggaaaag
64861 agatcaatgg aacagaatag tctagaaaaa gacccaagta atatatataa attagtttat
64921 gatgaaagtg acatttcata ctagtaggga aaaagttgga attttcaaag aaaaaaaatg
64981 atgtgacaga acaaatcgtt cttcatctga taaaataata agcttagact catgtcacaa
65041 atcataaaac aaaaaataaa atcttccaaa agaaccagaa gtaaatacag aatagttgaa
65101 aaaatgtgaa aataaagcct tctgtcctag gtaagacctt aaaacctaga acgtataaaa
65161 aaggctgacg ttttaaatca taaaaatttt aaagcttttt catgaccaaa aaaatgcagt
65221 ttaaagacaa ggaagagtat gggataaacc atttcaaca tacataaaca aaagatttca
65281 agtcagactg tatcagggag tcctttatac tataaaacta tttgtaccat aactatgaga
65341 actggacaga agatataaat aattcacaga aaaaatgtta ataaacaaga tatgtgaaat
65401 atactcaagg ttttaggtaa atgcaaatta gaacagcact tttttggcca cagaagcata
65461 aattaacaat tttcatataa atcctatttt gaaaccaact cgatagttga taaaaattct
65521 aaatccagaa ttctagtttt cttaacttat cccaaagaat tacttgcatc tatgtgaaaa
65581 gatttatata taataatgct cattatggca ctgtttttat tagcaaaaaa cttaatgggt
65641 taaatatatt acgatatatc tatatggttt tgtagagtag tcaaattcag agaaagaaag
65701 tagaatggta gttgccaggg gctggggga gaggaatggg aagttattat ttaatggata
65761 cacagtttca gtttaagatg atgaaaaagt tctggagatg gatgattgtg atggctgttg
65821 cacaacaaca tgaatgtact taatgcatct aaactgtata cttcaaaatg gtaaattttg
65881 tattttacca ctatttaaaa aaagtgttca tctaaatgta cttatgaggt agtctccaat
65941 gtatagtttt aagggaaaca aatatgttgt agaataaagt ataattccat ttatctttaa
66001 aagaatgttt ttaaggagat gtacacataa ctataaatgt aggtgcagag aaaggcccct
66061 taaacagcat atattaaatt attgatgaag gaggaaaaag gtgacttata ttttgctctg
66121 cataattaca ctcaatcata ataatatatt catgcattac ttgcttaatt gtaaaaatcg
66181 tatcaaccta gtcttaaaat agtttgttta aaactcact tttgtgatga taacttcttg
66241 cttctgacca agtctatggc atctgtcaaa gcactgatct tcagcagcag gattccaggc
66301 ctaacaagaa catggatgag ttacttact actgccctga tctttcagtg ttttgcattt
66361 gtcctttcat ttcactagta ttcattcatc ttttctgac tgaaagtttt ctgcctgaag
66421 tcagatacta acatcacaaa tactctgggg aaaaatccac cctcccaatc actatgatga
66481 taggcatcct cccctacta ctacttctaa tacctaatac aggcccccgac atatgtatca
66541 gcacccaaaa taagtatttg ttgattaatc aatttggttt ttttttttcat ttttaaaga
66601 atctatgtgt gcttaacagc agaaaaaggt tatacatcct cttaaatgac ttaatttata
```

Fig. 28 (Cont.)

```
66661 tgagaaaaga cacaattctt gggcctattt agttttctcc cccttttctg gttttctttc
66721 actttcctct gttcatgaaa taaaagtata aaaaagggt ttctcctggc taacacagtg
66781 aaacccgtc tctactaaaa atagaaaaaa ttagccggga gaggtggcgg gcgcctgtag
66841 tcccagctac tcaggaggct gaggcaggag aatggcctga accccgggag gcggagcctg
66901 cagtgagccg agatcgcgcc actgcactcc agactgggcg acagcgagac tccgtctcaa
66961 aaaaaaaaaa aaaaaaaaaa aaaaggggg ttttaagagt cagtaagtcc taaaaattat
67021 ttttttgttg atgctatttt ctgtatcagt atttgacgtt agtttgactt taaagctgag
67081 ctaaaaaaag taccattagc taattaacac agacatgatc atgagaactg ttttaagcta
67141 aaaaataaaa tgatgggtcc ggcacagtgg ctcacgcctg taatcccagc actttgggag
67201 gccgaggcag gcagatcacg agttcaggag atcgagacca tcctggctaa cacggtgaaa
67261 ccccatctct actaaaata caaaaaatta gccgggcgtg gtggcaggcg cctgtagtcc
67321 cagctactcg ggaggctgag gcaggagaat ggcgtgaacc caggaggcgg agctggcagt
67381 gagccgagat cgcgccactg cactccagcc tgggcgacag agcgagacta catctcaaaa
67441 aaaacaaaa aacaaaaaac acaacaacag caataaaatg gtgcaacaat gaaagggaa
67501 gaataaccaa aaagatatag accctggta agtggttttt aaatagtatc atgaattgtt
67561 tggataagga tcattaaatt ttaaattaaa actatgaggt ttttttttg agatggagtc
67621 tcgctctgtc accaggctgg agtgcagtgg cacgatctca gctcagtgca acctccacct
67681 cctgggttca agcgattctc ctgcctcagc ctcccaagta gctgggatta caggcgcttg
67741 ccaccatgcc ccgctaattt ttgtattttt agtagagacg gggtttcacc atgttggcca
67801 agatggtctc aatctcttga cctcatgatc cgcccacctc ggcctcccac aaagtgctgg
67861 gattacaggc atgagcctcc gcgccaggcc atattacccc aatacttata caatgttcaa
67921 tgaaaaggta aagaaagct gggcacagtg ccatatgcct gtaatccag ctactcaaga
67981 ggctgaggga ggattgcttg agctcaggag tttgagacca gcctgggcaa aagaggaaga
68041 ccctgtctct taaaaaaga aaaaaaatt taatggtaaa agactttcat gagcaaattt
68101 ttatttttt attgaatcat tatgtttctc ggacctgact tttaagttag aaacaacatt
68161 ggaaagcttg atatgttcaa tgaagaacac tcaacttact ataaaactgc taaaacgttc
68221 tgtaaatttt taaaaactgt taacacgttt agtctctgat caactttttc atactaatta
68281 ttttggtatt aacctctttg gtactaagat tataagcaag aaaaataaaa tttgggattt
68341 gttctaaaaa tcagcttcta gaattatcac tggattaatt aatattcaac aatctatagt
68401 tacaaatatt ttttatagta gccataaaat actgcaaaca aagatttcaa acttcatcca
68461 cagtacaaag gcaagaaaat acaacagacc ggctgggcgc ggtggctcat gcctgtaatc
68521 ccagcacttt gggaggctga ggcaggtgga tcatgaggtc aggagttcaa gaccagcctg
68581 gccaacatgg taaaaccccg tctctactaa aaatgcaaaa attagccacg cgtggtggca
68641 ggtgcctgta atcccagcta ctcaggaggc tgaggcagtg aaccgcttga cccaggagg
68701 tggaggttgc agtgagccaa gattgtgcca ccacactcca gcatgggcga cagagcaaga
68761 ctctgtctca aaaaaaaaaa aaaagaaaa aagaaaatac aacagaccat accatatcca
68821 tgatattcac ccatgaaggc ctaagtatga tgacccagt tataatctta ctgagaagga
68881 taccgtcagt tgagggagga aaaaggaagc ctgagtaaac atatatgcat caacaaggta
68941 gcctcaccca agtaactaaa atttatatct cagtagtatt cctacatgta tctcagtaga
69001 attcctacat gttaaaaatc ttctgagttt caggtaacaa gttacaacca caaatcttaa
69061 gtctgaatgc acagaaacag cagagggttg cctttagccc acatagtacc cagtgcaaat
69121 tagaaactga attagtccaa ggtcctctca ggccaaacag cccctttgta cacgtagaaa
69181 aacacgctcc tatgtgaatg cacgtccagg tcacacagct tggtgagtaa agttcaaagt
69241 gaattttagc ctctgttcta ccttcatgcc tgtactacac aaccacaact gactgcacta
69301 tattaggcat taaaacgtac tcagaacatt ccattaatga taatttgttt ctcaaattgt
69361 gatcctagac cacctgtacc tcaatcacct atgatatatg ctaaaaatgc agcttcctgg
69421 gtctaatcct agaactccta agtctctacg ttgaatgcaa aggaaattgc attttaccta
```

Fig. 28 (Cont.)

```
69481 attcttatgc acattaaagc ttaagactac tagaaccgtg atggtaatca ttttgtctat
69541 cttgtttata gttagattcc cagtgcctat aaaaactgac gcaaagcagg atctcattat
69601 ttgctggctg aatgaaccac taccctaaaa agcattacag ttaatattta ttatagaaga
69661 aaagtagaat agcatagcat aatagtactt aaatatttac atggactatg attctggttt
69721 tgcctattac taactgtatg atactgggca cattatttac ttttctgtgc ttcagttgcc
69781 tcttcagtaa aacagagcat tttttttctt tttttctttt cagagacggg ttcttgctct
69841 gtcacccagg ctggagtgca gtgacaggag catggctcac tgaaacttca acctcctggg
69901 cccaagcaat caatctttcc gacttagccc tgcaagtagc tgggactaca agcacaaacc
69961 actacaccag agtaactttt ctggtacttt ttttgtaga gatggggttt tgccatgttg
70021 cctaggctgc tctcaaactc ctgagctcag gcaatccatt caccttggcc tcccaaagtg
70081 ctgggattac aggcatgtgc cacagcacct ggccaaaaca gagcatttaa taatggtatc
70141 tacctcataa ggatgttgtg aggatttcag taaagtgctt aagagaaagc tcttaatcca
70201 catttactaa gttttttgtta tttatttcta aagtttgcct aagaattttc acagttaatt
70261 ataactatga aggtatttac caaatagttt tttgtcttat ttttttgaaa gaagtactaa
70321 gattctgaaa aaatttacag aactacttac tggatccatt aaaaacactc gagaagctgc
70381 agacagattc aaaccaactc cacctgcttt taaggacaga agcattatag ttggagatcc
70441 tgcttcagtg tttgaaaaac actgaattga ttcaactctt ttcttttggg ccatggaacc
70501 atccaaacga gtaaacacaa atccagaggc tctaaagggg ggaagaaaag agacaagtaa
70561 caaacactat tattataaaa ataaaacaaa gttaagtaac tacaaatctc ttcaataaat
70621 tctttcactc atttattta acaaatgttt attgaacact tattaatatg ctaggcactg
70681 agtcagtcat tttctgataa attcaggact taatctttaa attcttgtgc tgccaggaag
70741 tattctctat tgtgactctg aatatctttc agataaaatg actaaaactg gcaaaacaaa
70801 ttaagttttt tttttgcta tccaaatcaa tatgattata taaaatcctt ttactgaaag
70861 tgaaaaacac tgtggaactt acttaagtgg tatttctatt aaagacagga atgttgtaaa
70921 ctgagaaaca accaaacttt ttatgttggg attcttcttt cttaagtcag tcaatgcgtg
70981 cattagcgca ttaatctgca aaaatatta agatgtccat tagattccat tttaaatcag
71041 taaaattagt ctaaagtttt ttatcataaa gaaaaggtcc tgaaatgtta tttccctaaa
71101 atgcaaaaga ctactcattt aaaacaaaaa attaagactg aaagaacact ctaataatct
71161 gaacccattc catttcccct caaattcacc actaaaaata aaagccagt ggtcaacaac
71221 agaacactaa aatgacagga atgaaagcag aattacgatt ttgatatact gtgtatattt
71281 ccttatataa aggtaaaaca aatactcaaa tatttgcaca tgagtacttt acctttgaac
71341 tggatgtcca ttccatatca gactttttct cactgtcacg tgctaattct tctggaggac
71401 attctaataa attatcttca tgtatatcat ttctgcataa agggcattta gcatgtggct
71461 atataagaaa gaacgaagta tgagcaacac ttaacagaag aacaaatata aatatgccta
71521 aaaatttta aatgtatgct aaaatctgta tctctcatag ctaacatttt attaaacctt
71581 ttaatggatt tcatccattt aagagacatc tgaacatgct gaactccaga cataatgtgg
71641 taagtagaac ggataaagga gggagcaaaa gtatgtgatc tggactagct agaagcaaga
71701 gcaagaaacc aaaaattata acattgtaag caagtttaaa aaaaaatct atgaataaca
71761 atttattgaa cctaaataca atacagctac actatttagt actattcttt aaaaaaaaat
71821 ccatcttaat ggcttataaa gctattaagc ttataaagct tataatagct tataaagcta
71881 ctaggatctg ttaaatccta tcaagttcat tccaaagcaa catctgttgt acccgtttga
71941 acctgttaat aaaataagat tatatcttaa ataactatat ataaacacc attacaatta
72001 aataattctg aagctaaaat tatttaaaag tcaatacagt ggggttactt ttggggaaga
72061 gggagagggt aaatggttgg gagggccac aaggggacct aggcagcaga tacaggaata
72121 tgtttacctc ataattgact gagctattta attatgaatt tatacatttt ttctacatat
```

Fig. 28 (Cont.)

```
72181 gttatatatc aatttaaaat gtttaaaaaa attctacccc agctgaatga ctgcttaaca
72241 gactagtcaa cttcaaaaaa attctaccac acaaaagaat ctagacctac cttatccaac
72301 acaatagcca ataatcacat ggggcaatta cgtccttgaa atgtggctaa gccaaattga
72361 ggtgtgctgt aagtatacac caccaccaaa ttctgaagat ttagttttt gtaaaaagca
72421 cattaatact ttttatattt tagatatatt gggttaaata caaatgtatt aaaattagct
72481 taatgtttct ttttacttaa gagtatgact actagaaaac tgaaaattat ctttgtgtct
72541 cacattatca atccatttat tgaacagcaa tgatataaac agcggaatta agatattgac
72601 tgtgaacatc tttttatgtt gcaaatgttg cattagaaga aatatatcac ctattaaaat
72661 actggaataa ttaactatca aaggtatatt attaaatcca agtgcaaaac tccatatact
72721 atcttttatt atattaaaga caggtacact actctatcaa acactgaacc tgtactgagc
72781 aaaaaactaa cctgctcatt ctgaatgact tggcaaatac agggtttaca aaatacatgt
72841 gcacaatgtg ttatcacagg aactgttaaa gaatccaggc aaattgcaca ttcctcatct
72901 gaacctgagc tcagaattaa cttcatcttc cttattaact tctttctcag ttcttcaggt
72961 gtatcatttc ctagagaaaa ggctgaaaaa ttaatttcag agcaaggttt gtaatatgac
73021 aagttaatct atcttataag gaaaagtttc gcttgccagt agggaaagtc tctcatcatt
73081 ttctgccata ggcaaaaagc ataatttaaa tttgaaattt aagaaacatt cagaagccaa
73141 aatagtagcc aactcacata atatacctca tagagaagca tcattataac atgacaataa
73201 cataccacca cacaataaaa ggcagatcca atatgaatct ttcatcaaag ggtatctatc
73261 accggaattc ctggaaagac ctcattataa ttccatttca ttggtaaaaa aattattgga
73321 tgtattccta gctgagtctc acactaaaag caatctccat ttgacagaac aaaataaact
73381 aaatgtatgc cacataaaaa aaatttatca ctcttattta agtatctctg acaaatacaa
73441 tgatatgaag caatcaaatt tacctacctg aggggccatt ggaagacact gcatttgtaa
73501 gaaggtaagt atggcaacaa atttgccgca gtctaagcaa aagacccagg acatctgcat
73561 aatgtgccag gacagtccct tcattaaaat acctagagat taaaatgtca aatattatta
73621 agtccgctaa acaataataa cttcctattc taaaacagca gagtaaaatg gcatttttct
73681 tttcttctct agaaattact ccaaaacaag aatgaaaagc agaaaagcaa ctctaataaa
73741 accaagagag atctataaca ataaggcaca atatatgaga aatggctgcc aattgcagtc
73801 taagtcagat aggaagatgc tgagagggat gactgcagat ctcaaacaga gctgccaaaa
73861 cacaattctt taaaatggat ggcatgccct gaggggaaaa tcaatacctc tcatgtgcag
73921 aaacaggaac agggtgcatg cttggtgact tgagcttcca tggagaaatt tatatcaaaa
73981 aaagagggaa ggtaaactga atacagaaac atacaggtgc actgtatttt caaaaaaaga
74041 ctatgggcac agcactctac actccaagca cccctaaagt ttctgatctc tgtttatgtg
74101 tactaataaa acctaagta actcaacatg taaccctgag tcttaagtaa attgggttat
74161 ttcctgctgg tcggggacat gattgtgacc tttcccttt gtatatctgg actagcaaat
74221 agctagtcca agaagaactc aagatattca aatataagta ataatcagca gagagcaaag
74281 gtaggggaca catggcagtg aaagaaaact cagcagaaaa atgttgccac agagcaaata
74341 aaaattatga ccaaggatac tgtcacaatt taacaccact caataaaaca attcctccaa
74401 aaaaaaaaaa tcttaaagca aagacaaaga gctttgaaaa aatatgcaa gagaacagga
74461 agagatgaaa gatgagctgg tatggctcaa gaaagtgaaa gaaacagtg aatcatcaga
74521 gaaatgaaag tcacactgaa accaatataa gccaatataa aaaagacta gtcactgata
74581 aaaacataga aaggatgta ggaaacagga ctgagaaaat caaaattaaa caaaaaaatg
74641 taaaagatca gaaataaaat gatacctatg gaacacagat aaaagacatc taacatacac
74701 agagagaaat aaaataatgg aacagaaaac aatatttaaa gaaagctttc caggaaagag
74761 aaggggggaa aagcctggaa tctaaagatt taaataatat cacatgtccc aggggaaagt
74821 caacaaagaa gttgctgaac ttcagaggga aaaaaaaaaa aaaaaaaaa accaggcttc
74881 cccacagaaa cattctatac aaaatacagt ggtacaatga caacatagat tcttaaggaa
```

Fig. 28 (Cont.)

```
74941 atgggtgatc caaaaattat ataaccaggc catctgatat ttaagtattt taaggcaaca
75001 gaagaaatat agcctaacgg ctaagagtac aaatttttag agctagctgg tcatgaattc
75061 aaaacctggc tgtgccaatt taattatgta accttggaca ggttgcttaa cctatgtctt
75121 gagcttcctc agttctaaca gtggcattgt aaaagtacct acctcataca actactgtta
75181 tttaatttaa tacatgtaaa gtatttaaaa tagtgcctgg actatattaa gtgctataca
75241 tgaatctgtt gctagtatta gtactggtag tattatggca acaaacattt ctgaatattc
75301 aagaatgcaa ggaataggca aaataataca aagattaaac ttacaagctc taaaccaaag
75361 tgccagagtt aatctgtcct gtcactcact agctgtgtga caacagtgta agtcacctaa
75421 actgctctgt gcctcagttt cctcacttat aagatgtgga taattatact gacctaatag
75481 gattgctgtg aatacattta aagcactaag atcaatgtat aacacctagt gagtgctaaa
75541 taaatgttag taaatatata gcctattaaa aagaatactt taaaaataac ttatttctg
75601 agaacagttt caataaagtt aatctttttc aactttttca aatagaataa cctttactaa
75661 cactaattat tccctggcat ggtcatatct tactgatact cagcatttca atttaagaga
75721 tctcttttga gtgcctacca tgtgctaaat attagaagct tccttcctcc tatttcacca
75781 gccattgcta tcttcacagt tagatctctt tcactttact cactcccttg gtgatctcat
75841 ggctttaatt accatccaca catagctgac tttgaactcg actctcctat ccaactaatt
75901 atttgatatc tctacttgga aaattcacgg gcatcctatg atcaatgtgt ccaaaactga
75961 gcttctgatc ttagcttaaa aaaatctctg ctcttcccat agacctgtct tggtaaacag
76021 caattccagc cttccactta tgcaggtaaa aaggcttgaa gttatctttg attcctcttt
76081 cacatgccat aacatatcaa ccagcaagtt ctgttggttc tacgttcaca atttaacaga
76141 atctaatcat ttctcactcc ctttatcact actatggtaa aaaccaccat catctcttgc
76201 tttgactgcc actggtctcc ctacttctga cctattcct attcaaataa cctaaatctg
76261 agcacagcag ccagagtgat ctttaaaaa tataaatcag attacgtccc tctcctggct
76321 caaaaccctt taaggtttcc tgtcataaaa agtaaaagcc aaagtccttg acatatgcgt
76381 tacataccccc cattccaata aatctctgat atcatgacta ttttctctcg ttcatactat
76441 ccagccacac ttgcttctct gttattcttc aagctcacca ggcatgttcc caactgggag
76501 catctacact tgctcttcct tctggctgaa acacccctta atcccaatct cctttagatc
76561 tttacctata tatcatcttc tcagtgaggt cttccttaat accctactaa aacagctttg
76621 gcattcccca tccccttttcg ttgctttatt ccttaaaact taatcatgtt tttaaattat
76681 ctgtttcttc ccattaaaat ataaattcct cgagtgcagg catttttgtc tgtttattc
76741 tgctgtatcc caatgggtat aagtgcctgg cacacagtgg gcacttaata aattttgtt
76801 gaaagaatat gaaaagaaag aagattttga actcagaaat ctgctgctta gaacaatctt
76861 tcccactctc tctaattcct atcaaacctg ctttgtacct acctcactga agttttatg
76921 ttttgaagat tccccttttca cagtcctatt ctgctttcac ttgtctctta ttcattctgt
76981 tccctgtggg ctcacattaa acctgatctt gcttggacca gaattcata ccttctacca
77041 atccttaatc ttcttgttaa acctatttca tcagttccta tttccagatt tccatacgat
77101 tttggaaata gaagcaagca aaatcttctg gctagcaatt gagaacttgt catttaaagt
77161 aagctttaaa ttatttccta acttaaaaaa ttacttacct ggtgaattat actattattt
77221 cattcacttt attgatttgt aaaaaacact gtaattcata gaagcaaatt atctttcagt
77281 atacttcaaa ctattgctaa cacatctaaa taatgtcatt cagtgaatgg gaaacaaagt
77341 aaacaaaaac taattttaa catggttttc tttctccata ccttccaata gtggctctgc
77401 cttcattttt cacagactga taaatctttc tctcttcatc tgaaagtgta atgtgctgaa
77461 taaatacttt acgttctggt aactccaaaa caggttttcc tttaattttg cttgtctttg
77521 ttcttctaag tgtaatattt ttaattaggg actgtaaacg cctaatcaga ataaaacaaa
77581 taattatgta acttttaatt tctacataaa ttgatccaag aagaacgaaa cagaacattt
```

Fig. 28 (Cont.)

```
77641 taatttgtta ctgttttata gcttctgtaa aagtgttttt aaaatccctt atttgggatt
77701 ttaaccaatc tgataatcac agaagtattc tacaaaaata aaattattaa aacaaatgta
77761 tggaaatttc ccctcaatac ctaacatagt ttaatctttt tatatcctgt ccttattttc
77821 gtaagttctg ttccccattt ttgttccaat cactaactct tttacttctc aactgtcctg
77881 tcaactccat caccgaatag tcaacactca aattctaagt atctattaag tgccaggcac
77941 tgaattaaat gttgtaagaa tacaaatatg ggtaagatac tacattctgt aatattaaaa
78001 tcaaaagtat ataaataagt aattgtataa agtaatgagt gccccaaaa taaaagata
78061 atatggtaat tcagaacaca gaaaatgct ttacaggttc cacaatcttt acatttcttt
78121 ctcagtactg gaaaaaaga gatgtatcaa ttcttgtttt ttcccaacat tgaaatataa
78181 atacaatttc ctggagttta aatagttggt tttgaggaat caagtggata gtactgccaa
78241 ctaggttagt ggctcttgaa gcttctcac tataactcac agtaagaaac acattctatc
78301 cagcaaaaat atacaaacac atacaaaaga aacaaatatt tcacaaaata atacttacta
78361 tgtatcatgc actccgatat ttactaatct cttctctatt tcattgtctt tttaaatgct
78421 ggctaccacc tttataatga ttttatatcc cactaatagc tctcaaatct tcagtctata
78481 aaccggtgct ttagccaaaa agttaacca cattacatct tgcaaaatgg ctatcactga
78541 gttttaattt atgttctcaa cttttatcta tctccaccag aaacaaccac ataaaacttt
78601 cctatacaac ttttgctaag gtcatggtac ctcacatcat tcactatata aagctatgta
78661 aggccaggtg tggtagctca tgcctgtaat cccagcactt gggaggtcg aggcaagagg
78721 ataacctgag gtcagaagtt tgagactagc ctggccaaca tggcgaaacc ccatctctac
78781 taaaaataca aaaattagcg gggcatgctg gcgcagacct gtaatctcag ctacttggga
78841 ggctgagaca ggagaatcgc ttgaacccag gaggcggagg ttgcagtgag ccaagatcgc
78901 gccactgccc tccagcatgg acgacagagc aagactccat ctcaaataaa taaatacata
78961 aataaataaa taaagctata taagatatga aaacttaatg catattagat cctcaaagga
79021 tatacgatgt ttcctgctaa atctgttaat gctggttttg gggctttggg gcttagcaac
79081 acacaaaaaa cagttatgtc tttcctttca gtttagccac aacaggggaa gggtagttat
79141 cgacaattag aaatctttgt ctttccaaac aagcatcact aggttctgaa agacaaaggt
79201 actgagccat aaacactttt tagaaggaaa agttaagagt caagttaaaa tagtaaagaa
79261 agtgccaact ggttcaagct actaacagtt atttgtaact aatattaatc actgtctgaa
79321 agtacttacc taagtcctcc ttcatctccc attgtgacag gacgctgtat tgttctatgc
79381 caccattctc tatcaataaa tggtttaagt tttaaaaagg aagaagaga ccacaagtcc
79441 tttaaagaat tctggattgg agtacctaga aataacagga aactgttata actctttaac
79501 cagagtatcc agtaagagta tctatttggc ccaatcagag aagacaacaa ttgaaaatgg
79561 gcactctgta ccaggctcat cattatcaat taaattaaac tatcaagtgt tgactataat
79621 catttattaa aaatatacac atctcaagat acagttttgc tctaattttt agctctcaca
79681 tgacacacta gccaagaaaa agactggaaa attcaacttt ctccttatca agtacatctg
79741 cttatttagt ttttaaagca gcagcactag cagaaggaaa aagcaactag tttaagttta
79801 cattcttttc cttaccttct agtaaaggta ctgtgaatgg caaacaggtt tgaggatggg
79861 aaacagaaat caagattatg actggatgac tagagtgtct actccatttc cactagagtg
79921 tctactccat ttccaaggtt caagaataag tctagtgact gttccataaa ttatcaataa
79981 gtcaaatgtt gttatatcac gggcaattat gaagaacaac tcaaaacatt tgattaaatt
80041 atttatatga ttaattttgg ggcagaattt acacccactt taagtttaca aagttacttt
80101 actaacttac ataatgatat atttagaga tttaaggttt tagtaagttt aatgctatga
80161 ttacctgtca aaacccatct tctttctgat tctaagtcaa gtacagcttt tgtctgctga
80221 gcatttggat ttcgtatggc atgtccttca tccaggatca ctcttagcca ccttatgcta
80281 tgtaatggac tatctccttt agtctgaaat aaatgtttta tatgaattaa aaaacacagg
80341 aaagtaaaat agtacttaat atgatttgct aactagttgt tatcattatt taatatcaaa
```

Fig. 28 (Cont.)

```
80401 tttactatgt gctaggtact gctttaagca ctacattaat tattgaatac tcacaagttt
80461 ataaaataag tacttattag cacacctaat tttacagata agaaaactga agcacaaact
80521 gctaagtaag tatgttaccc aaagcaccac aggtggcaga actagcattc aaacccaagc
80581 agcagtctag ctctctgttg agtcactggt caatacactg aactgttcta cctcggatta
80641 aaacatagca atgatataga aaatggcagt tgtaagaatt acttgaattc aacattactt
80701 tcttttatat aaaaggtaat attttactta gaagactgaa attttgatag caaggtattt
80761 ttcaaaaagt tttaactttt gaacaattgg aattataaag gtaaaaaaca attagactaa
80821 ctggaaaact tatgaactgt aactacaaaa aaagcatacc ttcaaactga gatattaatc
80881 aaatcattgt gatagaaaac aattttccag aatattaaaa aagaaaataa aattcattta
80941 caaattgctt catatactta caatccaaat ttaaaatctt aacttaaaat gttctaaatg
81001 aaaaatattc ctgtctgggt gtggtggcac acgcctgtaa tcccagcact tgggaggcc
81061 aaggtgggtg gatcacctga ggtcaggagt tcaagaccag cctgaccaag atggtgaaac
81121 ctcatctctg ctgaataaca aaaattagct gagtgtggtg atgcatgcct gtaatcccag
81181 ctacttggga ggctgaggca ggagaatcat ctgaaccag gaggcagagg ttgcagtgag
81241 ctgagatcac accattatat tccagcctgg gcaacaagag caaaactcca tcgagaggga
81301 gggggagggg aggagtggag aaaagaaaaa tactcctaaa ttagcatcta aataaaatgc
81361 aacccttca cgcaaaaagt caaaaaaaaa aaccatttat ttttctatat atcgttaagt
81421 atctaaagag aaaaaaaaag tataaagcct gaattttgga acactctaga aacctgtggc
81481 atatttctta cattcaatct ttaaaagatc tgttaagtat caacaatact tactccatag
81541 tcatgagtta aaatattata cgtagtcaaa acaatatcct gttttgaaag taaggccggt
81601 tctctaatac gatcaggacc ataataaaca taaaaattca agtgtacatc tgatttata
81661 tgttgtccaa actggtccta aagaaaaatt aggaatattt ttaacaatga gcagatttgt
81721 gtcagactta atagatgtat aaaaaagtaa ctgccctggc agtagtgtga caaatccaac
81781 tactaaaatt gtatgaaatc aagtttcctt cagtctagac caaaataata acaataagaa
81841 aaatgacaca tacacagtaa taataaatta tttaaaattt acttggccct accaatcagc
81901 aactgcttca tttttaggag gaaaaaccaa agttattgaa aacaataatg agttttataa
81961 aaatatttta attagaaggc cctttaatgc tgcattagtt agcagactta ataatataaa
82021 aattaaacag taaagaaca acaaccaata tttccaagga tgtgggcaga gattcaagca
82081 ctgtagccac tttctttcac tcatttatta ttggcctact atttgccagg tatcaaccac
82141 aatagtgatg taactaaaaa tgaagaacaa ataatcatcc ctgactttct tgaggacatg
82201 atcagtttta aaaactatt attatttttt taatcatgaa aaaaaccaga cctagaagat
82261 tttcagcaga aaaaaatagt ctgattaaac tgaaaagaga agataccagg gagacacagc
82321 tgggaagcta tgaggagaga gatgatgaag tcctaaacca gcaaggtaga agtaggaaca
82381 gggtggaaag gacaggtgtg aaaacagaa actaagacaa gactgatagg acttggggac
82441 taatgaaata tgaaatatga ataataataa taagactaag atgctctgat acttgaatga
82501 ctacctagaa ttgtgtgata aaaatataag gaagtttaaa aaaaaaaaaa aagaagggaa
82561 aagtgggcat ccaagtaaga aagagatgaa tattttagac ctttatcatt tttggtcact
82621 atagaatacc taactgaaga cgtatactag gaaaatgtaa ataattccct atagatagaa
82681 gtgagaggtg tagatatgaa ttttaaagtt aacaacagac agtatttaca gctgtaagaa
82741 tgaatgaaat ttcctaaaga gagcatgtac agtgagcaaa cgttagggac agagtctaca
82801 gaataccggt atgtaaggag aagacttgtt tttattggga gaaaacacat gatgcctggg
82861 gtataattaa aaatattcca ggccaggtgc agtagctcat gcctgtaatc ccggcacttt
82921 gggaggccaa ggcgggtgga tcacttgagg tcaggagttc gagaccagcc tagccaacat
82981 ggcgaaaccc tgcctctact aaaaatacaa aaattagctg ggcatggtgg tgatggtgat
83041 gcgcacctat aattccagct actcgggagg ctaaggcatg agaatcactt gaacccagga
83101 gacagaggtt gcagtgagct gagactgtgc cactgcactc cagcctgggt gatggaatga
```

Fig. 28 (Cont.)

```
83161 gattctttct ttaaaaaagg ccgggtgcag tggctcacac ctgttaattc caacactggg
83221 aggccgaggt gggcggaacg aggtcaggag ttcgagacca gcctgatcaa catggtgaaa
83281 ccccatctct actaaaaaaa caaaaattag ccgggcatgg tggcatgtgc ctgtaattcc
83341 acctactcaa gaggctgagg cagcaggatc acttgaacct gggaggtgga ggttgcagtg
83401 agctgagatc gcgccattgc actccagcct gggcgacaga gcaagactgt aaaaaaaaaa
83461 aaaaaaaaaa aaatcaatcc agcaaagaaa aaaggaaag cacatgtgtc agacttttgg
83521 taatttttga atcttgatga gtagatggag atctcattaa aatttttttaa aatactcttt
83581 ttaaaaaatt atatgttgta tggaaataca gaaaagacag atttaatagg aaccagaaca
83641 aagacagaga aaagttagg acaacaaata taaagggtaa aggcctggga tccaaagaat
83701 ataaaagttt caagaaaaaa aaccaaggtg gactttaat ttgtcatcta tcttcattcc
83761 agttctttac aagaaggttt agagatagct tacaaaataa gacataacaa ataataaatg
83821 aataacatat tcaaggcaga ggaaaagggg agctcattgt acatggcaat attgaagtct
83881 gaagatctct gcaaagggag tttctgtagt gagtggaagc aaaaaccaga ctaccaagga
83941 ctgaagaaag tattaaacat gaaataaagg caaaaatgca gagaggataa aacatgaaaa
84001 agtaaagctg aaaatgcaaa gaatttctta tagaaatttg gtaaagaaga aaaggaaatt
84061 agaatccagc atgacaaaga atccaatatg agaaaactga atcaatgggt ggccttgaaa
84121 tgggacagtg cattatttgt aaagggatta cacttggaac agaagaaaat cagcttttct
84181 ggagaataaa gggagagaac tatagttact ccatctctag acagtgttag gctctactgt
84241 atatgtatgt atgtatcatc ctctcaatag aaaacgaaat aggtgttatt tcatgagatt
84301 acttgtctaa atatccagaa caaatatgtg gtagaagtag gattggtacc caggttctat
84361 tcctttacct ggattatttg aagacaaaaa agggaatata agtcagttct agcctgctct
84421 gtagaatgct agatccttta cttgagagcc aggaagacgg tatcttgttc agattgtgaa
84481 attttaattc ttgatcattg aaatcgtttg gatgttcatc tcctccaaat ctcatgttga
84541 aatgtaatct ccagagttgg atgaggggcc tggaggtgga aggtgtatgg ctcatagcgg
84601 tggatccctc ctgagtggct tagtgctatc ccttggtga tgagtgagtt ctcactctaa
84661 gtccacacga gatctggttg tttctaagtt tgtagcacct ctccactctc tctcttactc
84721 ccactctggc aatgtgatgc tgggtcccca tcaccttctg ccaagagtgt aagcttcctg
84781 aggctgtgta agcttcctgt ggcctcacca gaagcagatg ccagcacgat acttcctgta
84841 aagcctgcag tatcatgagc caattaaaac tcttaaatta tccagcctca gttatttctt
84901 tatagcaatg caagaatgga ctaacacaac catgaatccc taaatgccaa accacctctc
84961 attcctttaa attcacagag tgtgcatgat ctcacttggc aagattttgc cacactttcc
85021 tttctgaact ttacattact tgaactttcc taaatataaa attataatta aatactgatt
85081 acccatttta aaaatacatc tctataccc aagccctcaa ataatcagtt agatagttta
85141 tacctccatt aatactctaa acctcatccc aaaactgcca ttcaagtacc catgtactat
85201 ccttcccata acaaacaaca aattaaagaa agaacagttt cgttggaata aaaaaatagc
85261 aacagaccat taacattcat tcttctggtc ctaagaggaa aaatgataca cttatcagga
85321 caaggtgtaa tttaaaaaat aaataaataa accaaaaact tatataaaaa aagataattc
85381 atgtcacgga aaaaagact ataaagccaa gaagaggcca ctaaatttga caattaaact
85441 atcacaagta gtcttttcca atgcaattta gagaactaat ggtacaagcc agattacaat
85501 gaattaagga attagtaagt aaaagcacaa agtagaaatt aacctccaag agtatgacag
85561 tgaaggaaag cagaagagta gcaacttta aagatgcata tcaagagaat gtattttaaa
85621 atgaaaaaac ctgagtatgt atcaggaaga gccagtggga agagactaaa taaacaaggg
85681 aaaaagaac agatgagcaa tgtgggaaaa gagagaatcc aatgtagaga ctaaatactg
85741 gtcttaaaaa gagtaggatc tcttcctcct ctgacataag aagaatggcg atgagagata
85801 aacagataac ttggaagtgg caagaacggt gagtggtcct tatattcaca gggattccaa
85861 gagagtcatt atttcatcat aacaagaagt ttgaagctca aactaggaag aaaacatatc
```

Fig. 28 (Cont.)

```
85921 caggctgcaa ataaacaatt aatcaagagg ttccattcca atgtcaatgt ttcagaacag
85981 aaaagcaatc tggaaaaaaa aaatttctga tgggtagtgt taaaaggaca ggctctagat
86041 tcaaaatgtt ggagactata tacaagatcc atcatttatt agctggatga ccttaggcaa
86101 cttaacctct ctgtgtttca atgtgggcac ctggaaaatc agggtaacag ttatgagaat
86161 taaatgagaa aaatccttaa aagaggttaa ggacaaacca aataaacagg agttcactaa
86221 ctgttgttat tgttataaaa ataagttatt gttggtatag ctcttagaaa agacagttcc
86281 aacagtcaat ctgtaaatgt agaggagtca aactatacat ctttcccact ttggggggaca
86341 aaaatagcaa aggcagaaat acaaaccaaa tcttatgtta gcaattgatt atgttccttt
86401 accttcttct ctactacaca tcttcaaaga aaaatttctt caattcagca aacataatcc
86461 aattcacctg atgattattt gaacttagat acgaactgat gaccaagtat atttacccca
86521 atgaatgact ctttaacaga atactttcta ccttgtagat aaaatataaa ttatgttaca
86581 tttttaaagg gcttaaagac ttacaatcca gttgcttaac acagaaagcg gacagatgat
86641 cagtgttgtt cttggtctct cctcaacatc agttttcttt gaccccctcca ctgcacaagc
86701 tcctaaaaaa atgaaccact gatagaacct ttagctgttt ttctgaaata tatatgtcaa
86761 taaggagatg gcaataatgt gcctccatga aaagataaat taggaacaat taaaatgaag
86821 cagatggact tttaacaggg aataaatttt acctcatcac ttaaaaaaac taaaaatcca
86881 catagtgatt atgagaagaa ccaaaggact atgacagaga gtaggtcaca aggaggaagt
86941 ctctaatatt ttctgatagt catagtcatt cattaagacg aacatttgtt ttatgcagtt
87001 ttctgaattt gtgttatatt taatttggta gccagccaag atggccctca atgatctcta
87061 cttcctgata ttcacaatct tgtgtaatct cctcccatac tccaccagga ctggtctgtg
87121 tgaccaacag aatatagcag agaagatagt atgtcacttc tgagatagat tacaaaagaa
87181 gtttccgtat tgggtgtgca agctcactct catactcatt ctctctctcc aatctttcac
87241 tctggtggag ccagctgcca cgatgtgagg ccactcaggc aacttatgga aggatgcaca
87301 tagtgaggat ctgaagacta cagttagcca gcaagtaatg aggtctgctg acaactatgt
87361 gagtgaactt ggaaatggat cctccctaag tccaatgttc agatgacggc ggccctgaa
87421 gaagagtttg actgcaacct cgtaagagac cataagccat taaaccatcc agctaagcca
87481 ctccgacttc cagccctgtc aaagtgtgtg agataataaa tgtctgattt taaatggcta
87541 agttttagga taatttgtta cacagtaata ggtaactaat atattacaac aaaaattctt
87601 aatacttttc tgtggagcat gtttaaaaat agtgataata aagtgttttt acaaattctt
87661 gaaataaatt ctagagatgg tatcccttac caatggagta tcttccagta aacttaaaat
87721 gcaaatttct gagttttttaa aaaattgtat tttcacacta atttcaaaat taaactggaa
87781 ggtgagcaaa gtatcatact gtatctacgt atcattcaca acttgctttt ttctctcagt
87841 gctatctaca gtagtccctc cttatccact gggggtatgt tccaagaccc tcaatagata
87901 cttaaaacca taaatagtac caaaccctat atataatgtt ttttcccctat atatacctac
87961 aataaagttt aatttataaa gtaggtgcag taagagattc gtaacaacaa agaataaaac
88021 agaacaatta taacaatata cagttgaccc ttaaacaata tgtttgaact atgtgatgca
88081 cttacatgca aatttttgtt aaccaaacgt ggattaaaaa tacagaatgg gccgggcgcg
88141 gtggctcacg cctgtaatcc cagcactttg ggaggccgag gcgggcggat cacgaggtca
88201 ggagctcgag accatcctgg ctaacacggt gaaacccgt ctctactaaa aatacaaaaa
88261 attagccggg ggaggtggcg ggcgcctgta gtcccagcta ctcgggaggc tgaggcagga
88321 gaatggcgtg aaccccaggg ggcggagcct gcagtgagcc gagattgcgc cactgcactc
88381 cagcctgggc gacagcgaga ctccgtctca aaaaaaaaaa aaaaaaaaa aaaaaaata
88441 cagaatgggc caggcatggt ggctcatgcc tgtaatccca gcactttgga agactgaggc
88501 gggtggatca tgaggtcagg agatcaagac catcttggct aacatggtga acccgtctc
88561 tattaaaaat acaaaaaatt agccgggcat ggtggcaggc gcctgtagtc tcagctactt
```

Fig. 28 (Cont.)

```
88621 gggaggctga cacaggagaa ttgcttgaac ccatgaggtg gaggttgcag tgcgccgtga
88681 tcgcaccact gcactctagc ctgggcgaca gagtgagact ccgtctcaaa acaaacaaac
88741 aaacaaacaa aaaaacagta tctgctgatt gcaaaactca tgtatatgga aggccaactt
88801 ttcatatata ctcgtcctgc agggcagact gtgggacttg agtatgcgca catttggta
88861 tacacagggg gccctggaac caaatccctg acaaatactg agggatgact gtactgtaat
88921 aaaacttatg tgaatgtggt cattctctgt ctctcaaaat accttattgt atataatatt
88981 ttagaactga aactgtagaa cgtgaaactg cagataaaga acaactgtgt ttgggattta
89041 cacttattag tatttgtagc tctagtgtat tcattttaac caattcatag catcatactg
89101 caaagtagat tacaatttat ttaccattcc cctactggac aacatgtaca ttatttctaa
89161 tattccatta aaataatgct gcaatgaaaa ccattttttc atgtctcctt atttatattt
89221 acagagttac agatggtcta tattcagctt cattatattt ttgtccagtt gctctccttg
89281 gtaattggcg ctcccatcaa caatgcacga attcctattg ctgcacaact ttgtcaatac
89341 ttggcattgt gagatttttt aatgtctgaa aatatgaagg gtaagagcat cccctattc
89401 ctttatttta tgttttgag acatggtctc gctctgtcac ccaggctgga atgcagtggc
89461 gctattatgg ctcactgcag ccttgacctc ccaggctcaa gtagctggga ctacaggcat
89521 gtgctaccat gcctggctaa ttttgtgtat tttttgtag aaacaggatt ttgccatgtt
89581 gcccacccct gatcttgaac tcatgggcct cggcctccca aagtgctgca atttcaggca
89641 tgtgccacca tgcctgctgc cactattcct taatttgca tctccccaat aattctgaat
89701 cagcatattt ttccagtgt taactggtta tttgggtttt ctttctatgg actccatatg
89761 tacatccttt gactattctc ctattgggtg gtcttttcc aattgtttgg aaagttctta
89821 catagtctag aattgaacct tttgtcagtt acacttaata cacattatct tcttcagttt
89881 tatcattttt tactttgttt atggcacctt ttgatgcatg gaaatttaaa atgtagtggc
89941 atttaatcaa tctttcctt atgacctttt gtgtcttact aaagagatca ctatctacca
90001 caaggacaat caggattatg gcttctgtct ccattcacag agttttgttt ctattctgct
90061 tctctttcaa agatatactt agtttggtta aaaccaaaat gacacacagc tgtgactttg
90121 aaaatgttct ctcttgtatc acagctatgc atctgcaact gaaagtggtt tctaatgtgt
90181 aatttaattc tatctcaacc gaaatttcca catttcttta aatttctaaa attagggtaa
90241 agaataatcc acccaacatg cctatatttt ctattcctaa ttatctgatt cttggaccaa
90301 aagtcggctc tttctcatga gtctatgtta gcttcataaa caagcccctt caggtcaatc
90361 tttacttcat tatcctcctt tttcttcaca ttacttctca ttatttaaaa ttatattgac
90421 ttgcttattg tatatttctc tcatcattac atcatatgct atatgaaaac agatagcctg
90481 ctatatcccc aacatgtaaa ataatggaga ccaaggggca gagatataat ttgtctcaga
90541 tcttctcaac cttagttcaa tctcttccca tctcaaatat ttagtctctt aagcagtgtt
90601 gttttcctat gaattacaaa atataaaatc ataacaaaga tcactaacat tttaaaatga
90661 aaagcaaatt ctaataccaa aaaattaaac ctttaactta aattaaccaa aattaaatta
90721 agctttaaag cagccacaaa ttgctttgtg ccatcactag aagaaatatc tctgctattc
90781 agaggagtaa gggcccccat cacatttggg ccctaactaa aacaaataca gtaggaaaat
90841 gcaccaaaag gaaaacaaat tatgaggtag ctttgttctt ttaatgggtt atatacttta
90901 aaaatagtc tctatttct aaacttcttg taatatggtt ttataactta aaattttaaa
90961 tttttttcatt caaaaacaga aaaaaaacca aaaactagaa aacaaggata tttactgacc
91021 cttttcaac attttctttt ttgttgtagg aacagatgaa gttaatgcac atgcaaatgc
91081 cacatcttct ataaccttag aagatcctgc tgataaaaca acaaagaatc ttaaatttt
91141 ttcaaattat ctcctgtgct agagtacagg tactttctaa gggtaagaaa tagaatatca
91201 ttttcaccct ctattgtaag agcttatatt attaagttaa aatatttggt aaccaaaatt
91261 actacctctg acactaagga tatcttttca actcagagaa acgatgtagt cattcatggt
91321 aagacttgag gagaagaaat gaaagtagga gcagtcatat gcaaagtaat tcggctctca
91381 ggtggaagga gaattttca aggaaacaaa cagtttgatt cctaatgata aggctgccaa
```

Fig. 28 (Cont.)

```
91441  attttcagat cagtcaagat gatcagttat tttccaaatg caatacaatt tctcaacgaa
91501  tgagaaatat agtatgatgt gaattacagg aaaataaaac atattttaaa gaaaagaaa
91561  aaatttgatt attttcacat ctgtataata atgtaaacaa taatagtatt gccaggaaga
91621  cattctcaac ctaattttgt aattactatt catactacac acataggttt tattgaagtc
91681  attttatagg tagtagaaaa ttgttttaag tatagtttaa atattattat cccttagatt
91741  ttaatttgca actatttatt cactttttcct cctttacaaa attaatttaa aacccatggt
91801  tagctccatg aagagttcaa atgtaaacat cagccaagtt taagagctat tactaaaaca
91861  ttccaaccta gcgagataca aatcaatgga gctgtacttt aataatcttg aagtctagat
91921  tatgggtata tagtatacac ataccctttcg ccctgccttt agtttcagac tgtacatttt
91981  tcagtttgcc taaaaataaa acaaaaataa acataaaaat gggcaaaaca ggacattaga
92041  ataggaca cattatcaaa tcaaatctat tacatgttac ctttcatttt ctgcggcaat
92101  tcacttgttt caatttcctc tgaatcactg ctttctatgt actggacagc agtttttctt
92161  ctaaaattaa gtatacacaa agaaattttt ggaccaaccc aaagcaaaat aagtatataca
92221  aacatgttta ataaatgcaa taaaaaactt ttgtcctact catttatttt ttgaaaaatt
92281  ttttaaagat tttgacaaat gaaagtcaga tctgctaaaa gcattctgct ttcataacca
92341  gatagatgca ttaactatac aaaatggagt accaccgtta ttgttttttg agacagggtc
92401  tcactctttt gcccaggatg gagtacagtg acacaatcag aagtcactgc aacctcatac
92461  tcctgggctc aagtgatcat cccgccttag cctcgggagt acctaggact acaggtgcgt
92521  gccactacac ccagcgaatt tcactattat taaaataaat ttgatagccg ggcgtggtgg
92581  tgggtgcctg tagtcccagc tactcgggag gctgaggcag gagaatgacg tgaagccagg
92641  agacggagtt tccagtgagc ggagattgcg ccactgcaca ccagcccgcc tgacagagcg
92701  acactccatc tcaaaaaaat aaaataaaat aaaataaaat aaaataaatt tgaaaaacta
92761  agtcattcta aaaattaaa aatttcaata ccaggtttaa tatttggtag ttcaattaaa
92821  gcatataaaa ctggaacaaa aaagaattgg ctcgtggcca ggcacggtgg ctcatgtctg
92881  caatcccagc actttgggag gcggaggtgg gcagatcacc tgaggtcagg agtttgagac
92941  cagactggct aacatggtga aaccccgttt ctactaaaaa tacaaaaact agccaggtgt
93001  ggtggtgcgt gcctgtagtt ctagctgctc aggaggctga ggcaggagaa ttgcttgaac
93061  ccgggaggca gaggttgcag tgagccgaga tcatgccatt gcactccagc ctgggcgaca
93121  ggagcaaaac tctgtctcaa aaaaaaaaa aagaaaaga aagaaaaaa gaattggctc
93181  ttatcaaaga aaatacttct aacacaatga aataagcagc caaaaggcaa aaatgtaatt
93241  cttttcacaat aggaaatttc ataaatttg tgtagaaagt ttaacagtga ttaagtgcct
93301  aagagcaata aattctgaag tcagactgcc tagctttaaa tcctcattcc accagtaatt
93361  tgttatgtga ttttaagtaa attacctaat attcttcaat gcctgtttcc tcataagaaa
93421  aatagaaata aaaatataat cctcatagaa taaaatgtta ctacatgcaa aagcccctaa
93481  aagagtgcct gttacacaat aacataacta ttagctataa catgtgtgtc agctgttgtt
93541  aagtttttct catgtcctca ccattattat ttctatgtcc tttaatctga tcttgtccaa
93601  ttaacagtgt tgtgttaccc aggtttatga taagttcaaa gttgtaacat tgtcatttta
93661  tctaaatctg aagcaattag atttagataa cactgatgag tgctggcttt tgcttagtt
93721  cagacagcta ttaatgacag aacaattaac atagccagtt tcaaaacctt tgttgatgaa
93781  atagctagca gagacaaatt tgcgatgact tgtgtagata ctgatggtag acaatacaac
93841  aaaagcccaa ttttagacc tacttcagaa gataaatgaa gtttgtaaag ttaacagatt
93901  caagacaaga tcagagggga attacatctt ttattcaaat tctccctcta gtctatgtta
93961  atataactct gtccacaaat aactttatca tgtcttattt ccactacatg tgaagaactg
94021  aaacgatcaa gaatgctttt gtcaagttat ctaataaaat attcttcagt tttcatcccc
94081  ttaaatccat aaagaaaact tctaaaatct caaaaaaaag caaaaatccc aagatctaga
94141  tcttagttcc ttgacaaaat agaaaaaaag tagtagaaag atgagtgatt attaaaattt
```

Fig. 28 (Cont.)

```
94201 accaattcat ttcttttata ggtcagtatc attcttcttc atctgtaaaa tgagaatact
94261 ctatctgcct aagtcatagt gatcttggta gtttcaaata aaagaatgta tttgaaagaa
94321 ctacttaaca aatataaggg tcatggtcat ctctatctct ctcttttttct tttttttttg
94381 agacggagtc tcactctgtc acccaggctg cagtgcagtg gtgcgatctt aactcactgc
94441 aagctctgcc tcccgggttc acgccattct cctgcctcag cctcctgggt aactgggact
94501 acaggcgccc acgaccacgc ctggctaatt tttgtctatt tttagtagag acggggtttc
94561 actgtgttag ccaggatggt ctcaatctcc tgacctcatg atccgcccgc ctcggcctcc
94621 caaagtgctg ggattacagg tgtgagccac cgtgcccagc ctctatctct tttacacata
94681 agaaaacaga gtctaaataa acatatgaca taatcaaacc ataatagttt acctttggg
94741 gcgggagcta gacaattctg acatgcgaaa cttactcttc tccttgatat ctgaaatact
94801 gggttgttca ctacatctag atgcgtctat tcaaagaaa aatgcaaata taagtatta
94861 gtaaggtgtc ttagaaacta gtattatccc tcttaaaacc ttggttttct aattactgat
94921 tttcagtttt cttaagatct tcattccttt cattactcta ttttctctac tttttccta
94981 atctagtatt tcctcatttc taattagaaa gtaccttcaa atttttatga cccagtcttt
95041 tctttgtact catccagccc atccccacac tagctgaatg tcttgctgta ccaaggcagc
95101 taagagctat tggaaaaaaa aatcaacaga accacaaata ggtgctgtta taaatttaca
95161 tgttcaaatc tcagatgtca ccttgtgtca cttggtaact cttttacta aacactgttc
95221 ggctcccta cccatttatc agaatgatcc ataccagaat gatccatact acattgaccc
95281 ctttgcctag attataactc cttttattcc aagatgacct atttcacttt acaaagaaaa
95341 tgagaaggta tcttccataa aaatctcaat tttcctatct tttaatccac tcatttatct
95401 atactttcct tcaaccttac ttctttcctt ctactgctaa ctcatctacc taactcatct
95461 aggtagatga gttagaccac agaacaaaat caaaaacaaa aaaaacctca tcttacccta
95521 actcgccacc tttctatttc tttcctgttc caaacttaag taatagcacc aattgttatt
95581 tacaattttt cacctactac tcttaaaata ttttcagtct gctctaatct atctttagaa
95641 ataagcttta tgagggtcat ttaagtaaaa tccacagatc tctttccatt tctcctatga
95701 cttcagaatt tggctctaaa gctagctttc tagcattatc tgctgttatc catgcatatt
95761 acatttaaa tacaacaaaa ttcactgagg tcccagaata aaacatgctc ttttttaaagt
95821 acccttttcat gagattttt ttcacaaccc aaaatgctct tccccagttc tctaaatgtt
95881 atactaccca attcaatcat ctccttcatg aaacctttcc tatcagtact cagggaagac
95941 cttttaaaaa agagatccta aattttgta cagtacaaag ccaaaactag aattacaata
96001 ttaggctgaa aaaacgcaaa tcaaatattg ggtcatattc aaattaaagt ttaccagatc
96061 aaatattgga tcatttcaaa attagcattt acctttgctt agtccatctg cctttcact
96121 ggtattgttt cctccaagtt tcatagagtc atcgttaaca ttatattcct gggtaaatag
96181 gcatatttct taaacagtac tgctatcagt tttaaataac tttaaatgca tcctgtttta
96241 tattgcttta ctttgcataa taaaacgac ttaaattgct acccaattct ggagcaactg
96301 aaggggaggg tgaataagtg aagaggaaaa tatacaaact gatttaaaat tttttcacgg
96361 gttatctcaa aaaaaaaaaa ataaataaaa ctacttggcc ttcaccttt cgaaggaat
96421 accgaaagca aatctcaatt ataaatgaca cattattgtg agaaaaattc aagaactggg
96481 atttacttta taattaagaa ttctcagact tcaaactttt caaaccaatg ttccatgttc
96541 agatctttaa tgaggctgcc attgtcatcc tctctttctc tagaatttgc agggcaaata
96601 actctaatat ataatagtac aggtcccaga gtgtcctctc ttcttactcc atggggtatt
96661 ttcctgctag cccatttct tttcttttcc aatgtaccct tgtttccaaa ggcaccaatg
96721 tacatgaatt gaaaacaatt ttataaaatt tgaattgtaa gcacttaaaa aatcccccct
96781 tagagttaag tcttactaaa aatgtggttg aaaaggttca tcctctttaa aggtaccaat
96841 caaaaaaaac taaaatctg ccgggcgcag tggctcatgc cagcactttg ggagaccgag
96901 gcgggcggat cacctaagat caggagctcg agactagcct ggccaacaca gcaaaccct
```

Fig. 28 (Cont.)

```
96961  gtctctacta aatagacaca gattagccag gcatggtggc gggcacctgt aatcccagct
97021  acttgggagg ctgaggcagg agaattgctt gaactgagga ggtggaggtt gtagtgagcc
97081  aaggttgcgc cactgcactc cctctgtctc aaaaaataaa attaaattaa tttaaaatcc
97141  caaatacaat atttttagag atacgtaact agaagagtta ctttagacag ttaatgtcta
97201  agcattagct ccaagaaaga gatggtaaaa atgcttttca tcaaacatcc tatcaagtct
97261  acaataatta ctataaccat ttatattaaa cagtatgcaa aaaaactaaa tgtttattca
97321  aacataaagg atgtcctttg cattcatctt cttttttttt tttctgagac agagtttcac
97381  tcttgttgcc caggctggag tgcaacggca caatctcggc tcattgaaac ctctacctcc
97441  tgagttcaag tgattctcct gcctcagcct cccaagtaac tgagattaca ggtatgcgcc
97501  accacaccca gctaattttg tatttcagt agagacaggg cttcatcatg ttggtcagac
97561  tggtcttgaa ctcctaacct caggtgatct gcccgcctca gcctcccaaa gtgctgggat
97621  tacaggaatg agtcactatg cccagctttg cattattctt tatattaaaa tattttgctc
97681  agcaaacttt ttctctataa agttcaaaga taaactttt atcaagtcca agctggatga
97741  aataatagta tgttagaatc taggggaatt taaatcaata tttcagtcta cttatgtttg
97801  gaatatctaa acatacttga aagagtgaca atttttttt tttttttaat aaatccctgg
97861  ctggaaatca catcttcagc tgccatttca attaatgtag caacccaaat attctaaaac
97921  ctttctacta taaaacacac tttaaatata taacttatct tggggaaaaa taagagaaat
97981  ccttattgtt aattgataat ttctcaatta ataattgaga ctaaagcagt aagtagtctt
98041  atgtgcttct atcaaatctg gtaacctaaa acttcagttt caataaccaa atgtaggaag
98101  aacaagacat aaaacattag gttgctcagg gtgaggaatt gaacctgaga cttcaacagg
98161  tttaactctc aataaaagta gaaagtagga agtaaaacta agtgcagaca ttaataaaat
98221  aaaatctcaa tagcactgac aggaaactga tgtactgcct tctctgaaaa ctaaaaacta
98281  ggaagaatgg taattcagaa gagttcagaa aagaagtata ttgcatacat cttttgcta
98341  tttccttcta tttaagttac ttgaattttc aggtaagaaa agaagtaact gttcctctct
98401  agtaacattt attttctca ctaaactaat ttttaattct tagaaaccaa atataaatgt
98461  atgtttatat tatatacata tatatatgta tatatataca cacacacaca caaatttca
98521  agaaaagtca cccttattct catcactagg acataagtta ttattaacat tttggtacag
98581  atagtgtagt gaatggactt aaaacacaca tgaatatatt atttacaaag tgaggaacca
98641  aactccacac aaagatttgt acctgtcatt ttttaactaa aaagaatcat gaaagtgatt
98701  attcatcaaa aataatactt aatggttaca taatagtaag ttttatggct atatcgttta
98761  actgttccct tgtcaaaaga tgtttcaaat tgtccacctt tatttattt ttatttgttt
98821  tagagacagg gtctcacagt gtcactgaag gtggagtgca atagtgcaat catagctgac
98881  cataggctca aactcctggg ctccagcaat cctcctgctt cagcctccca agtaggtgga
98941  actacaggtg ccagtcacta tgcccagcct ttaaaacaat gttgagggaa aaaaaataa
99001  taataataaa aaaaaacctg tatttctttt ggaaaaaatg aatttctggt aactcctttc
99061  agatagtttc ttagaaatgg cattattgac tggcaaaatt gttcaaagat tataaacaat
99121  tttaagactc ctgatacaaa ttatcaattg ttctcaagaa tgtgatacct gctggtggct
99181  cacacctata gccccagcac tttgggaggc tgaggcaggt agatggcttg agctcatgag
99241  ttcgagacca gcctggacaa catggcgaaa tcccacgact gagcctggg aagcagaggt
99301  tacagtgagc tgagattgcg ccactgcact ccagcctggg caacagagcc acaccttgtc
99361  tgaaaacgta aaagaatgt gacacgaact ttcattctta tcagcaacac ataaaagaca
99421  gagagaccat tcatcgcatt tctgaaaaca caatttcttg gtagtttttt ttaatgatga
99481  aatttaaaga tttcacaata aactggaggt ttcacataaa gcgcacttac tactacttta
99541  ccttcttcag tagattcttt ttaactcttt caataggaag aggtctgcca tcatggaagt
99601  tggtaaggat tactgcaatg gccgtaagag ttttacccctt aaaaatgttt taaaaagata
```

Fig. 28 (Cont.)

```
 99661 aatggtcaga ttgtgaaacc cagttcacca gaaaaacgtt cccattttaa aatcaagtaa
 99721 tcgaatatca aatatcattc aaggtcacaa aagtgtactg tatattaatg aaaaatgagt
 99781 atttcattta gttagaaaat gctttccccc actgcattat tagggaatta ttaaatgatt
 99841 tacactataa aatactacaa gtatctctga gaagtgtcat tttattgaat gactgctatt
 99901 ctacaattct acatttaatc ctgaactctt gatttttatc atgcaactat ttataactac
 99961 tcatttgcca tgaagttcgg agctaaagtg attagtaatt ccagtatgca tataatcatt
100021 ttattaaaat ttgacttaaa gataatacca agcttaaaag tcataacttc tccataaagc
100081 ataaaagata tatttcttat gcattttctc taagtggaag tatgtaattt ttcaatattt
100141 actgcagctt aattcatagt tggcaataca ttagtaaatc tctggcaatt taaagcagt
100201 gtaaataaca gcagttttca aagtgtggtc cacaggccac tggggatggg gagggtttcc
100261 caggagccct tcacgaaaat gcaaagtcaa aactgttttt ataatactac taagacagac
100321 cttactctgt taacatctgc actaatccta caaaaagccc aaatagcaat ggtcaaaaaa
100381 gtgcctcagc ataaaacaaa gcagttggca ctaaggtata ttagtactag tcatcatatt
100441 cttaactgcc acatacagtt aaaaaaaaaa gttttcctta agaatgttct tggctgggca
100501 cagtggctca ggcctgtaat cccagcactt tgggaggccg aagcaggtgg atcacctgag
100561 gtaggagttc aagaccagcc tggaccaaca cggtgaaacc ccgtctctac taaatacaaa
100621 aaattagcta ggtgtggtgg tgcatgcctg taatcccagc tacttgggag gctaaggaag
100681 gagaatcact tgaacctggg aggcggaggg tgcagtgagc caagactgaa ccattactcc
100741 agcctgggca acaagagtga aactccatct caagaaaaaa aaaaaaaaag aagaagaatg
100801 ttcttgacga agcagtacac attaattta ttaagtctca ttacttcagt acaaatcttt
100861 ttaatattct gtgtagtgaa atggaaacta catattaact acttctgttg catatcaaac
100921 tatgagggtt agctagagaa aaatcactca agatgggagt tataagctca actagtcact
100981 tttttcatgc gacaccattt ttacttgaat gacaactatc aatcacgact gagtgtctga
101041 aagatacttt ctagaaaatg aacaaagtga ggctgtcatc tacaaaggaa acaactgagc
101101 ttgtcaatga taaaatgtga gttttcaata gaaaattaga atgttggaaa agttgtgtgt
101161 gacactatga acatagtgcc ttcccaaaat gtaaatgatt ttctaataac atcagtggta
101221 atattaatga atgtaagttt tggatattgc atatgaaata catcaacatt tagtaggtct
101281 gcccaactca atgaaccaac attttctaaa tgagcaatgc ctggtgttat aaaatcatac
101341 atgggtaaaa tattcattca atgagcaaga tacacaaata gattttaaca aaacagggta
101401 taaaagctc actgatatga tttagcgttc catattacaa caattaacct ttaataaact
101461 aatatttatt gaattttgat gcagtatatc aaagaaatct gcaattatct aaaaagctat
101521 tacaatactc ctctctttac agcaacatac cgtcgtaagg acaaattttc ttcatatact
101581 tcaaccaaaa caacctaaca gaacagactg aatgaagaag caggtgagaa ttcagctgcc
101641 atctattcgg ccaaacacag agatgtgcaa aaatgtgaca atgccagttg ttgcaacaaa
101701 aatgttaatg ttttggcata gttatttttc ttttaaaaat atgctattta tgttaacaag
101761 caatgagttt gtactgctat ctttagctac cactgcctaa tactataact actgataaca
101821 gcacacaaaa gcaaagctc tttgaaatca gtaattttta tgagtagaaa gggttactga
101881 gactgaaaaa tataaaaact gctagtgtaa ggacacataa gtatctattt aatactctgc
101941 ataacacaat atttgtgatg gaatacaatt tcacataaca ttgttttgtc tttactttt
102001 aaaagaaaac ctatgaaaga caggtcaccc tgaatttcaa agagcaaaga aaattgagaa
102061 acatggccag gcagggtggc tcacatctgt aaccccagca ctttgggagg ccaaggcggg
102121 cggatcactt gaagtcagga gttcaaaacc agcctggcca acgtggtaaa accctgtctc
102181 tactaaaaat acaaaaatta gctgggcatg gtggcacatg cctgtaatcc cagctatttg
102241 gaagtctgag acaggagaac tgcttgaacc tgggaggcgg aggctgcagt gagccaagat
102301 cgcgtcactg cactccagcc tgggtgacag agcaagactc catctcaaaa aaaaaaaaaa
102361 gaaaactgag gaacacatct ttataccact attttaacta aaactacag gaaaaactgt
```

Fig. 28 (Cont.)

```
102421 gttctacaaa gatagtaaga tctagtccca aactggtacc aacatattcc tatctctttt
102481 tacttcaaaa ttactttcta gaaaatcata atcacaaaat tagattttat taactaaaga
102541 aaaaaataat taccaaaccc atatcatcag ctaaaattcc tccatggaca ttttctggtc
102601 ggtccttctc agaaaaattt gttattgtgt tatagtataa gtcatttcgc tgttcccaga
102661 atggtggaag ttctttgcta ttttcccgtg acaccatcca agctagagct tgttttgat
102721 gtggaagcag tggtgtttca atagcctata aataaaaagt cataaagcga aatacattaa
102781 gccattcctt tttcacatgc agatcctgtg attaaacaaa aagtagattc taagtatatt
102841 taaacattct gagtagtctt aaataaaaaa tattggttca atacctcagc tggttccatt
102901 tcatgggttt tatcatcttc ttttaaatct tcaaacaatt tgtcaaattc tgttttaagc
102961 tacaataaac agcaacaaga aacaatgtaa aacaaactaa ttaaaataat acttgcattt
103021 aagtcagatt tgaaatcatt taattaactg gcgttaatgt caaacgggcc aggagtggtg
103081 gctcatgcca ataatctcag cactttggga gaccaaggtg ggaggatcac ttgagctcag
103141 gagtttgaga ccagcctgga taacatagtg agagatccca tctctacaaa aaaattttta
103201 aaaaattagc caggcatggg ggtgcatgcc tgtagttctg gctcctaggg atgctgagat
103261 gggaggatca cttcagccta gtaggtagag gatagagtga accatgatta tgccactgca
103321 ctccagcctg ggcaagaaag tgagaccctg tcccaaaaaa ttaagaaatt gaaattaaat
103381 taaatttaaa aaccacaaac tagtcaaacg ccaaaaaggc acataaatca actctagaat
103441 tacactactc actgaagagc gaatgaacag gtgctttagt tgttaggagg taaaagaata
103501 taaagaatt ttaagtcccg agtttcagtc acagttttat cacaaataag cttatatgta
103561 agtttcagca agacttgacc tttatggccc catgtcttat tcctataaaa tgaaagggat
103621 gaactaaatt tagattgtct ctaaggttcc ttctgccatt aaaattctgt gatgctatca
103681 gttgtattca aaatattttc tcagtcctac caggtcaatg acattccatt tattattact
103741 gcaataagga acttgccatg cactatagga tacttttatt attatgctaa cttaattgac
103801 tatttaaact aggttagtcc aatttatat caacatatat gtgatacaga tatttttgaa
103861 aattaacaca tgaacacagc agcagctcag aagaaatcag gccaggtcta aaaaatcaga
103921 agtaaccggg ggcttatcta ccagaaacaa gctcaagtcc ttctaacaat aagcagggta
103981 aatatggtaa ctacaattag tagataaaag gactaacact ggtagataca aacatcaaaa
104041 aagttttaat gttatttta aattgatctg cattaattac tttatatact ttttttcaa
104101 agaaattcag cataactcat cctaaattac aaattagaca atgtgaagaa tttggagtta
104161 aatctttagc actgcatttg caaaattact gaaaggagtt aagtctcagc ttcaattttt
104221 ttcttaaaat tactacttga acatttaaaa catttcagat acaaaaatat gccgtgcata
104281 aacaggaacg tgtgtgtttt gtatgttggg tacaaatgtt cacgtatgga tttattcctt
104341 atcagtactt tttatataaa atgttaacat atatatattc tatttattct ataacatgtt
104401 tcattataac ttaatatatt tgaagaccac aaatacccac acgtacatat tcatcctgtt
104461 cttttaaata caaacctgca acatttaaaa ttcactttta gattacaaaa taaaagagaa
104521 gcacacctgt tcagttgtca tctgtactgc agcatgcact ggcatactat agcttggtcc
104581 agctcttcca gagccccaac cactttccaa attgaatcct aaagctataa tttacaaaat
104641 aaaagaata aagccatcaa ataagtagg tttttatctt ttattaagta gcttttaaaa
104701 tatgcattaa cagggctggg tgctgtggct catgcctgta acccaagcac tttgggaggc
104761 caaggcaggt ggtttgcctg agtccagtag tttgagacta gcctgggcaa catggtgaga
104821 ttctgtctct acaaaaaata caaaaattag cagagcgtga tggtgtgcgc ctgtagtccc
104881 agctactcag gaggctcagg tggaaggact gctggagccc aggaggtcaa ggttgcactc
104941 agccactgat cgtggccact gtactctagc ctgggtgaca gagcaagact ctgtctcaaa
105001 atatatacac aaataaataa ataaaacgtg cataacaaac tgcattaaaa gccttgtatt
105061 ttagaggtat tttaaaagct aaatactaaa tcactaaaaa aacaagtaat tccacattat
105121 ttgaacaaac tcttgccaag caatcctttt cattcgctat cagaagatta ttttgccta
```

Fig. 28 (Cont.)

```
105181 aaatttatca aaaagaatgt ttaaagtcag gggtttccag atgttaccat tagggaaaat
105241 taggggaggg tatatatgag acttcattgc atatatactt tttctttaat ttttttaata
105301 tccctcact cttactgtgt atatttttat gtgtgaatct atttcaatag aggcaaaagg
105361 aaaatcaga gatttcctca aaaagactcc tgaaaaaaag ttgtaccttg gagccttgag
105421 cacaaattag ccaacaaact ccaagagaga ataaatgttt cataatccct gcatcttaca
105481 atatcagaat aatattaagt gaaaccctaa acttactttt tggtgcagga cccaatttaa
105541 atccatgttt cttcaactga tctgaaaccg cttttctatt ttcttctttt ccccaaaaag
105601 tcatatgcag aggcatggta aaagcattgt ttgcaccaaa aggaactacc ctattatatt
105661 tgggagaaaa agaaagggaa atcagaagca ttactttta tccccactaa gaattagttc
105721 aatattttaa gtgtatcatt tacatttac attgaagtaa agtaataagg aactagttgg
105781 gcagacttga aagaaaaaaa ggaaaagaaa tagaaccata aacaatcaga agggtgattt
105841 ttagaaacag agtgccagaa aaaattgaga aaatggaata aagcagtttt aaaaatgcaa
105901 ggatggcctg taaacaagat tgtaatataa gtaaaataag ttaaatcaaa gggtagagtt
105961 tggctaacgg aaccactgag ggtagtaact cattctgctt ggaaaatggg aaatgcaaga
106021 acttgtgatt cactaagtta ttctcaataa ctgaaaaacc tgataaactg aaaaaggaga
106081 aaacaaagtg agacattatg agcatttatt ttctcttcaa actcacctag gattatatga
106141 atatcctaaa aattagaatt agaatatcaa gatcctaaat attccagata cttaaattga
106201 gatcacaagt acaaatgcct aaaagagaaa aggtaactga aagattgaaa gagtttagaa
106261 aaagaaaaaa gaaacaggtg ataaaactgg gagagcatat gccctagcta aagggagagt
106321 tccagtcaac tattgtcata tggaagtgac aactcatcct gcattgccag atttcccact
106381 tgtcaagaga aaaataagtt ttttgtattt aagaaaataa attaatatgt ataaaatgcg
106441 gacttagcta tttcaataat tagtactgaa cgaaaaaatg tctaaaacac tgcagggcaa
106501 aatgaaattc acctacatca tatcacagaa taccagttta taacctctga tataaacaaa
106561 cacttccagg ctgggcacgg tggctcacgc ctgtaatccc agcattttgg gaggccgagg
106621 cgggcagatc acctgaggtc aggagttcga gacagcctgg ccaacatggc aaatctctgt
106681 ctctactaaa aaatacaaaa attaattggg catggtggca ggcacctgta gctactcagg
106741 aggctaaggc agggagagtt gcttgaaccc tggaggcgga ggttgcagtc agccgagatc
106801 acacaactgc actgcagcct gggcaacaga gtgagacttc gtctcaaaat aaataaataa
106861 ataaataaac aaataaacac ttccaaattc ctaaacctag gtaccaaaag gtttggagaa
106921 atggaatgta cttcctaata tttgaaccaa ggtctatttt ctccatggta ataattccat
106981 aggaaaatga gaggacaatt gtttgatggc tggggtagta gaagtatgta aaaggagaaa
107041 taaacatttt atttaacacg taccaaaagt acagtgatag aaattgttag catacctta
107101 taggctctaa caagaagccc taacaagttc aaagatgact ataattcaca attattaaaa
107161 ctaaattctg aaagtacatt accttcaat ttgtgccaat tgttgtcca tgatataggc
107221 caaagcacct gcaagctctt tctttaaatg gccaacttga tttccattca cattgtttac
107281 tttaattgca ttcttatcat aagggttatt aggatctcgt tgtaatgcaa ccatttcatt
107341 attattaacc taataaaaat gataaacaga taatattaca ttataaataa tagacaataa
107401 ctttgttata ctttatctgg gatttccatt cattttttaa tgctactgct aaacactgca
107461 cataagaaaa atatattttc tagacacaaa ctacagaaat attaatatat attattatga
107521 ctccttaata ttattttct aatctatatt cattaggaag ttaacaaatc cttaatgtct
107581 taaaaatag tcaatgtaa actagcaaat tcaaattatc taaattttc aacatcataa
107641 cttctgaaaa atagccaacc cttattgagc gcttactatg tgccaagcat tggtctaagt
107701 acattgcaca gactgacttt ttaaatcctc acagctctat tgggaggtac tatcattatt
107761 cccatttac aaatgaagaa actgaagcac agaaaagtaa cttgcccaag gtcacaaagc
107821 taaaggtag cagagctagg atctgaaccc acacagggtg gttcctgagc ctcaattctc
```

```
107881  cagaatataa aagtcaggga ataaggcatt tataagtcag gatggaacta ggtaagaaaa
107941  atatatccag ccttcaactc atgccattct gattctactt tattaaaaac tgtatgattt
108001  aacttaaata ttatgatgta tatttttaaa aactgaagga gggtaacaca ataaagaatg
108061  gtagaatgag gactttcaaa aattcctcaa taaaggcaac aaaaaaacta gataaattat
108121  ttgtcagaat caaatgtttc agaacactga gaactaaatc aaaggcttgc agaaatctgg
108181  gtaacattta ttcaagaata aaaagaataa acagctgaat atcagtactt cagtcccatc
108241  cccagcaatc ctgtagcctt taaaaatagc tcacggccag gcacagtagc tcacgccccc
108301  agcactttgg gaggccgagg tgggaagatc acgaggtcaa gagatcaaga ccatcctagc
108361  caacatggtg agaccccgt  ctctactaaa aatacaaaaa ttagctgggt gtggtggcac
108421  gcgcctgtag tcctagctac tgggaggct  gaggcaggag aaccacttga acccggcagg
108481  cagaggttgc agtgagccaa gatagtgccc ctgcactcca gcctggtgac agagcgagac
108541  ttcatctcaa aataaataaa taaataaata aataaataaa taaataaata aataaaaata
108601  atagcttgtt gggatcctag gtaaagcctg gcagtcacca gaaaaaaaga gaatggagtt
108661  acagttcttt cagagattca ttcccaaaga actgttattc tcctgaagtt ccccggaaga
108721  ccccacttgc aaggctgact gtatttaacc tctgagctca ccaagtacaa aaaaacctcc
108781  cttgggcgga tgtttgtcaa aacaatttta caggaaagtg ttttaacttc atggctacct
108841  gaggcagtgg ataacagctg aagcaaaaaa acaaaaaggc ttataaagaa gagctaggga
108901  atgagatgtc tgtgagggct ttgaaaagct ccagtgtatt tctggatatc tagaaggccg
108961  taagcaagca cagggctggt atgcatgacc agggctgtgc acattctcaa gaaagacctg
109021  agaaggccct aaacgctcac cttttgcctga acttgagcat ttaaacaagc cagaagtgaa
109081  agctaaagca gagttgtcag gggccttaga gtgttgaagg aatgccctaa catacagaag
109141  ttctcagcaa agaatgtacg atttattagt tccagcacaa tcatcagctg accgctaagc
109201  taaccaagta cagacttcag tgaccacaca cgataaagga tagacatcac agaattaatt
109261  caggaaagtc actaacaaac acacactaat tacaaaactc agcaacaaac caccctagaa
109321  gcctaacaaa cacacactaa ttacaaaact cagcaacaac aaaccaccct gatttccaga
109381  gctgccacat tatttaaaat gtcaattttt caagaaaaaa agtacaagac atgcaaaaaa
109441  aataagaaag tatggtctat acacagggaa aaaaagcaat caatgtcaac tgtccccaag
109501  aaagtataga tgtttgacat agtagaaaaa gaatttaagt cagttatttt aaatatgttc
109561  aaaggggctg ggcatggtgg ctcacacttg taatcccagc actttaggag gctgaagtgt
109621  gaggatctct tgaggccagg aatttgagac cagcctggga aacatagcaa gaccccattt
109681  ctacaaaata aaaatagaaa aattagccag gtatggtggt acatgcctgt agtcccagct
109741  attcaggagt ctgaggtggg aggactgctt gaatgcagga gttcaaggtt acagtgagct
109801  atgatcacgc cactgcactc cagcctgggt aatagagcaa gaacctatct ctaaaaaatt
109861  aaaaagttca aagacctggc cgggcacagt ggctcacgcc tgtaatccca gcactttggg
109921  aggccgaggt gggcggatca cgaggtcagg agatcgagac catcctggct aacacagtga
109981  aaccccgtct ctactaaaaa tacaaaaaat tagccgggcg aggtggcggg tgcctgtagt
110041  cccagttact cgggaagctg acacaggaga atgatgtgaa cctgggaggc agagcttgca
110101  gtgagccgag atcgtgccac tgcactccag cctgggcgac aaagcaagac tccgtctcaa
110161  aaaaaaaaaa aataagttca aagacctaa  agcaaatcat ttctttcgac atgaaaacgc
110221  atgtctaaaa gcatggagac gatgtctcac caaacagcaa ttctagagtc aaaaggtaca
110281  ataactgaag aaaaaattca ccagagagac tcaacagcaa atttgagcag gcataagaaa
110341  aatcagcgaa gctgaagata ggtcaattga gattatacaa tctaaggaac aaaaaaatga
110401  cacacaacag agcctcagaa acttgtaata tcaagcatac caacacacat acataagagt
110461  accataagga gaaagagaa  aggggcagaa aaaatattta agaaataac  agccaaaacc
110521  ttcccaattc gatggaaacc actactctac acatataaga agctcaacaa ctccaactaa
110581  aataaactca aagagatcca cacctggtca catcataatc aaactgtcaa aagaagtttg
```

Fig. 28 (Cont.)

113341 aaccaaaata gaccaaagaa gtacctaaat tatgctgagt gaaaaacgcc agacttaaaa
113401 tagtacatac tgtagaattc aatgtatatg aagttctaga ataggcaaaa cttatttata
113461 gtgatagaag acttgtgtgg ccgggcgcag tggctcacac ctgtaatccc agcactttgg
113521 gaggccgagg cgggcggatc acgaggtcag gagatacaga ccatcctggc taacacggtg
113581 aaaccccgtc tctaccaaaa atacaaaaaa attagccggg catggtggca ggcgcctgta
113641 gtcccagcta cttgggaggc tgaggcagga gaatggcatg aacttgggag gcggagcttg
113701 caatgagccg agatcccgcc actgcgctcc agcctgagaa acagagcgag actccgtctc
113761 aaaaaaaaca aaaaaaaaga aagaaatga gactcgtggc tgcctagggc aggaacaggg
113821 aaaaatgaat gcaataggat acaagatact ttgagggaga cggatacaat ctgtatcttg
113881 attggggtag tagttatcag gtatacatct ttgtcaaaac actaggatca tacatttaaa
113941 atatgtacat tttatcatac gtaaaccaca tctcaataaa gtagaaaaaa aattaaaata
114001 acaagtatgc aaagatagta tctcaatttt tattattttt ataatagtga ttaactcaaa
114061 aatgtccatc aacaaggaaa ttataagtcc aatatagatg atattcctaa tcacattagg
114121 cataatatga tctcatttt attaatacat aatatgattc caatttacat gcacatgctc
114181 acagaaacaa gtgtagaaga taagttatgg ttctggatga tagacttcag aagatttaat
114241 gccttttag ccatttaaaa ataatgaacg tggctgggcg cggtggctca tgcctgtaat
114301 cccagcactt tggaaggccg aggtgagtgg atcacctgag gtcaggggtt caagaccagc
114361 ctgaccaaca tggcaaaacc tcatctctcc taaatacaaa aaattagctg ggcatgatgg
114421 cgcatgcctg taatcccagc tacttaggag gctgttgcag gagaaccgct tgaacctggg
114481 aggcggaggt tgcagtgagc caagattgca ccattgcact ccagcctggg caatgcaagc
114541 aagactccgt ttcaaaaaaa aaacaaaaac aaataaaaga acatgcatta attataaaat
114601 aaatgatatc tcaacatagt gttcctggaa aaaaataaaa tttaaagtat atatatttgg
114661 caaaataaga aaactgatga ttacttttta tcaacacaca ctagagttta ccgaagtcat
114721 agagattatt ctcagatcaa aaatactgat tgttctaaga tcaataacta ccataatcta
114781 gtatttcatg gtggtataaa ataattatcg aaagcaatgt aagttttgaa aaattagcac
114841 aaatctgaaa cagaaaagct cagaaatgca tatgagagcc agagaatata tagatgtgaa
114901 ataagaactg atagagttca agaatctatt agaaaaaatt agaggccggg tgcagcatcc
114961 cagcacttgg agaggccaag gcggacggat cacttgagcc caggagttcc agatcagcct
115021 ggacaacatg ccaaaaccta aaaaaaaata caaaaaaaaa aatacaaaa attagctggg
115081 tatggtggtg aacgccagca gtcccagcta ctcaggaggc tgaattggga gaattgcttg
115141 agtctgggag gcagagattg cagtgaggcc agatcaggcc actgcactcc agcctgggca
115201 acaaaacgaa acttggtctc aaaaaaaag aaaaaaaaaa aaatccaatt cacttaagtg
115261 aaagaaaatc acactggcct gagaattcta tgcaacatta ggatatggag attttattac
115321 aaagatttta ttacaaagat atattacaaa gattttaaat tcagcccaac tgtcattaag
115381 tccttcataa ctttcatttt atgaaactgt cattcataaa atgccacaag tatgaaaata
115441 taaaaactta ggaaatattg tctcttccta aggaatctcc tagacaacac atttcagaca
115501 atcaaaaaac aatttgaaac gttccaatgt aaaggaaata caggagaaaa acaaatccag
115561 aacatgaaac tcctaaggaa tctcctgtcg aacatgcttc agacaccta ttgagaagct
115621 taaacataag aaacatacgg agaaatgaaa gaataaaatc cagaagattc cacaaaacga
115681 tctccttttt gcaacaaatc gatgacatga acaaggcgct ggggtgtggg ggtggggtgc
115741 tacccataat aaccaaacat aacgcactga ggccaagcat attggctcat tcctgtaatc
115801 ccaacactct gggaggctga ggtgggaggg tcacttaagg tatttgttat ttttgcgta
115861 caaatattta actaacttaa agtaaaataa agattaaccg cacacatcac ctgcgaattc
115921 tcttattttc taggttaacg ccagaaatat aatcaaaatt taattatcta ctattatact
115981 cactactccc gtgtaatagc gtagtccaac cacatgacct ctcaaacttc caaataaaac
116041 ggaatctact tcttcatcac tagttagaaa gtcatctgga gggataacat cttggaattc
116101 aaaacgtgga aagaaagttg gatatgagag gcgtggaaaa tttccatgaa ctccatactg

Fig. 28 (Cont.)

```
116161 gacagtctgc aagtacttcc aaactggatc cctatttttt tttaaaggca aagaaaaaca
116221 atataatatt taagtatttc caaagaccat atgagtagtt ttctcatgct ttacttcagc
116281 aaatgaaatc ttacatggga atcacggtaa agattaatag ttactctcgt taaagcagga
116341 attgcagtga gtggagaagg cttctaggaa ctctacctgt tttcaatatt ggctcttcta
116401 cctgccccct aggtattcaa aatgaaaagc ctagtcagag ttcactaacc tctttcccag
116461 tgaaaatcat ctaaattgat atgtatatga tgtctgtaac tacaattatg ggccggatgc
116521 ggtggctcac gcctggaatc ccagcacttt gggaggcaga ggcaggtgga tcacctgagg
116581 tcaggaattt gagaccaacc tggccaacat tgtgaaaccc tgtctactac aaatacaaaa
116641 attagccagg cgtggtggcg cccatatgta atcccagcta ctcgggaggc tgaggcagga
116701 gaatcacttg aacccgggag gcgtaggttg cagcgagccg agattgtgcc actgcactcc
116761 agcctggacg acagagcgag actccatgtc aaaaaataa tttaaaaaat gaaatcatat
116821 gccaaaattt caatagggat tgagctatat aaaagactta taaaaataca actattaatg
116881 taccagaagt tgtttataat tttccagaaa atacatccag catccatcac tgtaactccc
116941 tgcgagcaga acacctattc tggtatccaa accacgccac cgtgggaaat tggccccaag
117001 ccacccgtac ccgccttccg tcgccggttt aagcataacc ccaaacccat taggtgtaac
117061 tgtttcggga atgaccataa ataccaattt ggacaatgaa aagtgaaggg gagtctactg
117121 gagcattgca aaaagtttcc attctcctaa gaacagtcgc ttatttgcga tgcgttttcc
117181 ttgcaagtgg cgcatatctc tactagcgcc tctgcaaata cttatctgca cgtctgtgca
117241 tacagataag ctgtgagcca cttggggaca aggactgtct tactcggccc tccaccgagc
117301 acaatgcctg gcgcacagtg ggtatctaat ggatgttttg ttaaataaag cactggccga
117361 gatgctttaa gccccaggcc ccccacagtc ggtgacagag atttcccaag tccctaacac
117421 gggactcgcc ctaggagccc ctactcgcca gcgaagacaa tgcatttatt tctccggcgg
117481 ccacatatgc gaccaacaga acgaatacag ctgcacaaat cgcccaggga acgcagagga
117541 acgcggggaa ggtcaggttc atttggggac gcctccaggc cgttagaccg agcgccccac
117601 cccctccgcc cccttcacct cttgaacatc caggacatgg cgctgagtgg gatgacaaga
117661 ggagcgcctc ggctcccctg gatcgttttc gagccgcctc gatacgcctc cttccaggcc
117721 ccgcagccct gaagccgggg acaaattccg agcgccggat caggagcgca cgactgaaag
117781 gtaagtcgcc gcgagtccag tcagacgtcg acgccgtctc cttctgcaac aatctgggag
117841 accagcgtcg ctctgtgact ggcactagga aagcccaatc acgaagagga gagtgcggag
117901 ccaaaccagt cagagcacag aagggagggc aactccgccc cgctgccatt caaagacggc
117961 gggggggtccg ggctgcaagg gtggttccat ccgggttctt ccccgccccc aaggcgggcg
118021 cgcgggaaag ccacgaggcc ccaggagtgc gactgcggtg cctgcggtgc cggtgttttg
118081 tttgattccc tgcctcaaac ggagggaaac gaccttcctt tatcctacga gtcctaagac
118141 tgaacccccat tctaaaggct ctaccgtatc cttcctctta ttttcttctc atctaatgtg
118201 gcacataata gggccttata ctaaaggagc tccacggttt acgagaccta gagctaccgg
118261 cgagatactt tacttcattc cctgtggtga accgtgggga ctttcgctcc aaattttcat
118321 gttaagcctc agcgtatgca tgagacacaa cgagtttgga aaatcttaaa tggaacttag
118381 agtcccctcc ccacctcttt ttgttatttt taaggaaaat ttcctttct tggtgcagga
118441 aacccatcac atgtttatta cagctatggg ggcgtttgcc tgaaatggtg gacgggacca
118501 ttttccccgt gggcacttgg ctgctccagc caagaggggg aggcccttgt tttcctcaag
118561 gaactgcaga ggggcgctct gaggccctcc atggctctct tccagagtc tgaggtgacc
118621 ggaaggagaa tgcggccctg ggaccgtcaa ccttggacca gctgcagccg acgcctggca
118681 gggctggtcg ctttgcgttg aggaggctgc tgtccccgaa gctggccttt taatcgcaca
118741 gggcaggaag ctggtggtgg cgcccagctg cacaggcggc accatgtaac tgccagataa
118801 tacttgcgcg tcacagagag gtccatgtta cacgcctgtc agcacaataa tattaggtgg
118861 tcagcttttc ttttttcttt ttttgttttt ttttctttt ttattgagat ggagtcttgc
118921 tctgtccccc aggctggagt gcaatggggg tgatcttggc tcactgcaac ctccgcctcc
```

Fig. 28 (Cont.)

```
118981 cggattcaag cgattctcct gcctcagcct ccggagtagc cgggattgca ggagcccgcc
119041 accacgccca gctaattttt gtattttag tagagacggg gtttcaccat attggccagg
119101 ctggtcttga actcctgacc tcaggtgatc cgcccgcctc ggcctcccag agtgctggga
119161 ttacaggcat gagccaccgt gccaggccgg tagtcagctt ttcaagacac atttgttcat
119221 tatcgtaaat aaactgtagt gatctctaat catgaaccat ggatgagcaa tagaatttga
119281 aacaatgtat tatttcattt gaccaaagtt gatgaggaag ataaagacaa tggcatttca
119341 aattatttta attgttgtat gttcttcttg aagtgtgttg aggcaaatgg caatacagtt
119401 cagcttttag tatgccagat tttaaataaa ttcttggaaa atatgccaga aattgctcaa
119461 attgatgttt tgtaagagta agaaagtcat gctcactaga caaagaaaaa attccaaata
119521 tgagaacata gctctttcag acttaagact ggccaggcgc aatggctcac acctataatc
119581 ccagcacttt gggaggccga gttgggtgga tcacctgagg tcaggagttc gagaccagcc
119641 tggccaacat ggtgaaagcc tgactctact aagaaaatac aaaaattaag cagacgtggt
119701 ggcacgcacc tgtagtccta gctactggg aggctgaggc aggagaatcg cttgaaccag
119761 ggagacatgg gttgcagtga gccgagatca agccactgca ctccagcctg agcaacagag
119821 cgagactcca tctcaaaaaa ataaaaagac ttaagatcta tgaataatga ctgtcccatg
119881 gttaaagaat gtgctttgaa tgaactaaaa tttgctattt aaaggaatgg tatggaaagg
119941 aaaggaatcc aaaatttctc catccagcca cttcccagtc acaaacacac ttctcatctg
120001 cacccccagc cacacacaca cacatgcccg cgcgcgcgca cacacacaca cacacacaca
120061 cacacacaga acctttatgc aaattaatca tgtcatgtca ctcccctgtt tgattcagtg
120121 agcctgaaat ccaagaatgg catatgtggc tcttcctccc acagtatgtt ttctctatgt
120181 tatcaatatt tcacatccca gaaccaggag taaaacattc tttcccttaa tcattctttg
120241 ttttatattt aaagatcaag tacaatttgt actagtttga ttaaaatgtt acagcaatta
120301 caatttcaaa actattatac taaataatgt tttctgaaaa attaactttt ttggtttttt
120361 cttgatttat tctgataaca gcatcacaag tagatatgaa aaatgaacac ttgtaactgg
120421 aaaatgaact gtagggtggc ttgtggggtt tggctggtga gtaagaagga aagtggcact
120481 aaaaggacgg tggggaagat aagggccagg ttacatagga acttaagagt ctccagtaaa
120541 atttgtgttt taactgcaat ggaaagccat tgaatgtttc gagcaggagg ataacgactt
120601 gatttaggct tttaaaaatg ctggcagctc tgtggagaat tacaggaaac aaggatagaa
120661 gcaactgata gaaaattatt gtgttcagat aagagatggt ggtggcttgg aaagggaagg
120721 tgatgaagcc aagagaacca aaatgttcac tgataaattt aggtaggaat ggtatggaaa
120781 ggaaaggaat ccaaaatttc tccagccagc cacttcccag tcacaaacac acttctcatc
120841 tgcaccccta gccacacaca cacatgcccg tgcacacaca cacacacaca cacacacaga
```

Fig. 28 (Cont.)

SEQUENCE LISTING

<160> NUMBER OF SEQ ID NOS: 51

<210> SEQ ID NO 1
<211> LENGTH: 1009
<212> TYPE: PRT
<213> ORGANISM: Homo sapiens

<400> SEQUENCE: 1

```
Met Ser Trp Met Phe Lys Arg Asp Pro Val Trp Lys Tyr Leu Gln Thr
1               5                   10                  15

Val Gln Tyr Gly Val His Gly Asn Phe Pro Arg Leu Ser Tyr Pro Thr
            20                  25                  30

Phe Phe Pro Arg Phe Glu Phe Gln Asp Val Ile Pro Pro Asp Asp Phe
        35                  40                  45

Leu Thr Ser Asp Glu Glu Val Asp Ser Val Leu Phe Gly Ser Leu Arg
    50                  55                  60

Gly His Val Val Gly Leu Arg Tyr Tyr Thr Gly Val Val Asn Asn Asn
65                  70                  75                  80
```

```
Glu Met Val Ala Leu Gln Arg Asp Pro Asn Asn Pro Tyr Asp Lys Asn
                85                  90                  95

Ala Ile Lys Val Asn Asn Val Asn Gly Asn Gln Val Gly His Leu Lys
            100                 105                 110

Lys Glu Leu Ala Gly Ala Leu Ala Tyr Ile Met Asp Asn Lys Leu Ala
            115                 120                 125

Gln Ile Glu Gly Val Val Pro Phe Gly Ala Asn Asn Ala Phe Thr Met
130                 135                 140

Pro Leu His Met Thr Phe Trp Gly Lys Glu Glu Asn Arg Lys Ala Val
145                 150                 155                 160

Ser Asp Gln Leu Lys Lys His Gly Phe Lys Leu Gly Pro Ala Pro Lys
                165                 170                 175

Thr Leu Gly Phe Asn Leu Glu Ser Gly Trp Gly Ser Gly Arg Ala Gly
            180                 185                 190

Pro Ser Tyr Ser Met Pro Val His Ala Ala Val Gln Met Thr Thr Glu
            195                 200                 205

Gln Leu Lys Thr Glu Phe Asp Lys Leu Phe Glu Asp Leu Lys Glu Asp
            210                 215                 220

Asp Lys Thr His Glu Met Glu Pro Ala Glu Ala Ile Glu Thr Pro Leu
225                 230                 235                 240

Leu Pro His Gln Lys Gln Ala Leu Ala Trp Met Val Ser Arg Glu Asn
                245                 250                 255

Ser Lys Glu Leu Pro Pro Phe Trp Glu Gln Arg Asn Asp Leu Tyr Tyr
            260                 265                 270

Asn Thr Ile Thr Asn Phe Ser Glu Lys Asp Arg Pro Glu Asn Val His
            275                 280                 285

Gly Gly Ile Leu Ala Asp Asp Met Gly Leu Gly Lys Thr Leu Thr Ala
            290                 295                 300

Ile Ala Val Ile Leu Thr Asn Phe His Asp Gly Arg Pro Leu Pro Ile
305                 310                 315                 320

Glu Arg Val Lys Lys Asn Leu Lys Lys Glu Tyr Asn Val Asn Asp
                325                 330                 335

Asp Ser Met Lys Leu Gly Gly Asn Asn Thr Ser Glu Lys Ala Asp Gly
            340                 345                 350

Leu Ser Lys Asp Ala Ser Arg Cys Ser Glu Gln Pro Ser Ile Ser Asp
            355                 360                 365

Ile Lys Glu Lys Ser Lys Phe Arg Met Ser Glu Leu Ser Ser Ser Arg
            370                 375                 380

Pro Lys Arg Arg Lys Thr Ala Val Gln Tyr Ile Glu Ser Ser Asp Ser
385                 390                 395                 400

Glu Glu Ile Glu Thr Ser Glu Leu Pro Gln Lys Met Lys Gly Lys Leu
                405                 410                 415

Lys Asn Val Gln Ser Glu Thr Lys Gly Arg Ala Lys Ala Gly Ser Ser
            420                 425                 430

Lys Val Ile Glu Asp Val Ala Phe Ala Cys Ala Leu Thr Ser Ser Val
            435                 440                 445

Pro Thr Thr Lys Lys Met Leu Lys Lys Gly Ala Cys Ala Val Glu
450                 455                 460

Gly Ser Lys Lys Thr Asp Val Glu Glu Arg Pro Arg Thr Thr Leu Ile
465                 470                 475                 480

Ile Cys Pro Leu Ser Val Leu Ser Asn Trp Ile Asp Gln Phe Gly Gln
                485                 490                 495

His Ile Lys Ser Asp Val His Leu Asn Phe Tyr Val Tyr Tyr Gly Pro
```

```
                500             505             510
Asp Arg Ile Arg Glu Pro Ala Leu Leu Ser Lys Gln Asp Ile Val Leu
        515                 520                 525

Thr Thr Tyr Asn Ile Leu Thr His Asp Tyr Gly Thr Lys Gly Asp Ser
        530                 535                 540

Pro Leu His Ser Ile Arg Trp Leu Arg Val Ile Leu Asp Glu Gly His
545                 550                 555                 560

Ala Ile Arg Asn Pro Asn Ala Gln Gln Thr Lys Ala Val Leu Asp Leu
                565                 570                 575

Glu Ser Glu Arg Arg Trp Val Leu Thr Gly Thr Pro Ile Gln Asn Ser
        580                 585                 590

Leu Lys Asp Leu Trp Ser Leu Leu Ser Phe Leu Lys Leu Lys Pro Phe
        595                 600                 605

Ile Asp Arg Glu Trp Trp His Arg Thr Ile Gln Arg Pro Val Thr Met
        610                 615                 620

Gly Asp Glu Gly Gly Leu Arg Arg Leu Gln Ser Leu Ile Lys Asn Ile
625                 630                 635                 640

Thr Leu Arg Arg Thr Lys Thr Ser Lys Ile Lys Gly Lys Pro Val Leu
                645                 650                 655

Glu Leu Pro Glu Arg Lys Val Phe Ile Gln His Ile Thr Leu Ser Asp
                660                 665                 670

Glu Glu Arg Lys Ile Tyr Gln Ser Val Lys Asn Glu Gly Arg Ala Thr
        675                 680                 685

Ile Gly Arg Tyr Phe Asn Glu Gly Thr Val Leu Ala His Tyr Ala Asp
        690                 695                 700

Val Leu Gly Leu Leu Leu Arg Leu Arg Gln Ile Cys Cys His Thr Tyr
705                 710                 715                 720

Leu Leu Thr Asn Ala Val Ser Ser Asn Gly Pro Ser Gly Asn Asp Thr
                725                 730                 735

Pro Glu Glu Leu Arg Lys Lys Leu Ile Arg Lys Met Lys Leu Ile Leu
                740                 745                 750

Ser Ser Gly Ser Asp Glu Glu Cys Ala Ile Cys Leu Asp Ser Leu Thr
        755                 760                 765

Val Pro Val Ile Thr His Cys Ala His Val Phe Cys Lys Pro Cys Ile
        770                 775                 780

Cys Gln Val Ile Gln Asn Glu Gln Pro His Ala Lys Cys Pro Leu Cys
785                 790                 795                 800

Arg Asn Asp Ile His Glu Asp Asn Leu Leu Glu Cys Pro Pro Glu Glu
                805                 810                 815

Leu Ala Arg Asp Ser Glu Lys Lys Ser Asp Met Glu Trp Thr Ser Ser
                820                 825                 830

Ser Lys Ile Asn Ala Leu Met His Ala Leu Thr Asp Leu Arg Lys Lys
        835                 840                 845

Asn Pro Asn Ile Lys Ser Leu Val Val Ser Gln Phe Thr Thr Phe Leu
        850                 855                 860

Ser Leu Ile Glu Ile Pro Leu Lys Ala Ser Gly Phe Val Phe Thr Arg
865                 870                 875                 880

Leu Asp Gly Ser Met Ala Gln Lys Lys Arg Val Glu Ser Ile Gln Cys
                885                 890                 895

Phe Gln Asn Thr Glu Ala Gly Ser Pro Thr Ile Met Leu Leu Ser Leu
                900                 905                 910

Lys Ala Gly Gly Val Gly Leu Asn Leu Ser Ala Ala Ser Arg Val Phe
        915                 920                 925
```

```
Leu Met Asp Pro Ala Trp Asn Pro Ala Ala Glu Asp Gln Cys Phe Asp
        930                 935                 940

Arg Cys His Arg Leu Gly Gln Lys Gln Glu Val Ile Ile Thr Lys Phe
945                 950                 955                 960

Ile Val Lys Asp Ser Val Glu Glu Asn Met Leu Lys Ile Gln Asn Lys
                965                 970                 975

Lys Arg Glu Leu Ala Ala Gly Ala Phe Gly Thr Lys Lys Pro Asn Ala
            980                 985                 990

Asp Glu Met Lys Gln Ala Lys Ile  Asn Glu Ile Arg Thr  Leu Ile Asp
        995                 1000                1005

Leu

<210> SEQ ID NO 2
<211> LENGTH: 3000
<212> TYPE: DNA
<213> ORGANISM: Homo sapiens

<400> SEQUENCE: 2
attgccattt gcctcaacac acttcaagaa gaacatacaa caattaaaat aatttgaaat      60
gccattgtct ttatcttcct catcaacttt ggtcaaatga ataatacat tgtttcaaat      120
tctattgctc atccatggtt catgattaga gatcactaca gtttatttac gataatgaac     180
aaatgtgtct tgaaaagctg actaccggcc tggcacggtg gctcatgcct gtaatcccag     240
cactctggga ggccgaggcg gcggatcac ctgaggtcag gagttcaaga ccagcctggc      300
caatatggtg aaaccccgtc tctactaaaa atacaaaaat tagctgggcg tggtggcggg     360
ctcctgcaat cccggctact ccggaggctg aggcaggaga atcgcttgaa tccgggaggc    420
ggaggttgca gtgagccaag atcaccccca ttgcactcca gcctggggga cagagcaaga    480
ctccatctca ataaaaaga aaaaaaaca aaaaaagaa aaagaaaag ctgaccacct         540
aatattattg tgctgacagg cgtgtaacat ggacctctct gtgacgcgca agtattatct    600
ggcagttaca tggtgccgcc tgtgcagctg gcgccacca ccagcttcct gcctgtgcg      660
attaaaaggc cagcttcggg gacagcagcc tcctcaacgc aaagcgacca gccctgccag    720
gcgtcggctg cagctggtcc aaggttgacg gtcccagggc cgcattctcc ttccggtcac    780
ctcagactct ggaagagag ccatggaggg cctcagagcg cccctctgca gttccttgag     840
gaaaacaagg gcctccccct cttggctgga gcagccaagt gcccacgggg aaaatggtcc    900
cgtccaccat ttcaggcaaa cgcccccata gctgtaataa acatgtgatg ggtttcctgc    960
accaagaaag gaaatttttc cttaaaaata acaaaaagag gtggggaggg gactctaagt   1020
tccatttaag atttccaaa ctcgttgtgt ctcatgcata cgctgaggct taacatgaaa    1080
atttggagcg aaagtcccca cggttcacca cagggaatga agtaaagtat ctcgccggta   1140
gctctaggtc tcgtaaaccg tggagctcct ttagtataag gccctattat gtgccacatt    1200
agatgagaag aaaataagag gaaggatacg gtagagcctt tagaatgggg ttcagtctta   1260
ggactcgtag gataaaggaa ggtcgttttcc ctccgtttga ggcagggaat caaacaaaac   1320
accggcaccg caggcaccgc agtcgcactc ctggggcctc gtggctttcc cgcgcgcccg   1380
ccttgggggc ggggaagaac ccggatggaa ccacccttgc agcccggacc cccgccgtc    1440
tttgaatggc agcggggcgg agttgccctc ccttctgtgc tctgactggt ttggctccgc    1500
actctcctct tcgtgattgg gctttcctag tgccagtcac agagcgacgc tggtctccca   1560
gattgttgca gaaggagacg gcgtcgacgt ctgactggac tcgcggcgac ttacctttca   1620
```

```
gtcgtgcgct cctgatccgg cgctcggaat ttgtccccgg cttcagggct gcggggcctg    1680
gaaggaggcg tatcgaggcg gctcgaaaac gatccagggg agccgaggcg ctcctcttgt    1740
catcccactc agcgccatgt cctggatgtt caagaggtga agggggcgga gggggtgggg    1800
cgctcggtct aacggcctgg aggcgtcccc aaatgaacct gaccttcccg gcgttcctct    1860
gcgttccctg ggcgatttgt gcagctgtat tcgttctgtt ggtcgcatat gtggccgccg    1920
gagaaataaa tgcattgtct tcgctggcga gtaggggctc ctagggcgag tcccgtgtta    1980
gggacttggg aaatctctgt caccgactgt gggggggctg gggcttaaag catctcggcc    2040
agtgctttat ttaacaaaac atccattaga tacccactgt gcgccaggca ttgtgctcgg    2100
tggagggccg agtaagacag tccttgtccc caagtggctc acagcttatc tgtatgcaca    2160
gacgtgcaga taagtatttg cagaggcgct agtagagata tgcgccactt gcaaggaaaa    2220
cgcatcgcaa ataagcgact gttcttagga gaatggaaac ttttttgcaat gctccagtag    2280 actccccttc acttttcatt gtccaaattg gtatttatgg tcattcccga aacagttaca    2340
cctaatgggt ttggggttat gcttaaaccg gcgacggaag gcgggtacgg gtggcttggg    2400
gccaatttcc cacggtggcg tggtttggat accagaatag gtgttctgct cgcagggagt    2460
tacagtgatg gatgctggat gtattttctg gaaaattata aacaacttct ggtacattaa    2520
tagttgtatt tttataagtc ttttatatag ctcaatccct attgaaattt tggcatatga    2580
tttcattttt taaattattt ttttgacatg gagtctcgct ctgtcgtcca ggctggagtg    2640
cagtggcaca atctcggctc gctgcaacct acgcctcccg ggttcaagtg attctcctgc    2700
ctcagcctcc cgagtagctg ggattacata tgggcgccac cacgcctggc taattttttgt    2760 atttgtagta gacagggttt cacaatgttg gccaggttgg tctcaaattc ctgacctcag    2820
gtgatccacc tgcctctgcc tcccaaagtg ctgggattcc aggcgtgagc caccgcatcc    2880
ggcccataat tgtagttaca gacatcatat acatatcaat ttagatgatt ttcactggga    2940
aagaggttag tgaactctga ctaggctttt cattttgaat acctaggggg caggtagaag    3000
```

<210> SEQ ID NO 3
<211> LENGTH: 2001
<212> TYPE: DNA
<213> ORGANISM: Homo sapiens

<400> SEQUENCE: 3

```
tggcagttac atggtgccgc ctgtgcagct gggcgccacc accagcttcc tgccctgtgc      60
gattaaaagg ccagcttcgg ggacagcagc ctcctcaacg caaagcgacc agccctgcca     120
ggcgtcggct gcagctggtc caaggttgac ggtcccaggg ccgcattctc cttccggtca     180
cctcagactc tggaaagaga gccatggagg gcctcagagc gcccctctgc agttccttga     240
ggaaaacaag ggcctccccc tcttggctgg agcagccaag tgcccacggg aaaatggtc      300 ccgtccacca tttcaggcaa acgcccccat agctgtaata aacatgtgat gggtttcctg     360
caccaagaaa ggaaaatttt ccttaaaaat aacaaaaaga ggtggggagg ggactctaag     420
ttccatttaa gattttccaa actcgttgtg tctcatgcat acgctgaggc ttaacatgaa     480
aatttggagc gaaagtcccc acggttcacc acagggaatg aagtaaagta tctcgccggt     540
agctctaggt ctcgtaaacc gtggagctcc tttagtataa ggcccctatta tgtgccacat     600 tagatgagaa gaaataagag ggaaggatac ggtagagcct ttagaatggg gttcagtctt     660
aggactcgta ggataaagga aggtcgtttc cctccgtttg aggcagggaa tcaaacaaaa     720
```

```
caccggcacc gcaggcaccg cagtcgcact cctggggcct cgtggctttc ccgcgcgccc      780
gccttggggg cggggaagaa cccggatgga accacccttg cagcccggac cccccgccgt      840
ctttgaatgg cagcggggcg gagttgccct cccttctgtg ctctgactgg tttggctccg      900
cactctcctc ttcgtgattg ggctttccta gtgccagtca cagagcgacg ctggtctccc      960
agattgttgc agaaggagac ggcgtcgacg tctgactgga ctcgcggcga cttacctttc     1020
agtcgtgcgc tcctgatccg gcgctcggaa tttgtccccg gcttcagggc tgcggggcct     1080
ggaaggaggc gtatcgaggc ggctcgaaaa cgatccaggg gagccgaggc gctcctcttg     1140
tcatcccact cagcgccatg tcctggatgt tcaagaggtg aaggggcgg aggggtggg      1200 gcgctcggtc taacggcctg gaggcgtccc caaatgaacc tgaccttccc ggcgttcctc     1260
tgcgttccct gggcgatttg tgcagctgta ttcgttctgt tggtcgcata tgtggccgcc     1320
ggagaaataa atgcattgtc ttcgctggcg agtagggct cctagggcga gtcccgtgtt      1380
agggacttgg gaaatctctg tcaccgactg tgggggcct ggggcttaaa gcatctcggc      1440
cagtgcttta tttaacaaaa catccattag atacccactg tgcgccaggc attgtgctcg     1500
gtggagggcc gagtaagaca gtccttgtcc ccaagtggct cacagcttat ctgtatgcac     1560
agacgtgcag ataagtattt gcagaggcgc tagtagagat atgcgccact tgcaaggaaa     1620
acgcatcgca ataagcgac tgttcttagg agaatggaaa cttttgcaa tgctccagta       1680 gactcccctt cactttcat tgtccaaatt ggtatttatg gtcattcccg aaacagttac      1740
acctaatggg tttggggtta tgcttaaacc ggcgacggaa ggcgggtacg ggtggcttgg    1800
ggccaatttc ccacggtggc gtggtttgga taccagaata ggtgttctgc tcgcagggag    1860
ttacagtgat ggatgctgga tgtatttct ggaaaattat aaacaacttc tggtacatta     1920
atagttgtat ttttataagt cttttatata gctcaatccc tattgaaatt ttggcatatg    1980
atttcatttt ttaaattatt t                                              2001
```

```
<210> SEQ ID NO 4
<211> LENGTH: 551
<212> TYPE: DNA
<213> ORGANISM: Homo sapiens

<400> SEQUENCE: 4
gttcagtctt aggactcgta ggataaagga aggtcgtttc cctccgtttg aggcagggaa       60
tcaaacaaaa caccggcacc gcaggcaccg cagtcgcact cctggggcct cgtggctttc      120
ccgcgcgccc gccttggggg cggggaagaa cccggatgga accacccttg cagcccggac      180
cccccgccgt ctttgaatgg cagcggggcg gagttgccct cccttctgtg ctctgactgg      240
tttggctccg cactctcctc ttcgtgattg ggctttccta gtgccagtca cagagcgacg      300
ctggtctccc agattgttgc agaaggagac ggcgtcgacg tctgactgga ctcgcggcga      360
cttacctttc agtcgtgcgc tcctgatccg gcgctcggaa tttgtccccg gcttcagggc      420
tgcggggcct ggaaggaggc gtatcgaggc ggctcgaaaa cgatccaggg gagccgaggc      480
gctcctcttg tcatcccact cagcgccatg tcctggatgt tcaagaggtg aaggggcgg      540 aggggtggg g                                                            551
```

```
<210> SEQ ID NO 5
<211> LENGTH: 551
<212> TYPE: DNA
<213> ORGANISM: Homo sapiens

<400> SEQUENCE: 5
```

```
gtttagtttt aggattcgta ggataaagga aggtcgtttt ttttcgtttg aggtagggaa    60
ttaaataaaa tatcggtatc gtaggtatcg tagtcgtatt tttggggttt cgtggttttt   120
tcgcgcgttc gttttggggg cggggaagaa ttcggatgga attattttg tagttcggat    180 ttttcgtcgt ttttgaatgg tagcggggcg gagttgtttt ttttttttgtg ttttgattgg   240 tttggtttcg tatttttttt ttcgtgattg ggttttttta gtgttagtta tagagcgacg   300 ttggttttt agattgttgt agaaggagac ggcgtcgacg tttgattgga ttcgcggcga    360
tttatttttt agtcgtgcgt ttttgattcg gcgttcggaa tttgttttcg gttttagggt   420
tgcggggttt ggaaggaggc gtatcgaggc ggttcgaaaa cgatttaggg gagtcgaggc   480
gttttttttg ttattttatt tagcgttatg ttttggatgt ttaagaggtg aaggggggcgg   540 aggggggtggg g                                                        551

<210> SEQ ID NO 6
<211> LENGTH: 551
<212> TYPE: DNA
<213> ORGANISM: Homo sapiens

<400> SEQUENCE: 6
gtttagtttt aggatttgta ggataaagga aggttgtttt ttttttgtttg aggtagggaa   60 ttaaataaaa tattggtatt gtaggtattg tagttgtatt tttggggttt tgtggttttt   120
ttgtgtgttt gttttggggg tggggaagaa tttggatgga attattttg tagttttggat   180 tttttgttgt ttttgaatgg tagtggggtg gagttgtttt ttttttgtg ttttgattgg    240 tttggttttg tatttttttt tttgtgattg ggttttttta gtgttagtta tagagtgatg   300 ttggttttt agattgttgt agaaggagat ggtgttgatg tttgattgga tttgtggtga    360
tttatttttt agttgtgtgt ttttgatttg gtgtttggaa tttgttttg gttttagggt    420 tgtggggttt ggaaggaggt gtattgaggt ggtttgaaaa tgatttaggg gagttgaggt   480
gttttttttg ttattttatt tagtgttatg ttttggatgt ttaagaggtg aaggggtgg    540 aggggggtggg g                                                        551

<210> SEQ ID NO 7
<211> LENGTH: 551
<212> TYPE: DNA
<213> ORGANISM: Homo sapiens

<400> SEQUENCE: 7
caaatcaaaa tcctaagcat cctatttcct tccagcaaaa aaagcaaac tccatcccctt    60 aatttatttt atagccatag catccatagc atcagcataa aaccccaaa gcaccaaaaa    120 agcgcgcaag caaacccccc gcccccttctt aagcctacct taataaaaac atcaagccta   180
aaaagcagca aaacttacc atcgccccgc ctcaacaaaa aaaaaacac aaaactaacc    240 aaaccaaagc ataaaaaaaa aagcactaac ccaaaaaaat cacaatcaat atctcgctgc    300
aaccaaaaaa tctaacaaca tcttcctctg ccgcagctgc aaactaacct aagcgccgct    360
aaataaaaaa tcagcacgca aaactaagc cgcaagcctt aaacaaaagc caaaatccca    420
acgccccaaa ccttcctccg catagctccg ccaagctttt gctaaatccc ctcagctccg    480
caaaaaaaac aataaaataa atcgcaatac aaaacctaca aattctccac ttccccgcc    540 tccccaccc c                                                          551

<210> SEQ ID NO 8
```

```
<211> LENGTH: 551
<212> TYPE: DNA
<213> ORGANISM: Homo sapiens

<400> SEQUENCE: 8
caaatcaaaa tcctaaacat cctatttcct tccaacaaaa aaaacaaac tccatcccctt        60 aatttatttt ataaccataa catccataac atcaacataa aaccccaaa acaccaaaaa        120 aacacacaaa caaaacccc accccttctt aaacctacct taataaaaac atcaaaccta        180
aaaaacaaca aaaacttacc atcaccccac ctcaacaaaa aaaaaaacac aaaactaacc      240
aaaccaaaac ataaaaaaaa aaacactaac ccaaaaaaat cacaatcaat atctcactac      300
aaccaaaaaa tctaacaaca tcttcctcta ccacaactac aaactaacct aaacaccact     360
aaataaaaaa tcaacacaca aaaactaaac cacaaacctt aaacaaaaac caaatccca      420 acaccccaaa ccttcctcca cataactcca ccaaactttt actaaatccc ctcaactcca      480 caaaaaaac aataaaataa atcacaatac aaaacctaca aattctccac ttcccccacc      540
tcccccaccc c                                                            551

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
ggaaggtcgt ttccctccgt ttgag                                              25

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
cggctcccct ggatcgtttt cgag                                               24

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
tggggtttcg tggtttttc gcgc                                                24

<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12
ccgcgaatcc aatcaaacgt cgacg                                              25

<210> SEQ ID NO 13
<211> LENGTH: 29
<212> TYPE: DNA
<213> ORGANISM: Artificial Sequence
```

```
<220> FEATURE:
<223> OTHER INFORMATION: primer

<400> SEQUENCE: 13
atttttgggg ttttgtggtt tttttgtgt                                29

<210> SEQ ID NO 14
<211> LENGTH: 29
<212> TYPE: DNA
<213> ORGANISM: Artificial Sequence
<220> FEATURE:
<223> OTHER INFORMATION: primer

<400> SEQUENCE: 14
atcaccacaa atccaatcaa acatcaaca                                29

<210> SEQ ID NO 15
<211> LENGTH: 26
<212> TYPE: DNA
<213> ORGANISM: Artificial Sequence
<220> FEATURE:
<223> OTHER INFORMATION: primer

<400> SEQUENCE: 15
gcacgactaa aaataaatc gccgcg                                    26

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
aaacacacaa ctaaaaaata aatcaccaca                               30

<210> SEQ ID NO 17
<211> LENGTH: 25
<212> TYPE: DNA
<213> ORGANISM: Artificial Sequence
<220> FEATURE:
<223> OTHER INFORMATION: primer

<400> SEQUENCE: 17
taaaacctcg taactttccc gcgcg                                    25

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
gtcgcgagtt tagttagacg tcgac                                    25

<210> SEQ ID NO 19
<211> LENGTH: 28
<212> TYPE: DNA
<213> ORGANISM: Artificial Sequence
<220> FEATURE:
<223> OTHER INFORMATION: primer

<400> SEQUENCE: 19
tcctaaaacc tcataacttt cccacaca                                 28
```

<210> SEQ ID NO 20
<211> LENGTH: 29
<212> TYPE: DNA
<213> ORGANISM: Artificial Sequence
<220> FEATURE:
<223> OTHER INFORMATION: primer

<400> SEQUENCE: 20
agttgttgtg agtttagtta gatgttgat                              29

<210> SEQ ID NO 21
<211> LENGTH: 1301
<212> TYPE: DNA
<213> ORGANISM: Homo sapiens

<400> SEQUENCE: 21
tagatgagaa gaaaataaga ggaaggatac ggtagagcct ttagaatggg gttcagtctt     60
aggactcgta ggataaagga aggtcgtttc cctccgtttg aggcagggaa tcaaacaaaa    120
caccggcacc gcaggcaccg cagtcgcact cctgggcct cgtggctttc ccgcgcgccc    180
gccttggggg cggggaagaa cccggatgga accaccttg cagcccggac ccccgccgt     240 ctttgaatgg cagcggggcg gagttgccct cccttctgtg ctctgactgg tttggctccg    300
cactctcctc ttcgtgattg gcttttccta gtgccagtca cagagcgacg ctggtctccc    360
agattgttgc agaaggagac ggcgtcgacg tctgactgga ctcgcggcga cttacctttc    420
agtcgtgcgc tcctgatccg gcgctcggaa tttgtccccg gcttcagggc tgcgggggct    480
ggaaggaggc gtatcgaggc ggctcgaaaa cgatccaggg gagccgaggc gctcctcttg    540
tcatcccact cagcgccatg tcctggatgt tcaagaggtg aagggggcgg aggggtggg    600 gcgctcggtc taacggcctg gaggcgtccc caaatgaacc tgaccttccc ggcgttcctc    660
tgcgttccct gggcgatttg tgcagctgta ttcgttctgt tggtcgcata tgtggccgcc    720
ggagaaataa atgcattgtc ttcgctggcg agtaggggct cctagggcga gtcccgtgtt    780
agggacttgg gaaatctctg tcaccgactg tgggggggcct ggggcttaaa gcatctcggc    840
cagtgcttta tttaacaaaa catccattag atacccactg tgcgccaggc attgtgctcg    900
gtggagggcc gagtaagaca gtccttgtcc ccaagtggct cacagcttat ctgtatgcac    960
agacgtgcag ataagtattt gcagaggcgc tagtagagat atgcgccact tgcaaggaaa   1020
acgcatcgca aataagcgac tgttcttagg agaatggaaa cttttttgcaa tgctccagta   1080 gactccccctt cacttttcat tgtccaaatt ggtatttatg gtcattcccg aaacagttac   1140
acctaatggg tttggggtta tgcttaaacc ggcgacggaa ggcgggtacg ggtggcttgg   1200
ggccaatttc ccacggtggc gtggtttgga taccagaata ggtgttctgc tcgcagggag   1260
ttacagtgat ggatgctgga tgtattttct ggaaaattat a                       1301

<210> SEQ ID NO 22
<211> LENGTH: 1301
<212> TYPE: DNA
<213> ORGANISM: Homo sapiens

<400> SEQUENCE: 22
tagatgagaa gaaaataaga ggaaggatac ggtagagttt ttagaatggg gtttagtttt     60
aggattcgta ggataaagga aggtcgtttt ttttcgtttg aggtagggaa ttaaataaaa    120
tatcggtatc gtaggtatcg tagtcgtatt tttgggggttt cgtggttttt tcgcgcgttc    180
gttttggggg cggggaagaa ttcggatgga attattttg tagttcggat ttttcgtcgt    240

```
ttttgaatgg tagcggggcg gagttgtttt ttttttttgtg ttttgattgg tttggtttcg      300
tatttttttt ttcgtgattg ggttttttta gtgttagtta tagagcgacg ttggtttttt      360
agattgttgt agaaggagac ggcgtcgacg tttgattgga ttcgcggcga tttattttt       420 agtcgtgcgt ttttgattcg gcgttcggaa tttgttttcg gttttagggt tgcggggttt      480
ggaaggaggc gtatcgaggc ggttcgaaaa cgatttaggg gagtcgaggc gttttttttg      540
ttattttatt tagcgttatg ttttggatgt ttaagaggtg aaggggggcgg aggggggtggg      600 gcgttcggtt taacgttttg gaggcgtttt taaatgaatt tgattttttc ggcgtttttt      660
tgcgtttttt gggcgatttg tgtagttgta ttcgttttgt tggtcgtata tgtggtcgtc      720
ggagaaataa atgtattgtt ttcgttggcg agtaggggtt tttagggcga gtttcgtgtt      780
agggatttgg gaaattttttg ttatcgattg tggggggttt gggggtttaaa gtatttcggt      840 tagtgtttta tttaataaaa tatttattag atatttattg tgcgttaggt attgtgttcg      900
gtggagggtc gagtaagata gttttttgttt ttaagtggtt tatagtttat ttgtatgtat      960
agacgtgtag ataagtattt gtagaggcgt tagtagagat atgcgttatt tgtaaggaaa     1020
acgtatcgta aataagcgat tgttttttagg agaatggaaa ttttttgtaa tgttttagta     1080
gatttttttt tattttttat tgtttaaatt ggtatttatg gttatttttcg aaatagttat     1140 atttaatggg tttggggtta tgtttaaatc ggcgacggga ggcgggtacg ggtggtttgg     1200 ggttaattttt ttacggtggc gtggtttgga tattagaata ggtgttttgt tcgtagggag     1260
ttatagtgat ggatgttgga tgtattttttt ggaaaattat a                         1301

<210> SEQ ID NO 23
<211> LENGTH: 1301
<212> TYPE: DNA
<213> ORGANISM: Homo sapiens

<400> SEQUENCE: 23
tagatgagaa gaaaataaga ggaaggatat ggtagagttt ttagaatggg gtttagtttt       60
aggatttgta ggataaagga aggttgtttt tttttgtttg aggtagggaa ttaaataaaa      120
tattggtatt gtaggtattg tagttgtatt tttggggttt tgtggttttt ttgtgtgttt      180
gttttggggg tggggaagaa tttggatgga attattttttg tagtttggat ttttttgttgt      240 ttttgaatgg tagtggggtg gagttgtttt ttttttttgtg ttttgattgg tttggttttg      300
tatttttttt tttgtgattg ggttttttta gtgttagtta tagagtgatg ttggtttttt      360
agattgttgt agaaggagat ggtgttgatg tttgattgga tttgtggtga tttatttttt      420
agttgtgtgt ttttgatttg gtgttggaa tttgttttttg gttttagggt tgtgggtttt      480
ggaaggaggt gtattgaggt ggtttgaaaa tgatttaggg gagttgaggt gttttttttg      540
ttattttatt tagtgttatg ttttggatgt ttaagaggtg aaggggggtgg aggggggtggg      600 gtgtttggtt taatggtttg gaggtgtttt taaatgaatt tgatttttttt ggtgttttttt      660 tgtgtttttt gggtgatttg tgtagttgta tttgttttgt tggttgtata tgtggttgtt      720
ggagaaataa atgtattgtt tttgttggtg agtaggggtt tttagggtga gttttgtgtt      780
agggatttgg gaaattttttg ttattgattg tgggggggttt ggggtttaaa gtatttttggt      840 tagtgtttta tttaataaaa tatttattag atatttattg tgtgttaggt attgtgtttg      900 gtggaggggtt gagtaagata gtttttttgttt ttaagtggtt tatagtttat ttgtatgtat      960
agatgtgtag ataagtattt gtagaggtgt tagtagagat atgtgttatt tgtaaggaaa     1020
```

```
atgtattgta aataagtgat tgttttagg agaatggaaa ttttttgtaa tgttttagta    1080 gattttttt tatttttat tgtttaaatt ggtatttatg gttattttg aaatagttat     1140 atttaatggg tttggggtta tgtttaaatt ggtgatggaa ggtgggtatg ggtggtttgg   1200
ggttaatttt ttatggtggt gtggtttgga tattagaata ggtgttttgt ttgtagggag  1260
ttatagtgat ggatgttgga tgtatttttt ggaaaattat a                      1301
```

<210> SEQ ID NO 24
<211> LENGTH: 1301
<212> TYPE: DNA
<213> ORGANISM: Homo sapiens

<400> SEQUENCE: 24

```
atttatttt tttttatttt tttttttatg ctatttggga aatttatttt taagttagaa   60
ttttgagcat tttatttttt tttagcaaag ggaggcaaat tttgtttttt agtttgtttt  120
gtggctgtgg cgtttgtggc gttagcgtga ggattttgga gcattgaaag ggcgcgcggg  180
cggaattttt gcttttttt gggcttattt tggtgggaat gttgggcttg ggggcggca   240 gaaatttatt gttgctttgc tttaatggga gggaagatat gagattgatt aaattgaggc  300
gtgagaggag aagcattaat ttgaaaggat tatggttagt gttttgctgc gattagaggg  360
tttaataatg ttttttttg ctgcagctgc agattgattt gagcgctgct gaatggaaag  420
ttagcatgcg aggattaggc tgcgagcttt aaatagggc tgaagttttg atgctttgga  480 ttttttttg catagcttg ctgagctttt gctaggtttt tttggctttg cgaggagaat   540
agtagggtga gttgcggtat aggatttata agtttttat tttttttgct ttttttattt   600
tgcgagctag attgctggat ttttgcaggg gtttatttgg attggaaggg ctgcaaggag  660
atgcaaggga tttgctaaat atgttgatat aagcaagata attagcgtat atattggcgg  720
ctttttttat tatgtaatag aagcgattgc ttatttttga ggattttgct tagggcataa  780 ttttgaatt tttagagat agtggctgat attttttgga ttttgaattt tgtagagctg   840
gttatgaaat aaaattgttt gtaggtaatt tatgggtgat atgcggtttg taatatgagc  900
tattttttgg cttattttgt taggaatagg ggtttattga gtgttgaata gatatatgtg  960
tttgcatgtt tatttataaa tgttttgcg attattttta tatgcggtga atgttttttt   1020
tgcgtagcgt ttatttgctg ataagaattt tttatttttt gaaaaatgtt atgaggttat  1080
ttgaggggaa gtgaaaagta ataggtttaa ttataaatat tagtaagggc tttgttaatg  1140
tggattattt aaattttaat atgaatttgg ctgctgcttt ttgcttatgc ttattgaatt  1200
ttggttaaag ggtgctattg cattaaattt atggttttat ttataagatg agcgttttt   1260 aatgttatta tttatgattt atataaaaga ttttttaata t                      1301
```

<210> SEQ ID NO 25
<211> LENGTH: 1301
<212> TYPE: DNA
<213> ORGANISM: Homo sapiens

<400> SEQUENCE: 25

```
atttatttt tttttatttt tttttttatg ttatttggga aatttatttt taagttagaa   60
ttttgagtat tttatttttt tttagtaaag ggaggtaaat tttgtttttt agtttgtttt  120
gtggttgtgg tgtttgtggt gttagtgtga ggattttgga gtattgaaag ggtgtgtggg  180
tggaattttt gtttttttt gggtttattt tggtgggaat gttgggtttg ggggtggta   240 gaaatttatt gttgttttgt tttaatggga gggaagatat gagattgatt aaattgaggt  300
```

```
gtgagaggag aagtattaat ttgaaaggat tatggttagt gttttgttgt gattagaggg      360
tttaataatg ttttttttg ttgtagttgt agattgattt gagtgttgtt gaatggaaag      420
ttagtatgtg aggattaggt tgtgagtttt aaatagggt tgaagttttg atgttttgga      480 ttttttttg tatagttttg ttgagttttt gttaggtttt tttggttttg tgaggagaat      540
agtagggtga gttgtggtat aggatttata agtttttat ttttttgtt ttttttattt      600 tgtgagttag attgttggat ttttgtaggg gtttatttgg attggaaggg ttgtaaggag      660
atgtaaggga tttgttaaat atgttgatat aagtaagata attagtgtat atattggtgg      720 ttttttatt tatgtaatag aagtgattgt ttattttga ggattttgtt tagggtataa      780 ttttgaatt tttagagat agtggttgat atttttgga ttttgaattt tgtagagttg      840
gttatgaaat aaattgtttt gtaggtaatt tatgggtgat atgtggtttg taatatgagt      900 tattttgg tttatttgt taggaatagg ggtttattga gtgttgaata gatatatgtg      960
tttgtatgtt tatttataaa tgttttgtg attatttta tatgtggtga atgttttttt      1020
tgtgtagtgt ttatttgttg ataagaattt tttatttt gaaaatgtt atgaggttat      1080 ttgagggaa gtgaaaagta ataggtttaa ttataaatat tagtaagggt tttgttaatg      1140
tggattattt aaattttaat atgaatttgg ttgttgtttt ttgtttatgt ttattgaatt      1200
ttggttaaag ggtgttattg tattaaattt atggtttat ttataagatg agtgttttttt     1260 aatgttatta tttatgattt atataaaaga ttttttaata t                         1301
```

```
<210> SEQ ID NO 26
<211> LENGTH: 26
<212> TYPE: DNA
<213> ORGANISM: Artificial Sequence
<220> FEATURE:
<223> OTHER INFORMATION: primer

<400> SEQUENCE: 26
acgtcgacgt ctaactaaac tcgcga                                           26

<210> SEQ ID NO 27
<211> LENGTH: 27
<212> TYPE: DNA
<213> ORGANISM: Artificial Sequence
<220> FEATURE:
<223> OTHER INFORMATION: primer

<400> SEQUENCE: 27
atcgttttcg agtcgtttcg atacgtt                                          27

<210> SEQ ID NO 28
<211> LENGTH: 31
<212> TYPE: DNA
<213> ORGANISM: Artificial Sequence
<220> FEATURE:
<223> OTHER INFORMATION: primer

<400> SEQUENCE: 28
aaaacaacat caacatctaa ctaaactcac a                                     31

<210> SEQ ID NO 29
<211> LENGTH: 31
<212> TYPE: DNA
<213> ORGANISM: Artificial Sequence
<220> FEATURE:
<223> OTHER INFORMATION: primer
```

<400> SEQUENCE: 29
tttggttttt ttggattgt ttttgagttg t                      31

<210> SEQ ID NO 30
<211> LENGTH: 26
<212> TYPE: DNA
<213> ORGANISM: Artificial Sequence
<220> FEATURE:
<223> OTHER INFORMATION: primer

<400> SEQUENCE: 30
gacgttttta ggtcgttaga tcgagc                           26

<210> SEQ ID NO 31
<211> LENGTH: 29
<212> TYPE: DNA
<213> ORGANISM: Artificial Sequence
<220> FEATURE:
<223> OTHER INFORMATION: primer

<400> SEQUENCE: 31
ggggatgttt ttaggttgtt agattgagt                        29

<210> SEQ ID NO 32
<211> LENGTH: 25
<212> TYPE: DNA
<213> ORGANISM: Artificial Sequence
<220> FEATURE:
<223> OTHER INFORMATION: primer

<400> SEQUENCE: 32
gtcgtgcgtt tttgattcgg cgttc                            25

<210> SEQ ID NO 33
<211> LENGTH: 25
<212> TYPE: DNA
<213> ORGANISM: Artificial Sequence
<220> FEATURE:
<223> OTHER INFORMATION: primer

<400> SEQUENCE: 33
gcccaaaaaa cgcaaaaaaa cgccg                            25

<210> SEQ ID NO 34
<211> LENGTH: 32
<212> TYPE: DNA
<213> ORGANISM: Artificial Sequence
<220> FEATURE:
<223> OTHER INFORMATION: primer

<400> SEQUENCE: 34
ttttttagtt gtgtgttttt gatttggtgt tt                    32

<210> SEQ ID NO 35
<211> LENGTH: 30
<212> TYPE: DNA
<213> ORGANISM: Artificial Sequence
<220> FEATURE:
<223> OTHER INFORMATION: primer

<400> SEQUENCE: 35
aaatcaccca aaaaacacaa aaaaacacca                       30

<210> SEQ ID NO 36
<211> LENGTH: 28

<212> TYPE: DNA
<213> ORGANISM: Artificial Sequence
<220> FEATURE:
<223> OTHER INFORMATION: primer

<400> SEQUENCE: 36
gttctattaa tcgcatatat aaccgccg                                              28

<210> SEQ ID NO 37
<211> LENGTH: 29
<212> TYPE: DNA
<213> ORGANISM: Artificial Sequence
<220> FEATURE:
<223> OTHER INFORMATION: primer

<400> SEQUENCE: 37
ttggggataa ggattgtttt atttggttt                                             29

<210> SEQ ID NO 38
<211> LENGTH: 31
<212> TYPE: DNA
<213> ORGANISM: Artificial Sequence
<220> FEATURE:
<223> OTHER INFORMATION: primer

<400> SEQUENCE: 38
ttcattctat taatcacata tataaccacc a                                          31

<210> SEQ ID NO 39
<211> LENGTH: 62520
<212> TYPE: DNA
<213> ORGANISM: Homo sapiens

<400> SEQUENCE: 39
aggtgagaac tgggcaaaag ttgtgaagca gcaattctgt tatatggaca gtgttctgct           60
ttttaatcct atttagcttg tttcagaaat tctcactttt gttgactgcc aacatacaaa          120
gtaagggaaa ctcaagatat taagatggct gtatcagttc ttaaaatctg cagagcctgg          180
ttcaaaatca gtcactccct tcagaagcag acatggcatc tgttccttgc ttgcttgttg          240
gttgtgtacc tttcacgaga cctgaatttt agaattgccc agtgctgcca gagtgagtga          300
gtgtaattct cctttcaggt aaagataggc tatctcaaca ctgctgagtg attcataaac          360
atatcaacca atagcattaa cccatttat ttcctgtcct tagtgtctga agatgctcac           420
cagttttctg tgtacagtaa ggcagcatgc taaaatgctt ttgttcagtt ctgtatattt          480
gaaaatagca gtgtgttctc tgatggttac ctgcagtggc accctgtaca aaaaataaaa         540
gacttattgc tgtatcttgg ttgtttaatt aaattaagga atttcaccat acacccttga          600
acaaatctat tagggaattt ttcacaattt ttggaatttg tcatagttt aaaaaagtgt           660 aaagcttgac attgggatat atgctttaaa aactggtatc tatgatttca atctaattgt          720
ttttctgtga tggtgatgga tctgacagat cagaacaaac cgagatcaaa cttacatagt          780
gtcatccaca ctgcacctct ctattaagtg ggtatttagc tatttagaat attttaacct         840
taaagtcatt cctaactgtc agaatcaata ctgggtccag tccctactag tatttatct           900 atgatttaaa atgatagaat ggaaaagcgt atttattaaa tttatagatc attctaggtt          960
gtaagagatg gcaagctaaa gaagggtagg atccaagatg accttttaaa actaaaatga         1020
gtggtcagaa atgattctat ggaagaaaac aggacagtta accatgacag gaagaaactt         1080
tagaggtttg attgggcaaa agctgcaaag cttttgtgac ttagccttca aagtcaccct         1140

```
ccttattcat attgatgtga attaatatac aagcatatag acagcttaag tcaagaatgg    1200
ttggggccac cttgaaggct gttaccatag gagctcaata agaacctgag gatttaccta    1260
gaattataaa atattaaatg ataaatgact tctgaaacta gctatttgga ctggtgaaga    1320
atgagtcgct attgatcttc aagtacaatg aagcatttac caaagattta tttaagtgcc    1380
tccatgtgtc agatgctgtg gtacaaagaa ggacttctca aaattttagc tagtcagagg    1440
tctttctggc ttccgagtcc ctggttaaga tgaacagaaa cacagtcttc agatataaaa    1500
tgtcttattt ttgtggccat tcagttgcat tcaacgttaa tttttctat ttactaccgt    1560 tcattctcta tttttttacac agtagcataa caaagctcta aggtggaaaa gctgacatag    1620
ttttaaattt tttttttttt tttttttttt cttgaggcag agtcttgctc tgtcagtcag    1680
tcaccaggct ggagtgcagt ggtgcagtct cggctcactg caacctctgc ctcctggatt    1740
caagagattc tcctacctca gcctcctgag tagctgggac tacaggcacg caccaccacg    1800
cccagctaaa ttttgtattt ttagtagaga caggtttcac catgttgcca ggatggtctc    1860
aatctcttga cctcgtgatc caccggcctt ggcctcccaa agtgctggga ttacaggcgt    1920
gagccactgc acccagcaaa ttttaaaatt tcaaataagt agtgaaggct attattaact    1980
tttggaatca gaaagaatga caagcttacc ataagacata gcatataatg ctgtcaagtt    2040
atttggctag aaaatcactg aactaaacat tcttttcctt ctatgatcta tgtcttaagg    2100
tgaagtatta actaacttttt ccatgtaaag ctatacaaat attggaaaat cttttctagg    2160
gagtccagaa tactaagggt tacttagtaa aatgtataaa aaggcaacag taattcaaat    2220
tacaagattt atatttgcag aggtgatcca tatatactta tcccccttgca gtggctggta    2280 tgacctttgg ttgtaagaca aacttgccca caacagaggt caaatccatg cctttggaga    2340
ttagctccat ggtggatgga gctatggttt atgcataaag taaatgtttg tttaccttaa    2400
ttctccttat acccatattg tcctgctgta taacacattt tgcagatatt ttgaagttaa    2460
tgtgttaaaa acttgaggtt aaacatttga gttttttgtta agagccaaac atcaaatgtg    2520
cccttatatt tttaatgaat ctcatccaaa tgctaatgca taaaccttga caagtagtat    2580
aaataaaaca agaaaaaaat acagcaatgt ctttgccatt ccccaaaaca aagcacacac    2640
tgccgaagat cattagtact cactggtaac aaactacata gggttagttt gtatttccaa    2700
ttctagagct gtaattttaa ggacaaaatg tacaatgatt gattaagagt gctatctgtg    2760
tatatatagg tattatcaca actccttttt tccttccaga tgaagaaatt aattgggacc    2820
aatgttttta gatcaaggca ttttaaataa gcactcttga tttctgaaca agaatttcaa    2880
ccagctaaat tgagcaaaat aaagttagtt aggatatgag gacattattc tgttacagta    2940
atcttcatgt actctcaaaa aaatgtaaca cttgcataga aatgtcacaa ttaatgaagg    3000
attttatttg aagataaagt caaaattatg gcaccgagga aggtaataaa catttgaaat    3060
ttttattgat ttttaaattt aaaatccagt tttaaccaca aaattgtttg aatcacaagt    3120
ggtaatacaa tgtcttcaat attttttctaa agttattttt ctatataata ataagacaac    3180
agcatagcat ataggaagtt ttcattccag tggcttttttt atatatttat ccttcttagg    3240
aaggacaaat taaatttttt aaattaaact tttaaaatat aacaacatct aacagaactg    3300
tacaaaacaa agagacattt tttaaacaac ttgccaaact tacttatgag tgtgttttaa    3360
aaacaacttt gtaaatgtct gggcaaagaa gcaagctgtc ctcccttac cttcatagtg    3420 agtttgtaag gctttgtctt tgtaagcaga aagagtagac tgtgttgttt tttgccaaaa    3480
actgtttata cttaatctca ctgaagtatt gctatatgga gaacccatac tctgatcaac    3540
```

```
ttgattttttt gtgtgtaatg cttgatctac caggtaactt cccaactgct cctaatgcta    3600
gcgggctaat cccacattat tattccacta tcatccctgc agaaaggtct tggttttgat    3660
gaaaatcagc cctttcctta cctgctactg cctcaaaaag ggaccaggaa gattctagct    3720
ggctaattca ctgttccctt tgagcaagaa aacggcacag ggagaaaagg acttatctgg    3780
tgagagattt ggcatatacc ttcaatgtgt gccctataac acaacattgt ctccgatctc    3840
atctttctat caaatgactt ccaacactct taagtctcag gtattcttaa atctgtatca    3900
tcaaacatga agcttctctt gtttgttaga gtaattaatc tttctttgga ttaaagtttc    3960
cctttgaaat aaaaccacct acctaatctg actgctaaat ttctagcttc tttgttttaa    4020
atatgctcag gagtcaaccc aaattctgca gcaaataagt ttgcttatta acaaaaaagt    4080
aaaaaaaaaa gaaaagaaaa aagatgacta attctacaga tagctgtaag gatgaattac    4140
tcaagttcaa aatcaaattc tgattctaaa cacataacaa ttgtttacat tcaggattaa    4200
gatgtcttta agagttgaaa cgactttgga gatcatccag cccaacttcc atccagatat    4260
cacgcctctc acatatagta gtcttctgaa ttataaaaat ttataaagtt acttccaaaa    4320
aaagctacat aaataaaaat tatctattta tagaaatatc tatttagcag ttccataatt    4380
taaaatattc aaatcaaatt gggtaggact ggtttgcctc tcactcccac agactatatt    4440
tatacctcag acacagcaag ttacatttaa acaatgagtg tagtactact taactaaaat    4500
ggaaaaaata gtactcttaa cataatccct aattttttca tgaacataaa actccaagtc    4560
atttatgtga actatatctc aatgtagctg taggaaaaat aaaaacctgt gctaacctgg    4620
actttggtct catttaagat ttggttctgg aatgcaaata tggttttga aagcccaata    4680
aaattaattc ttgtatagtc tgtatatatt gtttacaagg actacaaaca ctgcatcaca    4740
aatcggaggc tttggtaaat aactaagtgt ccaacataga aaataactat ttggtcaaaa    4800
gtataaaagg tctgacctta tttgaaatac gaaaaagctg agtacttgga agatacgtga    4860
aaatactcag catagatatt atgaaaagct gaataacaaa gtaacctttt ttctcaaatt    4920
atttcaggcc acagtatata acggaactta ttgctatttg aagtttcatt aaaaataggt    4980
tcatatatag aagaaattgt gtcagtaata cctcttcact aatataaaat atgccccttt    5040
tagaagacgt gttctctaga tctcatttct aaaactctgt attttctca tttctaaaac    5100
ttaagtatcc aatcaaactg accttactaa aatcccacaa attataagtc aattaatgtt    5160
ctgatttcat taattttggc ttgtttcatt tcgtcagcat ttggttttt agttccaaag    5220
gctcctgctg caagttctct cttttttgtt tgtattttca gcatatttc ttcaacagag    5280
tcctttacaa tgaactttaa aaagaaaaaa aaaagttaag tagttttaa ggcatagtat    5340
ttaaaatctt tattaaaaaa actaaatgaa agatttgcct aatggcaaaa accgcaatta    5400
cttttgcacc aaactataat aactatttaa tagaactgaa ctttgctttc cttacccaat    5460
atggttttct tatataaaga atatggctgt acgaatagaa gttacagatc acaagataag    5520
caaagcaata aagaaaaaaa aagcaaacta tataggcaac tctggcaaaa tgacttcagc    5580
attgtattaa aaaggccatt ctggccgggc acggtggctc acacctgtaa tcccagcact    5640
ttgggaggcc gaggcgggca gatcatgagg tcaggagatc gagaccatcc tggctaacac    5700
ggtgaaatgc catctctact aaaaaataga aaaagttagc cgggcatggt ggtgggcgcc    5760
tgtagtccca gctactcggg aggctgagg aggagaatgg tgtgaacccg ggaggcggag    5820
cttgcagtaa gccgacattg cgccactgca ctccagcctg ggtgacagag cgacgtctca    5880
```

```
aaaaaaaaaa aaaaaaaaac aaaaaactat tcccagaaat tcaagaatga atctttagta    5940
taattcacaa cactaacaaa gagaaaaata aaacgtgatc atctcattcc tgataaaaac    6000
ttgattttaa ataccccaa ctaggaatga atgtctcaac cttacatatt taatgtgaaa     6060
caataaaagt attctacaac aaaacagaaa caagtcaaga atggtcacta tctgctacta    6120
tttaacattg tttaagaaga cccaattact gcaataacta aagctatata ataaaatttt    6180
actgaaatac atataagatc tacataaatg gagaaaggat actatgttcc tgtatggaaa    6240
cattcgttac ttataaagaa agatagttct cgaaagtaat aataaattca ataaatctca    6300
agatatctta aatgggattt tataactaaa atctaaagtt caattcaaga gcaataataa    6360
taaccaccaa tacaatttc aaaagggtc atcagaacat tttaccctat caggtatcaa      6420
aacttacttt aggaaaccat agttgttata agagtaaatac tgccctaaga aaaggaaaag   6480
agatcaatgg aacagaatag tctagaaaaa gacccaagta atatatataa attagtttat    6540
gatgaaagtg acatttcata ctagtaggga aaaagttgga attttcaaag aaaaaaaatg    6600
atgtgacaga acaaatcgtt cttcatctga taaaataata agcttagact catgtcacaa    6660
atcataaaac aaaaaataaa atcttccaaa agaaccagaa gtaaatacag aatagttgaa    6720
aaaatgtgaa aataaagcct tctgtcctag gtaagacctt aaaacctaga acgtataaaa    6780
aaggctgacg ttttaaatca taaaaatttt aaagcttttt catgaccaaa aaaatgcagt    6840
ttaaagacaa ggaagagtat gggataaacc attttcaaca tacataaaca aaagatttca    6900
agtcagactg tatcagggag tcctttatac tataaaacta tttgtaccat aactatgaga    6960
actggacaga agatataaat aattcacaga aaaaatgtta ataaacaaga tatgtgaaat    7020
atactcaagg ttttaggtaa atgcaaatta gaacagcact ttttggcca cagaagcata     7080 aattaacaat tttcatataa atcctatttt gaaaccaact cgatagttga taaaaattct    7140
aaatccagaa ttctagtttt cttaacttat cccaaagaat tacttgcatc tatgtgaaaa    7200
gatttatata taataatgct cattatggca ctgtttttat tagcaaaaaa cttaatgggt    7260
taaatatatt acgatatatc tatatggttt tgtagagtag tcaaattcag agaaagaaag    7320
tagaatggta gttgccaggg gctgggggga gaggaatggg aagttattat ttaatggata    7380
cacagtttca gtttaagatg atgaaaaagt tctggagatg gatgattgtg atggctgttg    7440
cacaacaaca tgaatgtact taatgcatct aaactgtata cttcaaaatg gtaaattttg    7500
tattttacca ctatttaaaa aaagtgttca tctaaatgta cttatgaggt agtctccaat    7560 gtatagttttt aagggaaaca aatatgttgt agaataaagt ataattccat ttatcttta    7620 aagaatgttt ttaaggagat gtacacataa ctataaatgt aggtgcagag aaaggcccct    7680
taaacagcat atattaaatt attgatgaag gaggaaaaag gtgacttata ttttgctctg    7740
cataattaca ctcaatcata ataatatatt catgcattac ttgcttaatt gtaaaaatcg    7800
tatcaaccta gtcttaaaat agtttgttta aaaactcact tttgtgatga aacttcttg     7860 cttctgacca agtctatggc atctgtcaaa gcactgatct tcagcagcag gattccaggc    7920
ctaacaagaa catggatgag ttacttact actgccctga tctttcagtg ttttgcattt     7980
gtcctttcat ttcactagta ttcattcatc tttttctgac tgaaagtttt ctgcctgaag    8040
tcagatacta acatcacaaa tactctgggg aaaaatccac cctcccaatc actatgatga    8100
taggcatcct ccccctacta ctacttctaa tacctaatac aggccccgac atatgtatca    8160
gcacccaaaa taagtatttg ttgattaatc aatttggttt ttttttttcat ttttaaagaa   8220 atctatgtgt gcttaacagc agaaaaaggt tatacatcct cttaaatgac ttaatttata    8280
```

```
tgagaaaaga cacaattctt gggcctattt agttttctcc cccttttctg gtttctttc      8340
actttcctct gttcatgaaa taaaagtata aaaaagggt ttctcctggc taacacagtg       8400
aaacccgtc tctactaaaa atagaaaaaa ttagccggga gaggtggcgg gcgcctgtag       8460
tcccagctac tcaggaggct gaggcaggag aatggcctga accccgggag gcggagcctg      8520
cagtgagccg agatcgcgcc actgcactcc agactgggcg acagcgagac tccgtctcaa      8580
aaaaaaaaaa aaaaaaaaa aaaaggggg ttttaagagt cagtaagtcc taaaaattat        8640
ttttttgttg atgctatttt ctgtatcagt atttgacgtt agtttgactt taaagctgag      8700
ctaaaaaaag taccattagc taattaacac agacatgatc atgagaactg ttttaagcta     8760
aaaaataaaa tgatgggtcc ggcacagtgg ctcacgcctg taatcccagc actttgggag     8820
gccgaggcag gcagatcacg agttcaggag atcgagacca tcctggctaa cacggtgaaa    8880
ccccatctct actaaaaata caaaaaatta gccgggcgtg gtggcaggcg cctgtagtcc    8940
cagctactcg ggaggctgag gcaggagaat ggcgtgaacc caggaggcgg agctggcagt   9000
gagccgagat cgcgccactg cactccagcc tgggcgacag agcgagacta catctcaaaa  9060
aaaacaaaa aacaaaaaac acaacaacag caataaaatg gtgcaacaat gaaagggaa    9120
gaataaccaa aaagatatag acccctggta agtggttttt aaatagtatc atgaattgtt   9180
tggataagga tcattaaatt ttaaattaaa actatgaggt tttttttttg agatggagtc   9240
tcgctctgtc accaggctgg agtgcagtgg cacgatctca gctcagtgca acctccacct   9300
cctgggttca agcgattctc ctgcctcagc ctcccaagta gctgggatta caggcgcttg   9360
ccaccatgcc ccgctaattt ttgtattttt agtagagacg gggtttcacc atgttggcca   9420
agatggtctc aatctcttga cctcatgatc cgcccacctc ggcctccac aaagtgctgg    9480
gattacaggc atgagcctcc gcgccaggcc atattcccc aatacttata caatgttcaa     9540
tgaaaaggta aagaaaagct gggcacagtg ccatatgcct gtaatcccag ctactcaaga   9600
ggctgaggga ggattgcttg agctcaggag tttgagacca gcctgggcaa agaggaaga    9660
ccctgtctct taaaaaaaga aaaaaaatt taatggtaaa agactttcat gagcaaattt      9720
ttatttttt attgaatcat tatgtttctc ggacctgact tttaagttag aaacaacatt     9780
ggaaagcttg atatgttcaa tgaagaacac tcaacttact ataaaactgc taaaacgttc   9840
tgtaaatttt taaaaactgt taacacgttt agtctctgat caacttttc atactaatta     9900
ttttggtatt aacctctttg gtactaagat tataagcaag aaaataaaa tttgggattt     9960
gttctaaaaa tcagcttcta gaattatcac tggattaatt aatattcaac aatctatagt   10020
tacaaatatt ttttatagta gccataaaat actgcaaaca aagatttcaa acttcatcca   10080
cagtacaaag gcaagaaaat acaacagacc ggctgggcgc ggtggctcat gcctgtaatc   10140
ccagcacttt ggaggctga ggcaggtgga tcatgaggtc aggagttcaa gaccagcctg    10200
gccaacatgg taaaccccg tctctactaa aaatgcaaaa attagccacg cgtggtggca    10260
ggtgcctgta atcccagcta ctcaggaggc tgaggcagtg aaccgcttga acccaggagg   10320
tggaggttgc agtgagccaa gattgtgcca ccacactcca gcatgggcga cagagcaaga  10380
ctctgtctca aaaaaaaaa aaaagaaaa agaaaatac aacagaccat accatatcca        10440
tgatattcac ccatgaaggc ctaagtatga tgaccctagt tataatctta ctgagaagga   10500
taccgtcagt tgagggagga aaaggaagc ctgagtaaac atatatgcat caacaaggta    10560
gcctcaccca agtaactaaa atttatatct cagtagtatt cctacatgta tctcagtaga   10620
```

```
attcctacat gttaaaaatc ttctgagttt caggtaacaa gttacaacca caaatcttaa    10680
gtctgaatgc acagaaacag cagagggttg cctttagccc acatagtacc cagtgcaaat    10740
tagaaactga attagtccaa ggtcctctca ggccaaacag ccccttttgta cacgtagaaa    10800 aacacgctcc tatgtgaatg cacgtccagg tcacacagct tggtgagtaa agttcaaagt    10860
gaattttagc ctctgttcta ccttcatgcc tgtactacac aaccacaact gactgcacta    10920
tattaggcat taaaacgtac tcagaacatt ccattaatga taatttgttt ctcaaattgt    10980
gatcctagac cacctgtacc tcaatcacct atgatatatg ctaaaaatgc agcttcctgg    11040
gtctaatcct agaactccta agtctctacg ttgaatgcaa aggaaattgc attttaccta    11100
attcttatgc acattaaagc ttaagactac tagaaccgtg atggtaatca ttttgtctat    11160
cttgtttata gttagattcc cagtgcctat aaaaactgac gcaaagcagg atctcattat    11220
ttgctggctg aatgaaccac taccctaaaa agcattacag ttaatattta ttatagaaga    11280
aaagtagaat agcatagcat aatagtactt aaatatttac atggactatg attctggttt    11340
tgcctattac taactgtatg atactgggca cattatttac ttttctgtgc ttcagttgcc    11400
tcttcagtaa aacagagcat ttttttttctt tttttcttt cagagacggg ttcttgctct    11460
gtcacccagg ctggagtgca gtgacaggag catggctcac tgaaacttca acctcctggg    11520
cccaagcaat caatctttcc gacttagccc tgcaagtagc tgggactaca agcacaaacc    11580
actacaccag agtaacttttt ctggtacttt tttttgtaga gatggggttt tgccatgttg    11640
cctaggctgc tctcaaactc ctgagctcag gcaatccatt cccttggcc tcccaaagtg    11700 ctgggattac aggcatgtgc cacagcacct ggccaaaaca gagcatttaa taatggtatc    11760
tacctcataa ggatgttgtg aggatttcag taaagtgctt aagagaaagc tcttaatcca    11820
catttactaa gttttttgtta tttatttcta agtttgcct aagaattttc acagttaatt    11880
ataactatga aggtatttac caaatagttt tttgtcttat tttttttgaaa gaagtactaa    11940 gattctgaaa aaatttacag aactacttac tggatccatt aaaaacactc gagaagctgc    12000
agacagattc aaaccaactc cacctgcttt taaggacaga agcattatag ttggagatcc    12060
tgcttcagtg ttttgaaaac actgaattga ttcaactctt ttctttttggg ccatggaacc    12120 atccaaacga gtaaacacaa atccagaggc tctaaagggg ggaagaaaag agacaagtaa    12180
caaacactat tattataaaa ataaaacaaa gttaagtaac tacaaatctc ttcaataaat    12240
tctttcactc atttatttta acaaatgttt attgaacact tattaatatg ctaggcactg    12300
agtcagtcat tttctgataa attcaggact taatctttaa attcttgtgc tgccaggaag    12360
tattctctat tgtgactctg aatatctttc agataaaatg actaaaactg gcaaaacaaa    12420
ttaagttttt tttttttgcta tccaaatcaa tatgattata taaaatcctt ttactgaaag    12480
tgaaaaacac tgtggaactt acttaagtgg tatttctatt aaagacagga atgttgtaaa    12540
ctgagaaaca accaaacttt ttatgttggg attcttcttt cttaagtcag tcaatgcgtg    12600
cattagcgca ttaatctgca aaaaatatta agatgtccat tagattccat tttaaatcag    12660
taaaattagt ctaaaagttt ttatcataaa gaaaaggtcc tgaaatgtta tttccctaaa    12720
atgcaaaaga ctactcattt aaaacaaaaa attaagactg aaagaacact ctaataatct    12780
gaacccattc catttcccct caaattcacc actaaaaata aaaagccagt ggtcaacaac    12840
agaacactaa aatgacagga atgaaagcag aattacgatt ttgatatact gtgtatattt    12900
ccttatataa aggtaaaaca aatactcaaa tatttgcaca tgagtacttt accttttgaac    12960 tggatgtcca ttccatatca gacttttttct cactgtcacg tgctaattct tctggaggac    13020
```

```
attctaataa attatcttca tgtatatcat ttctgcataa agggcattta gcatgtggct  13080
atataagaaa gaacgaagta tgagcaacac ttaacagaag aacaaatata aatatgccta  13140 aaaatttta  aatgtatgct aaaatctgta tctctcatag ctaacatttt attaaacctt  13200
ttaatggatt tcatccattt aagagacatc tgaacatgct gaactccaga cataatgtgg  13260
taagtagaac ggataaagga gggagcaaaa gtatgtgatc tggactagct agaagcaaga  13320
gcaagaaacc aaaaattata acattgtaag caagtttaaa aaaaaaatct atgaataaca  13380
atttattgaa cctaaataca atacagctac actatttagt actattcttt aaaaaaaaat  13440
ccatcttaat ggcttataaa gctattaagc ttataaagct tataatagct tataaagcta  13500
ctaggatctg ttaaatccta tcaagttcat tccaaagcaa catctgttgt acccgtttga  13560
acctgttaat aaaataagat tatatcttaa ataactatat ataaacacc  attacaatta  13620 aataattctg aagctaaaat tatttaaaag tcaatacagt ggggttactt ttggggaaga  13680
gggagagggt aaatggttgg gaggggccac aaggggacct aggcagcaga tacaggaata  13740
tgtttacctc ataattgact gagctatta  attatgaatt tatacatttt ttctacatat  13800
gttatatatc aatttaaaat gtttaaaaaa attctacccc agctgaatga ctgcttaaca  13860
gactagtcaa cttcaaaaaa attctaccac acaaaagaat ctagacctac cttatccaac  13920
acaatagcca ataatcacat ggggcaatta cgtccttgaa atgtggctaa gccaaattga  13980
ggtgtgctgt aagtatacac caccaccaaa ttctgaagat ttagtttttt gtaaaaagca  14040
cattaatact tttatatttt tagatatatt gggttaaata caaatgtatt aaaattagct  14100
taatgtttct ttttacttaa gagtatgact actagaaaac tgaaaattat ctttgtgtct  14160
cacattatca atccatttat tgaacagcaa tgatataaac agcggaatta agatattgac  14220
tgtgaacatc tttttatgtt gcaaatgttg cattagaaga aatatatcac ctattaaaat  14280 actgaataa  ttaactatca aaggtatatt attaaatcca agtgcaaaac tccatatact  14340
atcttttatt atattaaaga caggtacact actctatcaa acactgaacc tgtactgagc  14400
aaaaaactaa cctgctcatt ctgaatgact tggcaaatac agggtttaca aaatacatgt  14460
gcacaatgtg ttatcacagg aactgttaaa gaatccaggc aaattgcaca ttcctcatct  14520
gaacctgagc tcagaattaa cttcatcttc cttattaact tctttctcag ttcttcaggt  14580
gtatcatttc ctagagaaaa ggctgaaaaa ttaatttcag agcaaggttt gtaatatgac  14640 aagtaatct  atcttataag gaaaagtttc gcttgccagt agggaaagtc tctcatcatt  14700
ttctgccata ggcaaaaagc ataatttaaa tttgaaattt aagaaacatt cagaagccaa  14760
aatagtagcc aactcacata atatacctca tagagaagca tcattataac atgcacaataa  14820 cataccacca cacaataaaa ggcagatcca atatgaatct ttcatcaaag ggtatctatc  14880
accggaattc ctggaaagac ctcattataa ttccatttca ttggtaaaaa aattattgga  14940
tgtattccta gctgagtctc acactaaaag caatctccat ttgacagaac aaaataaact  15000
aaatgtatgc cacataaaaa aaatttatca ctcttattta agtatctctg acaaatacaa  15060
tgatatgaag caatcaaatt tacctacctg agggggccatt ggaagacact gcatttgtaa  15120
gaaggtaagt atggcaacaa atttgccgca gtctaagcaa aagacccagg acatctgcat  15180
aatgtgccag gacagtccct tcattaaaat acctagagat taaaatgtca atatattatta  15240 agtccgctaa acaataataa cttcctattc taaaacagca gagtaaaatg gcatttttct  15300
tttcttctct agaaattact ccaaaacaag aatgaaaagc agaaaagcaa ctctaataaa  15360
```

```
accaagagag atctataaca ataaggcaca atatatgaga aatggctgcc aattgcagtc    15420
taagtcagat aggaagatgc tgagagggat gactgcagat ctcaaacaga gctgccaaaa    15480
cacaattctt taaaatggat ggcatgccct gaggggaaaa tcaatacctc tcatgtgcag    15540
aaacaggaac agggtgcatg cttggtgact tgagcttcca tggagaaatt tatatcaaaa    15600
aaagagggaa ggtaaactga atacagaaac atacaggtgc actgtatttt caaaaaaaga    15660
ctatgggcac agcactctac actccaagca cccctaaagt ttctgatctc tgtttatgtg    15720
tactaataaa acctaaagta actcaacatg taaccctgag tcttaagtaa attgggttat    15780
ttcctgctgg tcggggacat gattgtgacc tttcccttttt gtatatctgg actagcaaat    15840
agctagtcca agaagaactc aagatattca aatataagta ataatcagca gagagcaaag    15900
gtaggggaca catggcagtg aaagaaaact cagcagaaaa atgttgccac agagcaaata    15960
aaaattatga ccaaggatac tgtcacaatt taacaccact caataaaaca attcctccaa    16020
aaaaaaaaaa tcttaaagca aagacaaaga gctttgaaaa aatatggcaa gagaacagga    16080
agagatgaaa gatgagctgg tatggctcaa gaaagtgaaa gaaaacagtg aatcatcaga    16140
gaaatgaaag tcacactgaa accaatataa gccaatataa aaaagacta gtcactgata    16200 aaacataga aaggatgta ggaaacagga ctgagaaaat caaaattaaa caaaaaatg    16260 taaaagatca gaaataaaat gatacctatg gaacacagat aaaagacatc taacatacac    16320
agagagaaat aaaataatgg aacagaaaac aatatttaaa gaaagctttc caggaaagag    16380 aagggggga aagcctggaa tctaaagatt taaataatat cacatgtccc aggggaaagt    16440
caacaaagaa gttgctgaac ttcagaggga aaaaaaaaaa aaaaaaaaaa accaggcttc    16500
cccacagaaa cattctatac aaaatacagt ggtacaatga caacatagat tcttaaggaa    16560
atgggtgatc caaaaattat ataaccaggc catctgatat ttaagtattt taaggcaaca    16620
gaagaaatat agcctaacgg ctaagagtac aaatttttag agctagctgg tcatgaattc    16680
aaaacctggc tgtgccaatt taattatgta accttggaca ggttgcttaa cctatgtctt    16740
gagcttcctc agttctaaca gtggcattgt aaaagtacct acctcataca actactgtta    16800
tttaatttaa tacatgtaaa gtatttaaaa tagtgcctgg actatattaa gtgctataca    16860
tgaatctgtt gctagtatta gtactggtag tattatggca acaaacattt ctgaatattc    16920
aagaatgcaa ggaataggca aaataataca aagattaaac ttacaagctc taaaccaaag    16980
tgccagagtt aatctgtcct gtcactcact agctgtgtga caacagtgta agtcacctaa    17040
actgctctgt gcctcagttt cctcacttat aagatgtgga taattatact gacctaatag    17100
gattgctgtg aatacattta aagcactaag atcaatgtat aacacctagt gagtgctaaa    17160
taaatgttag taaatatata gcctattaaa aagaatactt taaaaataac ttattttctg    17220
agaacagttt caataaagtt aatcttttttc aacttttttca aatagaataa cctttactaa    17280
cactaattat tccctggcat ggtcatatct tactgatact cagcatttca atttaagaga    17340
tctcttttga gtgcctacca tgtgctaaat attagaagct tccttcctcc tatttcacca    17400
gccattgcta tcttcacagt tagatctctt tcactttact cactcccttg gtgatctcat    17460
ggctttaatt accatccaca catagctgac tttgaactcg actctcctat ccaactaatt    17520
atttgatatc tctacttgga aaattcacgg gcatcctatg atcaatgtgt ccaaaactga    17580
gcttctgatc ttagcttaaa aaaatctctg ctcttcccat agacctgtct tggtaaacag    17640
caattccagc cttccactta tgcaggtaaa aaggcttgaa gttatctttg attcctcttt    17700
cacatgccat aacatatcaa ccagcaagtt ctgttggttc tacgttcaca atttaacaga    17760
```

```
atctaatcat ttctcactcc ctttatcact actatggtaa aaaccaccat catctcttgc    17820
tttgactgcc actggtctcc ctacttctga ccttattcct attcaaataa cctaaatctg    17880
agcacagcag ccagagtgat cttttaaaaa tataaatcag attacgtccc tctcctggct    17940 caaaacccctt taaggtttcc tgtcataaaa agtaaaagcc aaagtccttg acatatgcgt    18000
tacatacccc cattccaata aatctctgat atcatgacta ttttctctcg ttcatactat    18060
ccagccacac ttgcttctct gttattcttc aagctcacca ggcatgttcc caactgggag    18120
catctacact tgctcttcct tctggctgaa acaccccctta atcccaatct cctttagatc    18180
tttacctata tatcatcttc tcagtgaggt cttccttaat accctactaa aacagctttg    18240
gcattcccca tcccctttcg ttgctttatt ccttaaaact taatcatgtt tttaaattat    18300
ctgtttcttc ccattaaaat ataaattcct cgagtgcagg cattttttgtc tgttttattc    18360 tgctgtatcc caatgggtat aagtgcctgg cacacagtgg gcacttaata aatttttgtt    18420
gaaagaatat gaaaagaaag aagatttttga actcagaaat ctgctgctta gaacaatctt    18480
tcccactctc tctaattcct atcaaacctg ctttgtacct acctcactga gttttttatg    18540
ttttgaagat tccccttttca cagtcctatt ctgctttcac ttgtctctta ttcattctgt    18600
tccctgtggg ctcacattaa acctgatctt gcttggacca gaatttcata ccttctacca    18660
atccttaatc ttcttgttaa acctatttca tcagttccta ttttccagatt tccatacgat    18720 tttggaaata gaagcaagca aaatcttctg gctagcaatt gagaacttgt catttaaagt    18780
aagctttaaa ttatttccta acttaaaaaa ttacttacct ggtgaattat actattattt    18840
cattcacttt attgatttgt aaaaaacact gtaattcata gaagcaaatt atctttcagt    18900
atacttcaaa ctattgctaa cacatctaaa taatgtcatt cagtgaatgg gaaacaaagt    18960
aaacaaaaac taattttttaa catggttttc tttctccata ccttccaata gtggctctgc    19020 cttcatttt cacagactga taaatctttc tctcttcatc tgaaagtgta atgtgctgaa    19080
taaatacttt acgttctggt aactccaaaa caggttttcc tttaattttg cttgtctttg    19140
ttcttctaag tgtaatatttt ttaattaggg actgtaaacg cctaatcaga ataaaacaaa    19200
taattatgta acttttaatt tctacataaa ttgatccaag aagaacgaaa cagaacattt    19260
taatttgtta ctgtttttata gcttctgtaa aagtgttttt aaaatccctt atttgggatt    19320
ttaaccaatc tgataatcac agaagtattc tacaaaaata aaattattaa aacaaatgta    19380 tggaaattttc ccctcaatac ctaacatagt ttaatctttt tatatcctgt ccttatttttc    19440 gtaagttctg ttccccatttt ttgttccaat cactaactct tttacttctc aactgtcctg    19500
tcaactccat caccgaatag tcaacactca aattctaagt atctattaag tgccaggcac    19560
tgaattaaat gttgtaagaa tacaaatatg ggtaagatac tacattctgt aatattaaaa    19620
tcaaaagtat ataaataagt aattgtataa agtaatgagt gccccccaaaa taaaaagata    19680 atatggtaat tcagaacaca gaaaaatgct ttacaggttc cacaatcttt acatttcttt    19740
ctcagtactg gaaaaaaaga gatgtatcaa ttccttgtttt ttcccaacat tgaaatataa    19800
atacaatttc ctggagttta aatagttggt tttgaggaat caagtggata gtactgccaa    19860
ctaggttagt ggctcttgaa gctttctcac tataactcac agtaagaaac acattctatc    19920
cagcaaaaat atacaaacac atacaaaaga aacaaatatt tcacaaaata atacttacta    19980
tgtatcatgc actccgatat ttactaatct cttctctatt tcattgtctt tttaaatgct    20040
ggctaccacc tttataatga ttttatatcc cactaatagc tctcaaatct tcagtctata    20100
```

```
aaccggtgct ttagccaaaa agttgaacca cattacatct tgcaaaatgg ctatcactga    20160
gttttaattt atgttctcaa cttttatcta tctccaccag aaacaaccac ataaaacttt    20220
cctatacaac ttttgctaag gtcatggtac ctcacatcat tcactatata aagctatgta    20280
aggccaggtg tggtagctca tgcctgtaat cccagcactt gggaggtcg aggcaagagg     20340 ataacctgag gtcagaagtt tgagactagc ctggccaaca tggcgaaacc ccatctctac    20400
taaaaataca aaaattagcg gggcatgctg gcgcagacct gtaatctcag ctacttggga   20460
ggctgagaca ggagaatcgc ttgaacccag gaggcggagg ttgcagtgag ccaagatcgc    20520
gccactgccc tccagcatgg acgacagagc aagactccat ctcaaataaa taaatacata    20580
aataaataaa taaagctata taagatatga aaacttaatg catattagat cctcaaagga    20640
tatacgatgt ttcctgctaa atctgttaat gctggttttg gggctttggg gcttagcaac    20700
acacaaaaaa cagttatgtc tttcctttca gtttagccac aacaggggaa gggtagttat    20760
cgacaattag aaatctttgt ctttccaaac aagcatcact aggttctgaa agacaaaggt    20820
actgagccat aaacactttt tagaaggaaa agttaagagt caagttaaaa tagtaaagaa    20880
agtgccaact ggttcaagct actaacagtt atttgtaact aatattaatc actgtctgaa    20940
agtacttacc taagtcctcc ttcatctccc attgtgacag gacgctgtat tgttctatgc    21000
caccattctc tatcaataaa tggtttaagt tttaaaagg aaagaagaga ccacaagtcc     21060
tttaaagaat tctggattgg agtacctaga ataacagga aactgttata actctttaac     21120
cagagtatcc agtaagagta tctatttggc ccaatcagaa aagacaacaa ttgaaaatgg    21180
gcactctgta ccaggctcat cattatcaat taaattaaac tatcaagtgt tgactataat    21240
catttattaa aaatatacac atctcaagat acagttttgc tctaattttt agctctcaca    21300
tgacacacta gccaagaaaa agactggaaa attcaacttt ctccttatca agtacatctg    21360
cttatttagt ttttaaagca gcagcactag cagaaggaaa aagcaactag tttaagttta    21420
cattcttttc cttaccttct agtaaaggta ctgtgaatgg caaacaggtt tgaggatggg    21480
aaacagaaat caagattatg actggatgac tagagtgtct actccatttc cactagagtg    21540
tctactccat ttccaaggtt caagaataag tctagtgact gttccataaa ttatcaataa    21600
gtcaaatgtt gttatatcac gggcaattat gaagaacaac tcaaaacatt tgattaaatt    21660
atttatatga ttaattttgg ggcagaattt acacccactt taagtttaca aagttacttt    21720
actaacttac ataatgatat attttagaga tttaaggttt tagtaagttt aatgctatga    21780
ttacctgtca aaacccatct tctttctgat tctaagtcaa gtacagcttt tgtctgctga    21840
gcatttggat ttcgtatggc atgtccttca tccaggatca ctcttagcca ccttatgcta    21900
tgtaatggac tatctccttt agtctgaaat aaatgtttta tatgaattaa aaaacacagg    21960
aaagtaaaat agtacttaat atgatttgct aactagttgt tatcattatt taatatcaaa    22020
tttactatgt gctaggtact gctttaagca ctacattaat tattgaatac tcacaagttt    22080
ataaaataag tacttattag cacacctaat tttacagata agaaaactga agcacaaact    22140
gctaagtaag tatgttaccc aaagcaccac aggtggcaga actagcattc aaacccaagc    22200
agcagtctag ctctctgttg agtcactggt caatacactg aactgttcta cctcggatta    22260
aaacatagca atgatataga aaatggcagt tgtaagaatt acttgaattc aacattactt    22320
tcttttatat aaaaggtaat attttttacta gaagactgaa attttgatag caaggtatt    22380 ttcaaaaagt tttaacttt gaacaattgg aattataaag gtaaaaaaca attagactaa     22440
ctggaaaact tatgaactgt aactacaaaa aaagcatacc ttcaaactga gatattaatc    22500
```

-continued

```
aaatcattgt gatagaaaac aattttccag aatattaaaa aagaaaataa aattcattta   22560
caaattgctt catatactta caatccaaat ttaaaatctt aacttaaaat gttctaaatg   22620
aaaaatattc ctgtctgggt gtggtggcac acgcctgtaa tcccagcact ttgggaggcc   22680
aaggtgggtg gatcacctga ggtcaggagt tcaagaccag cctgaccaag atggtgaaac   22740
ctcatctctg ctgaataaca aaaattagct gagtgtggtg atgcatgcct gtaatcccag   22800
ctacttggga ggctgaggca ggagaatcat ctgaaaccag gaggcagagg ttgcagtgag   22860
ctgagatcac accattatat tccagcctgg gcaacaagag caaaactcca tcgagaggga   22920
gggggagggg aggagtggag aaaagaaaaa tactcctaaa ttagcatcta aataaaatgc   22980 aacccttttca cgcaaaaagt caaaaaaaaa aaccatttat ttttctatat atcgttaagt   23040
atctaaagag aaaaaaaaag tataaagcct gaattttgga acactctaga aacctgtggc   23100
atatttctta cattcaatct ttaaaagatc tgttaagtat caacaatact tactccatag   23160
tcatgagtta aaatattata cgtagtcaaa acaatatcct gttttgaaag taaggccggt   23220
tctctaatac gatcaggacc ataataaaca taaaaattca agtgtacatc tgattttata   23280
tgttgtccaa actggtccta aagaaaaatt aggaatattt ttaacaatga gcagatttgt   23340
gtcagactta atagatgtat aaaaaagtaa ctgccctggc agtagtgtga caaatccaac   23400
tactaaaatt gtatgaaatc aagtttcctt cagtctagac caaaataata acaataagaa   23460
aaatgacaca tacacagtaa taataaatta tttaaaattt acttggccct accaatcagc   23520
aactgcttca tttttaggag gaaaaaccaa agttattgaa aacaataatg agttttataa   23580
aaatatttta attagaaggc cctttaatgc tgcattagtt agcagactta ataatataaa   23640
aattaaacag taaagaaaca acaaccaata tttccaagga tgtgggcaga gattcaagca   23700
ctgtagccac tttctttcac tcatttatta ttggcctact atttgccagg tatcaaccac   23760
aatagtgatg taactaaaaa tgaagaacaa ataatcatcc ctgactttct tgaggacatg   23820
atcagtttta aaacttatt attattttt taatcatgaa aaaaaccaga cctagaagat   23880
tttcagcaga aaaaaatagt ctgattaaac tgaaaagaga agataccagg gagacacagc   23940
tgggaagcta tgaggagaga gatgatgaag tcctaaacca gcaaggtaga agtaggaaca   24000
gggtggaaag gacaggtgtg aaaaacagaa actaagacaa gactgatagg acttggggac   24060
taatgaaata tgaaatatga ataataataa taagactaag atgctctgat acttgaatga   24120
ctacctagaa ttgtgtgata aaaatataag gaagtttaaa aaaaaaaaaa aagaagggaa   24180
aagtgggcat ccaagtaaga aagagatgaa tattttagac ctttatcatt tttggtcact   24240
atagaatacc taactgaaga cgtatactag gaaaatgtaa ataattaccct atagatagaa   24300 gtgagaggtg tagatatgaa ttttaaagtt aacaacagac agtatttaca gctgtaagaa   24360
tgaatgaaat ttcctaaaga gagcatgtac agtgagcaaa cgttagggac agagtctaca   24420
gaataccggt atgtaaggag aagacttgtt tttattggga gaaaacacat gatgcctggg   24480
gtataattaa aaatattcca ggccaggtgc agtagctcat gcctgtaatc ccggcacttt   24540
gggaggccaa ggcgggtgga tcacttgagg tcaggagttc gagaccagcc tagccaacat   24600
ggcgaaaccc tgcctctact aaaaatacaa aaattagctg gcatggtgg tgatggtgat   24660 gcgcacctat aattccagct actcgggagg ctaaggcatg agaatcactt gaacccagga   24720
gacagaggtt gcagtgagct gagactgtgc cactgcactc cagcctgggt gatggaatga   24780
gattctttct ttaaaaaagg ccgggtgcag tggctcacac ctgttaattc caacactggg   24840
```

```
aggccgaggt gggcggaacg aggtcaggag ttcgagacca gcctgatcaa catggtgaaa    24900
ccccatctct actaaaaaaa caaaaattag ccgggcatgg tggcatgtgc ctgtaattcc    24960
acctactcaa gaggctgagg cagcaggatc acttgaacct gggaggtgga ggttgcagtg    25020
agctgagatc gcgccattgc actccagcct gggcgacaga gcaagactgt aaaaaaaaaa    25080
aaaaaaaaaa aaatcaatcc agcaagaaaa aaaggaaag cacatgtgtc agacttttgg     25140 taattttga atcttgatga gtagatggag atctcattaa aattttttaa aatactcttt     25200
ttaaaaaatt atatgttgta tggaaataca gaaaagacag atttaatagg aaccagaaca    25260
aagacagaga aaagttagg acaacaaata taaagggtaa aggcctggga tccaaagaat     25320 ataaagttt caagaaaaaa aaccaaggtg gactttaat ttgtcatcta tcttcattcc      25380
agttctttac aagaaggttt agagatagct tacaaaataa gacataacaa ataataaatg    25440
aataacatat tcaaggcaga ggaaaagggg agctcattgt acatggcaat attgaagtct    25500
gaagatctct gcaagggag tttctgtagt gagtggaagc aaaaaccaga ctaccaagga     25560
ctgaagaaag tattaaacat gaaataaagg caaaatgca gagaggataa acatgaaaa      25620 agtaaagctg aaaatgcaaa gaatttctta tagaaatttg gtaaagaaga aaaggaaatt    25680
agaatccagc atgacaaaga atccaatatg agaaaactga atcaatgggt ggccttgaaa    25740
tgggacagtg cattatttgt aaagggatta cacttggaac agaagaaaat cagcttttct    25800
ggagaataaa gggagagaac tatagttact ccatctctag acagtgttag gctctactgt    25860
atatgtatgt atgtatcatc ctctcaatag aaaacgaaat aggtgttatt tcatgagatt    25920
acttgtctaa atatccagaa caaatatgtg gtagaagtag gattggtacc caggttctat    25980
tcctttacct ggattatttg aagacaaaaa agggaatata agtcagttct agcctgctct    26040
gtagaatgct agatccttta cttgagagcc aggaagacgg tatcttgttc agattgtgaa    26100
attttaattc ttgatcattg aaatcgtttg gatgttcatc tcctccaaat ctcatgttga    26160
aatgtaatct ccagagttgg atgaggggcc tggaggtgga aggtgtatgg ctcatagcgg    26220
tggatccctc ctgagtggct tagtgctatc cccttggtga tgagtgagtt ctcactctaa    26280
gtccacacga gatctggttg tttctaagtt tgtagcacct ctccactctc tctcttactc    26340
ccactctggc aatgtgatgc tgggtcccca tcaccttctg ccaagagtgt aagcttcctg    26400
aggctgtgta agcttcctgt ggcctcacca gaagcagatg ccagcacgat acttcctgta    26460
aagcctgcag tatcatgagc caattaaaac tcttaaatta tccagcctca gttatttctt    26520
tatagcaatg caagaatgga ctaacacaac catgaatccc taaatgccaa accacctctc    26580
attcctttaa attcacagag tgtgcatgat ctcacttggc aagattttgc cacactttcc    26640
tttctgaact ttacattact tgaactttcc taaatataaa attataatta aatactgatt    26700
acccatttta aaaatacatc tctataccc aagccctcaa ataatcagtt agatagttta    26760
tacctccatt aatactctaa acctcatccc aaaactgcca ttcaagtacc catgtactat    26820 ccttccata caaacaaca aattaaagaa agaacagttt cgttggaata aaaaaatagc      26880
aacagaccat taacattcat tcttctggtc ctaagaggaa aaatgataca cttatcagga    26940
caaggtgtaa tttaaaaaat aaataaataa accaaaaact tatataaaaa aagataattc    27000
atgtcacgga aaaaagact ataaagccaa gaagaggcca ctaaatttga caattaaact     27060
atcacaagta gtcttttcca atgcaattta gagaactaat ggtacaagcc agattacaat    27120
gaattaagga attagtaagt aaaagcacaa agtagaaatt aacctccaag agtatgcacag   27180 tgaaggaaag cagaagagta gcaacttta aagatgcata tcaagagaat gtattttaaa    27240
```

```
atgaaaaaac ctgagtatgt atcaggaaga gccagtggga agagactaaa taaacaaggg   27300
aaaaaagaac agatgagcaa tgtgggaaaa gagagaatcc aatgtagaga ctaaatactg   27360
gtcttaaaaa gagtaggatc tcttcctcct ctgacataag aagaatggcg atgagagata   27420
aacagataac ttggaagtgg caagaacggt gagtggtcct tatattcaca gggattccaa   27480
gagagtcatt atttcatcat aacaagaagt ttgaagctca aactaggaag aaaacatatc   27540
caggctgcaa ataaacaatt aatcaagagg ttccattcca atgtcaatgt ttcagaacag   27600
aaaagcaatc tggaaaaaaa aaatttctga tgggtagtgt taaaaggaca ggctctagat   27660
tcaaaatgtt ggagactata tacaagatcc atcatttatt agctggatga ccttaggcaa   27720
cttaacctct ctgtgtttca atgtgggcac ctggaaaatc agggtaacag ttatgagaat   27780
taaatgagaa aaatccttaa aagaggttaa ggacaaacca aataaacagg agttcactaa   27840
ctgttgttat tgttataaaa ataagttatt gttggtatag ctcttagaaa agacagttcc   27900
aacagtcaat ctgtaaatgt agaggagtca aactatacat ctttcccact ttgggggaca   27960
aaaatagcaa aggcagaaat acaaaccaaa tcttatgtta gcaattgatt atgttccttt   28020
accttcttct ctactacaca tcttcaaaga aaaatttctt caattcagca aacataatcc   28080
aattcacctg atgattattt gaacttagat acgaactgat gaccaagtat atttacccca   28140
atgaatgact ctttaacaga atactttcta ccttgtagat aaaatataaa ttatgttaca   28200
tttttaaagg gcttaaagac ttacaatcca gttgcttaac acagaaagcg acagatgat   28260 cagtgttgtt cttggtctct cctcaacatc agttttcttt gaccctcca ctgcacaagc   28320 tcctaaaaaa atgaaccact gatagaacct ttagctgttt ttctgaaata tatatgtcaa   28380
taaggagatg gcaataatgt gcctccatga aagataaat taggaacaat taaatgaag   28440 cagatggact tttaacaggg aataaatttt acctcatcac ttaaaaaaac taaaaatcca   28500
catagtgatt atgagaagaa ccaaaggact atgacagaga gtaggtcaca aggaggaagt   28560
ctctaatatt ttctgatagt catagtcatt cattaagacg aacatttgtt ttatgcagtt   28620
ttctgaattt gtgttatatt taatttggta gccagccaag atggccctca atgatctcta   28680
cttcctgata ttcacaatct tgtgtaatct cctcccatac tccaccagga ctggtctgtg   28740
tgaccaacag aatatagcag agaagatagt atgtcacttc tgagatagat tacaaaagaa   28800
gtttccgtat tgggtgtgca agctcactct catactcatt ctctctctcc aatctttcac   28860
tctggtggag ccagctgcca cgatgtgagg ccactcaggc aacttatgga aggatgcaca   28920
tagtgaggat ctgaagacta cagttagcca gcaagtaatg aggtctgctg acaactatgt   28980
gagtgaactt ggaaatggat cctccctaag tccaatgttc agatgacggc ggccctgaa   29040 gaagagtttg actgcaacct cgtaagagac cataagccat taaaccatcc agctaagcca   29100
ctccgacttc cagccctgtc aaagtgtgtg agataataaa tgtctgattt taaatggcta   29160
agttttagga taatttgtta cacagtaata ggtaactaat atattacaac aaaaattctt   29220 aatactttc tgtggagcat gtttaaaaat agtgataata aagtgttttt acaaattctt   29280
gaaataaatt ctagagatgg tatcccttac caatggagta tcttccagta aacttaaaat   29340
gcaaatttct gagtttttaa aaaattgtat tttcacacta atttcaaaat taaactggaa   29400
ggtgagcaaa gtatcatact gtatctacgt atcattcaca acttgctttt ttctctcagt   29460
gctatctaca gtagtccctc cttatccact gggggtatgt tccaagaccc tcaatagata   29520
cttaaaacca taaatagtac caaaccctat atataatgtt ttttccctat atatacctac   29580
```

-continued

```
aataaagttt aatttataaa gtaggtgcag taagagattc gtaacaacaa agaataaaac    29640
agaacaatta taacaatata cagttgaccc ttaaacaata tgtttgaact atgtgatgca    29700
cttacatgca aattttttgtt aaccaaacgt ggattaaaaa tacagaatgg gccgggcgcg    29760
gtggctcacg cctgtaatcc cagcactttg ggaggccgag gcgggcggat cacgaggtca    29820
ggagctcgag accatcctgg ctaacacggt gaaaccccgt ctctactaaa aatacaaaaa    29880
attagccggg ggaggtggcg ggcgcctgta gtcccagcta ctcgggaggc tgaggcagga    29940
gaatggcgtg aaccccaggg ggcggagcct gcagtgagcc gagattgcgc cactgcactc    30000
cagcctgggc gacagcgaga ctccgtctca aaaaaaaaaa aaaaaaaaaa aaaaaaaata    30060
cagaatgggc caggcatggt ggctcatgcc tgtaatccca gcactttgga agactgaggc    30120
gggtggatca tgaggtcagg agatcaagac catcttggct aacatggtga aacccgtctc    30180
tattaaaaat acaaaaaatt agccgggcat ggtggcaggc gcctgtagtc tcagctactt    30240
gggaggctga gacaggagaa ttgcttgaac ccatgaggtg gaggttgcag tgcgccgtga    30300
tcgcaccact gcactctagc ctgggcgaca gagtgagact ccgtctcaaa acaaacaaac    30360
aaacaaacaa aaaacagta tctgctgatt gcaaaactca tgtatatgga aggccaactt    30420
ttcatatata ctcgtcctgc agggcagact gtgggacttg agtatgcgca cattttggta    30480
tacacagggg gccctggaac caaatccctg acaaatactg agggatgact gtactgtaat    30540
aaaacttatg tgaatgtggt cattctctgt ctctcaaaat accttattgt atataatatt    30600
ttagaactga aactgtagaa cgtgaaactg cagataaaga acaactgtgt ttgggattta    30660
cacttattag tatttgtagc tctagtgtat tcattttaac caattcatag catcatactg    30720
caaagtagat tacaaatttat ttaccattcc cctactggac aacatgtaca ttatttctaa    30780
tattccatta aaataatgct gcaatgaaaa ccattttttc atgtctcctt atttatattt    30840
acagagttac agatggtcta tattcagctt cattatattt ttgtccagtt gctctccttg    30900
gtaattggcg ctcccatcaa caatgcacga attcctattg ctgcacaact ttgtcaatac    30960
ttggcattgt gagattttttt aatgtctgaa aatatgaagg gtaagagcat ccccctattc    31020
ctttatttta tgttttgag acatggtctc gctctgtcac ccaggctgga atgcagtggc    31080
gctattatgg ctcactgcag ccttgacctc ccaggctcaa gtagctggga ctacaggcat    31140
gtgctaccat gcctggctaa ttttgtgtat tttttttgtag aaacaggatt ttgccatgtt    31200
gcccacccct gatcttgaac tcatgggcct cggcctccca aagtgctgca atttcaggca    31260
tgtgccacca tgcctgctgc cactattcct ttaatttgca tctccccaat aattctgaat    31320
cagcatattt tttccagtgt taactggtta tttgggtttt cttttctatgg actccatatg    31380 tacatccttt gactattctc ctattgggtg gtcttttttcc aattgtttgg aaagttctta    31440
catagtctag aattgaacct tttgtcagtt acacttaata cacattatct tcttcagttt    31500
tatcattttt tactttgttt atggcacctt ttgatgcatg gaaatttaaa atgtagtggc    31560
atttaatcaa tcttttcctt atgacctttt gtgtcttact aaagagatca ctatctacca    31620
caaggacaat caggattatg gcttctgtct ccattcacag agttttgttt ctattctgct    31680
tctctttcaa agatatactt agtttggtta aaaccaaaat gacacacagc tgtgactttg    31740
aaaatgttct ctcttgtatc acagctatgc atctgcaact gaaagtggtt tctaatgtgt    31800
aatttaattc tatctcaacc gaaatttcca cattctttta aatttctaaa attagggtaa    31860
agaataatcc acccaacatg cctatatttt ctattcctaa ttatctgatt cttggaccaa    31920
aagtcggctc tttctcatga gtctatgtta gcttcataaa caagccccctt caggtcaatc    31980
```

```
tttacttcat tatcctcctt tttcttcaca ttacttctca ttatttaaaa ttatattgac    32040
ttgcttattg tatatttctc tcatcattac atcatatgct atatgaaaac agatagcctg    32100
ctatatcccc aacatgtaaa ataatggaga ccaaggggca gagatataat ttgtctcaga    32160
tcttctcaac cttagttcaa tctcttccca tctcaaatat ttagtctctt aagcagtgtt    32220
gttttcctat gaattacaaa atataaaatc ataacaaaga tcactaacat tttaaaatga    32280
aaagcaaatt ctaataccaa aaaattaaac ctttaactta aattaaccaa aattaaatta    32340
agctttaaag cagccacaaa ttgctttgtg ccatcactag aagaaatatc tctgctattc    32400
agaggagtaa gggcccccat cacattttgg ccctaactaa aacaaataca gtaggaaaat    32460
gcaccaaaag gaaaacaaat tatgaggtag ctttgttctt ttaatgggtt atatacttta    32520
aaaaatagtc tctattttct aaacttcttg taatatggtt ttataactta aattttttaaa   32580 ttttttcatt caaaaacaga aaaaaaacca aaaactagaa aacaaggata tttactgacc    32640 cttttttcaac attttctttt ttgttgtagg aacagatgaa gttaatgcac atgcaaatgc    32700
cacatcttct ataaccttag aagatcctgc tgataaaaca acaagaatc ttaaattttt     32760 ttcaaattat ctcctgtgct agagtacagg tactttctaa gggtaagaaa tagaatatca    32820
ttttcaccct ctattgtaag agcttatatt attaagttaa aatatttggt aaccaaaatt    32880
actacctctg acactaagga tatcttttca actcagagaa acgatgtagt cattcatggt    32940
aagacttgag gagaagaaat gaaagtagga gcagtcatat gcaaagtaat tcggctctca    33000
ggtggaagga gaattttttca aggaaacaaa cagtttgatt cctaatgata aggctgccaa    33060
attttcagat cagtcaagat gatcagttat tttccaaatg caatacaatt tctcaacgaa    33120
tgagaaatat agtatgatgt gaattacagg aaaataaaac atattttaaa gaaaagaaa    33180 aaatttgatt attttcacat ctgtataata atgtaaacaa taatagtatt gccaggaaga    33240
cattctcaac ctaattttgt aattactatt catactacac acataggttt tattgaagtc    33300
attttatagg tagtagaaaa ttgttttaag tatagtttaa atattattat cccttagatt    33360
ttaatttgca actatttatt cacttttcct cctttacaaa attaatttaa aacccatggt    33420
tagctccatg aagagttcaa atgtaaacat cagccaagtt taagagctat tactaaaaca    33480
ttccaaccta gcgagataca aatcaatgga gctgtacttt aataatcttg aagtctagat    33540
tatgggtata tagtatacac ataccctttcg ccctgccttt agtttcagac tgtacatttt    33600
tcagtttgcc taaaaataaa acaaaaataa acataaaaat gggcaaaaca ggacattaga    33660 ataggaca cattatcaaa tcaaatctat tacatgttac ctttcatttt ctgcggcaat    33720
tcacttgttt caatttcctc tgaatcactg cttttctatgt actggacagc agttttttctt   33780 ctaaaattaa gtatacacaa agaaattttt ggaccaaccc aaagcaaaat aagatataca    33840
aacatgttta ataaatgcaa taaaaaactt ttgtcctact catttatttt ttgaaaaatt    33900
ttttaaagat tttgacaaat gaaagtcaga tctgctaaaa gcattctgct ttcataacca    33960
gatagatgca ttaactatac aaaatggagt accaccgtta ttgttttttg agacagggtc    34020
tcactctttt gcccaggatg gagtacagtg acacaatcag aagtcactgc aacctcatac    34080
tcctgggctc aagtgatcat cccgccttag cctcggagt acctaggact acaggtcgt    34140 gccactacac ccagcgaatt tcactattat taaaataaat ttgatagccg ggcgtggtgg    34200
tgggtgcctg tagtcccagc tactcgggag gctgaggcag gagaatgacg tgaagccagg    34260
agacggagtt tccagtgagc ggagattgcg ccactgcaca ccagcccgcc tgacagagcg    34320
```

```
acactccatc tcaaaaaaat aaaataaaat aaaataaaat aaaataaatt tgaaaaacta    34380
agtcattcta aaaaattaaa aatttcaata ccaggtttaa tatttggtag ttcaattaaa    34440
gcatataaaa ctggaacaaa aaagaattgg ctcgtggcca ggcacggtgg ctcatgtctg    34500
caatcccagc actttgggag gcggaggtgg gcagatcacc tgaggtcagg agtttgagac    34560
cagactggct aacatggtga aaccccgttt ctactaaaaa tacaaaaact agccaggtgt    34620
ggtggtgcgt gcctgtagtt ctagctgctc aggaggctga ggcaggagaa ttgcttgaac    34680
ccgggaggca gaggttgcag tgagccgaga tcatgccatt gcactccagc ctgggcgaca    34740
ggagcaaaac tctgtctcaa aaaaaaaaa aagaaaaga aaagaaaaaa gaattggctc    34800
ttatcaaaga aaatacttct aacacaatga aataagcagc caaaaggcaa aaatgtaatt    34860 cttttcacaat aggaaatttc ataaattttg tgtagaaagt ttaacagtga ttaagtgcct    34920
aagagcaata aattctgaag tcagactgcc tagctttaaa tcctcattcc accagtaatt    34980
tgttatgtga ttttaagtaa attacctaat attcttcaat gcctgtttcc tcataagaaa    35040
aatagaaata aaaatataat cctcatagaa taaaatgtta ctacatgcaa aagcccctaa    35100
aagagtgcct gttacacaat aacataacta ttagctataa catgtgtgtc agctgttgtt    35160 aagttttct catgtcctca ccattattat ttctatgtcc tttaatctga tcttgtccaa    35220
ttaacagtgt tgtgttaccc aggtttatga taagttcaaa gttgtaacat ttgtcattta    35280
tctaaatctg aagcaattag atttagataa cactgatgag tgctggcttt gtgcttagtt    35340
cagacagcta ttaatgacag aacaattaac atagccagtt tcaaaaccctt tgttgatgaa    35400 atagctagca gagacaaatt tgcgatgact tgtgtagata ctgatggtag acaatacaac    35460
aaaagcccaa ttttttagacc tacttcgaaa gataaatgaa gtttgtaaag ttaacagatt    35520
caagacaaga tcagagggga attacatctt ttattcaaat tctccctcta gtctatgtta    35580
atataatact gtccacaaat aactttatca tgtcttattt ccactacatg tgaagaactg    35640
aaacgatcaa gaatgctttt gtcaagttat ctaataaaat attcttcagt tttcatcccc    35700
ttaaatccat aaagaaaact tctaaaatct caaaaaaag caaaaatccc aagatctaga    35760
tcttagttcc ttgacaaaat agaaaaaaag tagtagaaag atgagtgatt attaaaattt    35820
accaattcat ttcttttata ggtcagtatc attcttcttc atctgtaaaa tgagaatact    35880
ctatctgcct aagtcatagt gatcttggta gtttcaaata aaagaatgta tttgaaagaa    35940
ctacttaaca aatataaggg tcatggtcat ctctatctct ctcttttct tttttttg    36000 agacggagtc tcactctgtc acccaggctg cagtgcagtg gtgcgatctt aactcactgc    36060
aagctctgcc tcccgggttc acgccattct cctgcctcag cctcctgggt aactgggact    36120
acaggcgccc acgaccacgc ctggctaatt tttgtctatt tttagtagag acggggtttc    36180
actgtgttag ccaggatggt ctcaatctcc tgacctcatg atccgcccgc ctcggcctcc    36240
caaagtgctg ggattacagg tgtgagccac cgtgcccagc ctctatctct tttacacata    36300
agaaaacaga gtctaaataa acatatgaca taatcaaacc ataatagttt acctttgtgg    36360
gcgggagcta gacaattctg acatgcgaaa cttactcttc tccttgatat ctgaaatact    36420
gggttgttca ctacatctag atgcgtctat ttcaaagaaa aatgcaaata taagtatta    36480 gtaaggtgtc ttagaaacta gtattatccc tcttaaaacc ttggttttct aattactgat    36540
tttcagtttt cttaagatct tcattccttt cattactcta ttttctctac ttttttccta    36600
atctagtatt tcctcatttc taattagaaa gtaccttcaa attttatga cccagtcttt    36660 tctttgtact catccagccc atccccacac tagctgaatg tcttgctgta ccaaggcagc    36720
```

```
taagagctat tggaaaaaaa aatcaacaga accacaaata ggtgctgtta taaatttaca    36780
tgttcaaatc tcagatgtca ccttgtgtca cttggtaact ctttttacta aacactgttc    36840
ggctccccta cccatttatc agaatgatcc ataccagaat gatccatact acattgaccc    36900
ctttgcctag attataactc cttttattcc aagatgacct atttcactttt acaaagaaaa   36960 tgagaaggta tcttccataa aaatctcaat tttcctatct tttaatccac tcatttatct    37020
atactttcct tcaaccttac ttctttcctt ctactgctaa ctcatctacc taactcatct    37080
aggtagatga gttagaccac agaacaaaat caaaaacaaa aaaaacctca tcttacccta    37140
actcgccacc tttctatttc tttcctgttc caaacttaag taatagcacc aattgttatt    37200 tacaatttt cacctactac tcttaaaata ttttcagtct gctctaatct atctttagaa     37260
ataagcttta tgagggtcat ttaagtaaaa tccacagatc tctttccatt tctcctatga    37320
cttcagaatt tggctctaaa gctagctttc tagcattatc tgctgttatc catgcatatt    37380
acattttaaa tacaacaaaa ttcactgagg tcccagaata aaacatgctc ttttaaagt    37440 acccttccat gagatttttt ttcacaaccc aaaatgctct tccccagttc tctaaatgtt    37500
atactaccca attcaatcat ctccttcatg aaacctttcc tatcagtact cagggaagac    37560
cttttaaaaa agagatccta aattttttgta cagtacaaag ccaaaactag aattacaata   37620
ttaggctgaa aaaacgcaaa tcaaatattg ggtcatattc aaattaaagt ttaccagatc    37680
aaatattgga tcatttcaaa attagcattt acctttgctt agtccatctg ccttttcact    37740
ggtattgttt cctccaagtt tcatagagtc atcgttaaca ttatattcct gggtaaatag    37800
gcatatttct taaacagtac tgctatcagt tttaaataac tttaaatgca tcctgttta    37860 tattgcttta ctttgcataa taaaaacgac ttaaattgct acccaattct ggagcaactg    37920
aaggggaggg tgaataagtg aagaggaaaa tatacaaact gatttaaaat ttttcacgg    37980 gttatctcaa aaaaaaaaaa ataaataaaa ctacttggcc ttcaccttttt cgaaaggaat   38040 accgaaagca aatctcaatt ataaatgaca cattattgtg agaaaaattc aagaactggg    38100
atttacttta taattaagaa ttctcagact tcaaactttt caaaccaatg ttccatgttc    38160
agatctttaa tgaggctgcc attgtcatcc tctctttctc tagaatttgc agggcaaata    38220
actctaatat ataatagtac aggtcccaga gtgtcctctc ttcttactcc atgggtatt    38280 ttcctgctag cccatttcct tttctttcc aatgtacctt tgtttccaaa ggcaccaatg    38340
tacatgaatt gaaacaatt ttataaaatt tgaattgtaa gcacttaaaa atcccccct     38400 tagagttaag tcttactaaa aatgtggttg aaaaggttca tcctctttaa aggtaccaat    38460 caaaaaaac taaaaatctg ccgggcgcag tggctcatgc cagcactttg ggagaccgag    38520
gcgggcggat cacctaagat caggagctcg agactagcct ggccaacaca gcaaaaccct   38580
gtctctacta aatagacaca gattagccag gcatggtggc gggcacctgt aatcccagct    38640
acttgggagg ctgaggcagg agaattgctt gaactgagga ggtggaggtt gtagtgagcc    38700
aaggttgcgc cactgcactc cctctgtctc aaaaaataaa attaaattaa tttaaaatcc    38760
caaatacaat atttttagag atacgtaact agaagagtta ctttagacag ttaatgtcta    38820
agcattagct ccaagaaaga gatggtaaaa atgcttttca tcaaacatcc tatcaagtct    38880
acaataatta ctataaccat ttatattaaa cagtatgcaa aaaaactaaa tgtttattca    38940
aacataaagg atgtcctttg cattcatctt cttttttttt tttctgagac agagtttcac    39000
tcttgttgcc caggctggag tgcaacggca caatctcggc tcattgaaac ctctacctcc    39060
```

```
tgagttcaag tgattctcct gcctcagcct cccaagtaac tgagattaca ggtatgcgcc    39120
accacaccca gctaattttg tattttcagt agagacaggg cttcatcatg ttggtcagac    39180
tggtcttgaa ctcctaacct caggtgatct gcccgcctca gcctcccaaa gtgctgggat    39240
tacaggaatg agtcactatg cccagctttg cattattctt tatattaaaa tattttgctc    39300
agcaaacttt ttctctataa agttcaaaga taaacttttt atcaagtcca agctggatga    39360
aataatagta tgttagaatc taggggaatt taaatcaata tttcagtcta cttatgtttg    39420
gaatatctaa acatacttga aagagtgaca atttttttt tttttttaat aaatccctgg    39480
ctggaaatca catcttcagc tgccatttca attaatgtag caacccaaat attctaaaac    39540
ctttctacta taaaacacac tttaaatata taacttatct tggggaaaaa taagagaaat    39600
ccttattgtt aattgataat ttctcaatta ataattgaga ctaaagcagt aagtagtctt    39660
atgtgcttct atcaaatctg gtaacctaaa acttcagttt caataaccaa atgtaggaag    39720
aacaagacat aaaacattag gttgctcagg gtgaggaatt gaacctgaga cttcaacagg    39780
tttaactctc aataaaagta gaaagtagga agtaaaacta agtgcagaca ttaataaaat    39840
aaaatctcaa tagcactgac aggaaactga tgtactgcct tctctgaaaa ctaaaaacta    39900
ggaagaatgg taattcagaa gagttcagaa aagaagtata ttgcatacat cttttttgcta   39960 tttccttcta tttaagttac ttgaattttc aggtaagaaa agaagtaact gttcctctct    40020
agtaacattt attttttctca ctaaactaat ttttaattct tagaaaccaa atataaatgt   40080
atgtttatat tatatacata tatatatgta tatatataca cacacacaca caaattttca    40140
agaaaagtca cccttattct catcactagg acataagtta ttattaacat tttggtacag    40200
atagtgtagt gaatggactt aaaacacaca tgaatatatt atttacaaag tgaggaacca    40260
aactccacac aaagatttgt acctgtcatt ttttaactaa aaagaatcat gaaagtgatt    40320
attcatcaaa aataatactt aatggttaca taatagtaag ttttatggct atatcgttta    40380
actgttccct tgtcaaaaga tgtttcaaat tgtccacctt tatttttattt ttatttgttt   40440 tagagacagg gtctcacagt gtcactgaag gtggagtgca atagtgcaat catagctgac    40500
cataggctca aactcctggg ctccagcaat cctcctgctt cagcctccca agtaggtgga    40560
actacaggtg ccagtcacta tgcccagcct ttaaaacaat gttgagggaa aaaaaaataa    40620
taataataaa aaaaaacctg tattttcttt ggaaaaaatg aatttctggt aactcctttc    40680
agatagtttc ttagaaatgg cattattgac tggcaaaatt gttcaaagat tataaacaat    40740
tttaagactc ctgatacaaa ttatcaattg ttctcaagaa tgtgatacct gctggtggct    40800
cacacctata gccccagcac tttgggaggc tgaggcaggt agatggcttg agctcatgag    40860
ttcgagacca gcctggacaa catggcgaaa tcccacgact tgagcctggg aagcagaggt    40920
tacagtgagc tgagattgcg ccactgcact ccagcctggg caacagagcc acaccttgtc    40980 tgaaacgta aaaagaatgt gacacgaact ttcattctta tcagcaacac ataaaagaca    41040
gagagaccat tcatcgcatt tctgaaaaca caatttcttg gtagttttt ttaatgatga    41100 aatttaaaga tttcacaata aactggaggt ttcacataaa gcgcacttac tactacttta    41160
ccttcttcag tagattcttt ttaactcttt caataggaag aggtctgcca tcatggaagt    41220
tggtaaggat tactgcaatg gccgtaagag ttttacccct aaaaatgttt taaaagata   41280 aatggtcaga ttgtgaaacc cagttcacca gaaaaacgtt cccatttta aatcaagtaa    41340 tcgaatatca aatatcattc aaggtcacaa aagtgtactg tatattaatg aaaaatgagt    41400
atttcattta gttagaaaat gctttccccc actgcattat tagggaatta ttaaatgatt    41460
```

```
tacactataa aatactacaa gtatctctga gaagtgtcat tttattgaat gactgctatt   41520
ctacaattct acatttaatc ctgaactctt gatttttatc atgcaactat ttataactac   41580
tcatttgcca tgaagttcgg agctaaagtg attagtaatt ccagtatgca tataatcatt   41640
ttattaaaat ttgacttaaa gataatacca agcttaaaag tcataacttc tccataaagc   41700
ataaaagata tatttcttat gcattttcct aagtggaag tatgtaattt ttcaatattt    41760
actgcagctt aattcatagt tggcaataca ttagtaaatc tctggcaatt ttaaagcagt   41820
gtaaataaca gcagttttca aagtgtggtc cacaggccac tggggatggg gagggtttcc   41880
caggagccct tcacgaaaat gcaaagtcaa aactgttttt ataatactac taagacagac   41940
cttactctgt taacatctgc actaatccta caaaaagccc aaatagcaat ggtcaaaaaa   42000
gtgcctcagc ataaaacaaa gcagttggca ctaaggtata ttagtactag tcatcatatt   42060
cttaactgcc acatacagtt aaaaaaaaaa gttttcctta agaatgttct tggctgggca   42120
cagtggctca ggcctgtaat cccagcactt tgggaggccg aagcaggtgg atcacctgag   42180
gtaggagttc aagaccagcc tggaccaaca cggtgaaacc ccgtctctac taaatacaaa   42240
aaattagcta ggtgtggtgg tgcatgcctg taatcccagc tacttgggag gctaaggaag   42300
gagaatcact tgaacctggg aggcggaggg tgcagtgagc caagactgaa ccattactcc   42360
agcctgggca acaagagtga aactccatct caagaaaaaa aaaaaaaag aagaagaatg    42420 ttcttgacga agcagtacac attaatttta ttaagtctca ttacttcagt acaaatcttt   42480
ttaatattct gtgtagtgaa atggaaacta catattaact acttctgttg catatcaaac   42540
tatgagggtt agctagagaa aaatcactca agatgggagt tataagctca actagtcact   42600
tttttcatgc gacaccattt ttacttgaat gacaactatc aatcacgact gagtgtctga   42660
aagatacttt ctagaaaatg aacaaagtga ggctgtcatc tacaaaggaa acaactgagc   42720
ttgtcaatga taaaatgtga gttttcaata gaaaattaga atgttggaaa agttgtgtgt   42780
gacactatga acatagtgcc ttcccaaaat gtaaatgatt ttctaataac atcagtggta   42840
atattaatga atgtaagttt tggatattgc atatgaaata catcaacatt tagtaggtct   42900
gcccaactca atgaaccaac attttctaaa tgagcaatgc ctggtgttat aaaatcatac   42960
atgggtaaaa tattcattca atgagcaaga tacacaaata gattttaaca aaacagggta   43020
taaaaagctc actgatatga tttagcgttc catattacaa caattaaccct ttaataaact  43080 aatatttatt gaattttgat gcagtatatc aaagaaatct gcaattatct aaaaagctat   43140
tacaatactc ctctctttac agcaacatac cgtcgtaagg acaaattttc ttcatatact   43200
tcaaccaaaa caacctaaca gaacagactg aatgaagaag caggtgagaa ttcagctgcc   43260
atctattcgg ccaaacacag agatgtgcaa aaatgtgaca atgccagttg ttgcaacaaa   43320
aatgttaatg ttttggcata gttatttttc ttttaaaaat atgctattta tgttaacaag   43380
caatgagttt gtactgctat ctttagctac cactgcctaa tactataact actgataaca   43440
gcacacaaaa gcaaaagctc tttgaaatca gtaattttta tgagtagaaa gggttactga   43500
gactgaaaaa tataaaaact gctagtgtaa ggacacataa gtatctattt aatactctgc   43560
ataacacaat atttgtgatg gaatacaatt tcacataaca ttgttttgtc tttacttttt   43620
aaaagaaaac ctatgaaaga caggtcaccc tgaatttcaa agagcaaaga aaattgagaa   43680
acatggccag gcagggtggc tcacatctgt aaccccagca ctttgggagg ccaaggcggg   43740
cggatcactt gaagtcagga gttcaaaacc agcctggcca acgtggtaaa accctgtctc   43800
```

```
tactaaaaat acaaaaatta gctgggcatg gtggcacatg cctgtaatcc cagctatttg   43860
gaagtctgag acaggagaac tgcttgaacc tgggaggcgg aggctgcagt gagccaagat   43920
cgcgtcactg cactccagcc tgggtgacag agcaagactc catctcaaaa aaaaaaaaa    43980 gaaaactgag gaacacatct ttataccact attttaacta aaaactacag gaaaaactgt   44040
gttctacaaa gatagtaaga tctagtccca aactggtacc aacatattcc tatctctttt   44100
tacttcaaaa ttactttcta gaaaatcata atcacaaaat tagatttttat taactaaaga  44160 aaaaaataat taccaaaccc atatcatcag ctaaaattcc tccatggaca ttttctggtc   44220
ggtccttctc agaaaaattt gttattgtgt tatagtataa gtcatttcgc tgttcccaga   44280
atggtggaag ttctttgcta ttttcccgtg acaccatcca agctagagct tgttttttgat 44340 gtggaagcag tggtgtttca atagcctata aataaaaagt cataaagcga aatacattaa   44400
gccattcctt tttcacatgc agatcctgtg attaaacaaa aagtagattc taagtatatt   44460
taaacattct gagtagtctt aaataaaaaa tattggttca ataccctcagc tggttccatt  44520 tcatgggttt tatcatcttc ttttaaatct tcaaacaatt tgtcaaattc tgttttaagc   44580
tacaataaac agcaacaaga aacaatgtaa aacaaactaa ttaaaataat acttgcattt   44640
aagtcagatt tgaaatcatt taattaactg gcgttaatgt caaacgggcc aggagtggtg   44700
gctcatgcca ataatctcag cactttggga gaccaaggtg ggaggatcac ttgagctcag   44760
gagtttgaga ccagcctgga taacatagtg agagatccca tctctacaaa aaaatttta    44820 aaaaattagc caggcatggg ggtgcatgcc tgtagttctg gctcctaggg atgctgagat   44880
gggaggatca cttcagccta gtaggtagag gatagagtga accatgatta tgccactgca   44940
ctccagcctg ggcaagaaag tgagaccctg tcccaaaaaa ttaagaaatt gaaattaaat   45000
taaatttaaa aaccacaaac tagtcaaacg ccaaaaaggc acataaatca actctagaat   45060
tacactactc actgaagagc gaatgaacag gtgctttagt tgttaggagg taaaagaata   45120 taaagaatt ttaagtcccg agtttcagtc acagttttat cacaaataag cttatatgta    45180
agtttcagca agacttgacc tttatggccc catgtcttat tcctataaaa tgaaagggat   45240
gaactaaatt tagattgtct ctaaggttcc ttctgccatt aaaattctgt gatgctatca   45300
gttgtattca aaatattttc tcagtcctac caggtcaatg acattccatt tattattact   45360
gcaataagga acttgccatg cactatagga tactttttatt attatgctaa cttaattgac  45420
tatttaaact aggttagtcc aatttttatat caacatatat gtgatacaga tattttttgaa 45480 aattaacaca tgaacacagc agcagctcag aagaaatcag gccaggtcta aaaaatcaga   45540
agtaaccggg ggcttatcta ccagaaacaa gctcaagtcc ttctaacaat aagcagggta   45600
aatatggtaa ctacaattag tagataaaag gactaacact ggtagataca aacatcaaaa   45660 aagtttttaat gttattttta aattgatctg cattaattac tttatatact tttttttcaa  45720
agaaattcag cataactcat cctaaattac aaattagaca atgtgaagaa tttggagtta   45780
aatctttagc actgcatttg caaaattact gaaaggagtt aagtctcagc ttcaattttt   45840
ttcttaaaat tactacttga acatttaaaa catttcagat acaaaaatat gccgtgcata   45900
aacaggaacg tgtgtgtttt gtatgttggg tacaaatgtt cacgtatgga tttattcctt   45960
atcagtactt tttatataaa atgttaacat atatatattc tatttattct ataacatgtt   46020
tcattataac ttaatatatt tgaagaccac aaatacccac acgtacatat tcatcctgtt   46080
cttttaaata caaacctgca acatttaaaa ttcactttta gattacaaaa taaaagaaaa   46140
gcacacctgt tcagttgtca tctgtactgc agcatgcact ggcatactat agcttggtcc   46200
```

```
agctcttcca gagccccaac cactttccaa attgaatcct aaagctataa tttacaaaat    46260
aaaaagaata aagccatcaa ataaagtagg ttttatctt ttattaagta gcttttaaaa     46320
tatgcattaa cagggctggg tgctgtggct catgcctgta acccaagcac tttgggaggc    46380
caaggcaggt ggtttgcctg agtccagtag tttgagacta gcctgggcaa catggtgaga    46440
ttctgtctct acaaaaaata caaaaattag cagagcgtga tggtgtgcgc ctgtagtccc    46500
agctactcag gaggctcagg tggaaggact gctggagccc aggaggtcaa ggttgcactc    46560
agccactgat cgtggccact gtactctagc ctgggtgaca gagcaagact ctgtctcaaa    46620
atatatacac aaataaataa ataaaacgtg cataacaaac tgcattaaaa gccttgtatt    46680
ttagaggtat tttaaaagct aaatactaaa tcactaaaaa aacaagtaat tccacattat    46740
ttgaacaaac tcttgccaag caatccttt cattcgctat cagaagatta tttttgccta     46800
aaatttatca aaaagaatgt ttaaagtcag gggtttccag atgttaccat tagggaaaat    46860 tagggggaggg tatatatgag acttcattgc atatatactt tttctttaat tttttaata    46920 tccctcact cttactgtgt atattttat gtgtgaatct atttcaatag aggcaaaagg      46980
aaaaatcaga gatttcctca aaaagactcc tgaaaaaag ttgtaccttg gagccttgag     47040
cacaaattag ccaacaaact ccaagagaga ataaatgttt cataatccct gcatcttaca    47100
atatcagaat aatattaagt gaaaccctaa acttactttt tggtgcagga cccaatttaa    47160
atccatgttt cttcaactga tctgaaaccg cttttctatt ttcttctttt ccccaaaaag    47220
tcatatgcag aggcatggta aaagcattgt ttgcaccaaa aggaactacc ctattatatt    47280
tgggagaaaa agaaagggaa atcagaagca ttacttttta tccccactaa gaattagttc    47340 aatatttaa gtgtatcatt tacatttac attgaagtaa agtaataagg aactagttgg      47400
gcagacttga aagaaaaaaa ggaaaagaaa tagaaccata aacaatcaga agggtgattt    47460
ttagaaacag agtgccagaa aaaattgaga aaatggaata aagcagtttt aaaaatgcaa    47520
ggatggcctg taaacaagat tgtaatataa gtaaaataag ttaaatcaaa gggtagagtt    47580
tggctaacgg aaccactgag ggtagtaact cattctgctt ggaaaatggg aaatgcaaga    47640
acttgtgatt cactaagtta ttctcaataa ctgaaaaacc tgataaactg aaaaaggaga    47700
aaacaaagtg agacattatg agcatttatt ttctcttcaa actcacctag gattatatga    47760
atatcctaaa aattagaatt agaatatcaa gatcctaaat attccagata cttaaattga    47820
gatcacaagt acaaatgcct aaaagagaaa aggtaactga aagattgaaa gagtttagaa    47880
aaagaaaaaa gaaacaggtg ataaaactgg gagagcatat gccctagcta aagggagagt    47940
tccagtcaac tattgtcata tggaagtgac aactcatcct gcattgccag atttcccact    48000
tgtcaagaga aaaataagtt ttttgtattt aagaaaataa attaatatgt ataaaatgcg    48060
gacttagcta tttcaataat tagtactgaa cgaaaaaatg tctaaaacac tgcagggcaa    48120
aatgaaattc acctacatca tatcacagaa taccagttta taacctctga tataaacaaa    48180
cacttccagg ctgggcacgg tggctcacgc ctgtaatccc agcattttgg gaggccgagg    48240
cgggcagatc acctgaggtc aggagttcga gacagcctgg ccaacatggc aaatctctgt    48300
ctctactaaa aaatacaaaa attaattggg catggtggca ggcacctgta gctactcagg    48360
aggctaaggc agggagagtt gcttgaaccc tggaggcgga ggttgcagtc agccgagatc    48420
acacaactgc actgcagcct gggcaacaga gtgagacttc gtctcaaaat aaataaataa    48480
ataaataaac aaataaacac ttccaaattc ctaaacctag gtaccaaaag gtttggagaa    48540
```

```
atggaatgta cttcctaata tttgaaccaa ggtctatttt ctccatggta ataattccat   48600
aggaaaatga gaggacaatt gtttgatggc tggggtagta gaagtatgta aaaggagaaa   48660
taaaacattt atttaacacg taccaaaagt acagtgatag aaattgttag catacccttta  48720 taggctctaa caagaagccc taacaagttc aaagatgact ataattcaca attattaaaa   48780
ctaaattctg aaagtacatt acccttcaat ttgtgccaat tgttgtcca tgatataggc    48840 caaagcacct gcaagctctt tctttaaatg gccaacttga tttccattca cattgtttac   48900
tttaattgca ttcttatcat aagggttatt aggatctcgt tgtaatgcaa ccatttcatt   48960
attattaacc taataaaaat gataaacaga taatattaca ttataaataa tagacaataa   49020
ctttgttata ctttatctgg gatttccatt catttttaa tgctactgct aaacactgca    49080
cataagaaaa atatattttc tagacacaaa ctacagaaat attaatatat attattatga   49140
ctccttaata ttatttttct aatctatatt cattaggaag ttaacaaatc cttaatgtct   49200
taaaaaatag tcaaatgtaa actagcaaat tcaaattatc taaaattttc aacatcataa   49260
cttctgaaaa atagccaacc cttattgagc gcttactatg tgccaagcat tggtctaagt   49320
acattgcaca gactgacttt ttaaatcctc acagctctat tgggaggtac tatcattatt   49380
cccattttac aaatgaagaa actgaagcac agaaaagtaa cttgcccaag gtcacaaagc   49440
taaaaggtag cagagctagg atctgaaccc acacagggtg gttcctgagc ctcaattctc   49500
cagaatataa aagtcaggga ataaggcatt tataagtcag gatggaacta ggtaagaaaa   49560
atatatccag ccttcaactc atgccattct gattctactt tattaaaaac tgtatgattt   49620
aacttaaata ttatgatgta tattttaaaa aactgaagga gggtaacaca ataaagaatg   49680
gtagaatgag gactttcaaa aattcctcaa taaaggcaac aaaaaaacta gataaattat   49740
ttgtcagaat caaatgtttc agaacactga gaactaaatc aaaggcttgc agaaatctgg   49800
gtaacattta ttcaagaata aaaagaataa acagctgaat atcagtactt cagtcccatc   49860
cccagcaatc ctgtagcctt taaaaatagc tcacggccag gcacagtagc tcacgccccc   49920
agcactttgg gaggccgagg tgggaagatc acgaggtcaa gagatcaaga ccatcctagc   49980
caacatggtg agacccccgt ctctactaaa aatacaaaaa ttagctgggt gtggtggcac   50040
gcgcctgtag tcctagctac tcgggaggct gaggcaggag aaccacttga acccggcagg   50100
cagaggttgc agtgagccaa gatagtgccc ctgcactcca gcctggtgac agagcgagac   50160
ttcatctcaa aataaataaa taaataaata aataaataaa taaataaata aataaaaata  50220
atagcttgtt gggatcctag gtaaagcctg gcagtcacca gaaaaaaaga gaatggagtt   50280
acagttcttt cagagattca ttcccaaaga actgttattc tcctgaagtt ccccggaaga   50340
ccccacttgc aaggctgact gtatttaacc tctgagctca ccaagtacaa aaaaacctcc   50400
cttgggcgga tgtttgtcaa aacaatttta caggaaagtg ttttaacttc atggctacct   50460
gaggcagtgg ataacagctg aagcaaaaaa acaaaaaggc ttataaagaa gagctaggga   50520
atgagatgtc tgtgagggct ttgaaaagct ccagtgtatt tctggatatc tagaaggccg   50580
taagcaagca cagggctggt atgcatgacc agggctgtgc acattctcaa gaaagacctg   50640
agaaggccct aaacgctcac ctttgcctga acttgagcat ttaaacaagc cagaagtgaa   50700
agctaaagca gagttgtcag gggccttaga gtgttgaagg aatgccctaa catacagaag   50760
ttctcagcaa agaatgtacg atttattagt tccagcacaa tcatcagctg accgctaagc   50820
taaccaagta cagacttcag tgaccacaca cgataaagga tagacatcac agaattaatt   50880
caggaaagtc actaacaaac acacactaat tacaaaactc agcaacaaac cacccctagaa  50940
```

```
gcctaacaaa cacacactaa ttacaaaact cagcaacaac aaaccaccct gatttccaga    51000
gctgccacat tatttaaaat gtcaattttt caagaaaaaa agtacaagac atgcaaaaaa    51060
aataagaaag tatggtctat acacagggaa aaaagcaat caatgtcaac tgtccccaag     51120
aaagtataga tgtttgacat agtagaaaaa gaatttaagt cagttatttt aaatatgttc    51180
aaaggggctg ggcatggtgg ctcacacttg taatcccagc actttaggag gctgaagtgt    51240
gaggatctct tgaggccagg aatttgagac cagcctggga aacatagcaa gaccccattt    51300
ctacaaaata aaaatagaaa aattagccag gtatggtggt acatgcctgt agtcccagct    51360
attcaggagt ctgaggtggg aggactgctt gaatgcagga gttcaaggtt acagtgagct    51420
atgatcacgc cactgcactc cagcctgggt aatagagcaa gaacctatct ctaaaaaatt    51480
aaaaagttca aagacctggc cgggcacagt ggctcacgcc tgtaatccca gcactttggg    51540
aggccgaggt gggcggatca cgaggtcagg agatcgagac catcctggct aacacagtga    51600
aaccccgtct ctactaaaaa tacaaaaaat tagccgggcg aggtggcggg tgcctgtagt    51660
cccagttact cgggaagctg acacaggaga atgatgtgaa cctgggaggc agagcttgca    51720
gtgagccgag atcgtgccac tgcactccag cctgggcgac aaagcaagac tccgtctcaa    51780
aaaaaaaaaa aaataagttc aaagacctaa agcaaatcat ttctttcgac atgaaaacgc    51840
atgtctaaaa gcatggagac gatgtctcac caaacagcaa ttctagagtc aaaaggtaca    51900
ataactgaag aaaaaattca ccagagagac tcaacagcaa atttgagcag gcataagaaa    51960
aatcagcgaa gctgaagata ggtcaattga gattatacaa tctaaggaac aaaaaaatga    52020
cacacaacag agcctcagaa acttgtaata tcaagcatac caacacacat acataagagt    52080
accataagga gaaagagaa agggcagaa aaaatattta agaaataac agccaaaacc        52140
ttcccaattc gatggaaacc actactctac acatataaga agctcaacaa ctccaactaa    52200
aataaactca aagagatcca cacctggtca catcataatc aaactgtcaa agaagtttg     52260
agaccagcct gggcaaaagg gtaacgacag tttctaaaaa aaaaaaaaaa aaaaaaaaa     52320
aaaaaaaaaa aaaattattt aaaaaaataa aaatttttaa gtataatttt ttgtaatttt    52380
tgtcctatct cattaaaaag tataatta taaatctttg ttgataggta tactacatat       52440
ataaagatat aacttggata acagcacaaa ggaaggcaat aggatggagc tgtgagcaaa    52500
ggttttttg gggtttctt tgttgttgtt tttttgagac agagtcttgc tgtcaccagg      52560
ctggagtaca gtcgcacaat ctcggctcac tgcaacctct gactccctag ttcatgcgat    52620
tctcctgcct cagcctccca agtagctggg actacaggca ggtgccacca tgcccagcta    52680
attttttgtat ttttagtaga gatggggttt caccatgttg gccaggatgg tctcaatctc    52740
ctaacctcgt gatccactca ccttggcctc ccaaagcgct gggattacag gcgtgagcca    52800
ccatgccca tgcccagcca caagttttt tatatactgt taagttggca ctaatccaaa       52860
ctaggttctt ataaattaag ttgttaattg taatccctaa agcaatcata agtaactcaa    52920
aatatatagt aaaagaaaca agggaattaa aatagtacac taaaaaaaaa aatctattta    52980
acataaaaat gagtattgga ggccagaccc aaatgccaca tattgtatca tttcatttac    53040
gtgaaatgtc aagaggaggt aaatccatat acacaggaag aagactgatt catggttgcc    53100
agggactgag gggtagagat aatgggagtg actacaaatg ggaatgaggt ttcttttggg    53160
agtaatgaaa atgttttgga actagattgt agggatggtt gcacaacctt gtgagtattc    53220
taaaaactac tcaactgtac actttaaaat ggtaaatttt ataataaatg tatctcaatt    53280
```

```
ttaaaaaatt ccttgaaaat atacaagaaa gctgcttcaa acctctccca gcatgtctac    53340
tgactcaaga gattacagcc agaactaaac agagtattag acagatattc atctctagac    53400
ttttagagat attatctatg aggcagagct atgttctctc ccagtcgcca ccctctgcc     53460 actgcctaca ggatgatctt ttttaaaccg gattatgcaa atcctagaaa atacataacc    53520
aaaataaaaa agcagggcac aaaactaaca atttttgagc atttcatctc aaggtattac    53580
ataattgtaa tttatcataa taagctatca ttaattacaa ttagttaact gtcgttacaa    53640
ataagtaatt actagaattt taaataaaat atatatgagc caaatatttg gagactataa    53700
aaacaaaaac atggtcccag cagcaagaaa aaacaggaca tataaaaaaa caaaagaca     53760 aagacaagaa taacaaaagg aatgagaatt aatcataaca gtatagtcat accccgcata    53820
acaacatttc agcaatgaca gaccacatgc attatgcaac agttgttcca caagattata    53880
atggggctgc cctatagaag tgtaccattt ttcatatttt atacaatatt tttactgtac    53940
ttttttcatg ttatatatgc ttaaatacac aaatgtgtta caattgccca cagtattcag    54000
taaagtaaca tcttgttcac tctgtttcca caaagaaatc acctaacact tttctcagaa    54060
agtatcttca ttgttaagca acacataact gtattttaaa atagaaaaag aaataaacca    54120
cattataaaa taaagccttt gatgggtcaa aaaataaact taaccatatg cttattgaaa    54180
acacactaaa aaaaaaaaaa caaaaaataa aaatgaaata gaataagaa acaccagag     54240 ttaaaaataa agaatgctac tacataacaa aacgtggtgg ctaaaggcaa cgcaatactt    54300
aacacgttta aagattaaaa gattaaatga ctcaaattaa gtgctcaaat cgcaagtcca    54360
acagaaatga aaagaaaata aatctaagta gaaaaaccga atgtaagagt aattattaag    54420
ccaagaaaca caatcattaa gaaaaattca agagagcctg ccttgaaaag aaataatgtc    54480
atagctaatc aataaaaaag acacgaatgt gtaacacaaa gaataaaaac aggaatataa    54540 tcacctttt aaaaaagttt ttaaaaagtt taatggagcc aataaggcat ataaaattat    54600
gttctggcag acattaaaaa aatggcacat tttatcaaaa tttgacaatt cagagtaaag    54660
ggtactgaaa tttaaggttc agagcaccaa cttaaaacaa ccaaaaaaat ggttattcaa    54720
cttggaaaga gtaactagaa ccaaggcata aagggagtt taagtatgtg ttcctccaat    54780 tcaaatcct tcaggaatag gagttctggc cacttgtgag caacacatca taccaccaaa    54840
ccccaattcc agaaaattac agttacaatt ttataaggat aaatgattac tatgcacaat    54900
tctatgggaa taagtttgaa tatctaaata aaatggatgc ttttcttcaa aaatgtaact    54960
aaccaaaata gaccaaagaa gtacctaaat tatgctgagt gaaaaacgcc agacttaaaa    55020
tagtacatac tgtagaattc aatgtatatg aagttctaga ataggcaaaa cttatttata    55080
gtgatagaag acttgtgtgg ccgggcgcag tggctcacac ctgtaatccc agcactttgg    55140
gaggccgagg cgggcggatc acgaggtcag gagatacaga ccatcctggc taacacggtg    55200
aaaccccgtc tctaccaaaa atacaaaaaa attagccggg catggtggca ggcgcctgta    55260
gtcccagcta cttgggaggc tgaggcagga gaatggcatg aacttgggag gcggagcttg    55320
caatgagccg agatcccgcc actgcgctcc agcctgagaa acagagcgag actccgtctc    55380
aaaaaaaaca aaaaaaaaga aagaaatga gactcgtggc tgcctagggc aggaacaggg    55440 aaaatgaat gcaataggat acaagatact ttgagggaga cggatacaat ctgtatcttg    55500
attggggtag tagttatcag gtatacatct ttgtcaaaac actaggatca tacatttaaa    55560
atatgtacat tttatcatac gtaaaccaca tctcaataaa gtagaaaaaa attaaaata    55620 acaagtatgc aaagatagta tctcaatttt tattattttt ataatagtga ttaactcaaa    55680
```

```
aatgtccatc aacaaggaaa ttataagtcc aatatagatg atattcctaa tcacattagg   55740
cataatatga tctcattttt attaatacat aatatgattc caatttacat gcacatgctc   55800
acagaaacaa gtgtagaaga taagttatgg ttctggatga tagacttcag aagatttaat   55860 gccttttag ccatttaaaa ataatgaacg tggctgggcg cggtggctca tgcctgtaat    55920
```



```
aatgtccatc aacaaggaaa ttataagtcc aatatagatg atattcctaa tcacattagg   55740
cataatatga tctcattttt attaatacat aatatgattc caatttacat gcacatgctc   55800
acagaaacaa gtgtagaaga taagttatgg ttctggatga tagacttcag aagatttaat   55860 gccttttag  ccatttaaaa ataatgaacg tggctgggcg cggtggctca tgcctgtaat   55920
cccagcactt tggaaggccg aggtgagtgg atcacctgag gtcagggggtt caagaccagc  55980 ctgaccaaca tggcaaaacc tcatctctcc taaatacaaa aaattagctg gcatgatgg    56040 cgcatgcctg taatcccagc tacttaggag gctgttgcag gagaaccgct tgaacctggg   56100
aggcggaggt tgcagtgagc caagattgca ccattgcact ccagcctggg caatgcaagc   56160
aagactccgt ttcaaaaaaa aaacaaaaac aaataaaaga acatgcatta attataaaat   56220
aaatgatatc tcaacatagt gttcctggaa aaaataaaa tttaaagtat atatatttgg    56280
caaaataaga aaactgatga ttactttttta tcaacacaca ctagagttta ccgaagtcat   56340
agagattatt ctcagatcaa aaatactgat tgttctaaga tcaataacta ccataatcta   56400
gtatttcatg gtggtataaa ataattatcg aaagcaatgt aagttttgaa aaattagcac   56460
aaatctgaaa cagaaaagct cagaaatgca tatgagagcc agagaatata tagatgtgaa   56520
ataagaactg atagagttca agaatctatt tgaaaaaatt agaggccggg tgcagcatcc   56580
cagcacttgg agaggccaag gcggacggat cacttgagcc caggagttcc agatcagcct   56640
ggacaacatg ccaaaaccta aaaaaaaata caaaaaaaaa aaatacaaaa attagctggg   56700
tatggtggtg aacgccagca gtcccagcta ctcaggaggc tgaattggga gaattgcttg   56760
agtctgggag gcagagattg cagtgaggcc agatcaggcc actgcactcc agcctgggca   56820
acaaaacgaa acttggtctc aaaaaaaag aaaaaaaaaa aaatccaatt cacttaagtg    56880
aaagaaaatc acactggcct gagaattcta tgcaacatta ggatatggag attttattac   56940
aaagatttta ttacaaagat atattacaaa gattttaaat tcagcccaac tgtcattaag   57000
tccttcataa ctttcatttt atgaaactgt cattcataaa atgccacaag tatgaaaata   57060
taaaaactta ggaatatatg tctcttccta aggaatctcc tagacaacac atttcagaca   57120 atcaaaaaaac aatttgaaac gttccaatgt aaaggaaata caggagaaaa acaaatccag   57180
aacatgaaac tcctaaggaa tctcctgtcg aacatgcttc agacacccta ttgagaagct   57240
taaacataag aaacatacgg agaaatgaaa gaataaaatc cagaagattc cacaaaacga   57300
tctccttttt gcaacaaatc gatgacatga acaaggcgct ggggtgtggg ggtgggggtgc   57360 tacccataat aaccaaacat aacgcactga ggccaagcat attggctcat tcctgtaatc   57420
ccaacactct gggaggctga ggtgggaggg tcacttaagg tatttgttat ttttttgcgta   57480 caaatattta actaacttaa agtaaaataa agattaaccg cacacatcac ctgcgaattc   57540
tcttattttc taggttaacg ccagaaatat aatcaaaatt taattatcta ctattatact   57600
cactactccc gtgtaatagc gtagtccaac cacatgacct ctcaaacttc caaataaaac   57660
ggaatctact tcttcatcac tagttagaaa gtcatctgga gggataacat cttggaattc   57720
aaaacgtgga agaaagttg gatatgagag gcgtggaaaa tttccatgaa ctccatactg    57780
gacagtctgc aagtacttcc aaactggatc cctattttt tttaaaggca aagaaaaaca    57840
atataatatt taagtatttc caaagaccat atgagtagtt ttctcatgct ttacttcagc   57900
aaatgaaatc ttcatgggaa atcacggtaa agattaatag ttactctcgt taaagcagga   57960
attgcagtga gtggagaagg cttctaggaa ctctacctgt tttcaatatt ggctcttcta   58020
```

-continued

```
cctgcccct  aggtattcaa  aatgaaaagc  ctagtcagag  ttcactaacc  tctttcccag   58080
tgaaaatcat  ctaaattgat  atgtatatga  tgtctgtaac  tacaattatg  ggccggatgc   58140
ggtggctcac  gcctggaatc  ccagcacttt  gggaggcaga  ggcaggtgga  tcacctgagg   58200
tcaggaattt  gagaccaacc  tggccaacat  tgtgaaaccc  tgtctactac  aaatacaaaa   58260
attagccagg  cgtggtggcg  cccatatgta  atcccagcta  ctcggaggc   tgaggcagga   58320
gaatcacttg  aacccgggag  gcgtaggttg  cagcgagccg  agattgtgcc  actgcactcc   58380
agcctggacg  acagagcgag  actccatgtc  aaaaaataa   tttaaaaaat  gaaatcatat   58440
gccaaaattt  caatagggat  tgagctatat  aaaagactta  taaaaataca  actattaatg   58500
taccagaagt  tgtttataat  tttccagaaa  atacatccag  catccatcac  tgtaactccc   58560
tgcgagcaga  acacctattc  tggtatccaa  accacgccac  cgtgggaaat  tggcccaag   58620
ccacccgtac  ccgccttccg  tcgccggttt  aagcataacc  caaacccat   taggtgtaac   58680
tgtttcggga  atgaccataa  ataccaattt  ggacaatgaa  aagtgaaggg  gagtctactg   58740
gagcattgca  aaaagtttcc  attctcctaa  gaacagtcgc  ttatttgcga  tgcgttttcc   58800
ttgcaagtgg  cgcatatctc  tactagcgcc  tctgcaaata  cttatctgca  cgtctgtgca   58860
tacagataag  ctgtgagcca  cttggggaca  aggactgtct  tactcggccc  tccaccgagc   58920
acaatgcctg  gcgcacagtg  ggtatctaat  ggatgttttg  ttaaataaag  cactggccga   58980
gatgctttaa  gccccaggcc  ccccacagtc  ggtgacagag  atttcccaag  tccctaacac   59040
gggactcgcc  ctaggagccc  ctactcgcca  gcgaagacaa  tgcatttatt  tctccggcgg   59100
ccacatatgc  gaccaacaga  acgaatacag  ctgcacaaat  cgcccaggga  acgcagagga   59160
acgcggggaa  ggtcaggttc  atttggggac  gcctccaggc  cgttagaccg  agcgccccac   59220
cccctccgcc  cccttcacct  cttgaacatc  caggacatgg  cgctgagtgg  gatgacaaga   59280
ggagcgcctc  ggctcccctg  gatcgttttc  gagccgcctc  gatacgcctc  cttccaggcc   59340
ccgcagccct  gaagccgggg  acaaattccg  agcgccggat  caggagcgca  cgactgaaag   59400
gtaagtcgcc  gcgagtccag  tcagacgtcg  acgccgtctc  cttctgcaac  aatctgggag   59460
accagcgtcg  ctctgtgact  ggcactagga  aagcccaatc  acgaagagga  gagtgcggag   59520
ccaaaccagt  cagagcacag  aagggagggc  aactccgccc  cgctgccatt  caaagacggc   59580
gggggtccg   ggctgcaagg  gtggttccat  ccgggttctt  cccgccccc   aaggcgggcg   59640
cgcgggaaag  ccacgaggcc  ccaggagtgc  gactgcggtg  cctgcggtgc  cggtgttttg   59700
tttgattccc  tgcctcaaac  ggagggaaac  gaccttcctt  tatcctacga  gtcctaagac   59760
tgaaccccat  tctaaaggct  ctaccgtatc  cttcctctta  ttttcttctc  atctaatgtg   59820
gcacataata  gggccttata  ctaaaggagc  tccacggttt  acgagaccta  gagctaccgg   59880
cgagatactt  tacttcattc  cctgtggtga  accgtgggga  ctttcgctcc  aaattttcat   59940
gttaagcctc  agcgtatgca  tgagacacaa  cgagtttgga  aaatcttaaa  tggaacttag   60000
agtccctcc   ccacctcttt  ttgttatttt  taaggaaaat  tttcctttct  tggtgcagga   60060
aacccatcac  atgtttatta  cagctatggg  ggcgtttgcc  tgaaatggtg  gacgggacca   60120
ttttccccgt  gggcacttgg  ctgctccagc  caagagggg   aggcccttgt  tttcctcaag   60180
gaactgcaga  ggggcgctct  gaggccctcc  atggctctct  ttccagagtc  tgaggtgacc   60240
ggaaggagaa  tgcggccctg  ggaccgtcaa  ccttggacca  gctgcagccg  acgcctggca   60300
gggctggtcg  ctttgcgttg  aggaggctgc  tgtcccgaa   gctggccttt  taatcgcaca   60360
gggcaggaag  ctggtggtgg  cgcccagctg  cacaggcggc  accatgtaac  tgccagataa   60420
```

```
tacttgcgcg tcacagagag gtccatgtta cacgcctgtc agcacaataa tattaggtgg    60480
tcagcttttc ttttttcttt ttttgtttt tttttcttt ttattgagat ggagtcttgc    60540
tctgtccccc aggctggagt gcaatggggg tgatcttggc tcactgcaac ctccgcctcc    60600
cggattcaag cgattctcct gcctcagcct ccggagtagc cgggattgca ggagcccgcc    60660
accacgccca gctaattttt gtattttag tagagacggg gtttcaccat attggccagg    60720
ctggtcttga actcctgacc tcaggtgatc cgcccgcctc ggcctcccag agtgctggga    60780
ttacaggcat gagccaccgt gccaggccgg tagtcagctt tcaagacac atttgttcat    60840 tatcgtaaat aaactgtagt gatctctaat catgaaccat ggatgagcaa tagaatttga    60900
aacaatgtat tatttcattt gaccaaagtt gatgaggaag ataaagacaa tggcatttca    60960 aattattta attgttgtat gttcttcttg aagtgtgttg aggcaaatgg caatacagtt    61020
cagcttttag tatgccagat tttaaataaa ttcttggaaa atatgccaga aattgctcaa    61080
attgatgttt tgtaagagta agaaagtcat gctcactaga caaagaaaaa attccaaata    61140
tgagaacata gctcttttcag acttaagact ggccaggcgc aatggctcac acctataatc    61200
ccagcacttt gggaggccga gttgggtgga tcacctgagg tcaggagttc gagaccagcc    61260
tggccaacat ggtgaaagcc tgactctact aagaaaatac aaaaattaag cagacgtggt    61320
ggcacgcacc tgtagtccta gctacttggg aggctgaggc aggagaatcg cttgaaccag    61380
ggagacatgg gttgcagtga gccgagatca agccactgca ctccagcctg agcaacagag    61440
cgagactcca tctcaaaaaa ataaaaagac ttaagatcta tgaataatga ctgtcccatg    61500
gttaaagaat gtgctttgaa tgaactaaaa tttgctattt aaaggaatgg tatggaaagg    61560
aaaggaatcc aaaatttctc catccagcca cttcccagtc acaaacacac ttctcatctg    61620
cacccccagc cacacacaca cacatgcccg cgcgcgcgca cacacacaca cacacacaca    61680
cacacacaga acctttatgc aaattaatca tgtcatgtca ctccctgtt tgattcagtg    61740 agcctgaaat ccaagaatgg catatgtggc tcttcctccc acagtatgtt ttctctatgt    61800
tatcaatatt tcacatccca gaaccaggag taaaacattc tttcccttaa tcattctttg    61860
ttttatattt aaagatcaag tacaatttgt actagtttga ttaaaatgtt acagcaatta    61920
caatttcaaa actattatac taaataatgt tttctgaaaa attaactttt ttggtttttt    61980
cttgatttat tctgataaca gcatcacaag tagatatgaa aaatgaacac ttgtaactgg    62040
aaaatgaact gtagggtggc ttgtgggtt tggctggtga gtaagaagga aagtggcact    62100
aaaaggacgg tggggaagat aagggccagg ttacatagga acttaagagt ctccagtaaa    62160
atttgtgttt taactgcaat ggaaagccat tgaatgtttc gagcaggagg ataacgactt    62220
gatttaggct tttaaaaatg ctggcagctc tgtggagaat tacaggaaac aaggatagaa    62280
gcaactgata gaaaattatt gtgttcagat aagagatggt ggtggcttgg aaagggaagg    62340
tgatgaagcc aagagaacca aaatgttcac tgataaattt aggtaggaat ggtatggaaa    62400
ggaaaggaat ccaaaatttc tccagccagc cacttcccag tcacaaacac acttctcatc    62460
tgcaccccta gccacacaca cacatgcccg tgcacacaca cacacacaca cacacagaga   62520
```

<210> SEQ ID NO 40
<211> LENGTH: 27
<212> TYPE: DNA
<213> ORGANISM: Artificial Sequence
<220> FEATURE:
<223> OTHER INFORMATION: primer

<400> SEQUENCE: 40
tacgccactt acaaaaaaaa cgcatcg                                27

<210> SEQ ID NO 41
<211> LENGTH: 31
<212> TYPE: DNA
<213> ORGANISM: Artificial Sequence
<220> FEATURE:
<223> OTHER INFORMATION: primer

<400> SEQUENCE: 41
tttaagttat tcgtattcgt ttttcgtcgt c                           31

<210> SEQ ID NO 42
<211> LENGTH: 31
<212> TYPE: DNA
<213> ORGANISM: Artificial Sequence
<220> FEATURE:
<223> OTHER INFORMATION: primer

<400> SEQUENCE: 42
aatatacacc acttacaaaa aaaacacatc a                           31

<210> SEQ ID NO 43
<211> LENGTH: 34
<212> TYPE: DNA
<213> ORGANISM: Artificial Sequence
<220> FEATURE:
<223> OTHER INFORMATION: primer

<400> SEQUENCE: 43
ggttttaagt tatttgtatt tgttttttgt tgtt                        34

<210> SEQ ID NO 44
<211> LENGTH: 22
<212> TYPE: DNA
<213> ORGANISM: Artificial Sequence
<220> FEATURE:
<223> OTHER INFORMATION: primer

<400> SEQUENCE: 44
gctcctcttg tcatcccact ca                                     22

<210> SEQ ID NO 45
<211> LENGTH: 25
<212> TYPE: DNA
<213> ORGANISM: Artificial Sequence
<220> FEATURE:
<223> OTHER INFORMATION: primer

<400> SEQUENCE: 45
cgtctttgct tagtccatct gcctt                                  25

<210> SEQ ID NO 46
<211> LENGTH: 21
<212> TYPE: DNA
<213> ORGANISM: Artificial Sequence
<220> FEATURE:
<223> OTHER INFORMATION: primer

<400> SEQUENCE: 46
cgatggtcta tgaaacttgg a                                      21

<210> SEQ ID NO 47
<211> LENGTH: 27

```
<212> TYPE: DNA
<213> ORGANISM: Artificial Sequence
<220> FEATURE:
<223> OTHER INFORMATION: primer

<400> SEQUENCE: 47
gaaattgtgt cagtaatacc tcttcac                                27

<210> SEQ ID NO 48
<211> LENGTH: 24
<212> TYPE: DNA
<213> ORGANISM: Artificial Sequence
<220> FEATURE:
<223> OTHER INFORMATION: primer

<400> SEQUENCE: 48
tggggtttcg tggttttttc gcgc                                   24

<210> SEQ ID NO 49
<211> LENGTH: 25
<212> TYPE: DNA
<213> ORGANISM: Artificial Sequence
<220> FEATURE:
<223> OTHER INFORMATION: primer

<400> SEQUENCE: 49
ccgcgaatcc aatcaaacgt cgacg                                  25

<210> SEQ ID NO 50
<211> LENGTH: 29
<212> TYPE: DNA
<213> ORGANISM: Artificial Sequence
<220> FEATURE:
<223> OTHER INFORMATION: primer

<400> SEQUENCE: 50
atttttgggg ttttgtggtt tttttgtgt                              29

<210> SEQ ID NO 51
<211> LENGTH: 29
<212> TYPE: DNA
<213> ORGANISM: Artificial Sequence
<220> FEATURE:
<223> OTHER INFORMATION: primer

<400> SEQUENCE: 51
atcaccacaa atccaatcaa acatcaaca                              29
```

METHODS AND COMPOSITIONS FOR DETECTING COLON CANCERS

CROSS-REFERENCE TO RELATED APPLICATIONS

This application claims the benefit of priority of U.S. Provisional Application No. 60/327,537, filed Oct. 5, 2001, the specification of which is incorporated by reference herein in its entirety.

BACKGROUND

In 2001, over 1.2 million new cases of human cancer will be diagnosed and over 0.5 million people will die from cancer (American Cancer Society estimate). Despite this, more people than ever are living with and surviving cancer. In 1997, for example, approximately 8.9 million living Americans had a history of cancer (National Cancer Institute estimate). People are more likely to survive cancer if the disease is diagnosed at an early stage of development, since treatment at that time is more likely to be successful. Early detection depends upon availability of high-quality methods. Such methods are also useful for determining patient prognosis, selecting therapy, monitoring response to therapy and selecting patients for additional therapy. Consequently, there is a need for cancer diagnostic methods that are specific, accurate, minimally invasive, technically simple and inexpensive.

Colorectal cancer (i.e., cancer of the colon or rectum) is one particularly important type of human cancer. Colorectal cancer is the second most common cause of cancer mortality in adult Americans (Landis, et al., 1999, CA Cancer J Clin, 49:8-31). Approximately 40% of individuals with colorectal cancer die. In 2001, it is estimated that there will be 135,400 new cases of colorectal cancer (98,200 cases of colon and 37,200 cases of rectal cancer) and 56,700 deaths (48,000 colon cancer and 8,800 rectal cancer deaths) from the disease (American Cancer Society). As with other cancers, these rates can be decreased by improved methods for diagnosis.

Although methods for detecting colon cancer exist, the methods are not ideal. Digital rectal exams (i.e., manual probing of rectum by a physician), for example, although relatively inexpensive, are unpleasant and can be inaccurate. Fecal occult blood testing (i.e., detection of blood in stool) is nonspecific because blood in the stool has multiple causes. Colonoscopy and sigmoidoscopy (i.e., direct examination of the colon with a flexible viewing instrument) are both uncomfortable for the patient and expensive. Double-contrast barium enema (i.e., taking X-rays of barium-filled colon) is also an expensive procedure, usually performed by a radiologist.

Because of the disadvantages of existing methods for detecting colon cancer, new methods are needed.

SUMMARY OF THE INVENTION

In accordance with the present invention, new methods are provided for detection of colon cancer. In one aspect, the method comprises assaying for the presence of differentially methylated HLTF nucleotide sequences in a tissue sample or a bodily fluid sample from a subject. Preferred bodily fluids include blood, serum, plasma, a blood-derived fraction, stool, colonic effluent or urine. In one embodiment, the method involves restriction enzyme/methylation-sensitive PCR. In another embodiment, the method comprises reacting DNA from the sample with a chemical compound that converts non-methylated cytosine bases (also called "conversion-sensitive" cytosines), but not methylated cytosine bases, to a different nucleotide base. In a preferred embodiment, the chemical compound is sodium bisulfite, which converts unmethylated cytosine bases to uracil. The compound-converted DNA is then amplified using a methylation-sensitive polymerase chain reaction (MSP) employing primers that amplify the compound-converted DNA template if cytosine bases within CpG dinucleotides of the DNA from the sample are methylated. Production of a PCR product indicates that the subject has colon cancer. Other methods for assaying for the presence of methylated DNA are known in the art.

In another aspect, the method comprises assaying for decreased levels of an HLTF transcript in the sample. Examples of such assays include RT-PCR assays which employ primers that derived from the coding sequence of HLTF.

In another aspect, the present invention provides a detection method for prognosis of a colon cancer in a subject known to have or suspected of having colon cancer. Such method comprises assaying for the presence of differentially methylated HLTF nucleotide sequences in a tissue sample or bodily fluid from the subject. In certain cases, presence of differentially methylated HLTF nucleotide sequences in the tissue sample bodily fluid indicates that the subject is a good candidate for a particular therapy. In other cases, presence of the differentially methylated HLTF nucleotide sequences in the tissue sample or bodily fluid indicates that the colon cancer has a poor prognosis or the subject is a candidate for more aggressive therapy.

In another aspect, the present invention provides a method for monitoring over time the status of colon cancer in a subject. The method comprises assaying for the presence of differentially methylated HLTF nucleotide sequences in a tissue sample or bodily fluid taken from the subject at a first time and in a corresponding bodily fluid taken from the subject at a second time. Absence of differentially methylated HLTF nucleotide sequences from the bodily fluid taken at the first time and presence of differentially methylated HLTF nucleotide sequences in the bodily fluid taken at the second time indicates that the cancer is progressing. Presence of differentially methylated HLTF nucleotide sequences in the tissue sample or bodily fluid taken at the first time and absence of differentially methylated HLTF nucleotide sequences from the tissue sample or bodily fluid taken at the second time indicates that the cancer is regressing.

In another aspect the present invention provides a method for evaluating therapy in a subject suspected of having or having colon cancer. The method comprises assaying for the presence of methylated HLTF promoter DNA in a tissue sample or bodily fluid taken from the subject prior to therapy and a corresponding bodily fluid taken from the subject during or following therapy. Loss of methylated HLTF promoter DNA or a decrease in methylation of HLTF promoter DNA in the sample taken after or during therapy as compared to the levels or HLTF promoter DNA in the sample taken before therapy is indicative of a positive effect of the therapy on cancer regression in the treated subject The present invention also provides nucleotide primer sequences for use in the methylation-sensitive PCR assay.

The present invention also provides a method of inhibiting or reducing growth of colon cancer cells. The method comprises increasing the levels of the protein encoded by HLTF in colon cancer cells. In one embodiment, the cells are contacted with the HLTF protein or a biologically active equivalent or fragment thereof under conditions permitting uptake of the protein or fragment. In another embodiment, the cells are contacted with a nucleic acid encoding the HLTF protein and (ii) a promoter active in the cancer cell, wherein the promoter is operably linked to the region encoding the HLTF protein, under conditions permitting the uptake of the nucleic acid by the cancer cell. In another embodiment, the method comprises demethylating the methylated HLTF promoter DNA.

In one aspect, the application provides isolated or recombinant HLTF nucleotide sequences that are at least 80%, 85%, 90%, 95%, 98%, 99% or identical to the nucleotide sequence of any one of SEQ ID NOs: 2-4 and 21, fragments of said sequences that are 10, 15, 20, 25, 50, 100, or 150 base pairs in length wherein the HLTF nucleotide sequences are differentially methylated in an HLTF-associated disease cell.

BRIEF DESCRIPTION OF THE DRAWINGS

FIG. 2 shows methylation of HLTF 5' genomic sequence. A. Diagram of the HLTF 5' genomic region. CpG sites are shown with circles. Shaded circles represent CpG sites that are tested in MS-PCR assays. Hatched circles represent CpG sites that overlap HpaII restriction sites. B. MS-PCR assay of the HLTF 5' genomic sequence. Shown are the results of MS-PCR assay of the HLTF 5' genomic sequence by using primers specific for amplification of either methylated (M) or unmethylated (U) templates. C. HLTF MS-PCR of matched cell lines and tissues. Shown are the results of HLTF MS-PCR assay of colon cancer cell lines (C), matched antecedent tumor tissue (T) or matched normal colon mucosa (N).

FIG. 6 illustrates correlation of HLTF methylation with the CpG island methylator phenotype (i.e., CIMP status) and with hMLH1 methylation. A. Shown are the numbers of primary colon cancers in each of the categories defined by combined HLTF methylation and CIMP status. B. Shown are the numbers of colon cancers (tumors and cell lines) in each category defined by combined hMLH1 and HLTF methylation status.

FIG. 14 shows the amino acid sequence (SEQ ID NO: 1) of human HLTF protein.

Figure 15:
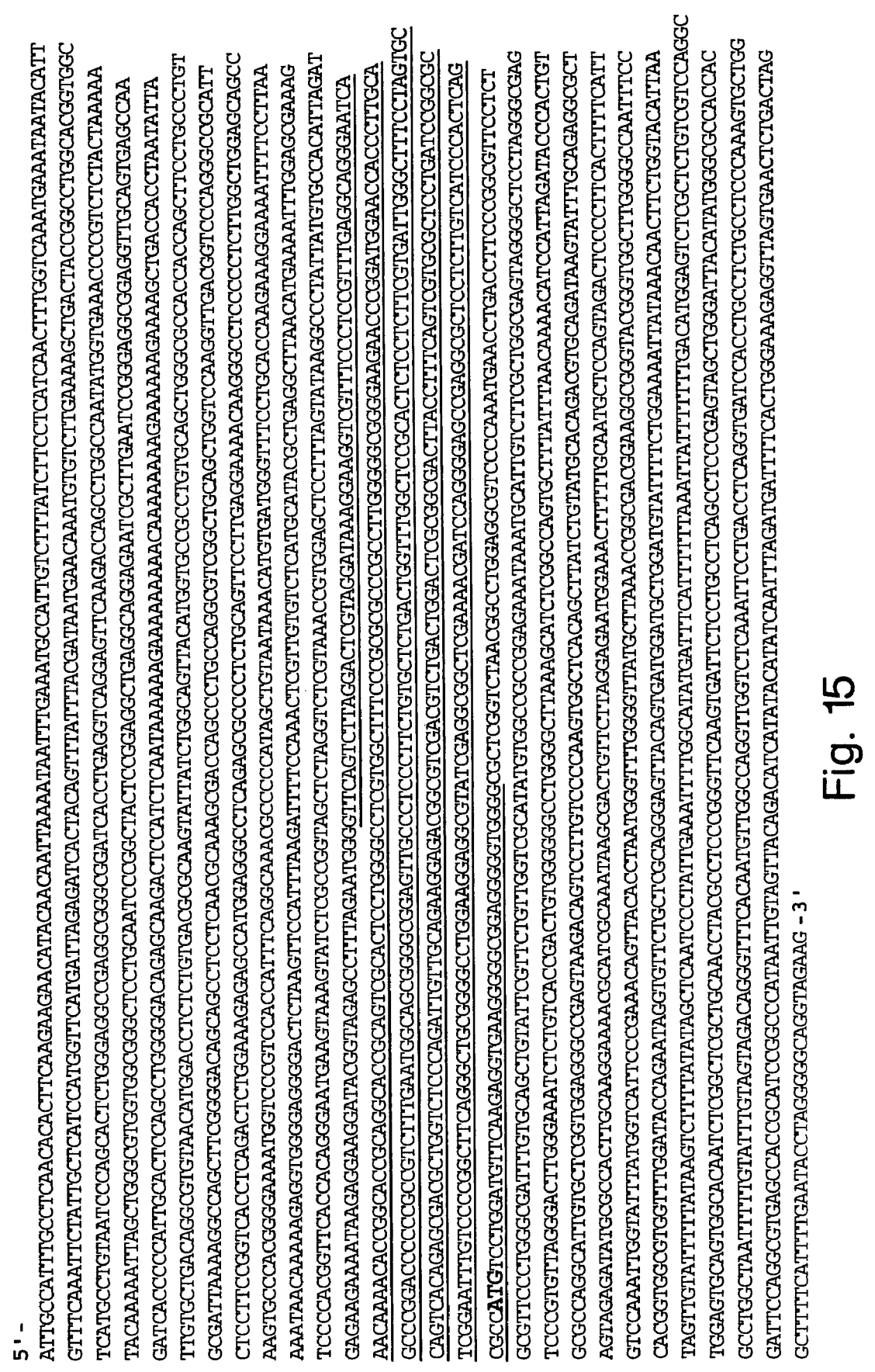

FIG. 15 shows the 5' genomic sequence of human HLTF gene (residues 1 to 3000, sense strand, SEQ ID NO: 2). The underlined region (residues 1250-1800, SEQ ID NO: 4) was tested by methylation specific PCR and by sensitivity to HpaII digestion. Alu1 and Alu2 regions are in bold. The start ATG is underlined and in bold, with the A at position 1757. There is currently one complete GeneBank entry "AC021059: *Homo sapiens* 3 BAC RP11-464E15 (Roswell Park Cancer Institute Human BAC Library) complete sequence", which contains the human HLTF gene. Residues 1-3000 correspond to positions 119396-116395 of this genomic clone (AC021059), and the A of the ATG relative to AC020159 will be 117640.

FIG. 16 shows the sequence of residue 600-2600 (SEQ ID NO: 3) that includes the differentially methylated region of residues 1200-2600, and a portion of the non-Alu constitutively methylated region within residues 600-1200.

FIG. 18 shows the sequences following bisulfite conversion of DNA derived from the sense strand of methylated template (top panel) and unmethylated template (bottom panel) of the HLTF 5' genomic sequence residues 1250-1800. CpG dinucleotides that are sites of cytosine methylation are in bold. Those CpG sites that are HpaII restriction sites are shown in italic and underlined. Sequences that are complementary to PCR primers that were used to selectively amplify the methylated but not unmethylated HLTF DNA after digestion with HpaII are shown as bold arrows. Those CpG site that are tested by specific MS-PCR assays described as examples in this invention are shown underlined. Sequences that were used to design specific MS-PCR primers that amplified methylated but not unmethylated templates following conversion with bisulfite are shown in smaller arrows.

FIG. 19 shows the corresponding complementary strands of the bisulfite-converted HLTF DNA base pairs 1250-1800 (methylated and unmethylated templates, as shown in FIG. 18). CpG dinucleotides that are sites of cytosine methylation are in bold. Those CpG sites that are HpaII restriction sites are shown in italic and underlined. Sequences that are complementary to PCR primers that were used to selectively amplify the methylated but not unmethylated HLTF DNA after digestion with HpaII are shown as bold arrows. Those CpG site that are tested by specific MS-PCR assays described as examples in this invention are shown underlined. Sequences that were used to design specific MS-PCR primers that amplified methylated but not unmethylated templates following conversion with bisulfite are shown in smaller arrows.

FIG. 21 shows the HLTF 5' genomic sequence (residues 1200-2500, sense strand, SEQ ID NO: 21). The region is differentially methylated as shown in FIG. 10.

FIG. 22 shows the sequence (SEQ ID NO: 22), derived from bisulfite conversion of DNA derived from the sense strand of methylated template of the HLTF 5' genomic sequence residues 1200-2500 (i.e., SEQ ID NO: 21). The underlined region (residues 1250-1800) was tested by MSP assay. The start ATG is in bold.

FIG. 23 shows the sequence (SEQ ID NO: 23), derived from bisulfite conversion of DNA derived from the sense strand of unmethylated template of the HLTF 5' genomic sequence residues 1200-2500 (i.e., SEQ ID NO: 21). The underlined region (residues 1250-1800) was tested by MSP assay. The start ATG is in bold.

Figure 24:
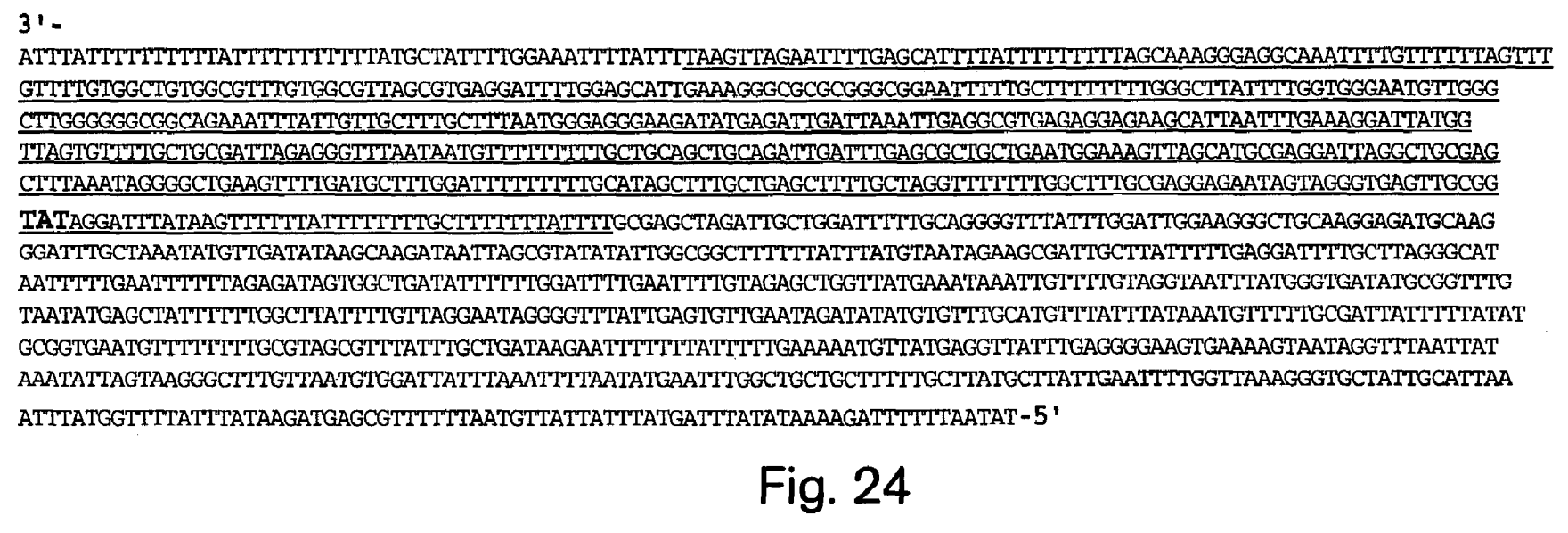

FIG. 24 shows the sequence (SEQ ID NO: 24), derived from bisulfite conversion of DNA derived from the antisense strand of methylated template of the HLTF 5' genomic sequence residues 1200-2500 (i.e., SEQ ID NO: 21). The underlined region (residues 1250-1800) was tested by MSP assay. The start ATG is in bold.

FIG. 25 shows the sequence (SEQ ID NO: 25), derived from bisulfite conversion of DNA derived from the antisense strand of unmethylated template of the HLTF 5' genomic sequence residues 1200-2500 (i.e., SEQ ID NO: 21). The underlined region (residues 1250-1800) was tested by MSP assay. The start ATG is in bold.

FIG. 27 shows the sequences of the proposed primer sets 4-8. MSP4, MSP5, MSP7, and MSP8 are primer sets for amplifying bisulfite-converted antisense sequences of the duplex methylated HLTF DNA, including: forward primer IP-HLTF1581MF(ASS) (SEQ ID NO: 26) and reverse primer 13P-HLTF1713MR(ASS) (SEQ ID NO: 27); forward primer 1P-HLTF1581MF(ASS) (SEQ ID NO: 26) and reverse primer 5P-HLTF1827MR(ASS) (SEQ ID NO: 30); forward primer 9P-HLTF1893MF(ASS) (SEQ ID NO: 36) and reverse primer ALU(MB)2133FR(ASS) (SEQ ID NO: 37); forward primer 15P-HLTF2201MF(ASS) (SEQ ID NO: 40) and reverse primer 1 IP-HLTF2400MR(ASS) (SEQ ID NO: 41). MSP6 are primer sets for amplifying bisulfite-converted sense sequences of the duplex methylated HLTF DNA, including forward primer 3P-HLTF1621MF (SEQ ID NO: 32) and reverse primer 7P-HLTF1873MR (SEQ ID NO: 33). Sequences underlined are the control primer sets used to amplify bisulfite-converted sequences (sense or antisense) of the duplex unmethylated HLTF DNA (designated as UF or UR), including: forward primer 2P-HLTF1575UF(ASS) (SEQ ID NO: 28) and reverse primer 14P-HLTF1728UR (ASS) (SEQ ID NO: 29); forward primer 2P-HLTF1575UF (ASS) (SEQ ID NO: 28) and reverse primer 6P-HLTF1829UR(ASS) (SEQ ID NO: 31); forward primer 4P-HLTF1614UF (SEQ ID NO: 34) and reverse primer 8P-HLTF1878UR (SEQ ID NO: 35); forward primer 10P-HLTF1890UF(ASS) (SEQ ID NO: 38) and reverse primer ALU(MB)2133FR(ASS) (SEQ ID NO: 37); forward primer 16P-HLTF2197UF(ASS) (SEQ ID NO: 42) and reverse primer 12P-HLTF2403UR(ASS) (SEQ ID NO: 43).

FIG. 28 shows a region of the Genomic clone AC021059 (residues 58381-120901) (SEQ ID NO: 39), encompassing the HLTF gene. The HLTF gene is located on the antisense strand of the clone.

DETAILED DESCRIPTION OF THE INVENTION

I. Definitions

Figure 1A:
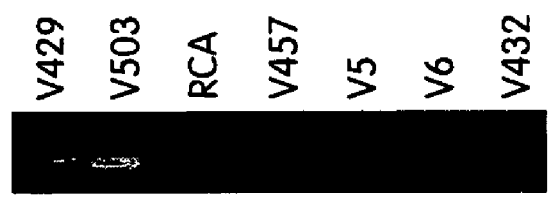
FIG. 1 illustrates HLTF silencing in colon cancer cell lines. A. HLTF RNA expression. Shown is an RT-PCR assay for HLTF expression in colon cancer cell lines. B. HLTF expression reactivation. Shown is an RT-PCR assay for HLTF expression in colon cancer cell lines treated (+) or untreated (−) with 5-azacytdine (5-azaC). Cell lines V429 and V503 are controls with constitutive HLTF expression. 5-azaC treatment reactivates HLTF expression in cell lines RCA, V457, SW480, V5, V6, and V432.

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The terms "adenoma", "colon adenoma," and "polyp" are used herein to describe any precancerous neoplasia of the colon.

The term "colon" as used herein is intended to encompass the right colon (including the cecum), the transverse colon, the left colon, and the rectum.

The terms "colorectal cancer" and "colon cancer" are used interchangeably herein to refer to any cancerous neoplasia of the colon (including the rectum, as defined above).

The term "blood-derived fraction" herein refers to a component or components of whole blood. Whole blood comprises a liquid portion (i.e., plasma) and a solid portion (i.e., blood cells). The liquid and solid portions of blood are each comprised of multiple components; e.g., different proteins in plasma or different cell types in the solid portion. One of these components or a mixture of any of these components is a blood-derived fraction as long as such fraction is missing one or more components found in whole blood.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The terms "compound", "test compound," "agent", and "molecule" are used herein interchangeably and are meant to include, but are not limited to, peptides, nucleic acids, carbohydrates, small organic molecules, natural product extract libraries, and any other molecules (including, but not limited to, chemicals, metals, and organometallic compounds).

The term "compound-converted DNA" herein refers to DNA that has been treated or reacted with a chemical compound that converts unmethylated C bases in DNA to a different nucleotide base. For example, one such compound is sodium bisulfite, which converts unmethylated C to U. If DNA that contains conversion-sensitive cytosine is treated with sodium bisulfite, the compound-converted DNA will contain U in place of C. If the DNA which is treated with sodium bisulfite contains only methylcytosine, the compound-converted DNA will not contain uracil in place of the methylcytosine.

The term "de-methylating agent" as used herein refers agents that restore activity and/or gene expression of target genes silenced by methylation upon treatment with the agent Examples of such agents include without limitation 5-azacytidine, 5-aza-2'-deoxycytidine, As used herein, the phrase "gene expression" or "protein expression" includes any information pertaining to the amount of gene transcript or protein present in a sample, as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information." Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

The term "detection" is used herein to refer to any process of observing a marker, or a change in a marker (such as for example the change in the methylation state of the marker), in a biological sample, whether or not the marker or the change in the marker is actually detected. In other words, the act of probing a sample for a marker or a change in the marker, is a "detection" even if the marker is determined to be not present or below the level of sensitivity. Detection may be a quantitative, semi-quantitative or non-quantitative observation.

"differentially methylated HLTF nucleotide sequence" refers to a region of the HLTF nucleotide sequence that is found to be methylated in an HLTF-associated neoplasia such as a region of the HLTF nucleotide sequence that is found to be methylated in colon cancer tissues or cell lines, but not methylated in the normal tissues or cell lines. For example, FIG. 10 delineates certain HLTF regions that are differentially methylated regions. Illustrative examples of such differentially methylated HLTF regions are set forth in SEQ ID NOs: 4 and 21.

"Expression vector" refers to a replicable DNA construct used to express DNA which encodes the desired protein and which includes a transcriptional unit comprising an assembly of (1) genetic element(s) having a regulatory role in gene expression, for example, promoters, operators, or enhancers, operatively linked to (2) a DNA sequence encoding a desired protein (in this case, an HLTF protein) which is transcribed into mRNA and translated into protein, and (3) appropriate transcription and translation initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

In the expression vectors, regulatory elements controlling transcription or translation can be generally derived from mammalian, microbial, viral or insect genes. The ability to replicate in a host, usually conferred by an origin of replication, and a selection gene to facilitate recognition of transformants may additionally be incorporated. Vectors derived from viruses, such as retroviruses, adenoviruses, and the like, may be employed.

The terms "healthy", "normal," and "non-neoplastic" are used interchangeably herein to refer to a subject or particular cell or tissue that is devoid (at least to the limit of detection) of a disease condition, such as a neoplasia, that is associated with HLTF such as for example neoplsia associated with silencing of HLTF gene expression due to methylation. These terms are often used herein in reference to tissues and cells of the colon. Thus, for the purposes of this application, a patient with severe heart disease but lacking a HLTF silencing-associated disease would be termed "healthy."

"HLTF-associated neoplasia" refers to neoplasia associated with reduced expression or no expression of the HLTF gene. Examples of HLTF-associated neoplasia include gastro-intestinal neoplasia, colon neoplasia etc.

"HLTF-associated proliferative disorder" refers to a disease that is associated with either reduced expression or overexpression of the HLTF gene.

"HLTF-methylation target regions" as used herein refer to those regions of HLTF that are found to be methylated. These regions include nucleotide regions that may be either constitutively or differentially methylated regions. For example, FIG. 10 discloses an HLTF region wherein certain regions of the sequence are constitutively methylated and certain other regions are differentially methylated regions. Illustrative examples of such HLTF methylation target regions are set forth in SEQ ID NO: 2-3 and 39.

"HLTF-nucleotide sequence" or "HLTF-nucleic acid sequence" as used herein refers to the HLTF-genomic sequences as set forth in SEQ ID NO: 39 and to the 5'-genomic flanking regulatory regions as set forth in SED ID NOs: 2-4 and 21.

"HLTF-silencing associated diseases" as used herein includes HLTF-associated neoplasia.

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, preferably less than 25% identity with a sequence of the present invention. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. The nucleic acid and protein sequences of the present invention may be used as a "query sequence" to perform a search against public databases to, for example, identify other family members, related sequences or homologs. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25(17): 3389-3402. When utilizing BLAST and Gapped BLAST programs, the default parameters of the respective programs (e.g., XBLAST and BLAST) can be used. See http://www.ncbi.nlm.nih.gov.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073, 1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990)). The well known Smith Waterman algorithm may also be used to determine identity.

The term "including" is used herein to mean, and is used interchangeably with, the phrase "including but not limited to."

The term "isolated" as used herein with respect to nucleic acids, such as DNA or RNA, refers to molecules in a form which does not occur in nature. Moreover, an "isolated nucleic acid" is meant to include nucleic acid fragments which are not naturally occurring as fragments and would not be found in the natural state.

The term "methylation-sensitive PCR" (i.e., MSP) herein refers to a polymerase chain reaction in which amplification of the compound-converted template sequence is performed. Two sets of primers are designed for use in MSP. Each set of primers comprises a forward primer and a reverse primer. One set of primers, called methylation-specific primers (see below), will amplify the compound-converted template sequence if C bases in CpG dinucleotides within the HLTF DNA are methylated. Another set of primers, called unmethylation-specific primers (see below), will amplify the compound-converted template sequences if C bases in CpG dinucleotides within the HLTF DNA are not methylated.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

"Operably linked" when describing the relationship between two DNA regions simply means that they are functionally related to each other. For example, a promoter or other transcriptional regulatory sequence is operably linked to a coding sequence if it controls the transcription of the coding sequence.

The term "or" is used herein to mean, and is used interchangeably with, the term "and/or", unless context clearly indicates otherwise.

The terms "proteins" and "polypeptides" are used interchangeably herein.

A "sample" includes any material that is obtained or prepared for detection of a molecular marker or a change in a molecular marker such as for example the methylation state, or any material that is contacted with a detection reagent or detection device for the purpose of detecting a molecular marker or a change in the molecular marker.

A "subject" is any organism of interest, generally a mammalian subject, such as a mouse, and preferably a human subject.

As used herein, the term "specifically hybridizes" refers to the ability of a nucleic acid probe/primer of the invention to hybridize to at least 12, 15, 20, 25, 30, 35, 40, 45, 50 or 100 consecutive nucleotides of a target sequence, or a sequence complementary thereto, or naturally occurring mutants thereof, such that it has less than 15%, preferably less than 10%, and more preferably less than 5% background hybridization to a cellular nucleic acid (e.g., mRNA or genomic DNA) other than the target gene. A variety of hybridization conditions may be used to detect specific hybridization, and the stringency is determined primarily by the wash stage of the hybridization assay. Generally high temperatures and low salt concentrations give high stringency, while low temperatures and high salt concentrations give low stringency. Low stringency hybridization is achieved by washing in, for example, about 2.0×SSC at 50° C., and high stringency is achieved with about 0.2×SSC at 50° C. Further descriptions of stringency are provided below.

As applied to polypeptides, "substantial sequence identity" means that two peptide sequences, when optimally aligned, such as by the programs GAP or BESTFIT using default gap which share at least 90 percent sequence identity, preferably at least 95 percent sequence identity, more preferably at least 99 percent sequence identity or more. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

As used herein, the term "transgene" means a nucleic acid sequence (encoding, e.g., an HLTF polypeptide), which is partly or entirely heterologous (i.e., foreign) to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). An HLTF transgene can include one or more transcriptional regulatory sequences and any other nucleic acid, such as introns, that may be necessary for optimal expression of a selected nucleic acid. An HLTF transgene can include a HLTF nucleotide sequence (SEQ ID NO: 3) or fragments thereof.

II. Overview

In certain aspects, the invention relates to methods for determining whether a patient is likely or unlikely to have a colon neoplasia. A colon neoplasia is any cancerous or precancerous growth located in, or derived from, the colon. The colon is a portion of the intestinal tract that is roughly three feet in length, stretching from the end of the small intestine to the rectum. Viewed in cross section, the colon consists of four distinguishable layers arranged in concentric rings surrounding an interior space, termed the lumen, through which digested materials pass. In order, moving outward from the lumen, the layers are termed the mucosa, the submucosa, the muscularis propria and the subserosa. The mucosa includes the epithelial layer (cells adjacent to the lumen), the basement membrane, the lamina propria and the muscularis mucosae. In general, the "wall" of the colon is intended to refer to the submucosa and the layers outside of the submucosa. The "lining" is the mucosa.

Precancerous colon neoplasias are referred to as adenomas or adenomatous polyps. Adenomas are typically small mushroom-like or wart-like growths on the lining of the colon and do not invade into the wall of the colon. Adenomas may be visualized through a device such as a colonoscope or flexible sigmoidoscope. Several studies have shown that patients who undergo screening for and removal of adenomas have a decreased rate of mortality from colon cancer. For this and other reasons, it is generally accepted that adenomas are an obligate precursor for the vast majority of colon cancers.

When a colon neoplasia invades into the basement membrane of the colon, it is considered a colon cancer, as the term "colon cancer" is used herein. In describing colon cancers, this specification will generally follow the so-called "Dukes" colon cancer staging system. The characteristics that the describe a cancer are generally of greater significance than the particular term used to describe a recognizable stage. The most widely used staging systems generally use at least one of the following characteristics for staging: the extent of tumor penetration into the colon wall, with greater penetration generally correlating with a more dangerous tumor; the extent of invasion of the tumor through the colon wall and into other neighboring tissues, with greater invasion generally correlating with a more dangerous tumor; the extent of invasion of the tumor into the regional lymph nodes, with greater invasion generally correlating with a more dangerous tumor; and the extent of metastatic invasion into more distant tissues, such as the liver, with greater metastatic invasion generally correlating with a more dangerous disease state.

"Dukes A" and "Dukes B" colon cancers are neoplasias that have invaded into the wall of the colon but have not spread into other tissues. Dukes A colon cancers are cancers that have not invaded beyond the submucosa. Dukes B colon cancers are subdivided into two groups: Dukes B1 and Dukes B2. "Dukes B1" colon cancers are neoplasias that have invaded upto but not through the muscularis propria. Dukes B2 colon cancers are cancers that have breached completely through the muscularis propria. Over a five year period, patients with Dukes A cancer who receive surgical treatment (i.e. removal of the affected tissue) have a greater than 90% survival rate. Over the same period, patients with Dukes B 1 and Dukes B2 cancer receiving surgical treatment have a survival rate of about 85% and 75%, respectively. Dukes A, B1 and B2 cancers are also referred to as T1, T2 and T3-T4 cancers, respectively.

"Dukes C" colon cancers are cancers that have spread to the regional lymph nodes, such as the lymph nodes of the gut. Patients with Dukes C cancer who receive surgical treatment alone have a 35% survival rate over a five year period, but this survival rate is increased to 60% in patients that receive chemotherapy.

"Dukes D" colon cancers are cancers that have metastasized to other organs. The liver is the most common organ in which metastatic colon cancer is found. Patients with Dukes D colon cancer have a survival rate of less than 5% over a five year period, regardless of the treatment regimen.

In general, colon neoplasia develops through one of at least three different pathways, termed chromosomal instability, microsatellite instability, and the CpG island methylator phenotype (CIMP). Although there is some overlap, these pathways tend to present somewhat different biological behavior. By understanding the pathway of tumor development, the target genes involved, and the mechanisms underlying the genetic instability, it is possible to implement strategies to detect and treat the different types of colon neoplasias.

This application is based at least in part, on the recognition that certain target genes may be silenced or inactivated by the differential methylation of CpG islands in the 5'flanking or promoter regions of the target gene. CpG islands are clusters of cytosine-guanosine residues in a DNA sequence, that are prominently represented in the 5-flanking region or promoter region of about half the genes in our genome. In particular, this application is based at least in part on the recognition that differential methylation of the HLTF nucleotide sequence may be indicative of colon neoplasia. In one aspect, this application discloses that the HLTF gene can be a common target for methylation and epigenetic gene silencing in cancer cells (e.g., a colon neoplasia), and function as a candidate tumor suppressor gene.

HLTF (helicase-like transcription factor, also called HIP116a, Zbu1, RUSH1a and Smarca3) is a member of the SWI/SNF family. The SWI/SNF family of genes encode members of multiprotein complexes that utilize the energy of ATP hydrolysis to alter nucleosome position or spacing (Muchardt, et al., 1999, *J. Mol. Biol.*, 293:187-198; Sudarsanam, et al., 2000, *Trends Genet.*, 16:345-351). HLTF has 5'-sequence-specific DNA-binding domains and can thus be targeted to specific promoters directly. For example, HLTF protein can bind to a promoter element (i.e., the B Box) of the plasminogen activator inhibitor-1 (PAI-1) gene and induce PAI-1 gene expression (Ding, et al., 1996, DNA Cell Biol. 15:429-442; Zhang, et al., 1997, Gene, 202:31-7). Functional interactions between Sp1 or Sp3 and HLTF were found to mediate basal expression from the PAI-I gene (Ding, et al., 1999, *J. Biol. Chem.*, 274:19573-19580). Recently, it has been found that HLTF is an activator of beta-globin transcription (Mahajan, et al., 2002, Blood, 99:348-56).

As noted above, early detection of colon neoplasia, coupled with appropriate intervention, is important for increasing patient survival rates. Present systems for screening for colon neoplasia are deficient for a variety of reasons, including a lack of specificity and/or sensitivity (e.g. Fecal Occult Blood Test, flexible sigmoidoscopy) or a high cost and intensive use of medical resources (e.g. colonoscopy). Alternative systems for detection of colon neoplasia would be useful in a wide range of other clinical circumstances as well. For example, patients who receive surgical and/or pharmaceutical therapy for colon cancer may experience a relapse. It would be advantageous to have an alternative system for determining whether such patients have a recurrent or relapsed colon neoplasia. As a further example, an alternative diagnostic system would facilitate monitoring an increase, decrease or persistence of colon neoplasia in a patient known to have a colon neoplasia. A patient undergoing chemotherapy may be monitored to assess the effectiveness of the therapy.

III. HLTF Nucleic Acids, Polypeptides, and Antibodies.

The present invention is based, at least in part, on the observation that HLTF nucleotide sequences are differentially methylated in certain HLTF-associated neoplasia, such as colon neoplasia. In one aspect, the application discloses HLTF nucleotide sequences having certain regions that are differentially methylated in HLTF-associated neoplasia as set forth in SEQ ID NOs: 2-4, 21, and 39. In other embodiments, the application provides nucleotide sequences that are differentially methylated in HLTF-associated neoplasia as set forth in SEQ ID NOs: 4 and 21. Accordingly, in one embodiment the application provides isolated or recombinant nucleotide sequences that are at least 80%, 85%, 90%, 95%, 97%, 98%, 99% or 100% identical to a nucleic acid sequence as set forth in SEQ ID NOs: 2-4, 21, and 39. In yet other aspects, the application provides oligonucleotide sequences having at least 50, 75, or 100 consecutive base pairs of any one of the sequences as set forth in SEQ ID NOs: 2-4 and 21.

In certain alternative embodiments, the application provides the differentially methylated HLTF nucleotide sequence set forth in SEQ ID NOs: 4 and 21 and fragments thereof, wherein detection of methylation in any one of said fragments would be indicative of an HLTF-associated neoplasia such as colon neoplasia. One of ordinary skill in the art will appreciate that HLTF nucleic acid sequences complementary to SEQ ID NOs: 2-4 and 21, variants of SEQ ID NOs: 2-4 and 21 are also within the scope of this invention. Such variant nucleotide sequences include sequences that differ by one or more nucleotide substitutions, additions or deletions, such as for example allelic variants.

In yet other embodiments, HLTF nucleotide sequences also include nucleotide sequences sequences that will hybridize under highly stringent conditions to nucleotide sequences designated in SEQ ID NOs: 2-4 and 21. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2× SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

In yet another aspect, the application provides the methylated forms of nucleotide sequences as set forth in SEQ ID NOs: 4 and 21, wherein the cytosine bases of the CpG islands present in said sequences are methylated. In other words, the HLTF nucleotide sequences may be either in the methylated status (e.g., as seen in HLTF-associated neoplasias) or in the unmethylated status (e.g., as seen in normal cells). In further embodiments, the HLTF nucleotide sequences of the invention can be isolated, recombinant, and/or fused with a heterologous nucleotide sequence, or in a DNA library.

Figure 10:
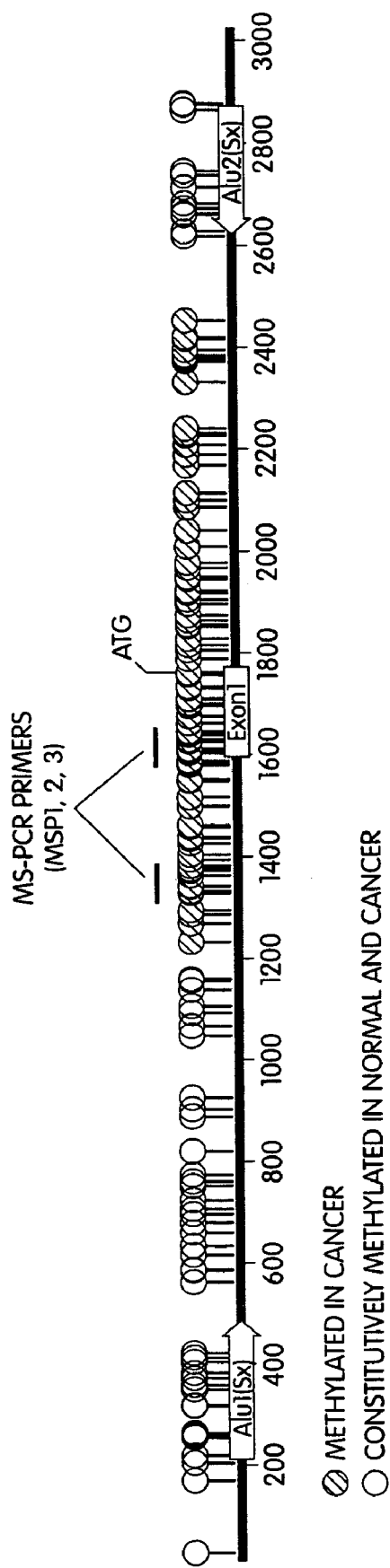
FIG. 10 summarizes the results of the sequencing across HLTF genomic residues 0-3000 of bisulfite converted genomic DNA from 6 different samples: Vaco5 (an HLTF silenced colon cancer cell line), Vaco206 (an HLTF expressing colon cancer cell line), and 4 normal colon epithelial tissue samples (19-1 IN, 587N, 421N, and 406N). Multiple individual DNA clones were sequenced for each of the bisulfite converted samples. The positions of Alu1, HLTF exon1, and Alu2 are shown in boxes. Open balloons denote CpG residues where cytosine methylation was found to be constitutive in normal colonic tissue. In both Alu1 and Alu2, all CpG residues are constitutively methylated in normal tissue. Additionally, CpG residues that are 3' of Alu1 from bases 550-1200 were also all found to be constitutively methylated. A differentially methylated region, that is methylated in HLTF silenced Vaco5 and is, in general, not methylated in normal colon or in HLTF expressing cancer is defined by the CpG dinucleotides lying between residues 1200 and 2600. The differential methylation of 5 HpaII sites between residues 1277 and 1742 was independently confirmed in multiple additional normal and cancer samples by assays of the resistance of these sites to HpaII digestion. Additionally, 3 sets of MS-PCR primers were designed to assay the methylation status of residues between 1352 and 1672 (as shown on the FIGURE), and these MS-PCR assays also confirmed that these residues were unmethylated in normal colon tissue and in HLTF expressing colon cancers, but were methylated in HLTF silenced colon cancers.
Figure 11:
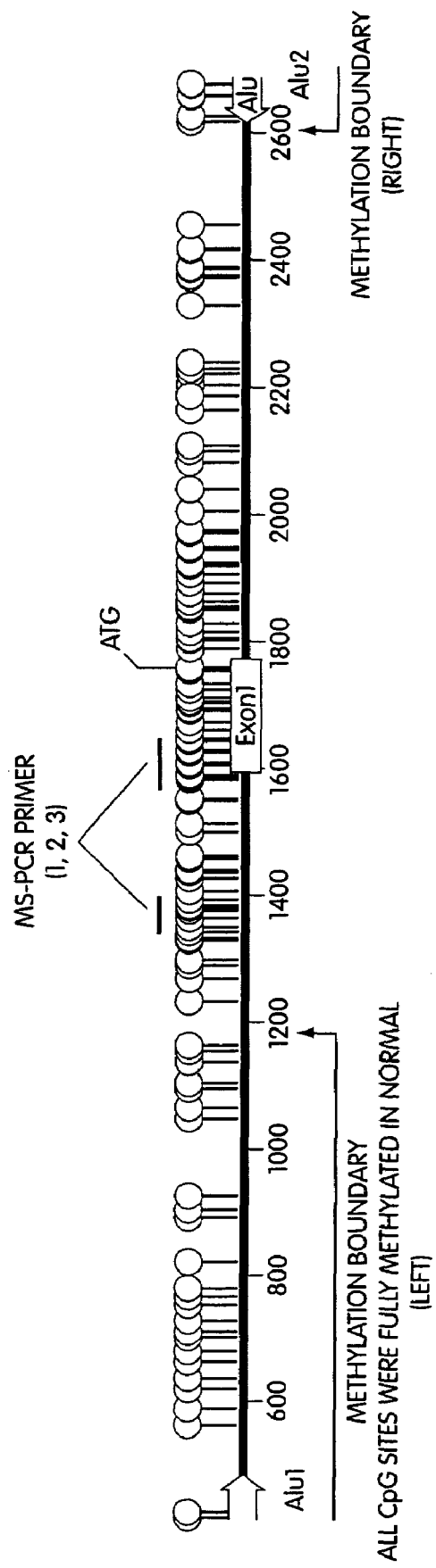
FIG. 11 shows a final diagramatic summary of the structure of the region between Alu1 and Alu2 repeats, and designates the boundaries of the base pair 1200-2500 region outside of which there is constitutive methylation of the adjacent CpG dinucleotides.
Figure 12:
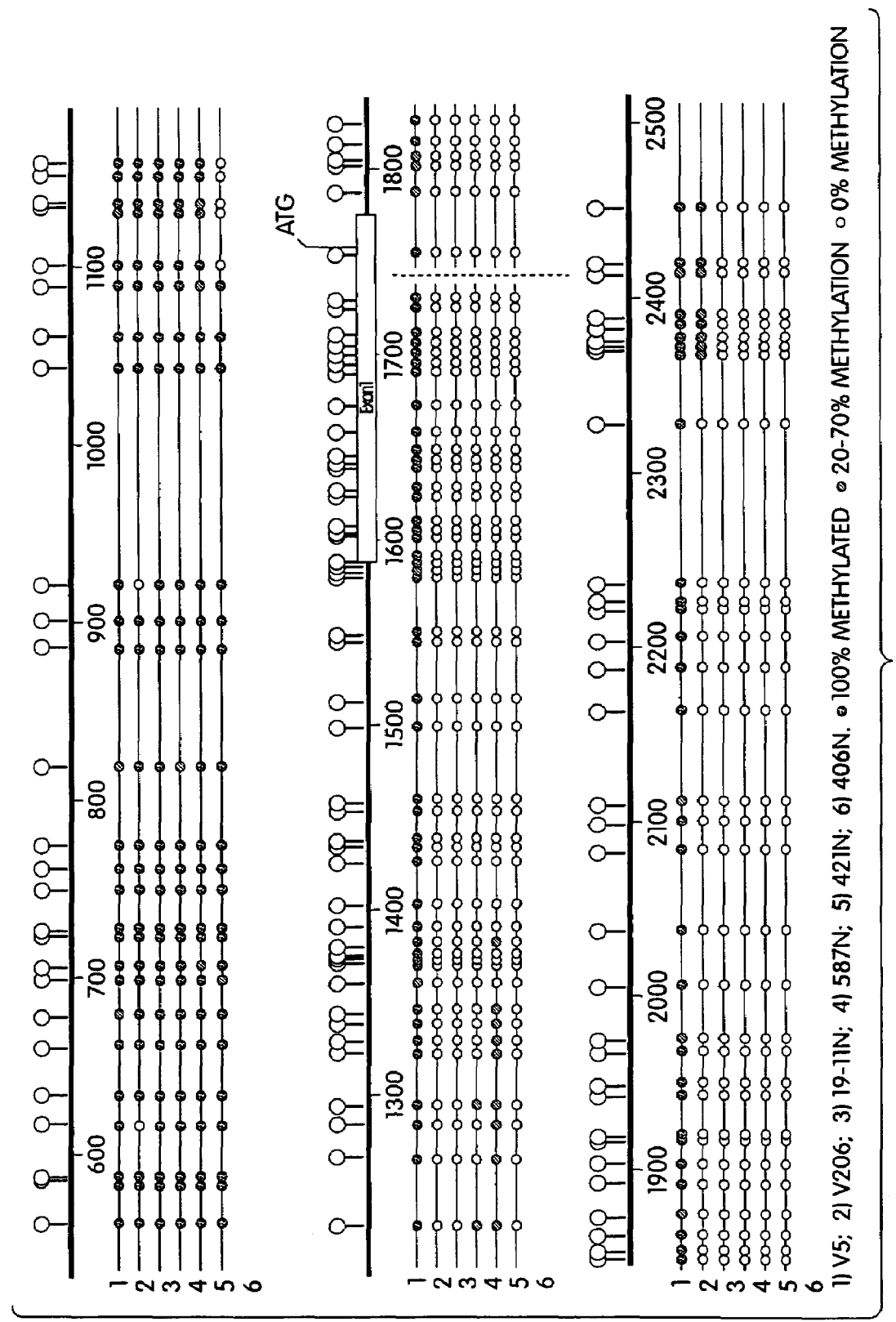
FIG. 12 summarizes for HLTF gene residues 550 to 2500 the primary results of the bisulfite sequencing in the 6 different samples (corresponding to the region flanked by the Alu1 and Alu2 repeats). The balloons indicate the position of the CpG dinucleotides. Data from the 6 samples is summarized by the 6 lines. At each CpG residue, an open circle indicates the residue was unmethylated in that sample, a black filled circle indicates the residue was methylated in every bisulfite converted clone derived from that sample, and a grey filled circle indicates that the residue was methylated in from 20%-70% of the clones derived from that sample. In the HLTF silenced Vaco5 sample, there basically is methylation of every residue from base pair 550 to 2500. However, the residues from base pairs 550 to 1200 are also seen to be methylated in the normal colon samples as well as in the HLTF expressing cancer cell line Vaco206. The residues between 1200 and 2500 essentially define a region that is differentially methylated in the HLTF silenced Vaco5 sample. Note is made of slight methylation of residues 1200 to 1400 in one normal sample, and of residues 2300 to 2500 in Vaco206. However, this slight methylation is distinguished from the core methylation of HLTF silenced cancers by all of the MS-PCR assays described in this application as well as by the described assay of methylation of the HpaII sites that span the 1277 to 1742 interval.
Figure 13:
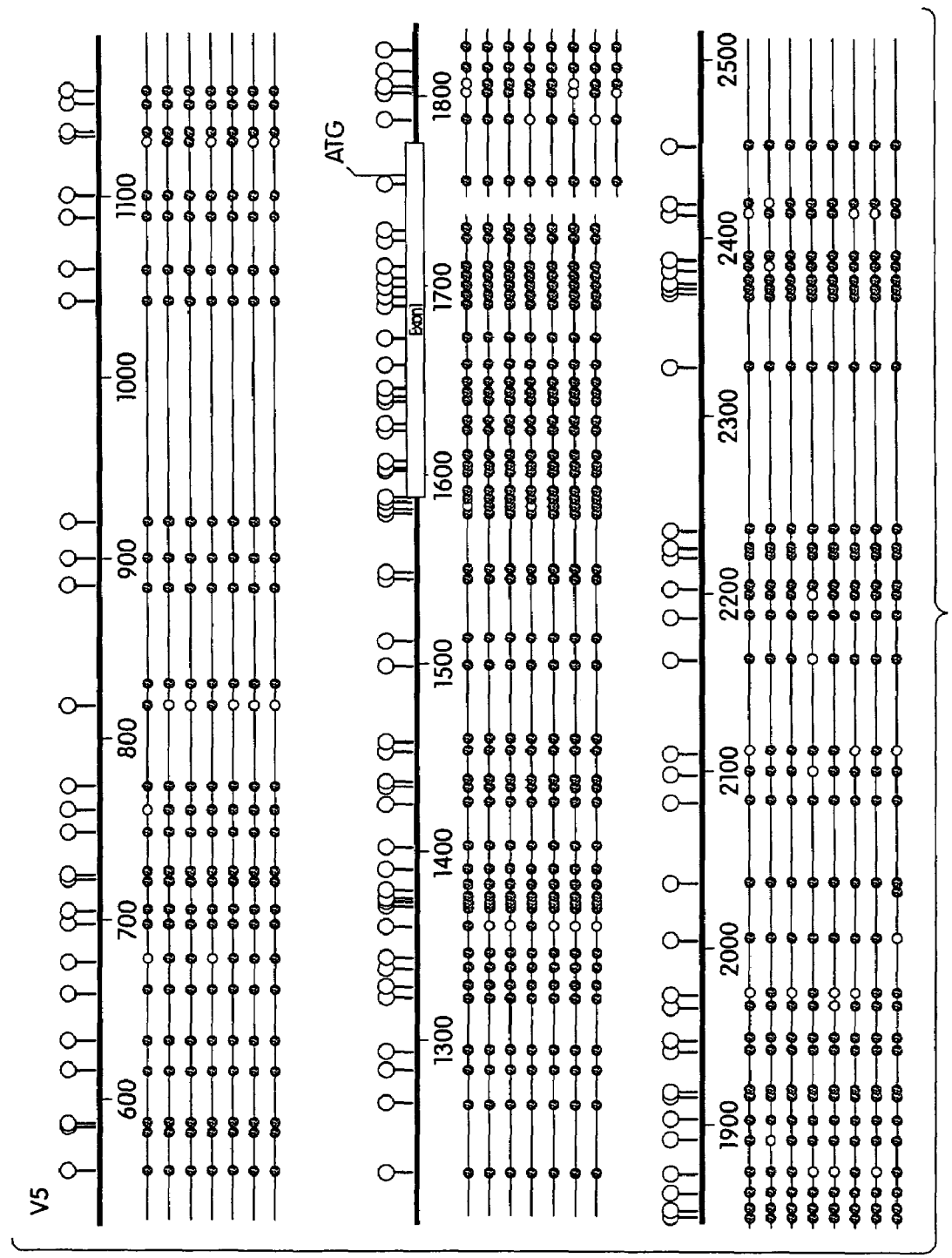
FIG. 13 shows the results of bisulfite sequencing of multiple individually derived DNA clones derived from bisulfite treated DNA from the Vaco5 colon cancer cell lines which do not express HLTF. In each of these Vaco5 derived DNA clones, essentially all of the CpG sites are methylated in the region from residues 550 to 2500.

In addition to the differentially methylated HLTF nucleotide sequences, the present application discloses constitutively methylated HLTF nucleotide sequences (such as the Alu repeats and the "non-Alu constitutively methylated region" as set forth in FIG. 10). Since such constitutively methylated HLTF nucleotide sequences are methylated in both normal cells and cancer cells, a person skilled in the art would appreciate the significance of detecting the differentially methylated HLTF nucleotide sequences as provided herein. Furthermore, although one of ordinary skill would expect the Alu's to be methylated, the finding of non-Alu constitutively methylated regions shows that one could not have computationally predicted the presence of the differentially methylated regions and their significance in the detection of HLTF-associated neoplasia.

In certain embodiments, the application contemplates any HLTF nucleotide sequence within the HLTF genomic sequence, SEQ ID NO: 39 (see FIG. 28) that is differentially methylated in HLTF-associated neoplasia cells, but not in normal cells. Thus, assaying of the methylation status of such an HLTF nucleotide sequence can differentiate cancer cells from normal cells.

In certain embodiments, the present invention provides bisulfite-converted HLTF template DNA sequences as set forth in SEQ ID NOs: 5-8 and 22-25. Such bisulfite-converted HLTF template DNA can be used for detecting the methylation status, for example, by an MSP reaction or by direct sequencing. In yet other embodiments, the bisulfite-converted HLTF nucleotide sequences of the invention also include nucleotide sequences that will hybridize under highly stringent conditions to any nucleotide sequence selected from SEQ ID NOs: 5-8 and 22-25.

In further aspects, the application provides methods for producing such bisulfite-converted nucleotide sequences, for example, the application provides methods for treating a nucleotide sequence with a bisulfite agent such that the unmethylated cytosine bases are converted to a different nucleotide base such as a uracil.

In yet other aspects, the application provides oligonucleotide primers for amplifying a region within the HLTF nucleic acid sequence of any one of SEQ ID NOs: 2-4 and 21. In certain aspects, a pair of the oligonucleotide primers (for example, SEQ ID NOs: 9-10) can be used in a detection assay, such as the HpaII assay. In certain aspects, primers used in an MSP reaction can specifically distinguish between methylated and non-methylated HLTF DNA, for example, SEQ ID NOs: 11-20, 26-38, and 40-43).

The primers of the invention have sufficient length and appropriate sequence so as to provide specific initiation of amplification of HLTF nucleic acids. Primers of the invention are designed to be "substantially" complementary to each strand of the HLTF nucleic acid sequence to be amplified. While exemplary primers are provided in SEQ ID NOs: 11-20, 26-38, and 40-43, it is understood that any primer that hybridizes with the bisulfite-converted HLTF sequence of any one of SEQ ID NOs: 2-4 and 21 are included within the scope of this invention and is useful in the method of the invention for detecting methylated nucleic acid, as described. Similarly, it is understood that any primers that would serve to amplify a methylation sensitive restriction site or sites within the differentially methylated region of SEQ ID NOs: 2-4 or 21 are included within the scope of this invention and is useful in the method of the invention for detecting nucleic methylated nucleic acid, as described.

The oligonucleotide primers of the invention may be prepared by using any suitable method, such as conventional phosphotriester and phosphodiester methods or automated embodiments thereof. In one such automated embodiment, diethylphosphoramidites are used as starting materials and may be synthesized as described by Beaucage, et al. (Tetrahedron Letters, 22:1859-1862, 1981). One method for synthesizing oligonucleotides on a modified solid support is described in U.S. Pat. No. 4,458,066.

The various Sequence Identification Numbers that have been used in this application are summarized below:

TABLE I

Figure 17:
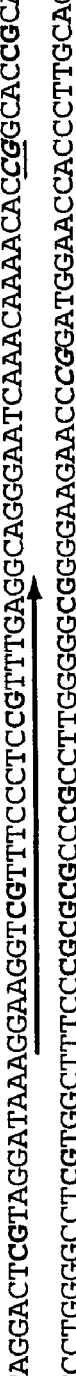
FIG. 17 shows the HLTF nucleotide sequence base pairs 1250-1800 (SEQ ID NO: 4). CpG dinucleotides that are sites of cytosine methylation are in bold. Those CpG sites that are HpaII restriction sites are shown in italic and underlined. Sequences that are complementary to PCR primers that were used to selectively amplify the methylated but not unmethylated HLTF DNA after digestion with HpaII are shown as bold arrows. Those CpG site that are tested by specific MS-PCR assays described as examples in this invention are underlined. Parent sequences that were used to design specific MS-PCR primers that amplified methylated but not unmethylated templates following conversion with bisulfite are shown in smaller arrows.
Figure 20:
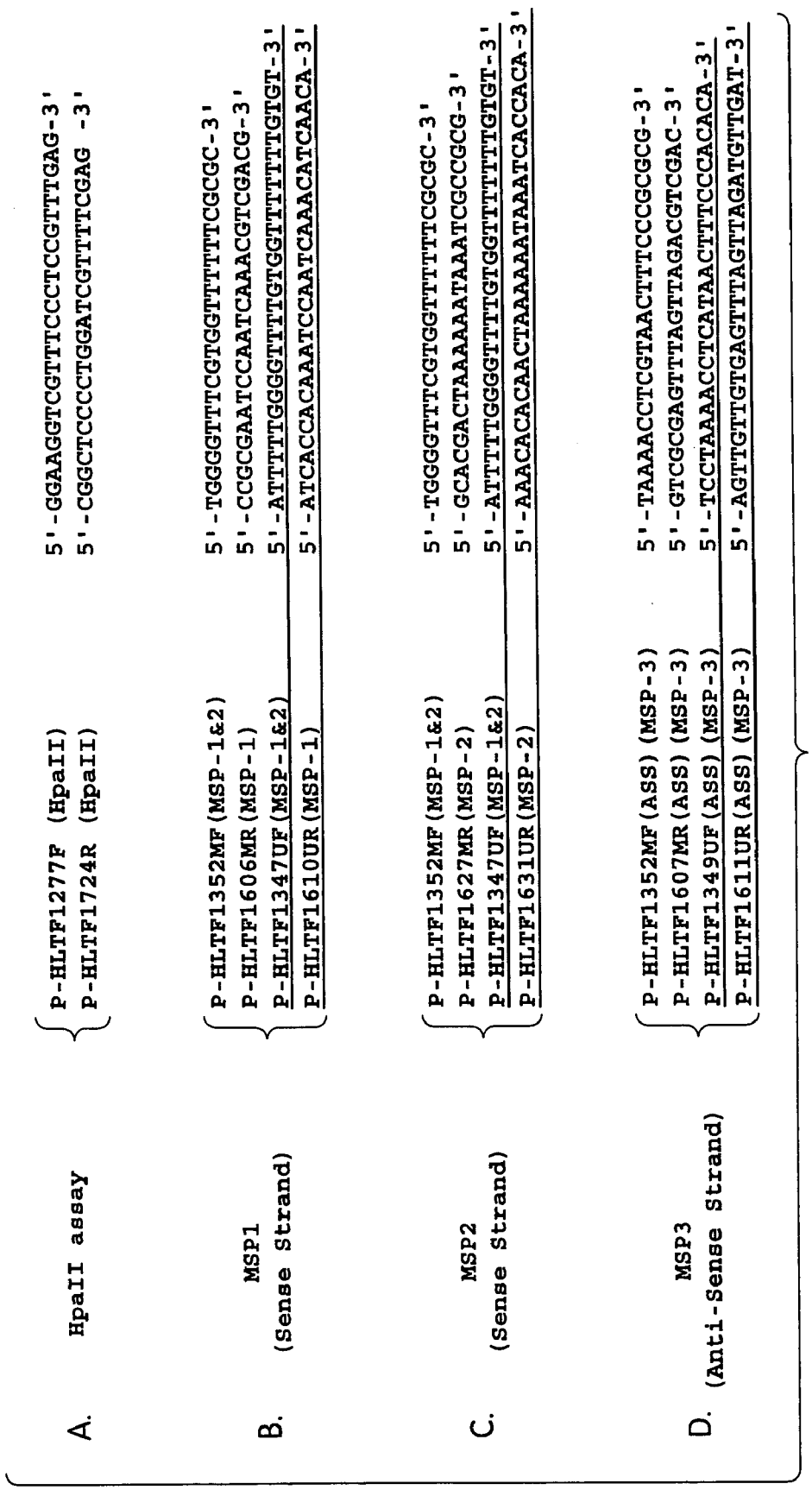
FIG. 20 shows primer sequences for amplifying HLTF. A. Forward PCR primer 1277F (SEQ ID NO: 9) and reverse PCR primer 1724R (SEQ ID NO: 10) selectively amplify the methylated but not unmethylated HLTF sequence after digestion with HpaII. Umnethylated DNAs are cut by HpaII and so cannot be PCR amplified B and C show primer sets for amplifying bisulfite-converted sense sequences of the duplex methylated HLTF DNA: forward PCR primer 1352MF (SEQ ID NO: 11) and reverse primer 1606MR (SEQ ID NO: 12); forward PCR primer 1352MF (SEQ ID NO: 11) and reverse primer 1627MR (SEQ ID NO: 15). D shows primer sets for amplifying bisulfite-converted antisense sequences of the duplex methylated HLTF DNA: forward primer 1352MF (ASS) (SEQ ID NO: 17) and reverse primer 1607MR(ASS) (SEQ ID NO: 18). Sequences underlined in B, C, and D are the control primer sets used to amply bisulfite-converted sequences (sense or antisense) of the duplex unmethylated HLTF DNA (designated as UF or UR): forward PCR primer 1347UF (SEQ ID NO: 13) and reverse primer 1610UR (SEQ ID NO: 14); forward PCR primer 1347UF (SEQ ID NO: 13) and reverse primer 1631UR (SEQ ID NO: 16); forward primer 1349UF(ASS) (SEQ ID NO: 19) and reverse primer 1611UR(ASS) (SEQ ID NO: 20).
Figure 26:
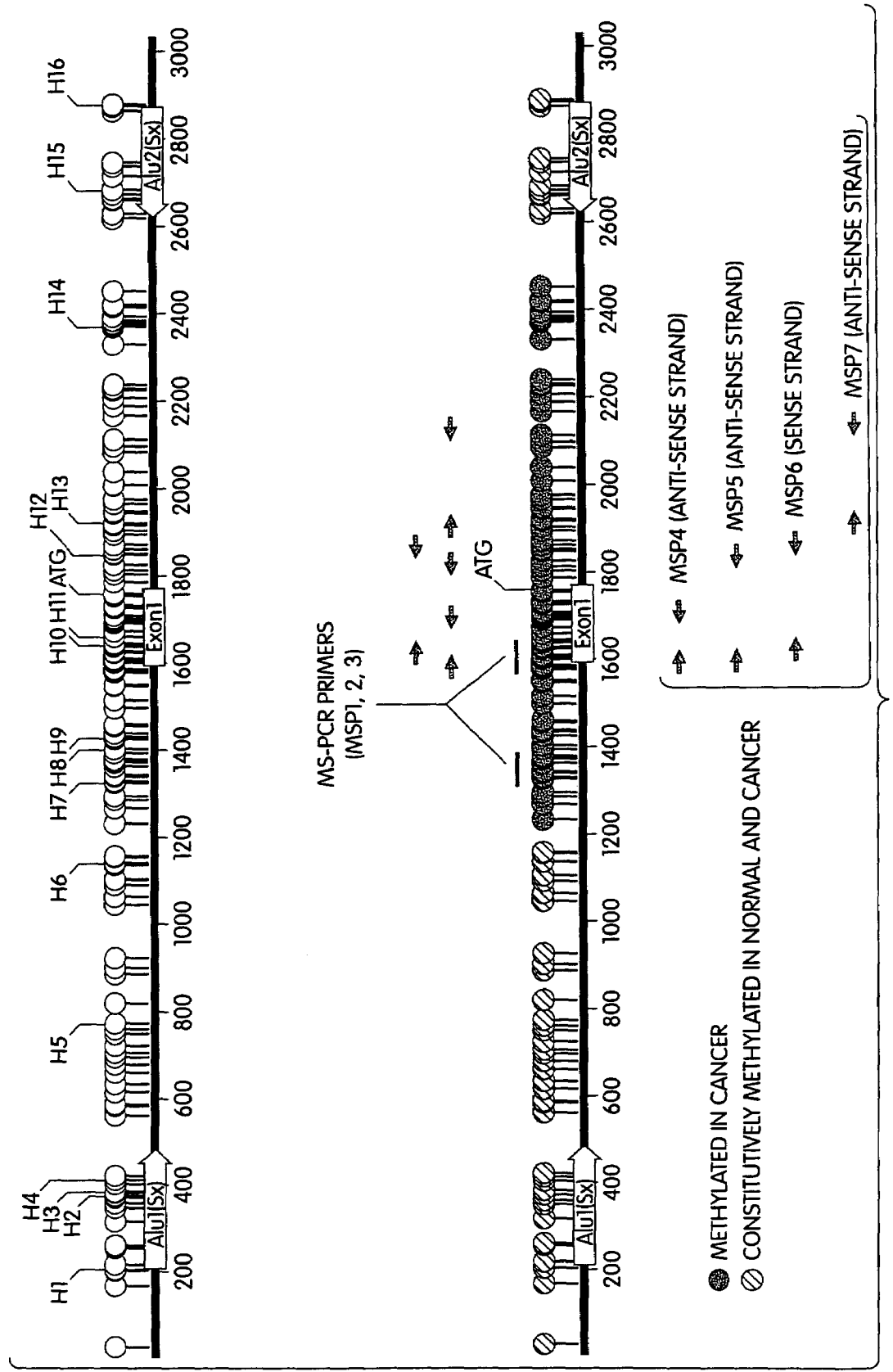
FIG. 26 shows digramatically the positions of newly designed primer sets 4-7 for detecting differential methylation of the 3' HLTF region that is beyond the previously-tested region.

| SEQ ID NO | Description/Name | Corresponding Figure |
|---|---|---|
| 1 | amino acid sequence of human HLTF protein. | FIG. 14. |
| 2 | 5' genomic sequence of human HLTF gene, residues 1-3000. | FIG. 15. |
| 3 | 5' genomic sequence of human HLTF gene, residues 600-2600. | FIG. 16. |
| 4 | 5' genomic sequence of human HLTF gene, residues 1250-1800. | FIG. 17. |
| 5 | methylated SEQ ID NO: 4, after bisulfite conversion. | FIG. 18, top panel. |
| 6 | unmethylated SEQ ID NO: 4, after bisulfite conversion. | FIG. 18, bottom panel. |
| 7 | complementary strand of SEQ ID NO: 5. | FIG. 19, top panel. |
| 8 | complementary strand of SEQ ID NO: 6. | FIG. 19, bottom panel. |
| 9 | P-HLTF1277F | FIG. 20. |
| 10 | P-HLTF1724R | FIG. 20. |
| 11 | P-HLTF1352MF | FIG. 20. |
| 12 | P-HLTF1606MR | FIG. 20. |
| 13 | P-HLTF1347UF | FIG. 20. |
| 14 | P-HLTF1610UR | FIG. 20. |
| 15 | P-HLTF1627MR | FIG. 20. |
| 16 | P-HLTF1631UR | FIG. 20. |
| 17 | P-HLTF1352MF(ASS) | FIG. 20. |
| 18 | P-HLTF1607MR(ASS) | FIG. 20. |
| 19 | P-HLTF1349UF(ASS) | FIG. 20. |
| 20 | P-HLTF1611UR(ASS) | FIG. 20. |
| 21 | 5' genomic sequence of human HLTF gene, residues 1200-2500, sense strand. | FIG. 21. |
| 22 | methylated SEQ ID NO: 21, after bisulfite conversion. | FIG. 22. |
| 23 | unmethylated SEQ ID NO: 21, after bisulfite conversion. | FIG. 23. |
| 24 | methylated antisense-strand of SEQ ID NO: 21, after bisulfite conversion. | FIG. 24. |
| 25 | unmethylated antisense-strand of SEQ ID NO: 21, after bisulfite conversion. | FIG. 25. |
| 26 | 1P-HLTF1581MF(ASS) | FIG. 27. |
| 27 | 13P-HLTF1713MR(ASS) | FIG. 27. |
| 28 | 2P-HLTF1575UF(ASS) | FIG. 27. |
| 29 | 14P-HLTF1728UR(ASS) | FIG. 27. |
| 30 | 5P-HLTF1827MR(ASS) | FIG. 27. |
| 31 | 6P-HLTF1829UR(ASS) | FIG. 27. |
| 32 | 3P-HLTF1621MF | FIG. 27. |
| 33 | 7P-HLTF1873MR | FIG. 27. |
| 34 | 4P-HLTF1614UF | FIG. 27. |
| 35 | 8P-HLTF1878UR | FIG. 27. |
| 36 | 9P-HLTF1893MF(ASS) | FIG. 27. |
| 37 | ALU(MB)2133FR(ASS) | FIG. 27. |
| 38 | 10P-HLTF1890UF(ASS) | FIG. 27. |
| 39 | HLTF genomic sequence (GenBank accession No. NT_005616, complementary residues 572873-629300) | FIG. 28. |
| 40 | 15P-HLTF2201MF(ASS) | FIG. 27 |
| 41 | 11P-HLTF2400MR(ASS) | FIG. 27 |
| 42 | 16P-HLTF2197UF(ASS) | FIG. 27 |
| 43 | 12P-HLTF2403UR(ASS) | FIG. 27 |

In certain other aspects, the invention relates to HLTF nucleic acids that encode the HTLF polypeptide of SEQ ID NO: 1 and variants thereof. Variant include sequences that differ by one or more nucleotide substitutions, additions or deletions, such as allelic variants; and will, therefore, include coding sequences that differ from the nucleotide sequence of the coding sequence e.g., due to the degeneracy of the genetic code. In certain embodiments, variant nucleic acids will also include sequences that will hybridize under highly stringent conditions to a nucleotide sequence encoding SEQ ID NO: 1.

Isolated HLTF nucleic acids which differ from the nucleic acids encoding SEQ ID NO: 1 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant HLTF nucleic acid may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects, the invention relates to HLTF polypeptide (SEQ ID NO: 1) described herein, and variants polypeptides thereof. In certain embodiments, variant polypeptides have an amino acid sequence that is at least 75% identical to an amino acid sequence as set forth in SEQ ID NO: 1. In other embodiments, the variant polypeptide has an amino acid sequence at least 80%, 85%, 90%, 95%, 97%, 98%, 99% or 100% identical to an amino acid sequence as set forth in SEQ ID NO: 1.

In certain aspects, variant HLTF polypeptides are agonists or antagonists of the HLTF polypeptide as set forth in SEQ ID NO: 1. Variants of these polypeptides may have a hyperactive or constitutive activity, or, alternatively, act to prevent the tumor suppressor activity of HLTF. For example, a truncated form lacking one or more domain may have a dominant negative effect.

In certain aspects, isolated peptidyl portions of the HLTF polypeptide can be obtained by screening polypeptides recombinantly produced from the corresponding fragment of the nucleic acid encoding the polypeptide as set forth in SEQ ID NO: 1. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments which can function as either agonists or antagonists of the tumor suppressor function of HLTF.

In certain aspects, variant HLTF polypeptides containing one or more fusion domains. Well known examples of such fusion domains include, for example, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion polypeptide by affinity chromatography. For the purpose of affinity purification, relevant matrices for affinity chromatography, such as glutathione-, amylase-, and nickel- or cobalt conjugated resins are used. Many of such matrices are available in "kit" form, such as the Pharmacia GST purification system and the QIAexpress$^{TM}$ system (Qiagen) useful with (HIS$_6$) fusion partners. Another fusion domain well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localization of the fusion HLTF polypeptide. The GFP tag is also useful for isolating cells which express the fusion HLTF polypeptide by flow cytometric methods such a fluorescence activated cell sorting (FACS). Fusion domains also include "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allow the relevant protease to partially digest the fusion HLTF polypeptide and thereby liberate the recombinant polypeptide therefrom. The liberated polypeptide can then be isolated from the fusion partner by subsequent chromatographic separation.

Another aspect of the invention pertains to an isolated antibody specifically immunoreactive with an epitope of an HLTF polypeptide. For example, by using immunogens derived from an HLTF polypeptide (e.g., based on its cDNA sequences), anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the HLTF peptide. Techniques for conferring immunogenicity on a protein or peptide include conjugation to carriers or other techniques well known in the art. An immunogenic portion of a polypeptide can be administered in the presence of adjuvant. The progress of immunization can be monitored by detection of antibody titers in plasma or serum. Standard ELISA or other immunoassays can be used with the immunogen as antigen to assess the levels of antibodies.

In certain embodiment, antibodies of the invention may be useful as diagnostic or therapeutic agents for detecting or treating HLTF-associated diseases.

The term "antibody" as used herein is intended to include fragments thereof which are also specifically reactive with one of the HLTF polypeptide. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragments can be treated to reduce disulfide bridges to produce Fab fragments. The antibody of the invention is further intended to include bispecific, single-chain, and chimeric and humanized molecules having affinity for the HLTF protein. In preferred embodiments, the antibody further comprises a label attached thereto and able to be detected, (e.g., the label can be a radioisotope, fluorescent compound, enzyme or enzyme co-factor).

IV. Assays and Drug Screening Methodologies

In certain aspects, the application provides assays and methods using the HLTF nucleotide sequences as molecular markers that distinguish between healthy cells and HLTF-associated diseased cells. For example, in one embodiment, the application provides methods and assays using the HLTF nucleotide sequences as markers that distinguish between healthy cells ands colon neoplasia cells. In one aspect, a molecular marker of the invention is a differentially methylated HLTF nucleotide sequence. In another aspect, another marker provided herein is the HLTF gene expression product.

In certain embodiments, the invention provides assays for detecting differentially methylated HLTF nucleotide sequences, such as the differential methylation patterns seen in any one of SEQ ID NOs: 2-4, 21 and 39, preferably, SED ID NOs: 4 and 21. Thus, a differentially methylated HLTF nucleotide sequence, in its methylated state, can be a HLTF-associated neoplasia-specific modification that serves as a target for detection using various methods described herein and the methods that are well within the purview of the skilled artisan in view of the teachings of this application.

In certain embodiments, methods of the present invention assaying for the methylation status of the HLTF nucleotide sequence in combination with one or more genes selected from HIC-1 (hypermethylated in cancer-1), p16, p14, TIMP-3, APC, PTEN, RARβ (retinoic acid receptor β), THBS1, hMLH1, and others. The present application provides that HLTF methylation correlates strongly with a pathway termed as the CpG island methylator phenotype (CIMP+), which may involve methylation of multiple genes, including p16, p14, HIC-1, TIMP-3, APC, PTEN, RARP, THBS1, and hMLH1.

In certain aspects, such methods for detecting methylated HLTF nucleotide sequences are based on treatment of HLTF genomic DNA with a chemical compound which converts non-methylated C, but not methylated C (i.e., 5 mC), to a different nucleotide base. One such compound is sodium bisulfite, which converts C, but not 5mC, to U. Methods for bisulfite treatment of DNA are known in the art (Herman, et al., 1996, Proc Natl Acad Sci USA, 93:9821-6; Herman and Baylin, 1998, Current Protocols in Human Genetics, N. E. A. Dracopoli, ed., John Wiley & Sons, 2:10.6.1-10.6.10; U.S. Pat. No. 5,786,146). To illustrate, when an DNA molecule that contains unmethylated C nucleotides is treated with sodium bisulfite to become a compound-converted DNA, the sequence of that DNA is changed (C→U). Detection of the U in the converted nucleotide sequence is indicative of an unmethylated C.

The different nucleotide base (e.g., U) present in compound-converted nucleotide sequences can subsequently be detected in a variety of ways. In a preferred embodiment, the present invention provides a method of detecting U in compound-converted HLTF DNA sequences by using "methylation sensitive PCR" (MSP) (see, e.g., Herman, et al., 1996, Proc. Natl. Acad. Sci. USA, 93:9821-9826; U.S. Pat. No. 6,265,171; U.S. Pat. No. 6,017,704; U.S. Pat. No. 6,200,756). In MSP, one set of primers (i.e., comprising a forward and a reverse primer) amplifies the compound-converted template sequence if C bases in CpG dinucleotides within the HLTF DNA are methylated. This set of primers is called "methylation-specific primers." Another set of primers amplifies the compound-converted template sequence if C bases in CpG dinucleotides within the HLTF 5' flanking sequence are not methylated. This set of primers is called "unmethylation-specific primers."

In methyl specific PCR the reactions use the compound-converted DNA from a sample in a subject. In assay for HLTF methylated DNA, methylation-specific primers are used. In the case where C within CpG dinucleotides of the target sequence of the DNA are methylated, the methylation-specific primers will amplify the compound-converted template sequence in the presence of a polymerase and an MSP product will be produced. If C within CpG dinucleotides of the target sequence of the DNA are not methylated, the methylation-specific primers will not amplify the compound-converted template sequence in the presence of a polymerase and an MSP product will not be produced It is often also useful to run a control reaction for the detection of unmethylated HLTF DNA. The reactions uses the compound-converted DNA from a sample in a subject and unmethylation-specific primers are used. In the case where C within CpG dinucleotides of the target sequence of the DNA are unmethylated, the unmethylation specific primers will amplify the compound-converted template sequence in the presence of a polymerase and an MSP product will be produced. If C within CpG dinucleotides of the target sequence of the DNA are methylated, the unmethylation-specific primers will not amplify the compound-converted template sequence in the presence of a polymerase and an MSP product will not be produced. Note that a biologic sample will often contain a mixture of both neoplastic cells that give rise to a signal with methylation specific primers, and normal cellular elements that give rise to a signal with unmethylation-specific primers. The unmethyl specific signal is often of use as a control reaction, but does not in this instance imply the absence of colon neoplasia as indicated by the positive signal derived from reactions using the methylation specific primers.

Primers for an MSP reaction are derived from the compound-converted HLTF template sequence. Herein, "derived from" means that the sequences of the primers are chosen such that the primers amplify the compound-converted template sequence in an MSP reaction. Each primer comprises a single-stranded DNA fragment which is at least 8 nucleotides in length. Preferably, the primers are less than 50 nucleotides in length, more preferably from 15 to 35 nucleotides in length. Because the compound-converted HLTF template sequence can be either the Watson strand or the Crick strand of the double-stranded DNA that is treated with sodium bisulfite, the sequences of the primers is dependent upon whether the Watson or Crick compound-converted template sequence is chosen to be amplified in the MSP. Either the Watson or Crick strand can be chosen to be amplified.

The compound-converted HLTF template sequence, and therefore the product of the MSP reaction, can be between 20 to 3000 nucleotides in length, preferably between 50 to 500 nucleotides in length, more preferably between 80 to 150 nucleotides in length. Preferably, the methylation-specific primers result in an MSP product of a different length than the MSP product produced by the unmethylation-specific primers.

A variety of methods can be used to determine if an MSP product has been produced in a reaction assay. One way to determine if an MSP product has been produced in the reaction is to analyze a portion of the reaction by agarose gel electrophoresis. For example, a horizontal agarose gel of from 0.6 to 2.0% agarose is made and a portion of the MSP reaction mixture is electrophoresed through the agarose gel. After electrophoresis, the agarose gel is stained with ethidium bromide. MSP products are visible when the gel is viewed during illumination with ultraviolet light. By comparison to standardized size markers, it is determined if the MSP product is of the correct expected size.

Other methods can be used to determine whether a product is made in an MSP reaction. One such method is called "real-time PCR." Real-time PCR utilizes a thermal cycler (i.e., an instrument that provides the temperature changes necessary for the PCR reaction to occur) that incorporates a fluorimeter (i.e. an instrument that measures fluorescence). The real-time PCR reaction mixture also contains a reagent whose incorporation into a product can be quantified and whose quantification is indicative of copy number of that sequence in the template. One such reagent is a fluorescent dye, called SYBR Green I (Molecular Probes, Inc.; Eugene, Oreg.) that preferentially binds double-stranded DNA and whose fluorescence is greatly enhanced by binding of double-stranded DNA. When a PCR reaction is performed in the presence of SYBR Green I, resulting DNA products bind SYBR Green I and fluorescence. The fluorescence is detected and quantified by the fluorimeter. Such technique is particularly useful for quantification of the amount of the product in the PCR reaction. Additionally, the product from the PCR reaction may be quantitated in "real-time PCR" by the use of a variety of probes that hybridize to the product including TaqMan probes and molecular beacons. Quantitation may be on an absolute basis, or may be relative to a constitutively methylated DNA standard, or may be relative to an unmethyled DNA standard. In one instance the ratio of methylated HLTF derived product to unmethylated derived HLTF product may be constructed.

Methods for detecting methylation of the HLTF DNA in this invention are not limited to MSP, and may cover any assay for detecting DNA methylation. Another example method for detecting methylation of the HLTF DNA is by using "methylation-sensitive" restriction endonucleases. Such methods comprise treating the genomic DNA isolated from a subject with an methylation-sensitive restriction endonuclease and then using the restriction endonuclease-treated DNA as a template in a PCR reaction. Herein, methylation-sensitive restriction endonucleases recognize and cleave a specific sequence within the DNA if C bases within the recognition sequence are not methylated. If C bases within the recognition sequence of the restriction endonuclease are methylated, the DNA will not be cleaved. Examples of such methylation-sensitive restriction endonucleases include, but are not limited to HpaII, SmaI, SacII, EagI, MspI, BstUI, and BssHII. In this technique, a recognition sequence for a methylation-sensitive restriction endonuclease is located within the template DNA, at a position between the forward and reverse primers used for the PCR reaction. In the case that a C base within the methylation-sensitive restriction endonuclease recognition sequence is not methylated, the endonuclease will cleave the DNA template and a PCR product will not be formed when the DNA is used as a template in the PCR reaction. In the case that a C base within the methylation-sensitive restriction endonuclease recognition sequence is methylated, the endonuclease will not cleave the DNA template and a PCR product will be formed when the DNA is used as a template in the PCR reaction. Therefore, methylation of C bases can be determined by the absence or presence of a PCR product (Kane, et al., 1997, Cancer Res, 57:808-11). No sodium bisulfite is used in this technique.

Yet another exemplary method for detecting methylation of the HLTF DNA is called the modified MSP, which method utilizes primers that are designed and chosen such that products of the MSP reaction are susceptible to digestion by restriction endonucleases, depending upon whether the compound-converted template sequence contains CpG dinucleotides or UpG dinucleotides.

Yet other methods for detecting methylation of the HLTF DNA include the MS-SnuPE methods. This method uses compound-converted HLTF DNA as a template in a primer extension reaction wherein the primers used produce a product, dependent upon whether the compound-converted template contains CpG dinucleotides or UpG dinucleotides (see e.g., Gonzalgo, et al., 1997, Nucleic Acids Res., 25:2529-31).

Another exemplary method for detecting methylation of the HLTF DNA is called COBRA (i.e., combined bisulfite restriction analysis). This method has been routinely used for DNA methylation detection and is well known in the art (see, e.g., Xiong, et al., 1997, Nucleic Acids Res, 25:2532-4).

In certain embodiments, the invention provides methods that involve directly sequencing the product resulting from an MSP reaction to determine if the compound-converted HLTF template sequence contains CpG dinucleotides or UpG dinucleotides. Molecular biology techniques such as directly sequencing a PCR product are well known in the art.

In alternative embodiments, the skilled artisan will appreciate that the present invention is based in part, on the recognition that HLTF functions as a tumor suppressor gene. Accordingly, in certain aspects, the invention provides assays for detecting molecular markers that distinguish between healthy cells and HLTF-associated diseases cells, such as colon neoplasia cells. As described above, one of the molecular markers of the present application includes that methylated HLTF nucleotide sequences. Thus, in one embodiment, assaying for the methylation status of the HLTF nucleotide sequence can be monitored for detecting an HLTF-silencing associated disease.

This application further provides another molecular marker: the HLTF gene expression transcript or the gene product. Thus, in another embodiment, expression of the HLTF nucleic acid or protein can be monitored for detecting an HLTF-silencing associated disease such as a colon neoplasia.

In certain embodiments, the invention provides detection methods by assaying the above-mentioned HLTF molecular markers so as to determine whether a patient has or does not have a disease condition. Further, such a disease condition may be characterized by decreased expression of HLTF nucleic acid or protein described herein. In certain embodiments, the invention provides methods for determining whether a patient is or is not likely to have a HLTF-associated disease by detecting the expression of the HLTF nucleotide sequences. In further embodiments, the invention provides methods for determining whether the patient is having a relapse or determining whether a patient's cancer is responding to treatment.

In a preferred embodiment, the application provides method for detecting colon neoplasia. In certain embodiments, the present invention provides methods for detecting a colon neoplasia that is associated with silencing of HLTF gene. Such methods comprise assaying for the presence of a methylated HLTF nucleotide sequence in a sample obtained from a subject. In other aspects, the invention relates to methods for determining whether a patient is likely or unlikely to have a colon cancer. In further aspects, the invention relates to methods for monitoring colon neoplasia in a subject.

In certain embodiments, the invention provides assays for detecting HLTF protein or nucleic acid transcript described herein. In certain embodiments, a method of the invention comprises providing a biological sample and probing the biological sample for the HLTF expression which include protein or nucleic acid transcript of the HLTF. Information regarding the HLTF expression status, and optionally the quantitative level of the HLTF expression, may then be used to draw inferences about the nature of the biological sample and, if the biological sample was obtained from a subject, the health state of the subject.

In certain embodiments, methods of the present invention further comprise assaying for detecting a protein or a nucleic acid transcript selected from p16, THBS1, and hMLH1. The present inventors discovered that HLTF methylation correlates strongly with a pathway termed as the CpG island methylator phenotype (CIMP+), which may involve methylation of multiple genes, including p16, THBS1, and HMLH1. Methylation of these genes may lead to aberrant expression of the gene or the protein.

In certain embodiments, a method of the invention comprises detecting the presence of HLTF protein in a sample. Optionally, the method involves obtaining a quantitative measure of the HLTF protein in the sample. In view of this specification, one of skill in the art will recognize a wide range of techniques that may be employed to detect and optionally quantitate the presence of a protein. In preferred embodiments, HLTF protein is detected with an antibody. In many embodiments, an antibody-based detection assay involves bringing the sample and the antibody into contact so that the antibody has an opportunity to bind to proteins having the corresponding epitope. In many embodiments, an antibody-based detection assay also typically involves a system for detecting the presence of antibody-epitope complexes, thereby achieving a detection of the presence of the proteins having the corresponding epitope. Antibodies may be used in a variety of detection techniques, including enzyme-linked immunosorbent assays (ELISAs), immunoprecipitations, Western blots. Antibody-independent techniques for identifying a protein may also be employed. For example, mass spectroscopy, particularly coupled with liquid chromatography, permits detection and quantification of large numbers of proteins in a sample. Two-dimensional gel electrophoresis may also be used to identify proteins, and may be coupled with mass spectroscopy or other detection techniques, such as N-terminal protein sequencing. RNA aptamers with specific binding for the protein of interest may also be generated and used as a detection reagent.

Samples should generally be prepared in a manner that is consistent with the detection system to be employed. For example, a sample to be used in a protein detection system should generally be prepared in the absence of proteases. Likewise, a sample to be used in a nucleic acid detection system should generally be prepared in the absence of nucleases. In many instances, a sample for use in an antibody-based detection system will not be subjected to substantial preparatory steps. For example, urine may be used directly, as may saliva and blood, although blood will, in certain preferred embodiments, be separated into fractions such as plasma and serum.

In certain embodiments, a method of the invention comprises detecting the presence of an HLTF-expressed nucleic acid, such as an mRNA, in a sample. Optionally, the method involves obtaining a quantitative measure of the HLTF-expressed nucleic acid in the sample. In view of this specification, one of skill in the art will recognize a wide range of techniques that may be employed to detect and optionally quantitate the presence of a nucleic acid. Nucleic acid detection systems generally involve preparing a purified nucleic acid fraction of a sample, and subjecting the sample to a direct detection assay or an amplification process followed by a detection assay. Amplification may be achieved, for example, by polymerase chain reaction (PCR), reverse transcriptase (RT) and coupled RT-PCR. Detection of a nucleic acid is generally accomplished by probing the purified nucleic acid fraction with a probe that hybridizes to the nucleic acid of interest, and in many instances detection involves an amplification as well. Northern blots, dot blots, microarrays, quantitative PCR, and quantitative RT-PCR are all well known methods for detecting a nucleic acid in a sample.

In certain embodiments, the invention provides nucleic acid probes that bind specifically to an HLTF nucleic acid. Such probes may be labeled with, for example, a fluorescent moiety, a radionuclide, an enzyme or an affinity tag such as a biotin moiety. For example, the TaqMang® system employs nucleic acid probes that are labeled in such a way that the fluorescent signal is quenched when the probe is free in solution and bright when the probe is incorporated into a larger nucleic acid.

Immunoscintigraphy using monoclonal antibodies directed at the HLTF marker may be used to detect and/or diagnose a cancer. For example, monoclonal antibodies against the HLTF marker labeled with $^{99}$Technetium, $^{111}$Indium, $^{125}$Iodine-may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

In certain embodiments, the present invention provides drug screening assays for identifying test compounds which potentiate the tumor suppressor function of the HLTF gene. In one aspect, the assays detect test compounds which potentiate the expression level of the HLTF. In another aspect, the assays detect test compounds which inhibit the methylation of the HLTF nucleotide sequences. In certain embodiments, drug screening assays can be generated which detect test compounds on the basis of their ability to interfere with stability or function of the HLTF polypeptide. Alternatively, simple binding assays can be used to detect compounds that inhibit or potentiate the interaction between the HLTF polypeptide and its interacting protein (e.g., Sp1 or Sp3) or the binding of the HLTF polypeptide to a target DNA.

A variety of assay formats may be used and, in light of the present disclosure, those not expressly described herein will nevertheless considered to be within the purview of ordinary skill in the art. Assay formats can approximate such conditions as HLTF expression level, methylation status of HLTF sequence, tumor suppressing activity, transcriptional activating activity and may be generated in many different forms. In many embodiments, the invention provides assays including both cell-free systems and cell-based assays which utilize intact cells.

Compounds to be tested can be produced, for example, by bacteria, yeast or other organisms (e.g., natural products), produced chemically (e.g., small molecules, including peptidomimetics), or produced recombinantly. The efficacy of the compound can be assessed by generating dose response curves from data obtained using various concentrations of the test compound. Moreover, a control assay can also be performed to provide a baseline for comparison. In the control assay, the formation of complexes is quantitated in the absence of the test compound.

In many drug screening programs which test libraries of compounds and natural extracts, high throughput assays are desirable in order to maximize the number of compounds surveyed in a given period of time. Assays of the present invention which are performed in cell-free systems, such as may be developed with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target.

In certain embodiments, test compounds identified from these assays may be used in a therapeutic method for treating an HLTF-associated proliferative disease.

Still another aspect of the application provides transgenic non-human animals which express a heterologous HLTF gene, or which have had one or more genomic HLTF gene(s) disrupted in at least one of the tissue or cell-types of the animal. For instance, transgenic mice that are disrupted at their HLTF gene locus can be generated.

In another aspect, the application provides an animal model for an HLTF-associated proliferative disease, which has a mis-expressed HLTF allele. For example, a mouse can be bred which has an HLTF allele deleted, or in which all or part of one or more HLTF exons are deleted. Such a mouse model can then be used to study disorders arising from mis-expression of the HLTF gene.

Accordingly, the present application discloses transgenic animals which are comprised of cells (of that animal) containing an HLTF transgene and which preferably (though optionally) express an exogenous HLTF protein in one or more cells in the animal. The HLTF transgene can encode the wild-type form of the protein, or can encode homologs thereof, including both agonists and antagonists, as well as antisense constructs. The HLTF transgene can include an HLTF nucleotide sequence (e.g., SEQ ID NOs: 2-4, 21 or 39) or fragments thereof. In preferred embodiments, the expression of the transgene is restricted to specific subsets of cells, tissues or developmental stages utilizing, for example, cis-acting sequences that control expression in the desired pattern.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the HLTF polypeptides. For example, excision of a target sequence which interferes with the expression of a recombinant HLTF gene can be designed to activate expression of that gene. This interference with expression of the protein can result from a variety of mechanisms, such as spatial separation of the HLTF gene from the promoter element or an internal stop codon. Moreover, the transgene can be made wherein the coding sequence of the gene is flanked recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the cre/loxP recombinase system of bacteriophage PI (Lakso et al., (1992) Proc. Natl. Acad. Sci. USA 89:6232-6236; Orban et al., (1992) Proc. Natl. Acad. Sci. USA 89:6861-6865) or the FLP recombinase system of Saccharomyces cerevisiae (O'Gorman et al., (1991) Science 251:1351-1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al., (1984) J. Biol. Chem. 259:1509-1514); catalyzing the excision of the target sequence when the loxP sequences are oriented as direct repeats and catalyzes inversion of the target sequence when loxP sequences are oriented as inverted repeats.

V. Subjects and Samples

In certain aspects, the invention relates to a subject suspected of having or has an HLTF-associated disease such as colon neoplasia. Alternatively, a subject may be undergoing routine screening and may not necessarily be suspected of having such an HLTF-associated disease or condition. In a preferred embodiment, the subject is a human subject and the HLTF associated disease is colon neoplasia.

Assaying for HLTF markers discussed above in a sample from subjects not known to have a colon neoplasia can aid in diagnosis of such a colon neoplasia in the subject. To illustrate, detecting the methylation status of the HLTF nucleotide sequence by MSP can be used by itself, or in combination with other various assays, to improve the sensitivity and/or specificity for detecting a colon neoplasia. Preferably, such a detection is made at an early stage in the development of cancer, so that treatment is more likely to be effective.

In addition to diagnosis, assaying of an HLTF marker in a sample from a subject not known to have colon neoplasia, can be prognostic for the subject (i.e., indicating the probable course of the disease). To illustrate, subjects having a predisposition to develop colon neoplasia may possess methylated HLTF nucleotide sequences. Assaying of HLTF markers in a samples from subjects can also be used to select a particular therapy or therapies which are particularly effective against the colon neoplasia in the subject, or to exclude therapies that are not likely to be effective.

Assaying of HLTF markers in samples from subjects that are known to have, or to have had, a cancer associated with silencing of the HLTF gene is also useful. For example, the present methods can be used to identify whether therapy is effective or not for certain subjects. One or more samples are taken from the same subject prior to and following therapy, and assayed for the HLTF markers. A finding that the HLTF marker is present in the sample taken prior to therapy and absent (or at a lower level) after therapy would indicate that the therapy is effective and need not be altered. In those cases where the HLTF marker is present in the sample taken before therapy and in the sample taken after therapy, it may be desirable to alter the therapy to increase the likelihood that the cancer will be eradicated in the subject. Thus, the present method may obviate the need to perform more invasive procedures which are used to determine a patient's response to therapy.

Cancers frequently recur following therapy in patients with advanced cancers. In this and other instances, the assays of the invention are useful for monitoring over time the status of an cancer associated with silencing of the HLTF gene. For subjects in which a cancer is progressing, an HLTF marker may be absent from some or all samples when the first sample is taken and then appear in one or more samples when the second sample is taken. For subjects in which cancer is regressing, an HLTF marker may be present in one or a number of samples when the first sample is taken and then be absent in some or all of these samples when the second sample is taken.

Samples for use with the methods described herein may be essentially any biological material of interest. For example, a sample may be a bodily fluid sample from a subject, a tissue sample from a subject, a solid or semi-solid sample from a subject, a primary cell culture or tissue culture of materials derived from a subject, cells from a cell line, or medium or other extracellular material from a cell or tissue culture, or a xenograft (meaning a sample of a cancer from a first subject, e.g., a human, that has been cultured in a second subject, e.g., an immuno-compromised mouse). The term "sample" as used herein is intended to encompass both a biological material obtained directly from a subject (which may be described as the primary sample) as well as any manipulated forms or portions of a primary sample. A sample may also be obtained by contacting a biological material with an exogenous liquid, resulting in the production of a lavage liquid containing some portion of the contacted biological material. Furthermore, the term "sample" is intended to encompass the primary sample after it has been mixed with one or more additive, such as preservatives, chelators, anti-clotting factors, etc.

In certain embodiments, a bodily fluid sample is a blood sample. In this case, the term "sample" is intended to encompass not only the blood as obtained directly from the patient but also fractions of the blood, such as plasma, serum, cell fractions (e.g., platelets, erythrocytes, and lymphocytes), protein preparations, nucleic acid preparations, etc. In certain embodiments, a bodily fluid sample is a urine sample or a colonic effluent sample. In certain embodiments, a bodily fluid sample is a stool sample.

A subject is preferably a human subject, but it is expected that the molecular markers disclosed herein, and particularly their homologs from other animals, are of similar utility in other animals. In certain embodiments, it may be possible to detect an HLTF marker directly in an organism without obtaining a separate portion of biological material. In such instances, the term "sample" is intended to encompass that portion of biological material that is contacted with a reagent or device involved in the detection process.

In certain embodiments, DNA which is used as the template in an MSP reaction is obtained from a bodily fluid sample. Examples of preferred bodily fluids are blood, serum, plasma, a blood-derived fraction, stool, colonic effluent or urine. Other body fluids can also be used. Because they can be easily obtained from a subject and can be used to screen for multiple diseases, blood or blood-derived fractions are especially useful. For example, it has been shown that DNA alterations in colorectal cancer patients can be detected in the blood of subjects (Hibi, et al., 1998, Cancer Res, 58:1405-7). Blood-derived fractions can comprise blood, serum, plasma, or other fractions. For example, a cellular fraction can be prepared as a "buffy coat" (i.e., leukocyte-enriched blood portion) by centrifuging 5 ml of whole blood for 10 min at 800 times gravity at room temperature. Red blood cells sediment most rapidly and are present as the bottom-most fraction in the centrifuge tube. The buffy coat is present as a thin creamy white colored layer on top of the red blood cells. The plasma portion of the blood forms a layer above the buffy coat. Fractions from blood can also be isolated in a variety of other ways. One method is by taking a fraction or fractions from a gradient used in centrifugation to enrich for a specific size or density of cells.

DNA is then isolated from samples from the bodily fluids. Procedures for isolation of DNA from such samples are well known to those skilled in the art. Commonly, such DNA isolation procedures comprise lysis of any cells present in the samples using detergents, for example. After cell lysis, proteins are commonly removed from the DNA using various proteases. RNA is removed using RNase. The DNA is then commonly extracted with phenol, precipitated in alcohol and dissolved in an aqueous solution.

VI. Therapeutic Methods for HLTF-Associated Diseases

Yet another aspect of this application pertains to methods of treating an HLTF-associated proliferative disease which arises from reduced expression or over-expression of the HLTF gene in cells. Such HLTF-associated proliferative diseases (for example, a colon neoplasia) can result from a wide variety of pathological cell proliferative conditions. In certain embodiments, treatment of an HLTF-associated proliferative disorder includes modulation of the HLTF gene expression or HLTF activity. The term "modulate" envisions the suppression of expression of HLTF when it is over-expressed, or augmentation of HLTF expression when it is under-expressed.

In an embodiment, the present invention provides a therapeutic method by using an HLTF gene construct as a part of a gene therapy protocol, such as to reconstitute the function of an HLTF protein (e.g., SEQ ID NO: 1) in a cell in which the HLTF protein is mis-expressed or non-expressed. To illustrate, cell types which exhibit pathological or abnormal growth presumably depend at least in part on a function of a HLTF protein. For example, gene therapy constructs encoding the HLTF protein can be utilized in a colon neoplasia that is associated with silencing of the HLTF gene.

In certain embodiments, the invention provides therapeutic methods using agents which induce re-expression of HLTF. Loss of HLTF gene expression in an HLTF-associated diseased cells may be due at least in part to methylation of the HLTF nucleotide sequence, methylation suppressive agents such as 5-deoxyazacytidine or 5-azacytidine can be introduced into the diseased cells. Other similar agents will be known to those of skill in the art. A preferred embodiments the HLTF-associated disease is colon neoplasia associated with increased methylation of HLTF nucleotide sequences.

In certain embodiments, the invention provides therapeutic methods using a nucleic acid approach, for example, antisense nucleic acid, ribozymes or triplex agents, to block transcription or translation of a specific HLTF mRNA, either by masking that mRNA with an antisense nucleic acid or triplex agent or by cleaving it with a ribozyme. Such disorders include neurodegenerative diseases, for example. Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate an mRNA that is double-stranded. Antisense oligomers of about 15 nucleotides are preferred, since they are easily synthesized and are less likely to cause problems than larger molecules when introduced into a target HLTF over-producing cell. Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991). Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988).

The present invention also provides gene therapy for the treatment of proliferative or immunologic disorders which are mediated by HLTF protein. Such therapy would achieve its therapeutic effect by introduction of the HLTF antisense polynucleotide into cells having the proliferative disorder. Alternatively, it may be desirable to introduce polynucleotides encoding full-length HLTF into diseased cells.

Delivery of antisense HLTF polynucleotide or the HLTF gene can be achieved using a recombinant expression vector such as a chimeric virus or a colloidal dispersion system. Especially preferred for therapeutic delivery of antisense sequences is the use of targeted liposomes. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting an HLTF sequence of interest into the viral vector, along with another gene which encodes the ligand for a receptor on a specific target cell, for example, the vector is target-specific. Retroviral vectors can be made target-specific by attaching, for example, a sugar, a glycolipid or a protein. Preferred targeting is accomplished by using an antibody to target the retroviral vector. Those skilled in the art will know of, or can readily ascertain without undue experimentation, specific polynucleotide sequences which can be inserted into the retroviral genome or attached to a viral envelope to allow target-specific delivery of the retroviral vector containing antisense HLTF polynucleotide or the HLTF gene.

The invention also relates to a medicament or pharmaceutical composition comprising an HLTF 5' flanking polynucleotide or an HLTF 5' flanking polynucleotide operably linked to the HLTF structural gene, respectively, in a pharmaceutically acceptable excipient or medium wherein the medicament is used for therapy of HLTF-associated cell proliferative disorders, such as a colon neoplasia.

Exemplification

The invention now being generally described, it will be more readily understood by reference to the following examples, which are included merely for purposes of illustration of certain aspects and embodiments of the present invention, and are not intended to limit the invention.

1. Amplification and Sequencing of HLTF cDNA.

HLTF cDNA sequence was obtained from Genbank (accession No. Z46606) and primers were chosen by using MacVector software (Oxford Molecular). The HLTF cDNA was amplified in two overlapping fragments (5' fragment 286F/1381R and 3' fragment 1317F/3456R). Primer sequences were as follows: HLTF-286F (5'-GCTCCTCT-TGTCATCCCACTCA, SEQ ID NO: 44), HLTF-1381R (5'-CGTCTTTGCTTAGTCCATCTGCCTT, SEQ ID NO: 45), HLTF-1317F (5"-CGATGGTCTATGAAACTTGGA, SEQ ID NO: 46), and HLTF-3456R (5'-GAAATTGTGTCAG-TAATACCTCTTCAC, SEQ ID NO: 47). The HLTF 5' genomic sequence was identified from Genbank genomic clone sequence (NT_005616).

2. Methylation-Specific PCR (MS-PCR).

500 ng DNA from each sample in a volume of 50 ul were denatured by NaOH (freshly made, final concentration, 0.2 M) at 37° C. for 15 min. Next, 30 ul 10 mM hydroquinone (fresh) and 520 ul 3.0 M NaHSO4 (freshly prepared sodium bisulfite, pH5.0) were added, and incubated at 55° C. for 16 hrs. Modified DNA was purified using Wizard DNA Clean-Up System (Promega). The reaction was desulphonated by NaOH at a final concentration of 0.3 M at room temperature for 15 min and neutralized by adding 10 M NH4OAc, pH7.0, to a final concentration of 3 M. DNA was precipitated with 3 volumes of absolute ethanol for 30 min at −80° C. The DNA pellet was then dissolved in distilled water to give approximately 10 ng/ul. Sodium bisulfite treated DNA was used as the template for subsequent methylation-specific PCR.

The primer sequences were based on the HLTF 5' genomic sequence and were specific for fully modified DNA. Primer set for the methylated DNA are P-HLTF1352MF: 5'-TGGGGTTTCGTGGTTTTTTCGCGC-3' (SEQ ID NO: 48) and P-HLTF1606MR: 5'-CCGCGAATCCAAT-CAAACGTCGACG-3' (SEQ ID NO: 49), which gives 254 bp product. The primer set for the unmethylated DNA are P-HLTF1347UF: 5'-ATTTTTGGGGTTTTGTG-GTTTTTTTGTGT -3' (SEQ ID NO: 50) and P-HLTF1610UR: ATCACCACAAATCCAATCAAACAT-CAACA-3' (SEQ ID NO: 51), which amplify 284 bp fragment. PCR was carried out using a hot start at 95° C. (9 minutes) and the following cycling parameters: 33 cycles of 95° C. (45s), 66° C. (45s), 72° C. (45s), 72° C. (5 minutes), and 4° C. to cool. The PCR products were run on 3.0% agarose gel.

3. Cell Culture and 5-Azacytidine Treatment.

The cultures were grown and treated as described previously (Veigl, et al., 1998, *Proc. Natl. Acad. Sci. USA*, 95:8698-8702). The optimal tolerated doses were determined for each treated line, and two doses were used for some lines, ranging from 1 µg/ml to 3 µg/ml.

4. Clonogenic Assays and Transfections.

Cells were plated in 6-well dishes (12,000-20,00 cells/well) 24 hours before transfection in a regular growing medium and transfected with 0.4 µg DNA/well with effectene (QIAGEN) according to manufacturers protocol. G418 (0.5 mg/ml for FET, 0.6 mg/ml for V457) was added to the wells 48 hours after transfection, and cell were kept in G418 media (replaced bi-weekly) for 3 weeks, until tight colonies were observed. Colonies were stained with trypan blue and counted.

5. Statistical Methods.

Comparisons of HLTF methylation with sex, MLH1 methylation status, and CIMP (i.e., CpG island methylator phenotype) status were done using a two tailed Fisher's exact test. Comparison of HLTF methylation status with tumor site or stage was done using a Pearson's chi-squared test, with test for trend using a Mantel chi-squared test. Comparison of age distribution of smarca3 methylation in cancers and in normal tissue was done using a Wilcoxin non-parametric test.

6. HLTF is not Mutated in Colon Cancers.

As several SWI/SNF family genes have been found to be altered in human cancers, we first determined the sequence of the HLTF cDNA amplified by RT-PCR from 34 colon cancer cell lines matched to primary patient samples in our colon cancer bank. Only one mutation was detected, a hemizygous nonsense mutation at codon 979. Thus HLTF is not a common target for gene mutation in colon cancer.

7. HLTF is Frequently Methylated and Silenced in Colon Cancer Cell Lines.

In the process of HLTF sequence analysis in colon cancer cell lines we noted that 9 out of 34 of these cell lines did not express HLTF cDNA (FIG. 1A). Southern analysis did not identify any alterations in the HLTF locus. Coincidentally, in some of the cell lines that had lost HLTF expression we previously had demonstrated silencing of the hMLH 1 gene due to promoter methylation (Veigl, et al., 1998, Proc. Natl. Acad. Sci. USA, 95:8698-8702). We therefore examined the genomic sequence upstream of and within the HLTF gene (herein referred to as 5'-HLTF genomic sequence) which contained a CpG dense region that could potentially be methylated (FIG. 2A). No TATA box consensus sequence was found within this region of 5' HLTF genomic sequence. However, it did contain a consensus initiator element, and two SP1 sites that are typical of TATA-less housekeeping gene promoters.

To test for methylation of this CpG-rich region, we used the technique of methylation specific PCR (Herman, et al., 1996, Proc. Natl. Acad. Sci. USA, 93:9821-9826), employing PCR primers specific for amplification of either methylated or unmethylated DNA templates (FIG. 2A). As shown in FIG. 2B, all colon cancer cell lines that lacked HLTF gene expression demonstrated methylation of CpG sites within the 5' HLTF genomic sequence; whereas, methylation was not detected in the HLTF expressing cell lines. These results were confirmed by two independent MS-PCR assays that tested different HLTF CpG sites, as well as by resistance of the 5' HLTF genomic sequence to digestion with a methylation-sensitive restriction enzyme, HpaII enzyme. Thus, cell lines that had silenced the HLTF gene demonstrated methylation across the CpG sites within this entire region, whereas HLTF-expressing cell lines assayed as free of methylated CpG sites.

For three of these HLTF methylated cell lines, DNA from matched normal and antecedant tumor DNA was additionally available (V6, V8, and V432). In each of these cases, HLTF DNA methylation was detected in the primary tumors, but was absent in the matched normal tissues (FIG. 2C), verifying that HLTF methylation and silencing was a true somatic event and was not an artifact of cell line cultures.

8. Re-Induction of HLTF Expression.

Figure 1B:
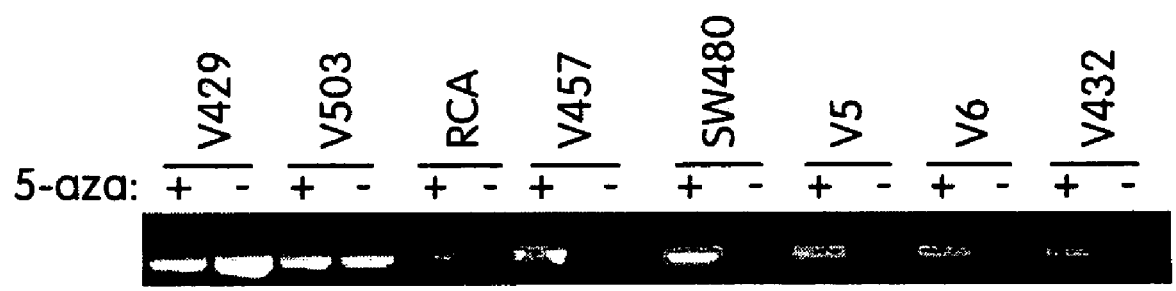

To establish that methylation was responsible for silencing HLTF gene expression, cell lines with HLTF DNA methylation were treated with 5-azacytidine (5-azaC), a demethylating agent. As shown in FIGS. 1B, 5-azaC treatment reactivated HLTF expression in all these cell lines, though Vaco457 required higher dose of 5-azaC for reactivation, compared to other cell lines. However, 5-AzaC did not further increase HLTF expression in control cell lines in which HLTF expression was constitutive and in which the basal HLTF DNA was unmethylated.

9. HLTF Methylation is Widespread in Primary Colon Cancer.

Figure 3:
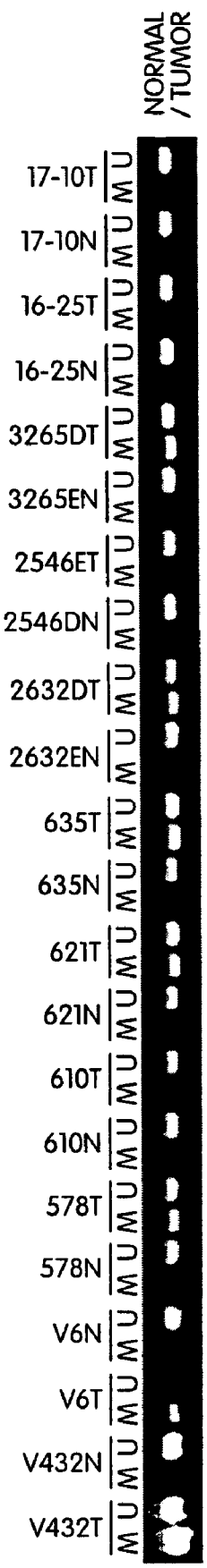
FIG. 3 shows methylation status of the HLTF 5' genomic region in primary tumors and matched normal tissues. Shown are the results of MS-PCR assay of the HLTF 5' genomic region in matched paired tumor (T) and normal (N) colon tissues samples amplified with primers specific for methylated (M) or unmethylated (U) templates.

To further establish the frequency of HLTF methylation in primary colon cancer tumors, we analyzed 63 pairs of primary colon tumors along with matched normal tissues (FIG. 3). HLTF methylation was detected in 27 of 63 (45%) colon cancer cases. In contrast, no evidence of HLTF gene silencing was detected in 30 lung tumor cell lines, or 8 breast cancer samples tested.

The finding of HLTF methylation in colon cancer tumors and cell lines was not correlated with patients' sex ($p=0.31$) or with age ($p=0.14$) (FIG. 4A), with a median age of 72 in persons with HLTF methylated cancers versus 68 in those with HLTF umnethylated cancers. In the overwhelming majority of cases (84%), HLTF methylation was detected only in the colon cancers, and was absent from the same individuals' normal colon tissues. HLTF methylation thus substantially arose in these individuals specifically during the neoplastic process. However, in 16% of individuals whose colon cancers demonstrated HLTF methylation, very faint HLTF methylation was also detectable in histologically normal colon tissue.

Figure 4B:
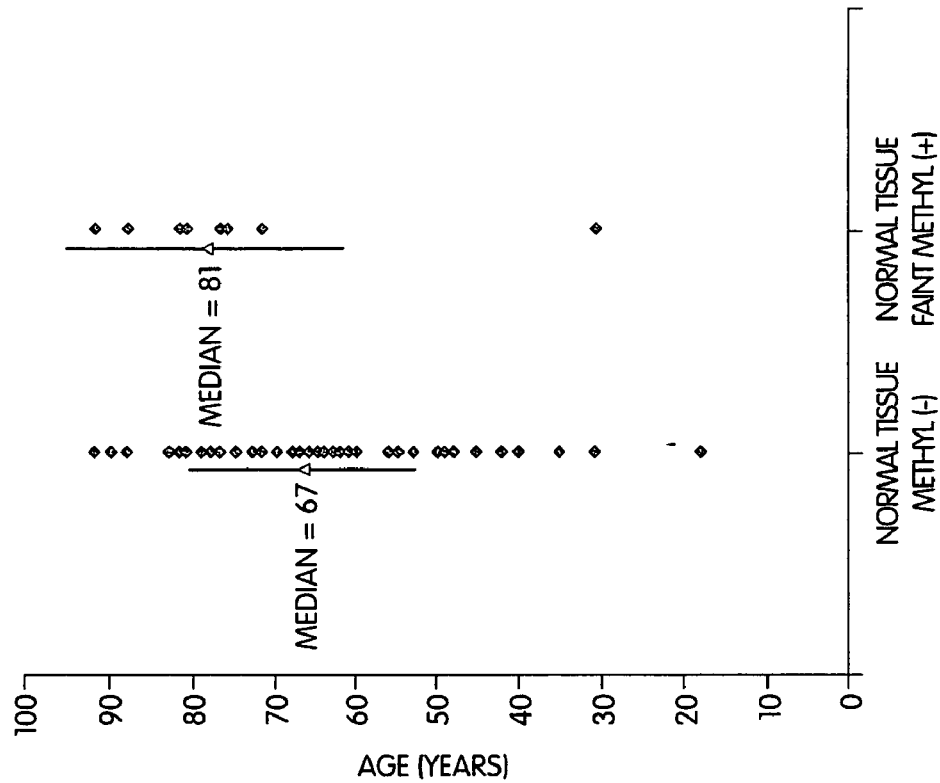
FIG. 4 shows correlation of HLTF 5' genomic region methylation with age. A. In colon cancer tumors and cell lines, B. In normal colon tissues.
Figure 4A:
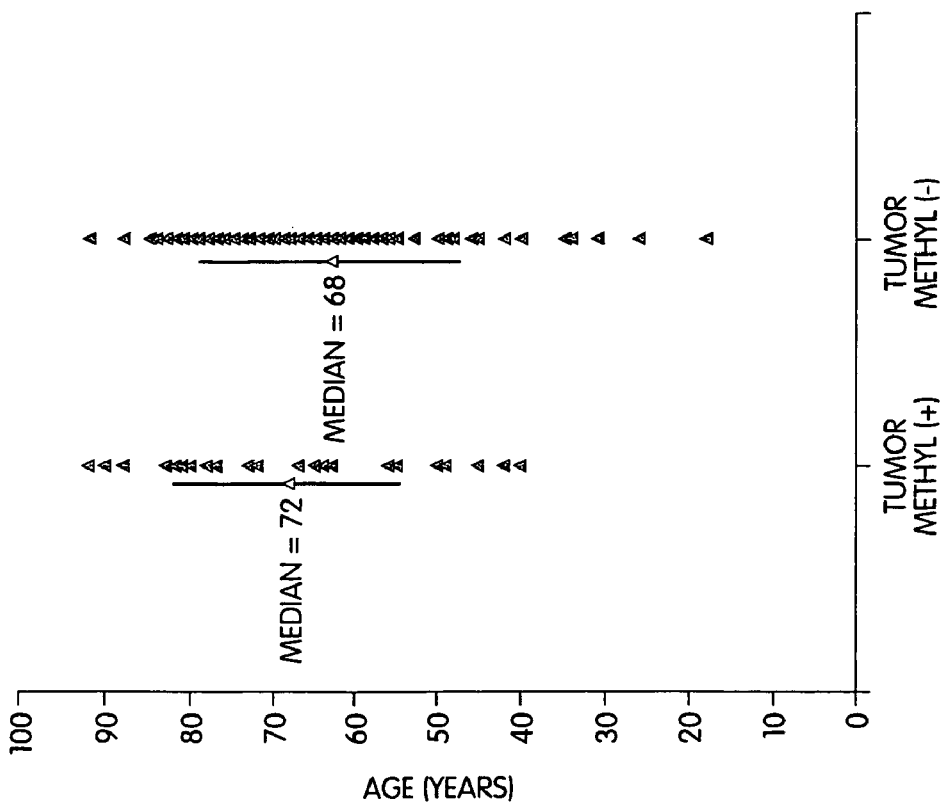
Figure 5A:
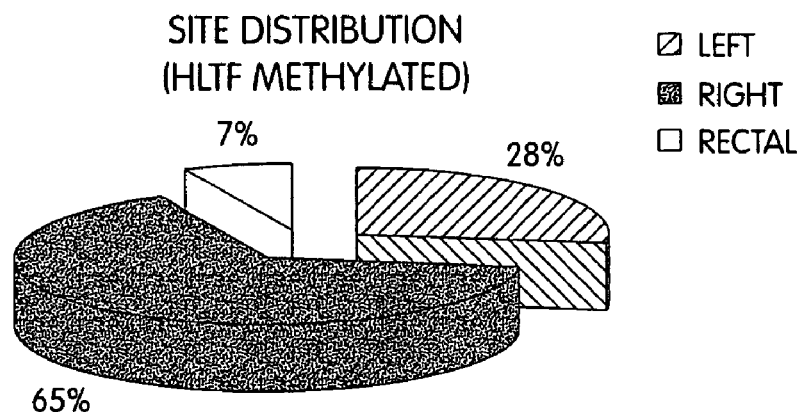
FIG. 5 shows correlation of HLTF 5' genomic region methylation with tumor site (A, B) or with tumor stage (C, D). Shown in A and B are percentage (%) of colon neoplasms (tumors and cell lines) in each category defined by location of the tumor in the colon and HLTF methylation status. Shown in C and D are percentage (%) of colon neoplasms (tumors and cell lines) in each category defined by clinical stage of the colon tumor and HLTF methylation status.
Figure 5B:
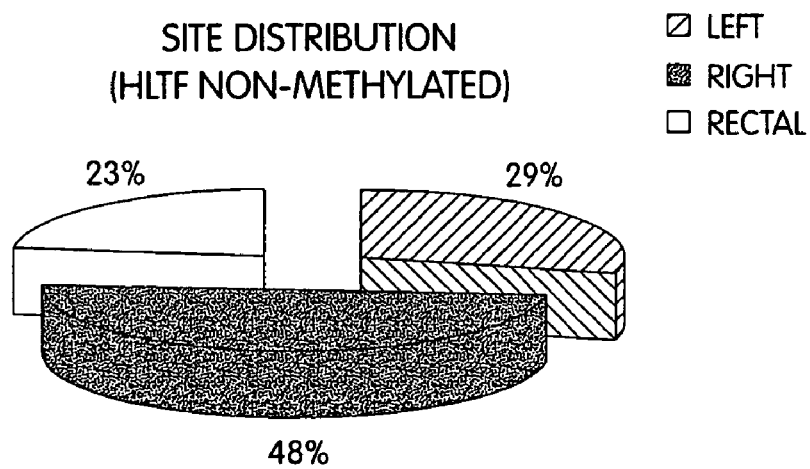
Figure 5C:
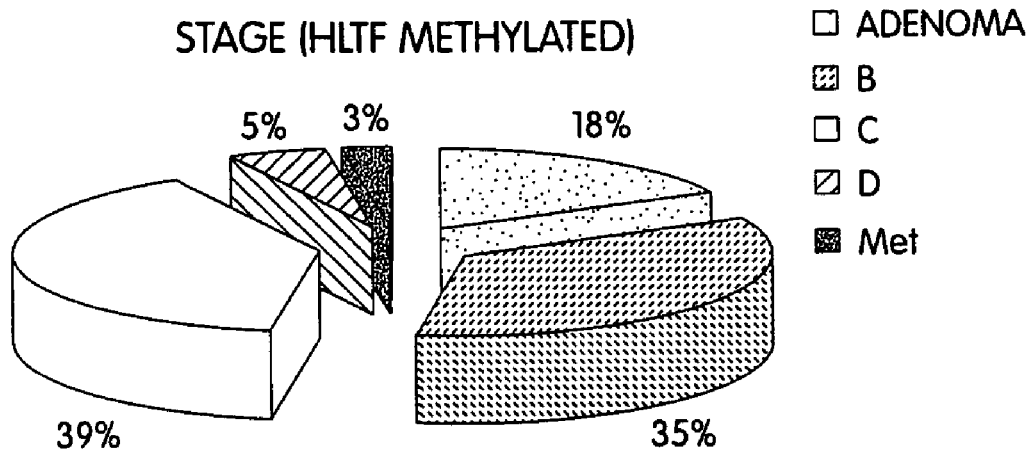
Figure 5D:
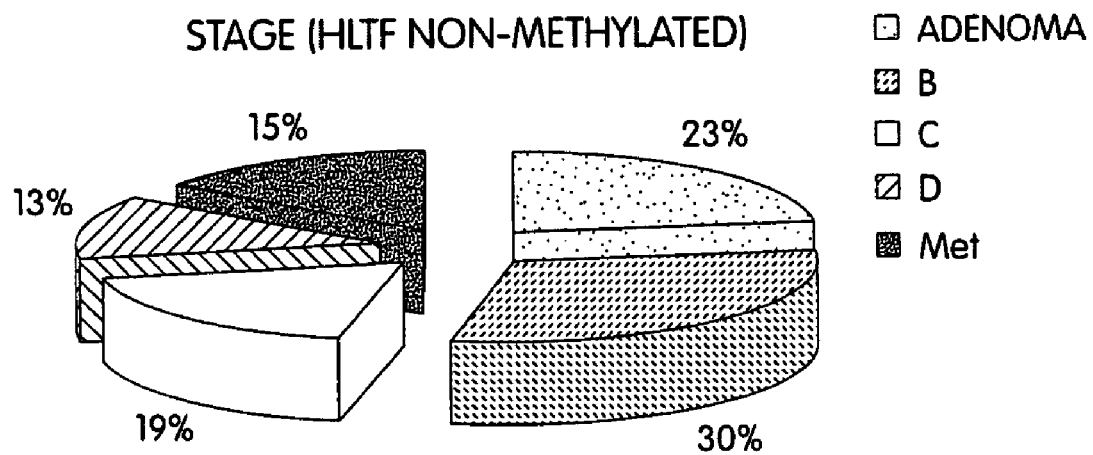

This was also the case in a small subset of all individuals from whom normal colon tissues were available to us, among whom faint HLTF methylation was detectable in 9 out of 78 normal colon samples (12%). Normal colon tissues showing faint HLTF methylation were in general those derived from the oldest individuals studied, with a median age of 81 for individuals demonstrating faint HLTF methylation in normal colon tissues versus 67 for those with whose normal colon tissue showed only unmethylated HLTF ($p=0.02$) (FIG. 4B). We cannot determine whether HLTF methylated cells when detected in normal colon tissues are derived from contamination by cancer cells derived from a frank cancer that was concurrently resected in the same colon specimen from which our normal sample was taken, are derived from microscopic early colon neoplasms, or alternatively whether in some instances HLTF methylation can be initiated in the aging colon separately from neoplasia, either as a stochastic event, or in response to endogenous or exogenous genotoxins. However, we favor the explanation that these signals arise from contaminating cancer cells, as no HLTF methylation was detected in colons from any of 12 individuals undergoing colon resection for non-malignant disease. Compared to HLTF expressing cancers, cancers with methylated and silenced HLTF alleles showed a borderline significant trend ($p=0.06$) to be more likely to arise in the proximal right colon and less likely to arise in the left colon or rectum, a trend similar to that previously observed for HNPCC and sporadic MSI colon cancers (Kinzler, et al., 1996, Cell, 87:159-170) (FIG. 5A vs. 5B). The distribution by tumor stage (adenoma; Dukes' stage B, C or D cancer primary; or metastatic lesion) was also significantly different between HLTF methylated and non-methylated colon neoplasms ($p=0.02$). An a postiori grouping of the tumors into a non-metastatic subset and a metastatic subset (Dukes D primary cancers or cancers from distant metastatic sites) suggests the hypothesis that this is due to a lesser likelihood of HLTF methylated tumors being metastastic (nominal p value=0.01) (FIG. 5C vs. 5D).

To determine the timing of onset of HLTF silencing during colon carcinogenesis, we additionally analyzed a group of 14 early and late adenomas for HLTF CpG island methylation. HLTF methylation was detected in 3 of the adenomas tested, all of which were greater than 1.5 cm in size, suggesting that HLTF methylation can occur as early as the late adenoma stage of colon neoplasia. Detection of HLTF methylation may thus be of value for detecting the early and most curable stages of colon neoplasia.

10. HLTF Methylation Defines a Singular Group of Colon Cancers.

Recently, it has been suggested that certain colon cancers are typified by a high frequency of gene promoter methylation and represent a distinct pathway termed the CpG island methylator phenotype (CIMP+) (Toyota, et al., 1999, Proc. Natl. Acad. Sci. USA, 96:8681-8686; Toyota, et al., 2000, Proc. Natl. Acad. Sci. USA, 97:710-715). Tumors exhibiting this phenotype (CIMP+) show concordant CpG island methylation affecting multiple genes, including HMLH1, p16, and THBS1. To establish whether HLTF methylation correlates with HMLH1 methylation, and/or with the CIMP+phenotype, 87 colon cancer cases examined for HLTF methylation were also examined for hMLH1 methylation, and 64 were further assayed for CIMP+ or CIMP-phenotype as determined by methylation status of MINT1, MINT2, MINT31, and MINT27 locii (Toyota, et al., 1999, Proc. Natl. Acad. Sci. USA, 96:8681-8686). HLTF methylation correlated with CIMP+phenotype (p<0.001) (FIG. 6A) and as well with hMLH1 gene methylation (p<0.0001) (FIG. 6B). However, HLTF-methylated tumors essentially defined a distinct subclass of colon cancers that did not fall exclusively into either the hMLH1 methylated or CIMP+groups.

To further determine whether HLTF methylation defines a singular group of colon cancers, we used restriction landmark genomic scanning (RLGS) analysis (Costello, et al., 2000, Nat. Genet., 24:132-138) to compare the patterns of global genome methylation in a group of twelve colon cancer cell lines, six of which demonstrated HLTF methylation and silencing and in six of which HLTF was umethylated and expressed. 497 loci demonstrated methylation present in at least one of the 12 colon cancer cell lines.

However, none of these loci demonstrated the presence of methylation across the six colon cancers in which HLTF was methylated and silenced, as well as the absence of methylation across the 6 colon cancers expressing an unmethylated HLTF allele. While RLGS analysis samples only a portion of the genome, this data independently suggests that HLTF methylation is a unique event, and does not necessarily reflect a genome-wide increase in promoter methylation.

11. HLTF Reconstitution Induces Growth Suppression.

Figure 7A:
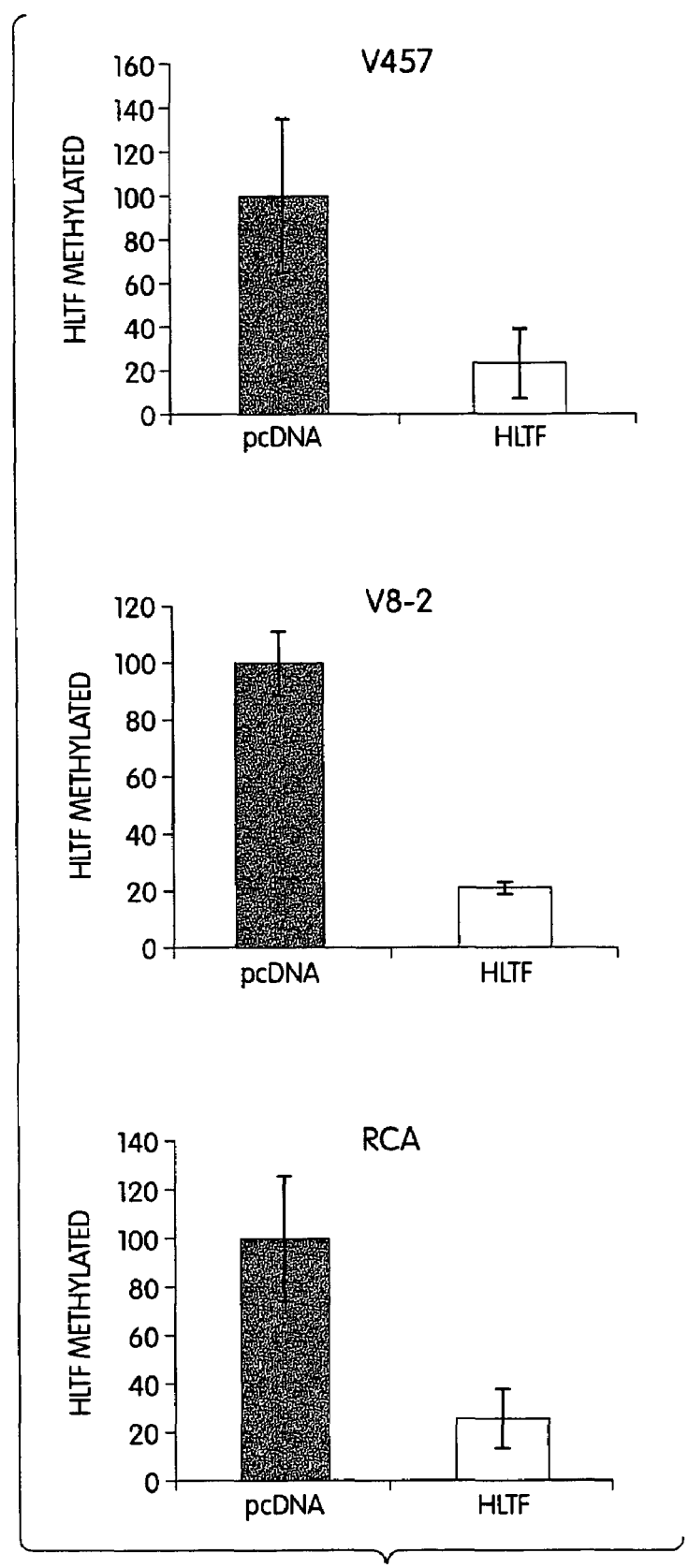
FIG. 7 shows HLTF colony suppressor activity. Shown are the number of G418 resistant colonies arising from transfection with an HLTF expression vector (HLTF) or a control empty expression vector (pcDNA) in HLTF unmethylated and expressing FET, V364 and V429 cells (B) as compared to HLTF methylated and deficient V457, V8-2, and RCA cells (A). C. Anti-V5 western blot assay of V5-epitope tagged HLTF introduced by transient transfection into HLTF methylated versus unmethylated cells. Control cells were transfected with an empty expression vector (pcDNA3.1).
Figure 7B:
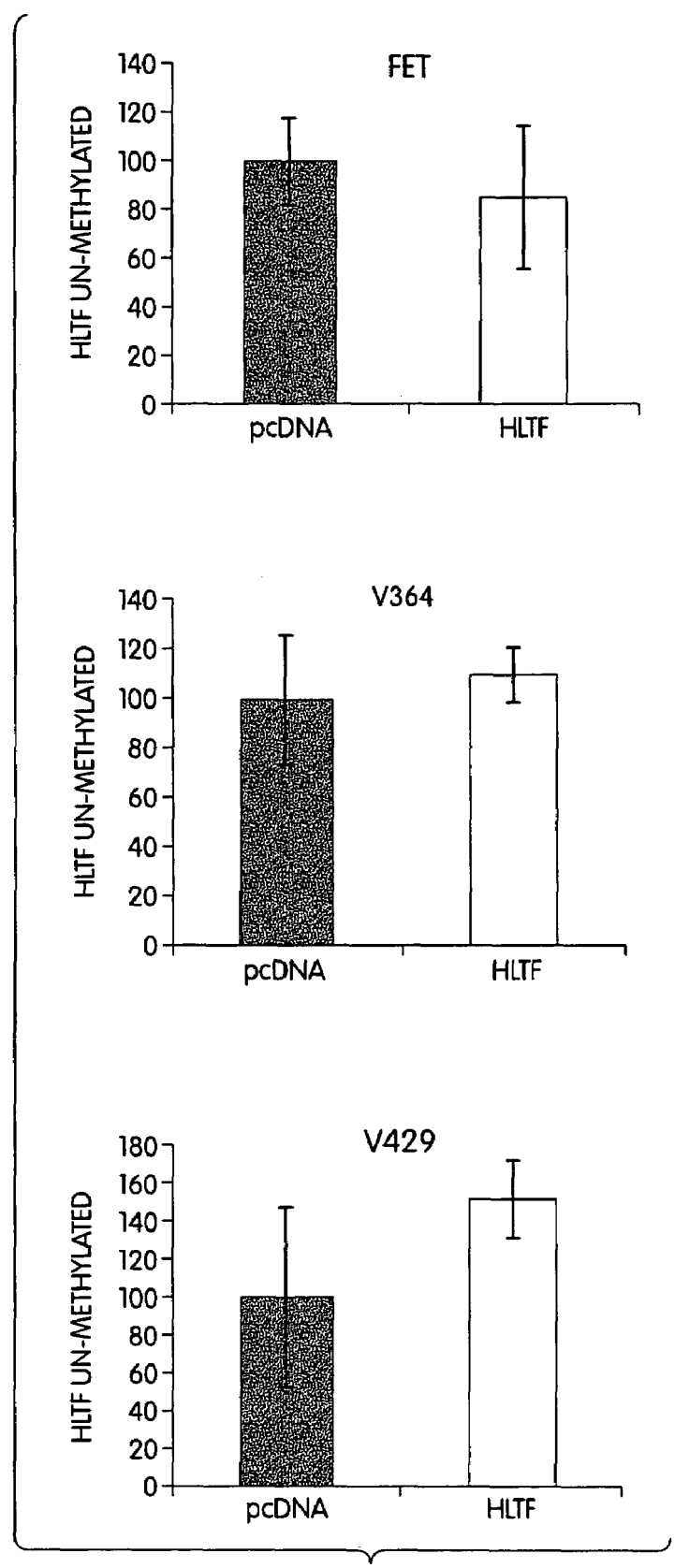
Figure 7C:
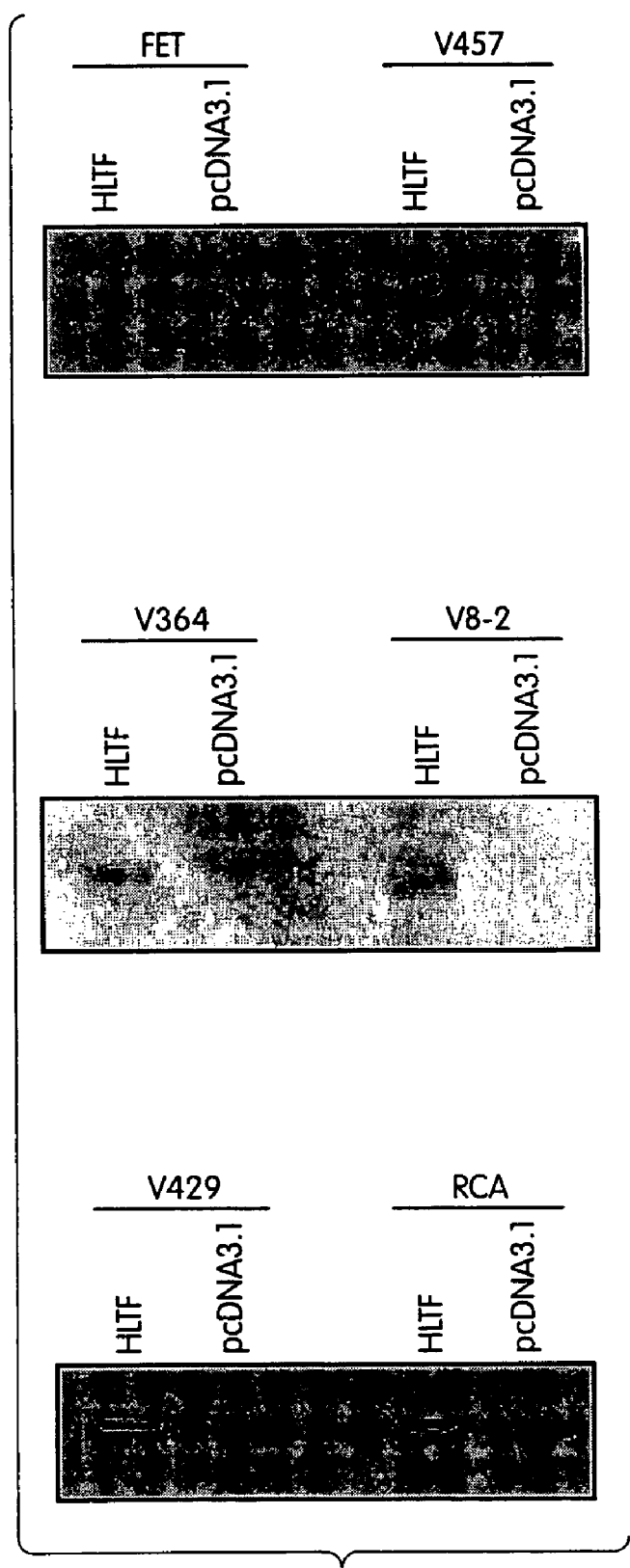
Figure 8:
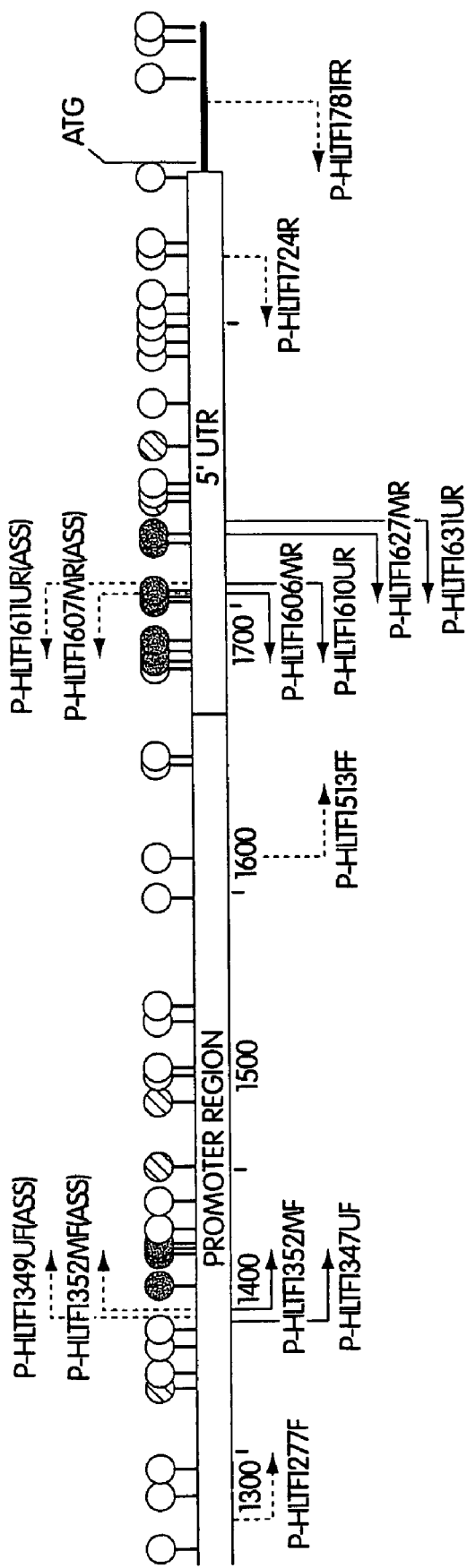
FIG. 8 shows a diagram of the HLTF 5' genomic region. CpG sites are shown with circles and stems. Hatched circles represent CpG sites that overlap HpaII restriction sites. Sequences that are complementary to PCR primers that were used to selectively amplify the methylated but not unmethylated HLTF 5' genomic sequence after digestion with HpaII are designated by the location of the arrows corresponding to forward PCR primer 1277F and reverse PCR primer 1724R. Shaded circles represent the CpG sites that are tested by MS-PCR assay primers described as examples in this application. Locations of specific primers used in the specific MS-PCR assays described as examples in this application are indicated with arrows and correspond to forward PCR primer 1352MF, designed as a forward primer for amplification of bisulfite converted sense sequences of duplex DNA derived from the methylated parental sense strand, and reverse primers 1606MR and 1627MR, designed as reverse primers for amplification of bisulfite converted sequences of duplex DNA derived from methylated parental sense strand. Primers 1352MF(ASS) and 1607MR(ASS) indicate the forward and reverse primers for amplification of duplex DNA derived from bisulfite converted sequences of methylated parental antisense strands. Further, the control primers (indicated as UF or UR) that are used to detect the unmethylated HLTF template in an MSP are also indicated in the diagram.
Figure 9:
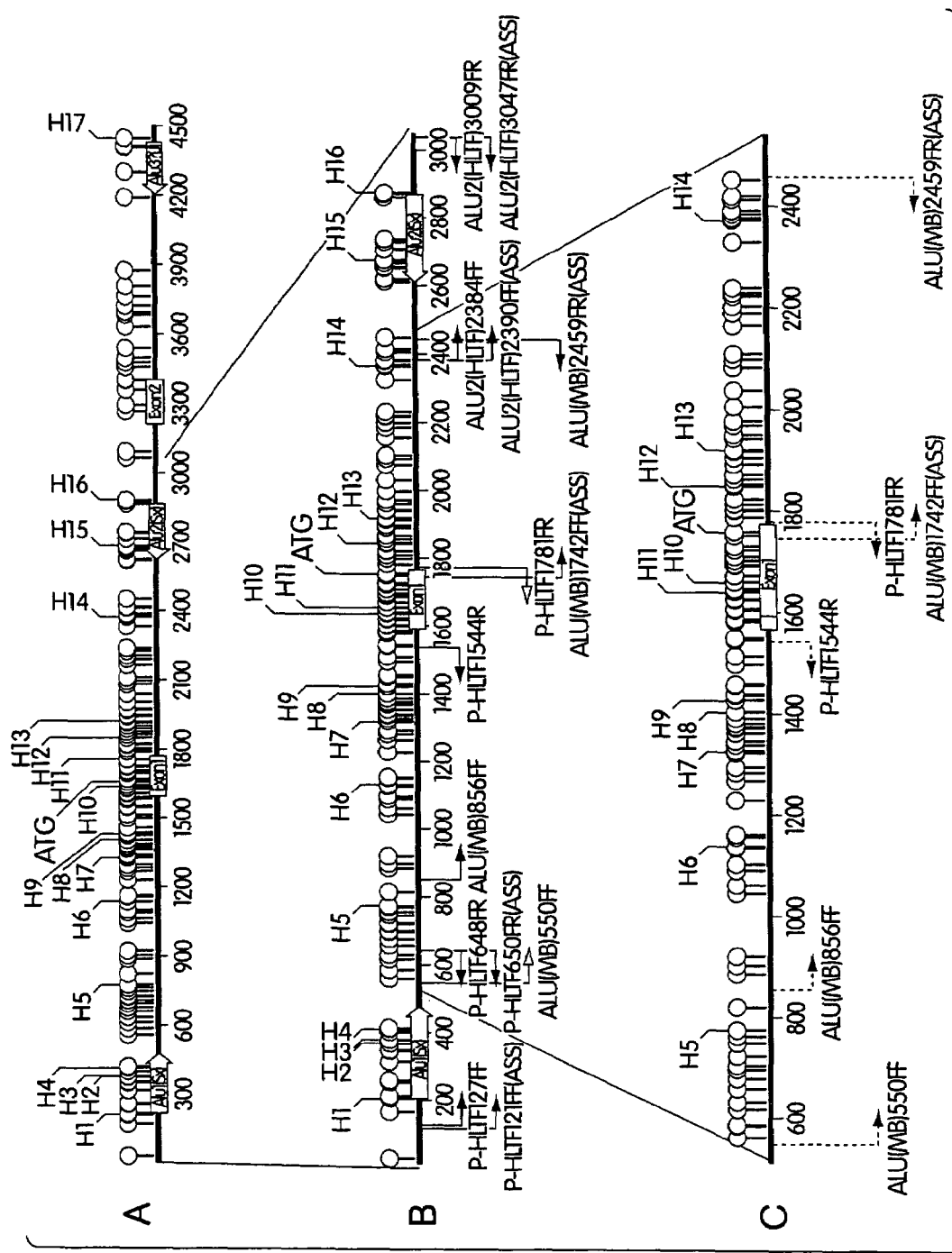
FIG. 9 shows the structure of the 5' region of HLTF at 3 levels of resolution. The top panel (A) depicts residues 0-4500 spanning exons 1 and exons 2, and depicting the position of three Alu repeats in which Alu1 is upstream of exon 1, Alu 2 is in intron 1, and Alu 3 is in intron 3. Balloons designate the positions of CpG dinucleotide sequences. The second panel (B) depicts at higher magnification the structure between residues 0-3000, spanning Alu1, exon1, and Alu2. The third panel (C) shows at higher magnification the region from residues 550 to 2459 that is between Alu1 and Alu2.

The high frequency of HLTF methylation observed in colon cancer suggested that inactivation of this gene might confer a selective advantage. To assay for such an advantage we examined the effect of HLTF transfection on colony formation in three HLTF methylated and non-expressing colon cancer cell lines (V457, V8-2, RCA) as compared to three HLTF unmethylated and expressing colon cancer cell lines (FET, V364, V429). Reconstitution of HLTF expression in HLTF methylated cells suppressed colony forming ability by 75% in each of the three lines tested (p<0.0001 for each) (FIG. 7A). In contrast, transfection of HLTF did not show significant colony suppression in the any of the three cell lines that already expressed endogenous HLTF (FIG. 7B). Growth suppression by exogenous HLTF was thus specific to colon cancers that had silenced the endogenous alleles (p<0.01 for the difference in effect of HLTF transfection in HLTF methylated versus unmethylated cell lines). Transient transfections showed both the HLTF methylated and unmethylated cells were well able to express exogenous HLTF, as determine by Western analysis for a V5 epitope tag attached to HLTF in the expression vector (FIG. 7C). These findings suggest that HLTF methylation and silencing indeed confers a growth advantage in a distinct subclass of colon cancers.

In sum, certainly future studies can be expected to further elucidate the presumptive pathogenetic role that we suggest for HLTF inactivation in colon cancer. Moreover, the high frequency of HLTF methylation in colon cancer may also be useful in potential translational applications. We and others have shown that methylated promoter DNA can be detected in the blood of some cancer patients (Grady, et al., 2001, Cancer Res., 61:900-902). Thus, it will also be attractive to explore the possibility that assays for methylation of HLTF in body fluids may be of future value for early detection of colon cancer incidence, relapse or prognosis.

Incorporation by Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method for detecting differential methylation patterns in an HLTF nucleotide sequence, comprising:
   a) obtaining a sample from a patient;
   b) assaying said sample for the presence of methylation within the nucleotide sequence as set forth in SEQ ID NO: 2;
   c) obtaining a sample from a healthy subject;
   d) assaying for the presence of methylation in the nucleotide sequence as set forth in SEQ ID NO: 2; and
   e) comparing the methylation patterns in the sample from the patient to the methylation patterns in the sample from the healthy subject.

2. A method for detecting colon or gastro-intestinal neoplasia, comprising:
   a) obtaining a sample from a patient; and
   b) assaying said sample for the presence of methylation within the nucleotide sequence as set forth in SEQ ID NO: 2;
   wherein methylation of said nucleotide sequence is indicative of colon or nastro-intestinal neoplasia.

3. The method of any one of claims 1 or 2, wherein the sample is a bodily fluid selected from the group consisting of blood, serum, plasma, a blood-derived fraction, stool, urine, and a colonic effluent.

4. The method of claim 3, wherein the bodily fluid is obtained from a subject suspected of having or is known to have colon or gastro-intestinal neoplasia.

5. The method of claim 2, wherein said method is for detecting colon neoplasia.

6. The method of any of claims 1 or 2, wherein the assay is methylation-specific PCR.

7. The method of claim 6, comprising:
   a) treating DNA from the sample with a compound that converts non-methylated cytosine bases in the DNA to a different base;
   b) amplifying a region of the compound converted HLTF nucleotide sequence with a forward primer and a reverse primer; and
   c) analyzing the methylation patterns of said HLTF nucleotide sequences.

8. The method of claim 6, comprising:
   a) treating DNA from the sample with a compound that converts non-methylated cytosine bases in the DNA to a different base;
   b) amplifying a region of the compound converted HLTF nucleotide sequence with a forward primer and a reverse primer; and
   c) detecting the presence and/or amount of the amplified product.

9. The method of claim 6, wherein the compound used to treat DNA is a bisulfite compound.

10. The method of any of claims 1 or 2, wherein the assay comprises digesting DNA from the sample with a methylation-specific restriction enzyme.

11. The method of claim 10, wherein said methylation-specific restriction enzyme is selected from HpaII, SmaI, SacII, EagI, MspI, BstUI, and BssHII.

12. A method for detecting colon or gastro-intestinal neoplasia in a subject, comprising detecting the level of a HLTF protein set forth in SEQ ID NO: 1 or a nucleic acid which encodes SEQ ID NO: 1 in a sample from the subject, wherein decreased level of the HLTF protein or nucleic acid relative to a control sample is indicative of colon or gastro-intestinal neoplasia.

13. The method of claim 12, wherein the sample is a bodily fluid selected from the group consisting of blood, serum, plasma, a blood-derived fraction, stool, urine, and a colonic effluent.

14. The method of claim 13, wherein the bodily fluid is from a subject suspected of having or known to have colon or gastro-intestinal neoplasia.

15. The method of claim 12, wherein said method is for detecting colon neoplasia.

\* \* \* \* \*